US011471196B2

(12) United States Patent
Sturm et al.

(10) Patent No.: US 11,471,196 B2
(45) Date of Patent: Oct. 18, 2022

(54) FACET JOINT REPLACEMENT DEVICE AND METHODS OF USE

(71) Applicant: Facet Dynamics, Inc., Milton, WI (US)

(72) Inventors: Christopher D. Sturm, Milton, WI (US); Shawn Van Dahm, Bolingbrook, IL (US); Robert Jones, Cedar Park, TX (US)

(73) Assignee: Facet Dynamics, Inc., Milton, WI (US)

( * ) Notice: Subject to any disclaimer, the term of this patent is extended or adjusted under 35 U.S.C. 154(b) by 188 days.

(21) Appl. No.: 16/808,203

(22) Filed: Mar. 3, 2020

(65) Prior Publication Data
US 2020/0337740 A1    Oct. 29, 2020

Related U.S. Application Data

(63) Continuation-in-part of application No. 16/786,753, filed on Feb. 10, 2020, now abandoned, which is a
(Continued)

(51) Int. Cl.
*A61B 17/70*  (2006.01)
*A61B 17/84*  (2006.01)

(52) U.S. Cl.
CPC ...... *A61B 17/7064* (2013.01); *A61B 17/7058* (2013.01); *A61B 17/84* (2013.01)

(58) Field of Classification Search
CPC .......... A61F 2/44; A61F 2/4405; A61F 2/442; A61B 17/7062; A61B 17/7064; A61B 17/7067; A61B 17/7058; A61B 17/84
See application file for complete search history.

(56) References Cited

U.S. PATENT DOCUMENTS 5,571,191 A    11/1996  Fitz
6,132,464 A    10/2000  Martin
(Continued)

FOREIGN PATENT DOCUMENTS

DE    10135771 A1    2/2003
DE    102007038996 A1    4/2009
(Continued)

OTHER PUBLICATIONS

International Search Report dated Jun. 22, 2017 in Application No. PCT/US2017/024591, filed on Mar. 28, 2017.
(Continued)

*Primary Examiner* — Eduardo C Robert
*Assistant Examiner* — Christina Negrellirodriguez
(74) *Attorney, Agent, or Firm* — Knobbe Martens Olson & Bear, LLP

(57) ABSTRACT

A facet joint replacement system includes a facet joint replacement device including an enclosing body and an articulating body. The enclosing body includes an interior surface defining an inner cavity of the enclosing body. The interior surface includes a first articulating surface and a projection extending inwardly relative to a surrounding area of the interior surface. The articulating body is positioned within the inner cavity of the enclosing body and is configured to move within the enclosing body. The articulating body includes a second articulating surface and a recess extending inwardly relative to a surrounding area of the articulating body and aligned with the projection of the interior surface of the enclosing body so as to allow movement of the projection along the recess of the enclosing body while constraining rotational motion of the articulating body within the enclosing body.

20 Claims, 117 Drawing Sheets

Related U.S. Application Data continuation of application No. 15/836,643, filed on Dec. 8, 2017, now Pat. No. 10,555,761, which is a continuation of application No. 15/472,021, filed on Mar. 28, 2017, now Pat. No. 9,839,451.

(60) Provisional application No. 62/314,634, filed on Mar. 29, 2016, provisional application No. 62/813,678, filed on Mar. 4, 2019.

(56) References Cited

U.S. PATENT DOCUMENTS

| | | | |
|---|---|---|---|
| 6,419,703 B1 | 7/2002 | Fallin | |
| 6,565,605 B2 | 5/2003 | Goble | |
| 6,579,319 B2 | 6/2003 | Goble | |
| 6,610,091 B1 | 8/2003 | Reiley | |
| 6,811,567 B2 | 11/2004 | Reiley | |
| 6,974,478 B2 | 12/2005 | Reiley | |
| 7,074,238 B2 | 7/2006 | Stinson | |
| 7,090,698 B2 | 8/2006 | Goble | |
| 7,101,398 B2 | 9/2006 | Dooris | |
| 7,338,527 B2 | 3/2008 | Blatt | |
| 7,377,942 B2 | 5/2008 | Berry | |
| 7,537,611 B2 | 5/2009 | Lee | |
| 7,588,590 B2 | 9/2009 | Chervitz | |
| 7,591,851 B2 | 9/2009 | Winslow | |
| 7,601,170 B2 | 10/2009 | Winslow | |
| 7,608,104 B2 | 10/2009 | Yuan | |
| 7,635,389 B2 | 12/2009 | Yu | |
| 7,655,044 B2 | 2/2010 | Kwak | |
| 7,662,183 B2 | 2/2010 | Haines | |
| 7,674,293 B2 | 3/2010 | Kuiper | |
| 7,691,145 B2 | 4/2010 | Reiley | |
| 7,695,514 B2 | 4/2010 | Kwak | |
| 7,722,647 B1 | 5/2010 | Wang | |
| 7,763,050 B2 | 7/2010 | Winslow | |
| 7,776,090 B2 | 8/2010 | Winslow | |
| 7,803,189 B2 | 9/2010 | Koske | |
| 7,811,326 B2 | 10/2010 | Braddock | |
| 7,846,183 B2 | 12/2010 | Blain | |
| 7,846,184 B2 | 12/2010 | Sasso | |
| 7,862,589 B2 | 1/2011 | Thramann | |
| 7,896,903 B2 | 3/2011 | Link | |
| 7,922,766 B2 | 4/2011 | Grob | |
| 7,935,136 B2 | 5/2011 | Alamin | |
| 7,947,063 B2 | 5/2011 | Arnin | |
| 7,988,712 B2 | 8/2011 | Hale | |
| 7,993,373 B2 | 8/2011 | Hoy | |
| 7,998,176 B2 | 8/2011 | Culbert | |
| 8,029,540 B2 | 10/2011 | Winslow | |
| 8,066,749 B2 | 11/2011 | Winslow | |
| 8,070,783 B2 | 12/2011 | Kwak | |
| 8,118,838 B2 | 2/2012 | Winslow | |
| 8,128,660 B2 | 3/2012 | Mitchell | |
| 8,172,877 B2 | 5/2012 | Winslow | |
| 8,182,512 B2 * | 5/2012 | Muhanna | A61F 2/4405 606/247 |
| 8,246,684 B2 | 8/2012 | Lee | |
| 8,409,254 B2 | 4/2013 | Yuan | |
| 8,460,341 B2 | 6/2013 | Chin | |
| 8,491,634 B2 | 7/2013 | Sasso | |
| 8,496,686 B2 | 7/2013 | Berg | |
| 8,556,936 B2 | 10/2013 | Goble | |
| 8,702,755 B2 | 4/2014 | Ralph | |
| 8,764,801 B2 | 7/2014 | Chervitz | |
| 8,840,647 B2 | 9/2014 | Siemionow | |
| 9,056,016 B2 | 6/2015 | Reiley | |
| 9,084,638 B2 | 7/2015 | Linares | |
| 9,089,436 B2 | 7/2015 | Overes | |
| 9,198,767 B2 | 12/2015 | Abdou | |
| 9,314,277 B2 | 4/2016 | Assell | |
| 9,339,394 B2 | 5/2016 | Chervitz | |
| 9,839,451 B2 | 12/2017 | Sturm | |
| 10,555,761 B2 | 2/2020 | Sturm | |
| 2003/0028254 A1 | 2/2003 | Hunter | |
| 2004/0230201 A1 | 11/2004 | Yuan | |
| 2005/0027361 A1 | 2/2005 | Reiley | |
| 2005/0033434 A1 | 2/2005 | Berry | |
| 2005/0197700 A1 | 9/2005 | Boehm | |
| 2005/0256578 A1 | 11/2005 | Blatt | |
| 2005/0261770 A1 | 11/2005 | Kuiper | |
| 2005/0267579 A1 | 12/2005 | Reiley | |
| 2006/0247633 A1 | 11/2006 | Winslow | |
| 2006/0247650 A1 | 11/2006 | Yerby | |
| 2006/0265074 A1 | 11/2006 | Krishna | |
| 2006/0276790 A1 | 12/2006 | Dawson | |
| 2007/0016196 A1 | 1/2007 | Winslow | |
| 2007/0016297 A1 | 1/2007 | Johnson | |
| 2007/0055373 A1 | 3/2007 | Hudgins | |
| 2007/0073290 A1 | 3/2007 | Boehm | |
| 2007/0088358 A1 | 4/2007 | Yuan | |
| 2007/0093833 A1 | 4/2007 | Kuiper | |
| 2007/0179617 A1 | 8/2007 | Brown | |
| 2007/0198091 A1 | 8/2007 | Boyer | |
| 2007/0233256 A1 | 10/2007 | Ohrt | |
| 2007/0288009 A1 | 12/2007 | Brown | |
| 2008/0027547 A1 | 1/2008 | Yu | |
| 2008/0017731 A1 | 7/2008 | Reiley | |
| 2008/0177311 A1 | 7/2008 | Winslow | |
| 2008/0183209 A1 | 7/2008 | Robinson | |
| 2008/0319483 A1 | 12/2008 | Triplett | |
| 2009/0216277 A1 | 8/2009 | Tornier | |
| 2009/0270917 A1 | 10/2009 | Boehm | |
| 2010/0004687 A1 | 1/2010 | Falahee | |
| 2010/0211107 A1 | 8/2010 | Muhanna | |
| 2010/0312283 A1 | 12/2010 | Kwak | |
| 2012/0221049 A1 | 8/2012 | Blain | |
| 2014/0277140 A1 | 9/2014 | Jarolem | |
| 2014/0288601 A1 | 9/2014 | Baynham | |
| 2015/0230833 A1 | 8/2015 | Chervitz | |
| 2015/0230933 A1 | 8/2015 | Fallin | |
| 2015/0342648 A1 | 12/2015 | Mccormack | |
| 2017/0095348 A1 | 4/2017 | Josse | |
| 2018/0071106 A1 | 3/2018 | Bydon | |
| 2018/0161074 A1 | 6/2018 | Sturm | |

FOREIGN PATENT DOCUMENTS

| | | |
|---|---|---|
| DE | 102007051782 A1 | 5/2009 |
| FR | 2832054 | 5/2003 |
| WO | WO 2005/048876 A2 | 6/2005 |

OTHER PUBLICATIONS

Extended European Search Report issued in EP Application No. 17776484.2, dated Nov. 5, 2019.

International Search Report issued in Application No. PCT/US2020/020810, dated Jun. 17, 2020.

\* cited by examiner

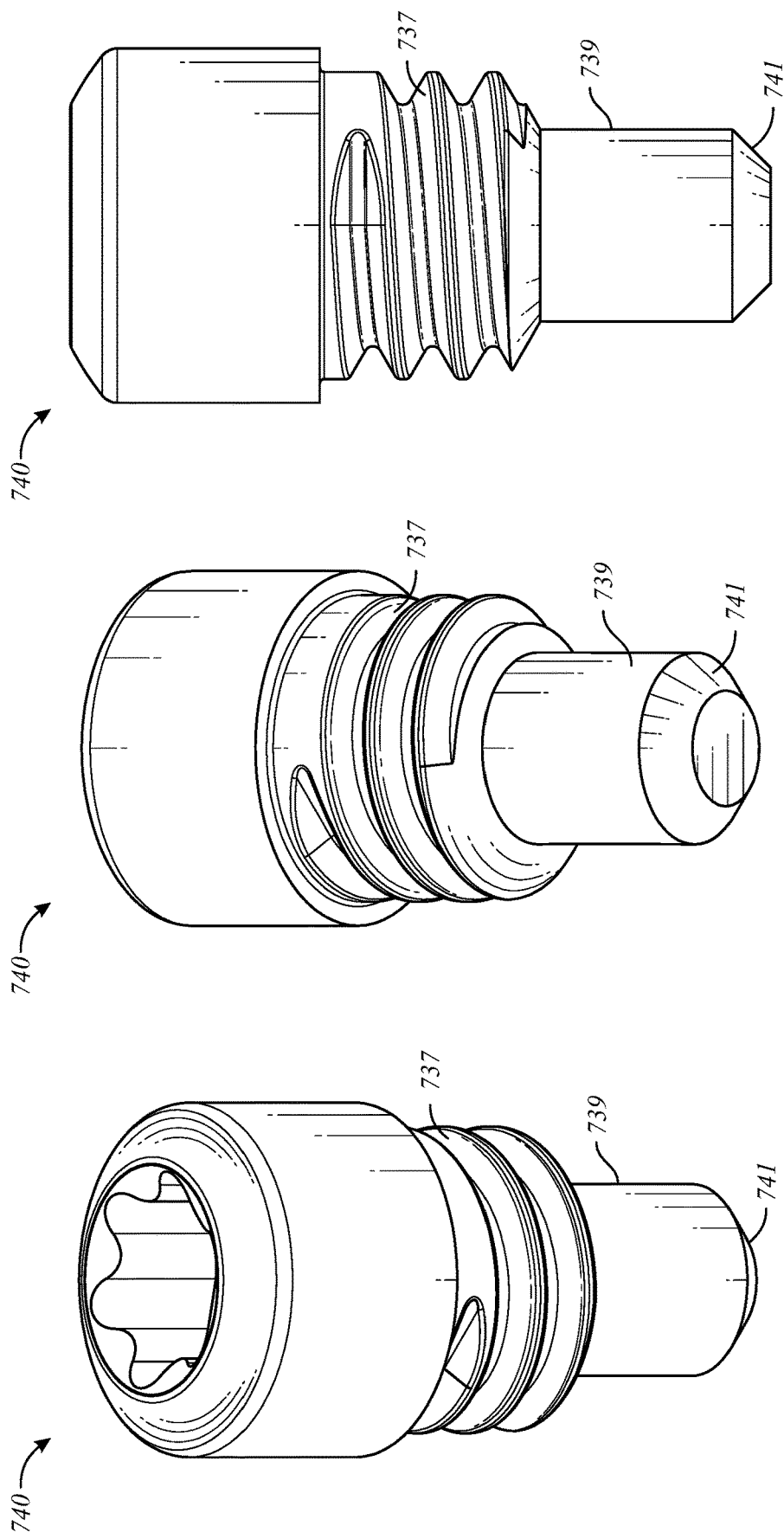

FACET JOINT REPLACEMENT DEVICE AND METHODS OF USE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

The present application claims priority benefit of Provisional Patent Application Ser. No. 62/813,678, entitled "FACET JOINT REPLACEMENT DEVICE AND METHODS OF USE", filed Mar. 4, 2019, and is a continuation-in-part of U.S. application Ser. No. 16/786,753, entitled "FACET JOINT REPLACEMENT DEVICE AND METHODS OF USE", filed Feb. 10, 2020, which is a continuation of U.S. application Ser. No. 15/836,643, entitled "FACET JOINT REPLACEMENT DEVICE AND METHODS OF USE", filed Dec. 8, 2017, which is a continuation of U.S. application Ser. No. 15/472,021, entitled "FACET JOINT REPLACEMENT DEVICE AND METHODS OF USE," filed Mar. 28, 2017, now U.S. Pat. No. 9,839,451, which claims priority benefit of U.S. Provisional Patent Application Ser. No. 62/314,634, entitled "Restore Unilateral or Bilateral Artificial Lumbar FACET joint surgical implant," filed Mar. 29, 2016, the entire disclosure of each of which is hereby expressly incorporated by reference.

BACKGROUND

Field

The present application relates to spinal surgery in general, and more particularly to methods, systems, and apparatuses for replacing a facet joint.

Description of the Related Art

The lumbar facet joint is a diarthrodial synovial joint consisting of a superior articular process having a superior articular surface, an inferior articular process having an inferior articular surface, and a capsule that encloses the superior and inferior articular surfaces. Each lumbar facet joint can provide mechanical support for axial loading along the spine, facilitate movement along a longitudinal axis of the spine, and limit relative rotation and translation of adjacent vertebra. Particularly, the articular processes support compressive loading and the capsule, resists forces developed across the facet joint due to movement of the adjacent vertebrae, such as, for example, rotational and translational forces. The facet joint capsule can provide resistance to separation of the superior and inferior articular surfaces and to relative motion between the superior and inferior articular surfaces.

Lumber facet joint dysfunction can develop as a result of degeneration, trauma, or neoplastic processes to the vertebrae and can result in spinal instability, malalignment, nerve compression, and pain, which can cause neurological deficits. Facet joint dysfunction is treated by partial or total resection of the dysfunctional lumbar facet joint. Resection can leave the addressed spinal motion segment with decreased strength, stiffness, and the ability to resist rotation.

Fusion procedures have evolved to address the spinal de-stabilization of motion segments caused by facet joint resection. Fusion procedures result in immobilization of the two adjacent vertebrae that comprise the motion segment. As physiologic loads are transmitted across contiguous motions segments of the lumbar spine, the introduction of an immobilized motion segment within the lumbar spine can result in non-physiologic transmission of these forces. This "disconnection" within the series of motion segments that comprise the lumbar spine has been postulated to create an altered force load application on the adjacent, non-treated, motion segments, potentially accelerating the degenerative process at these locations.

SUMMARY

Methods, systems and apparatuses are provided in certain embodiments of the present application to replace a dysfunctional facet joint.

In one embodiment, a facet joint replacement device is provided. The facet joint replacement device includes an enclosing element including an enclosing body and an inferior attachment member. The enclosing body includes a superior end having an opening, an inferior end, and an inner cavity defined by an interior surface of the enclosing body, wherein a portion of the interior surface of the enclosing body forms a superior articulating surface. The inferior attachment member extends from the enclosing body and is configured to attach to an inferior vertebral body. The facet joint replacement device also includes an inferior articulating element including an articulating body and a superior attachment member. The inferior articulating body is positioned within the inner cavity of the enclosing body of the enclosing element and is configured to move within the inner cavity of the enclosing body of the enclosing element. The inferior articulating body includes a superior end and an inferior end forming an inferior articulating surface. The superior attachment member extends from the superior end of the articulating body and superior to the opening of the superior end of the enclosing body. The superior attachment member is configured to attach to a superior vertebral body. The movement of the articulating body of the inferior articulating element is constrained in at least one direction within the inner cavity of the enclosing body of the enclosing element.

In another embodiment, a facet joint replacement system is provided. The facet joint replacement system includes the facet joint replacement device, an inferior fastener configured to secure the inferior attachment member to the inferior vertebral body, and a superior fastener configured to secure the superior attachment member to the superior vertebral body.

In another embodiment, a method of implanting a facet joint replacement device is provided. The method includes providing the facet joint replacement device, securing the superior attachment member to the superior vertebral body, and securing the inferior attachment member to the inferior vertebral body.

In another embodiment, a method of replacing a facet joint is provided. The method includes resecting at least a portion of a facet joint defined by an articular process of a superior vertebral body and an articular process of an inferior vertebral body, cannulating a pedicle of the inferior vertebral body and a pedicle of the superior vertebral body, inserting a first fastener into the pedicle of the inferior vertebral body and a second fastener into the pedicle of the superior vertebral body, and securing a facet joint replacement device to the first fastener and the second fastener, wherein the facet joint replacement device includes an enclosing body, an inferior articulating surface enclosed within the enclosing body, and a superior articulating surface enclosed within the enclosing body.

In another embodiment, a facet joint replacement system is provided. The facet joint replacement system includes a facet joint replacement device. The facet joint replacement device includes an enclosing body and an articulating body. The enclosing body includes an interior surface defining an inner cavity of the enclosing body. The interior surface includes a first articulating surface and a projection extending inwardly relative to a surrounding area of the interior surface. The articulating body is positioned within the inner cavity of the enclosing body and is configured to move within the inner cavity of the enclosing body. The articulating body includes a second articulating surface and a recess extending inwardly relative to a surrounding area of the articulating body and aligned with the projection of the interior surface of the enclosing body so as to allow movement of the projection along the recess of the enclosing body while constraining rotational motion of the articulating body within the enclosing body.

In another embodiment, a facet joint replacement system is provided. The facet joint replacement system includes a facet joint replacement device. The facet joint replacement device includes an enclosing body and an articulating body. The enclosing body includes an interior surface defining an inner cavity of the enclosing body. The interior surface includes a first articulating surface. The enclosing body includes a first channel extending through a portion of the enclosing body. The articulating body is positioned within the inner cavity of the enclosing body and is configured to move within the inner cavity of the enclosing body. The articulating body includes a second articulating surface and a second channel extending through at least a portion of the articulating body. The facet joint replacement system also includes a fastener configured to be removably received within the first channel and the second channel, the fastener configured to engage the enclosing body and articulating body to constrain movement of the articulating body within the enclosing body, and a plug configured to be removably received within the first channel.

In another embodiment, a facet joint replacement system is provided. The facet joint replacement system includes a facet joint replacement device. The facet joint replacement device includes an enclosing body and an articulating body. The enclosing body includes an outer shell defining an exterior surface of the enclosing body and a liner covering an interior surface of the outer shell, the liner including a low friction material and defining an inner cavity of the enclosing body, a portion of the liner defining a first articulating surface. The articulating body is positioned within the inner cavity of the enclosing body and is configured to move within the inner cavity of the enclosing body. The articulating body includes a second articulating surface configured to articulate against the first articulating surface.

In another embodiment, a method of replacing a facet joint is provided. The method includes introducing a facet joint replacement device into a body of a patient, the facet joint replacement device including an enclosing body and an articulating body positioned within an interior cavity of the enclosing body, wherein a fastener is positioned with respect to the enclosing body and the articulating body to constrain movement of the articulating body within the enclosing body. The method further includes securing the facet joint replacement device relative to a superior vertebral body and relative to an inferior vertebral body of the patient while the fastener constrains movement of the articulating body within the enclosing body. The method further includes removing the fastener after securing the facet joint replacement device relative to the superior vertebral body and relative to the inferior vertebral body to allow movement of the articulating body within the enclosing body.

In another embodiment, a facet joint replacement device is provided. The facet joint replacement device includes an enclosing body and an articulating body. The enclosing body is configured to be secured relative to one of a superior vertebral body and an inferior vertebral body. The enclosing body includes a first articulating surface. The articulating body is configured to be secured relative to the other of the superior vertebral body and the inferior vertebral body. The articulating body is positioned within an inner cavity of the enclosing body and includes a second articulating surface positioned within the inner cavity configured to articulate relative to the first articulating surface. When the enclosing body and the articulating body are secured relative to the superior and inferior vertebral bodies, the first articulating surface and the second articulating surface are configured such that they are located approximately at the location of a natural facet joint and are configured to articulate relative to each other by moving substantially only parallel to a superior/inferior axis of the patient.

In another embodiment, a method of replacing a facet joint is provided. The method includes introducing a facet joint replacement device into a body of a patient. The facet joint replacement device includes an enclosing body having a first articulating surface and an articulating body positioned within an inner cavity of the enclosing body having a second articulating surface. The method further includes securing the enclosing body of the facet joint replacement device relative to one of a superior vertebral body and an inferior vertebral body. The method further includes securing the articulating body of the facet joint replacement device relative to the other of the superior vertebral body and the inferior vertebral body, wherein after both the enclosing body and the articulating body are secured, the first and second articulating surfaces are located approximately at the location of a natural facet joint and are configured to articulate relative to each other by moving substantially only parallel to a superior/inferior axis of the patient.

In another embodiment, a method of replacing a facet joint is provided. The method includes introducing a facet joint replacement device into a body of a patient, the facet joint replacement device having an enclosing body and an articulating body positioned within an inner cavity of the enclosing body, wherein a device holder is coupled to the facet joint replacement device. The device holder includes a shaft, a handle positioned at a first end of the shaft, and a fastening head positioned at a second end of the shaft, wherein the fastening head is positioned with respect to the enclosing body and the articulating body to constrain movement of the articulating body within the enclosing body. The method further includes securing the facet joint replacement device relative to a superior vertebral body and relative to an inferior vertebral body of the patient while the fastening head constrains movement of the articulating body within the enclosing body, and disengaging the fastening head from the facet joint replacement device after securing the facet joint replacement device relative to the superior vertebral body and relative to the inferior vertebral body to allow movement of the articulating body within the enclosing body.

In any of the embodiments described above or elsewhere in this specification, the enclosing body can include a projection extending inwardly relative to a surrounding area of the interior surface of the enclosing body, and the articulating body can include a recess extending inwardly relative to a surrounding area of the articulating body and aligned with the projection of the interior surface of the enclosing body. In any of the embodiments described above or elsewhere in this specification, the projection can be configured to move within the recess parallel or substantially parallel to a longitudinal axis of articulation. In any of the embodiments described above or elsewhere in this specification, the longitudinal axis of articulation can be a superior/inferior axis. In any of the embodiments described above or elsewhere in this specification, the projection can be generally convex, and the recess can be generally concave. In any of the embodiments described above or elsewhere in this specification, the projection can be generally parabolic in shape.

In any of the embodiments described above or elsewhere in this specification, the facet joint replacement device can include a first attachment member configured to be secured relative to one of a superior vertebral body and an inferior vertebral body of a patient and a second attachment member configured to be secured to the other of the superior vertebral body and the inferior vertebral body. In any of the embodiments described above or elsewhere in this specification, the first attachment member can be part of the enclosing element, and the second attachment member can be part of the articulating element. In any of the embodiments described above or elsewhere in this specification, the first attachment member can extend from an articulating body. In any of the embodiments described above or elsewhere in this specification, the first attachment member can be configured to be secured relative to a superior vertebral body. In any of the embodiments described above or elsewhere in this specification, the second attachment member can extend from an enclosing body. In any of the embodiments described above or elsewhere in this specification, the second attachment member can be configured to be secured to an inferior vertebral body. In any of the embodiments described above or elsewhere in this specification, the first attachment member can be removably coupled to the articulating body. In any of the embodiments described above or elsewhere in this specification, the first attachment member can be removably secured to the articulating body via a tapered connection. In any of the embodiments described above or elsewhere in this specification, the first attachment member can include a bend in a section of the first attachment member lateral to the articulating body. In any of the embodiments described above or elsewhere in this specification, the second attachment member can be configured to extend from a lateral surface of the enclosing body. In any of the embodiments described above or elsewhere in this specification, the second attachment member can include a bend in a section of the second attachment member lateral to the enclosing body.

In any of the embodiments described above or elsewhere in this specification, the first articulating surface can be configured so that it is located approximately at the location of a natural facet joint when the facet joint replacement device is implanted within a body of a patient. In any of the embodiments described above or elsewhere in this specification, the first articulating surface can be shaped, dimensioned, or otherwise configured to correspond to the shape, size, and/or convexity of an articular surface of a healthy superior articular process. In any of the embodiments described above or elsewhere in this specification, the first articulating surface can be configured to perform the functions of an articular surface of a healthy superior articular process.

In any of the embodiments described above or elsewhere in this specification, the second articulating surface can be positioned on an anterior and medial section of the articulating body. In any of the embodiments described above or elsewhere in this specification, the second articulating surface can be positioned on a face of the articulating body opposite a recess of the articulating body. In any of the embodiments described above or elsewhere in this specification, the second articulating surface can be configured so that it is located approximately at the location of a natural facet joint when the facet joint replacement device is implanted within a body of a patient. In any of the embodiments described above or elsewhere in this specification, the second articulating surface can be shaped, dimensioned, or otherwise configured to correspond to the shape, size, and/or convexity of an articular surface of a healthy inferior articular process. In any of the embodiments described above or elsewhere in this specification, the second articulating surface can be configured to perform the functions of an articular surface of a healthy inferior articular process.

In any of the embodiments described above or elsewhere in this specification, the first articulating surface and the second articulating surface can be configured to articulate relative to each other by moving substantially only parallel to a superior/inferior axis of a patient when the facet joint replacement device is implanted within a body of the patient. In any of the embodiments described above or elsewhere in this specification, the first articulating surface and the second articulating surface can be configured to articulate relative to each other by moving substantially only parallel to an angle formed by the two juxtaposed articular surfaces.

In any of the embodiments described above or elsewhere in this specification, an angle between an axis parallel to a frontal anatomic plane and extending through a center point of the first articulating surface and an axis extending through the center point of the first articulating surface and perpendicular to a tangent of the first articulating surface at the center point can be between 30° and 60°, between 35° and 55°, between 40° and 50°, or any other suitable range. In any of the embodiments described above or elsewhere in this specification, an angle between an axis parallel to a frontal anatomic plane and extending through a center point of the first articulating surface and an axis extending through the center point of the first articulating surface and perpendicular to a tangent of the first articulating surface at the center point can be 30°, 35°, 40°, 45°, 50°, 55°, 60°, or any other suitable angle. In any of the embodiments described above or elsewhere in this specification, an angle between an axis parallel to a sagittal anatomic plane and extending through a center point of the first articulating surface and an axis extending through the center point of the first articulating surface and perpendicular to a tangent of first articulating surface at the center point can be between 30° and 60°, between 35° and 55°, between 40° and 50°, or any other suitable range. In any of the embodiments described above or elsewhere in this specification, an angle between an axis parallel to a sagittal anatomic plane and extending through a center point of the first articulating surface and an axis extending through the center point of the first articulating surface and perpendicular to a tangent of the first articulating surface at the center point can be 30°, 35°, 40°, 45°, 50°, 55°, 60°, or any other suitable angle. In any of the embodiments described above or elsewhere in this specification, an angle between an axis parallel to a transverse anatomic plane and extending through a center point of the first articulating surface and an axis extending through the center point of the first articulating surface and perpendicular to a tangent of the first articulating surface at the center point can be between 75° and 105°, between 80° to 100°, between 85° to 95° or any other suitable angle. In any of the embodiments described above or elsewhere in this specification, an angle between an axis parallel to a transverse anatomic plane and extending through a center point of the first articulating surface and an axis extending through the center point of the first articulating surface and perpendicular to a tangent of the first articulating surface at the center point can be 75°, 80°, 85°, 90°, 95°, 100°, 105°, or any other suitable angle.

In any of the embodiments described above or elsewhere in this specification, an angle between an axis parallel to a frontal anatomic plane and extending through a center point of the second articulating surface and an axis extending through the center point of the second articulating surface and perpendicular to a tangent of the second articulating surface at the center point can be between 30° and 60°, between 35° and 55°, between 40° and 50°, or any other suitable range. In any of the embodiments described above or elsewhere in this specification, an angle between an axis parallel to a frontal anatomic plane and extending through a center point of the second articulating surface and an axis extending through the center point of the second articulating surface and perpendicular to a tangent of the second articulating surface at the center point can be 30°, 35°, 40°, 45°, 50°, 55°, 60°, or any other suitable angle. In any of the embodiments described above or elsewhere in this specification, an angle between an axis parallel to a sagittal anatomic plane and extending through a center point of the second articulating surface and an axis extending through the center point of the second articulating surface and perpendicular to a tangent of second articulating surface at the center point can be between 30° and 60°, between 35° and 55°, between 40° and 50°, or any other suitable range. In any of the embodiments described above or elsewhere in this specification, an angle between an axis parallel to a sagittal anatomic plane and extending through a center point of the second articulating surface and an axis extending through the center point of the second articulating surface and perpendicular to a tangent of the second articulating surface at the center point can be 30°, 35°, 40°, 45°, 50°, 55°, 60°, or any other suitable angle. In any of the embodiments described above or elsewhere in this specification, an angle between an axis parallel to a transverse anatomic plane and extending through a center point of the second articulating surface and an axis extending through the center point of the second articulating surface and perpendicular to a tangent of the second articulating surface at the center point can be between 75° and 105°, between 80° to 100°, between 85° to 95° or any other suitable angle. In any of the embodiments described above or elsewhere in this specification, an angle between an axis parallel to a transverse anatomic plane and extending through a center point of the second articulating surface and an axis extending through the center point of the second articulating surface and perpendicular to a tangent of the second articulating surface at the center point can be 75°, 80°, 85°, 90°, 95°, 100°, 105°, or any other suitable angle.

In any of the embodiments described above or elsewhere in this specification, the enclosing body can be shaped, dimensioned, or otherwise configured to correspond to the shape and/or size of a facet joint capsule of a healthy facet joint. In any of the embodiments described above or elsewhere in this specification, the enclosing body can be configured to perform the functions of a facet joint capsule of a healthy facet joint.

In any of the embodiments described above or elsewhere in this specification, the articulating body can be configured to move superiorly and inferiorly within the enclosing body. In any of the embodiments described above or elsewhere in this specification, the articulating body can be configured to move along an axis parallel or substantially parallel with a superior/inferior axis of a patient. In any of the embodiments described above or elsewhere in this specification, the enclosing body can be configured to restrict movement of the articulating body within the enclosing body such that the articulating body moves only along the axis parallel or substantially parallel with the superior/inferior axis of the patient.

In any of the embodiments described above or elsewhere in this specification, the enclosing body can be configured to restrict movement of the articulating body within the enclosing body such that the second articulating surface moves only along an axis parallel or substantially parallel with the superior/inferior axis of the patient. In any of the embodiments described above or elsewhere in this specification, the enclosing body can be configured to restrict movement of the articulating body within the enclosing body such that the articulating body moves only along an axis parallel or substantially parallel with an angle formed by the juxtaposed first articulating surface and second articulating surface. In any of the embodiments described above or elsewhere in this specification, the enclosing body can be configured to restrict movement of the articulating body within the enclosing body such that the second articulating surface moves only along an axis parallel or substantially parallel with an angle formed by the two juxtaposed articulating surfaces.

In any of the embodiments described above or elsewhere in this specification, an angle between the transverse anatomic plane and a mean orientation of the second articulating surface can be between 0° and 98°, between 10° and 88°, between 20° and 78°, or any other suitable angle for a facet joint replacement device implanted within the cervical spine. In any of the embodiments described above or elsewhere in this specification, an angle between the transverse anatomic plane and a mean orientation of the second articulating surface can be between 35° and 100°, between 45° and 90°, between 55° and 80°, or any other suitable angle for a facet joint replacement device implanted within the thoracic spine. In any of the embodiments described above or elsewhere in this specification, an angle between the transverse anatomic plane and a mean orientation of the second articulating surface can be between 62° and 106°, between 72° and 96°, between 82° and 86°, or any other suitable angle for a facet joint replacement device implanted within the lumbar spine. In any of the embodiments described above or elsewhere in this specification, the transverse anatomic plane may be referred to as the 0° transverse plane. In any of the embodiments described above or elsewhere in this specification, the foregoing angles between the transverse anatomic plane and a mean orientation of the second articulating surface may be referred to as inclination angles of the second articulating surface within the sagittal anatomic plane.

In any of the embodiments described above or elsewhere in this specification, an angle between the sagittal anatomic plane and a mean orientation of the second articulating surface can be between 50° and 116°, between 60° and 106°, between 70° and 96°, or any other suitable angle for a facet joint replacement device implanted within the cervical spine. In any of the embodiments described above or elsewhere in this specification, an angle between the sagittal anatomic plane and a mean orientation of the second articulating surface can be between 65° and 140°, between 75° and 130°, between 85° and 120°, or any other suitable angle for a facet joint replacement device implanted within the thoracic spine. In any of the embodiments described above or elsewhere in this specification, an angle between the sagittal anatomic plane and a mean orientation of the second articulating surface can be between 0° and ° 90, between 5° and 80°, between 15° and 70°, or any other suitable angle for a facet joint replacement device implanted within the lumbar spine. In any of the embodiments described above or elsewhere in this specification, the sagittal anatomic plane may be referred to as the 0° sagittal plane. In any of the embodiments described above or elsewhere in this specification, the foregoing angles between the sagittal anatomic plane and a mean orientation of the second articulating surface may be referred to as inclination angles of the second articulating surface within the transverse anatomic plane.

In any of the embodiments described above or elsewhere in this specification, the second articulating surface can be configured to articulate relative to the first articulating surface by moving substantially only parallel to an axis defined by the inclination angles of the second articulating surface within the sagittal and transverse anatomic planes.

In any of the embodiments described above or elsewhere in this specification, an angle between the transverse anatomic plane and a mean orientation of the first articulating surface can be between 0° and 98°, between 10° and 88°, between 20° and 78°, or any other suitable angle for a facet joint replacement device implanted within the cervical spine. In any of the embodiments described above or elsewhere in this specification, an angle between the transverse anatomic plane and a mean orientation of the first articulating surface can be between 35° and 100°, between 45° and 90°, between 55° and 80°, or any other suitable angle for a facet joint replacement device implanted within the thoracic spine. In any of the embodiments described above or elsewhere in this specification, an angle between the transverse anatomic plane and a mean orientation of the first articulating surface can be between 62° and 106°, between 72° and 96°, between 82° and 86°, or any other suitable angle for a facet joint replacement device implanted within the lumbar spine. In any of the embodiments described above or elsewhere in this specification, the transverse anatomic plane may be referred to as the 0° transverse plane. In any of the embodiments described above or elsewhere in this specification, the foregoing angles between the transverse anatomic plane and a mean orientation of the first articulating surface may be referred to as inclination angles of the first articulating surface within the sagittal anatomic plane.

In any of the embodiments described above or elsewhere in this specification, an angle between the sagittal anatomic plane and a mean orientation of the first articulating surface can be between 50° and 116°, between 60° and 106°, between 70° and 96°, or any other suitable angle for a facet joint replacement device implanted within the cervical spine. In any of the embodiments described above or elsewhere in this specification, an angle between the sagittal anatomic plane and a mean orientation of the first articulating surface can be between 65° and 140°, between 75° and 130°, between 85° and 120°, or any other suitable angle for a facet joint replacement device implanted within the thoracic spine. In any of the embodiments described above or elsewhere in this specification, an angle between the sagittal anatomic plane and a mean orientation of the first articulating surface can be between 0° and ° 90, between 5° and 80°, between 15° and 70°, or any other suitable angle for a facet joint replacement device implanted within the lumbar spine. In any of the embodiments described above or elsewhere in this specification, the sagittal anatomic plane may be referred to as the 0° sagittal plane. In any of the embodiments described above or elsewhere in this specification, the foregoing angles between the sagittal anatomic plane and a mean orientation of the first articulating surface may be referred to as inclination angles of the first articulating surface within the transverse anatomic plane.

In any of the embodiments described above or elsewhere in this specification, the first articulating surface can be configured to articulate relative to the second articulating surface by moving substantially only parallel to an axis defined by the inclination angles of the first articulating surface within the sagittal and transverse anatomic planes.

In any of the embodiments described above or elsewhere in this specification, the facet joint replacement system can include a fastener configured to be removably received within the facet joint replacement device to constrain movement of the articulating body within the enclosing body. In any of the embodiments described above or elsewhere in this specification, the fastener can be configured to removably received within a first channel of the enclosing body and a second channel of the articulating body. In any of the embodiments described above or elsewhere in this specification, the fastener can contain an externally threaded portion configured to removably secure to complementary threads of one or both of the first channel and the second channel.

In any of the embodiments described above or elsewhere in this specification, the facet joint replacement system can include an instrument or device holder having a shaft, a handle positioned at a first end of the shaft, and a fastening head positioned at a second end of the shaft. In any of the embodiments described above or elsewhere in this specification, the fastening head can be configured to be removably received within a first channel of the enclosing body and a second channel of the artilating body. In any of the embodiments described above or elsewhere in this specification, the fastening head can contain an externally threaded portion configured to removably secure to complementary threads of one or both of the first channel and the second channel.

In any of the embodiments described above or elsewhere in this specification, the facet joint replacement system can include a plug configured to be received in the enclosing body. In any of the embodiments described above or elsewhere in this specification, the plug can be configured to be received within a channel of the enclosing body. In any of the embodiments described above or elsewhere in this specification, the plug can be configured to be received in a channel of the enclosing body after removal of a fastener from the channel. In any of the embodiments described above or elsewhere in this specification, the plug can be configured to seal the first channel relative to the external environment of the enclosing body. In any of the embodiments described above or elsewhere in this specification, the plug can include complementary threads within the channel of the enclosing body. In any of the embodiments described above or elsewhere in this specification, the plug can be dimensioned to extend through only a portion of the channel of the enclosing body. In any of the embodiments described above or elsewhere in this specification, the plug can be configured to fit flush with an exterior surface of the enclosing body. In any of the embodiments described above or elsewhere in this specification, the plug can be configured to removably couple to the fastening head of the device holder.

In any of the embodiments described above or elsewhere in this specification, the facet joint replacement system can include a plug assembly including the plug and a plug insertion section coupled to the plug by a frangible connection. In any of the embodiments described above or elsewhere in this specification, the frangible connection can be configured to break, shear, tear, and/or otherwise separate in response to application of a force to the plug assembly. In any of the embodiments described above or elsewhere in this specification, the frangible connection can be configured to break, shear, tear, and/or otherwise separate in response to application of a force to the plug insertion section. In any of the embodiments described above or elsewhere in this specification, the frangible connection can be configured to break, shear, tear, and/or otherwise separate in response to application of a force to the plug insertion section while the plug is maintained in a fixed position. In any of the embodiments described above or elsewhere in this specification, positioning the plug within the enclosing body can include inserting the plug into the enclosing body using the device holder while the plug assembly is coupled to the device holder. In any of the embodiments described above or elsewhere in this specification, the plug assembly can be configured such that while the plug is positioned within the enclosing body and the plug insertion portion is coupled to the plug, the handle of the device holder can be manipulated to cause the plug insertion section to separate from the plug at the frangible connection.

In any of the embodiments described above or elsewhere in this specification, the enclosing body can include an outer shell and a liner. In any of the embodiments described above or elsewhere in this specification, the liner can include ultra-high molecular weight polyethylene. In any of the embodiments described above or elsewhere in this specification, the liner can include Vitamin E impregnated ultra-high molecular weight polyethylene. In any of the embodiments described above or elsewhere in this specification, the liner can include a projection extending inwardly relative to a surrounding area of liner, the projection being shaped and positioned to restrict rotation of the articulating body within the enclosing body. In any of the embodiments described above or elsewhere in this specification, the outer shell can include a main body and a cap configured to secure to the main body. In any of the embodiments described above or elsewhere in this specification, the liner can include a main liner body and a liner cap. In any of the embodiments described above or elsewhere in this specification, the liner cap can be configured to be secured to the liner body. In any of the embodiments described above or elsewhere in this specification, the liner can circumferentially enclose the first articulating surface and the second articulating surface during relative movement between the first articulating surface and the second articulating surface. In any of the embodiments described above or elsewhere in this specification, the liner can enclose a circumferential portion of the articulating body that includes the second articulating surface.

In any of the embodiments described above or elsewhere in this specification, the enclosing body can include a retention plate. In any of the embodiments described above or elsewhere in this specification, the retention plate can include an opening positioned so that the first attachment member extends out of the opening of the retention plate. In any of the embodiments described above or elsewhere in this specification, a cross-sectional area of the opening can be less than the cross-sectional area of the articulating body. In any of the embodiments described above or elsewhere in this specification, the retention plate can be coupled to the liner and/or the outer shell of the enclosing body to form the enclosing body. In any of the embodiments described above or elsewhere in this specification, the retention plate can at least partially form a barrier to restrict movement of the articulating element in a superior direction relative to the enclosing body

BRIEF DESCRIPTION OF THE DRAWINGS

FIG. 32A depicts a top perspective view of the fastener 740.

FIG. 32B depicts a bottom perspective view of the fastener 740.

FIG. 32C depicts a front view of the fastener 740.

FIG. 38B depicts a top anterior perspective view of the articulating element 904.

FIG. 38C depicts a bottom posterior perspective view of the articulating element 904.

FIG. 38D depicts a bottom medial perspective view of the articulating element 904.

FIG. 38E depicts a posterior view of the articulating element 904.

FIG. 38F depicts an anterior view of the articulating element 904.

FIG. 38G depicts a first sagittal view of a lateral side of the articulating element 904.

FIG. 38H depicts a second sagittal view of a medial side of the articulating element 904.

FIG. 38I depicts a top view of the articulating element 904.

FIG. 38J depicts a bottom view of the articulating element 904.

FIG. 38K depicts a cross-sectional view of the articulating element 904.

FIG. 39 is an exploded view of the facet joint replacement device 900.

FIG. 40A depicts a posterior-medial cross-sectional view of the facet joint replacement device 900.

Figure 40A:
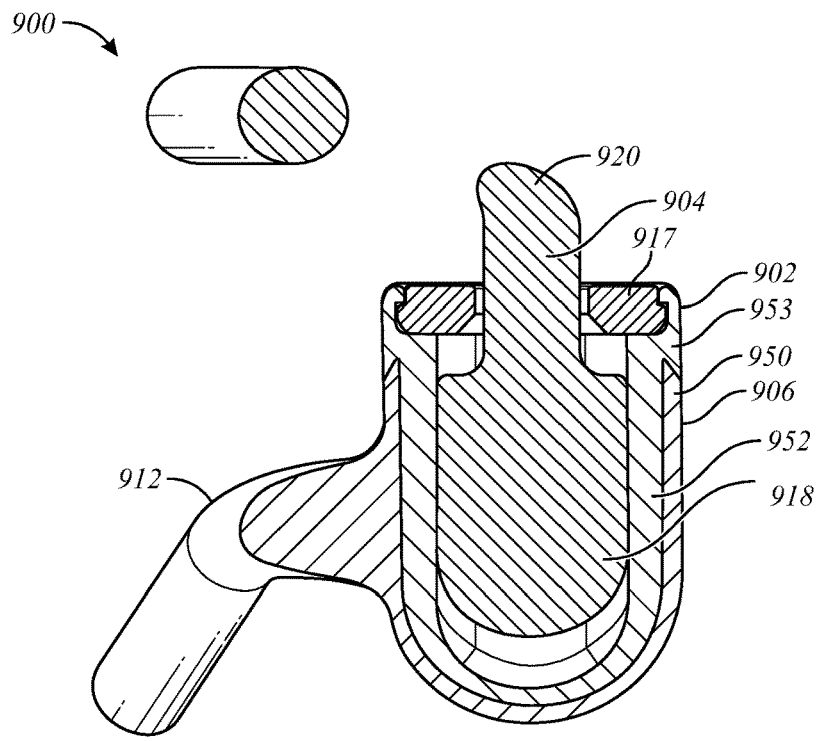
Figure 40B:
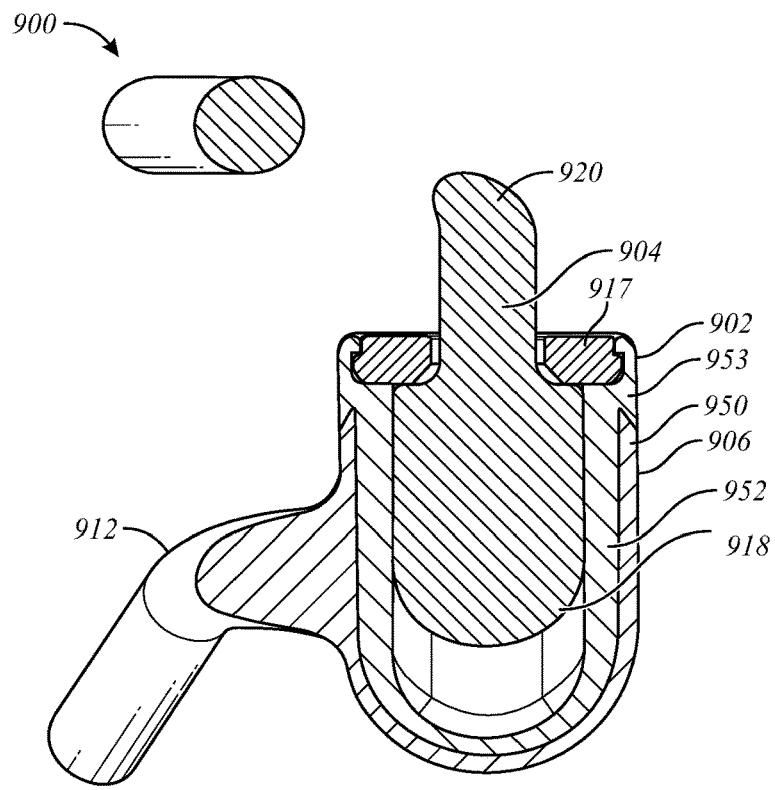

FIG. 40B depicts a posterior-medial cross-sectional view of the facet joint replacement device 900.

Figure 40C:
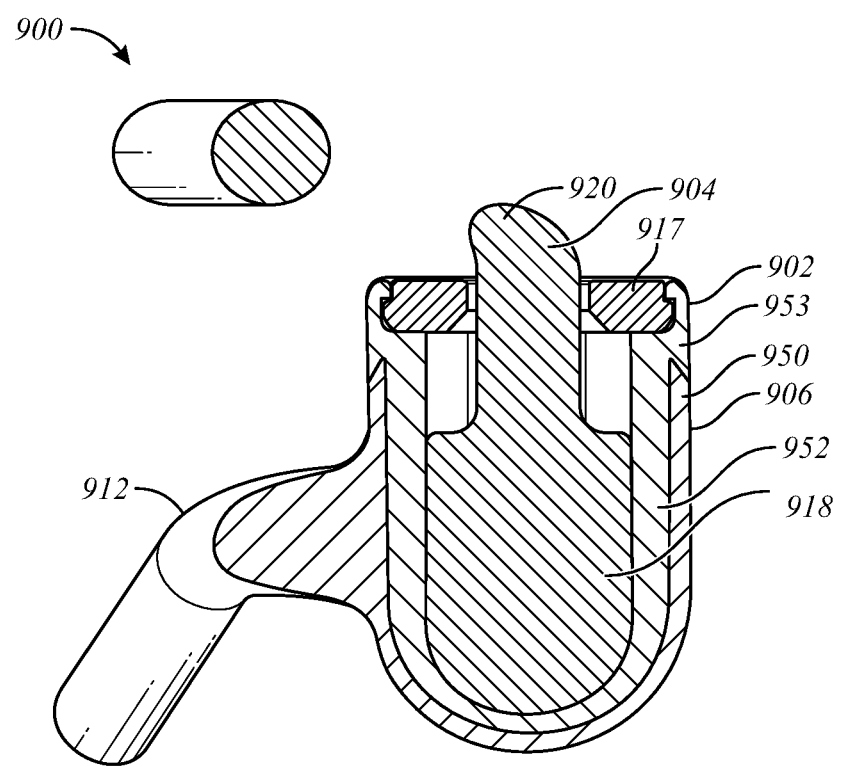

FIG. 40C depicts a posterior-medial cross-sectional view of the facet joint replacement device 900.

Figure 41A:
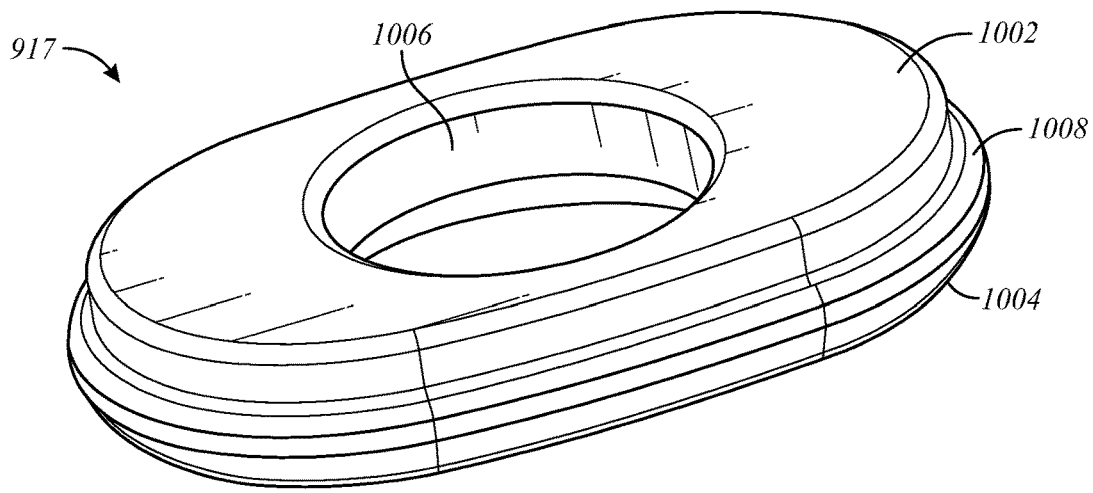

FIG. 41A depicts a top perspective of a retention plate 917.

Figure 41B:
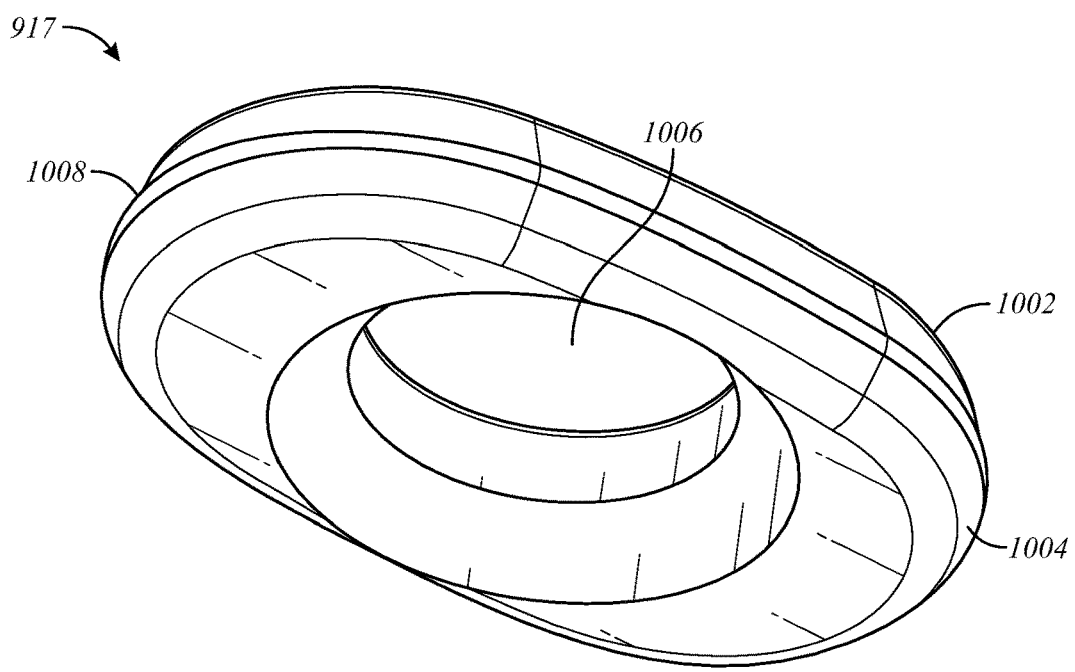

FIG. 41B depicts a bottom perspective view of the retention plate 917.

Figure 41C:
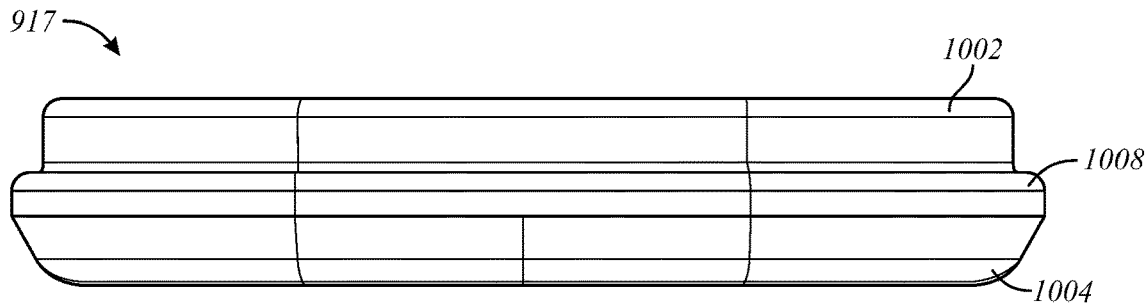

FIG. 41C depicts a front view of the retention plate 917.

Figures 42A, 42B, 42C:
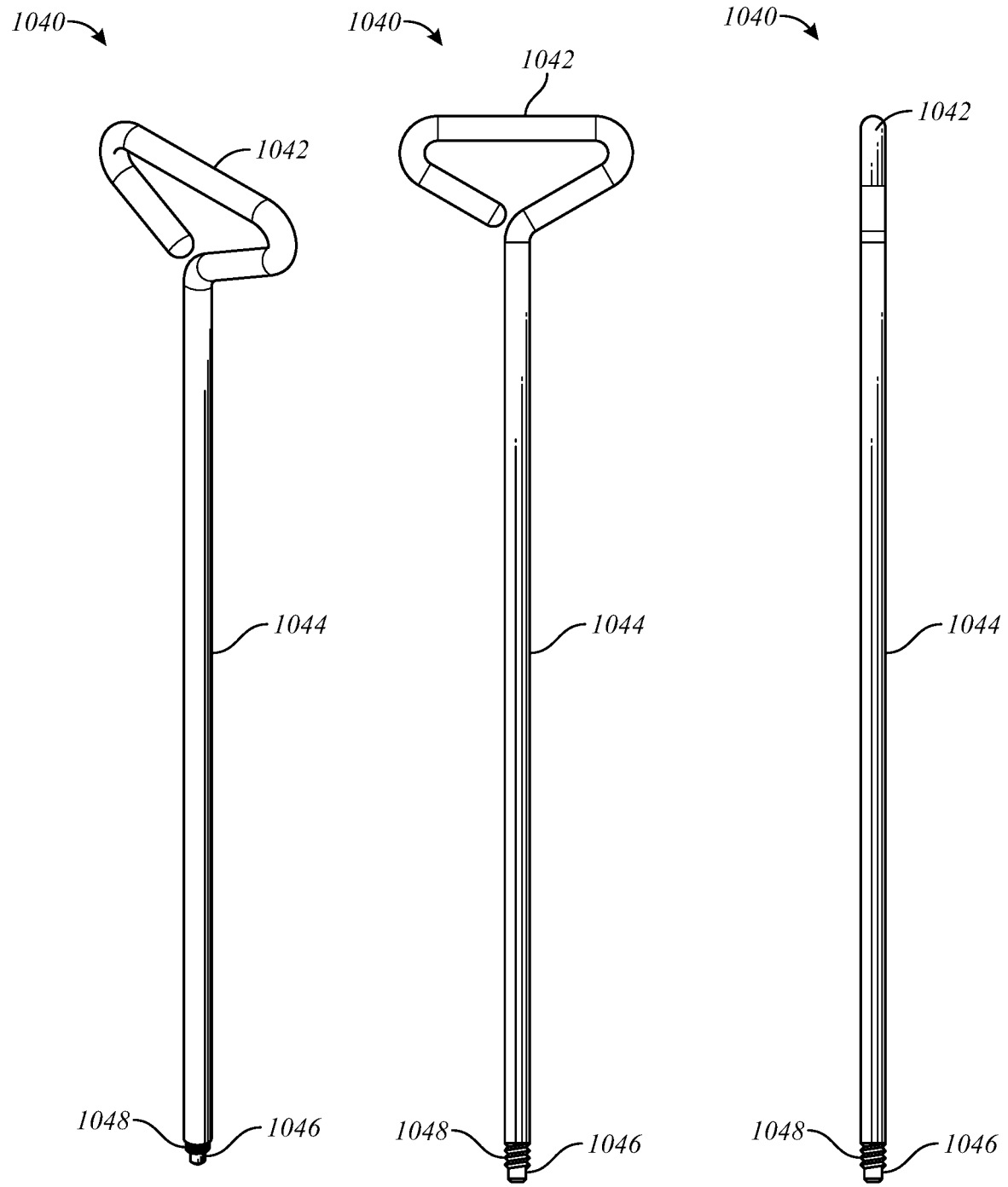

FIG. 42A depicts a perspective view of a device holder 1040.

FIG. 42B depicts a front view of the device holder 1040.

FIG. 42C depicts a side view of the device holder 1040.

Figure 42D:
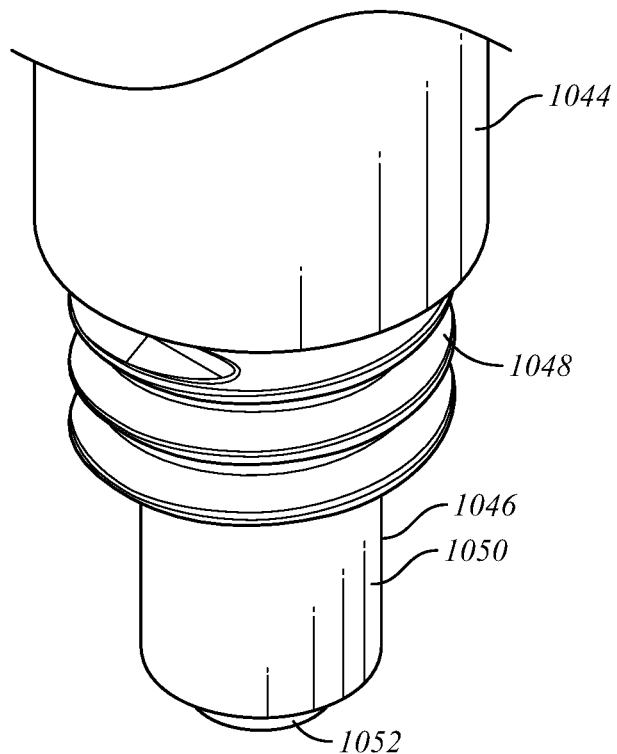

FIG. 42D depicts a top perspective enlarged view of a portion of the device holder 1040.

Figure 42E:
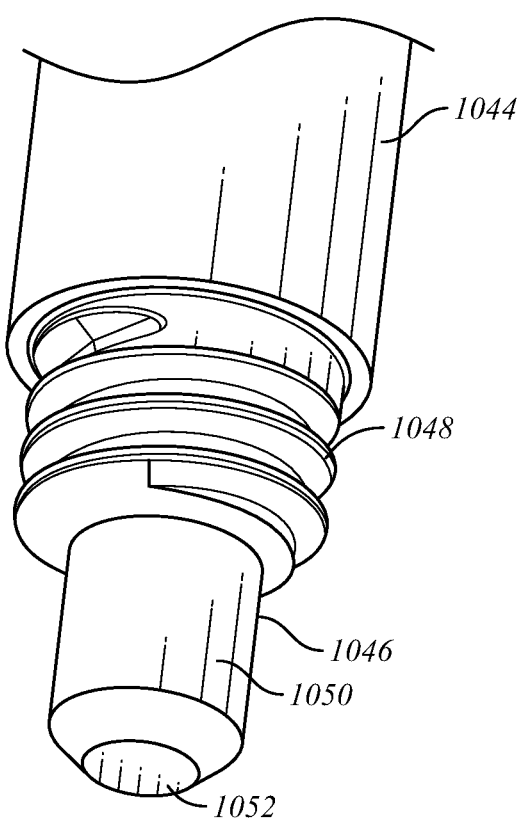

FIG. 42E depicts a bottom perspective enlarged view of a portion of the device holder 1040.

Figure 42F:
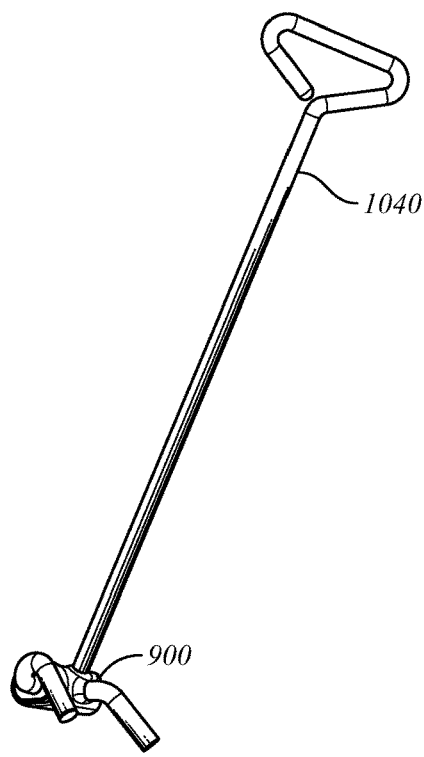

FIG. 42F depicts a perspective view of the device holder 1040 coupled to the facet joint replacement device 900.

Figure 42G:
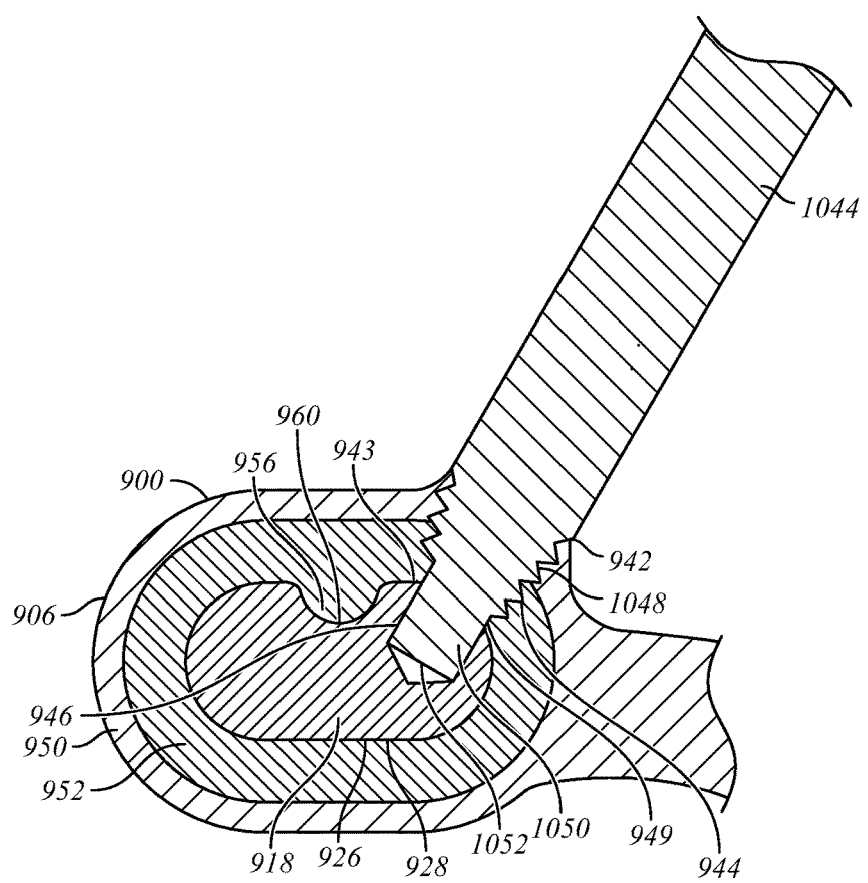

FIG. 42G depicts an enlarged cross-sectional view of a portion of the device holder 1040 coupled to the facet joint replacement device 900.

Figure 43A:
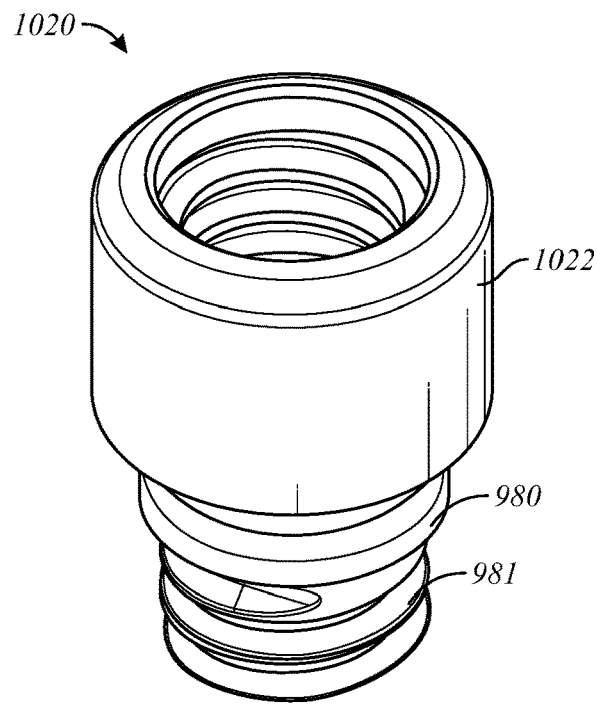

FIG. 43A depicts a top perspective view of a plug assembly 1020.

Figure 43B:
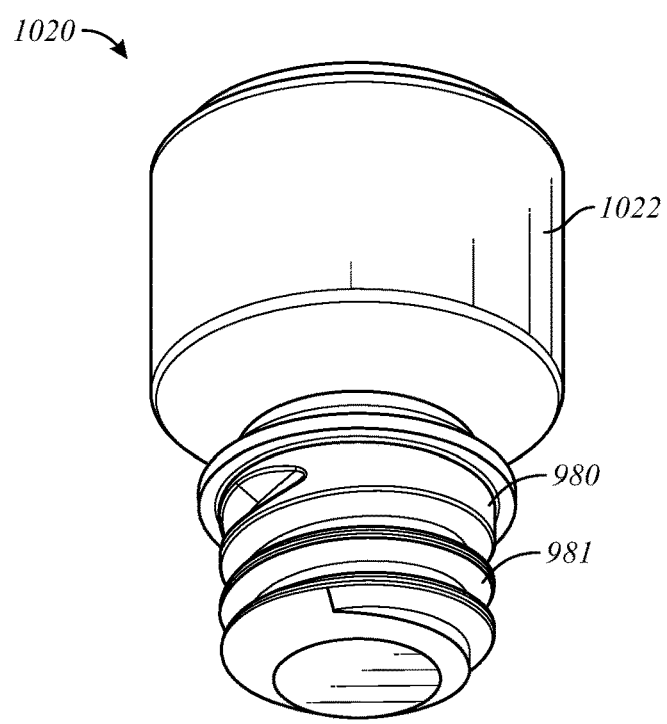

FIG. 43B depicts a bottom perspective view of the plug assembly 1020.

Figure 43C:
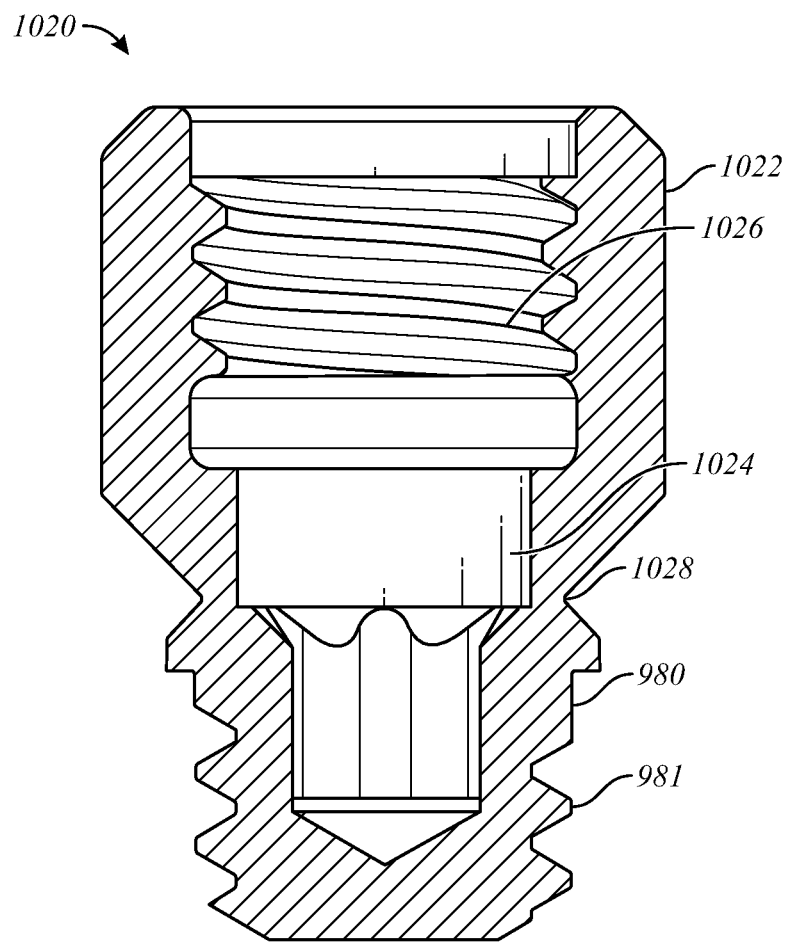

FIG. 43C depicts a first enlarged cross-sectional view of the plug assembly 1020.

Figure 43D:
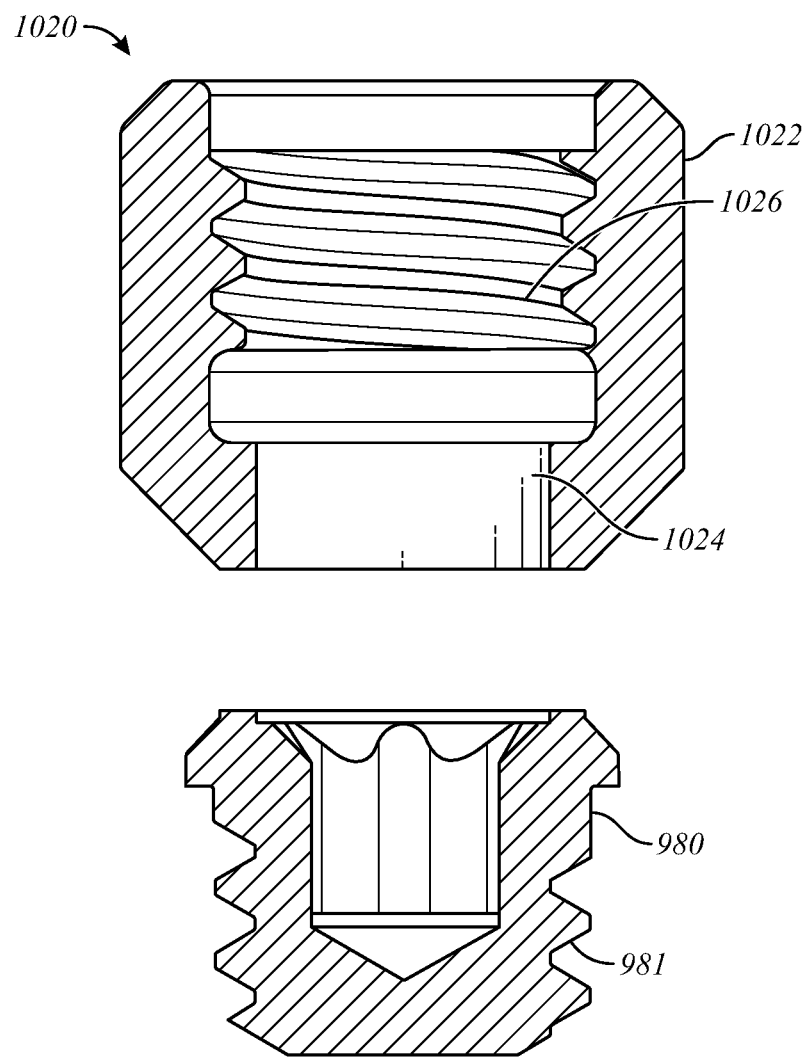

FIG. 43D depicts a second enlarged cross-sectional view of the plug assembly 1020 showing the plug assembly 1020 separated into two pieces.

Figure 44A:
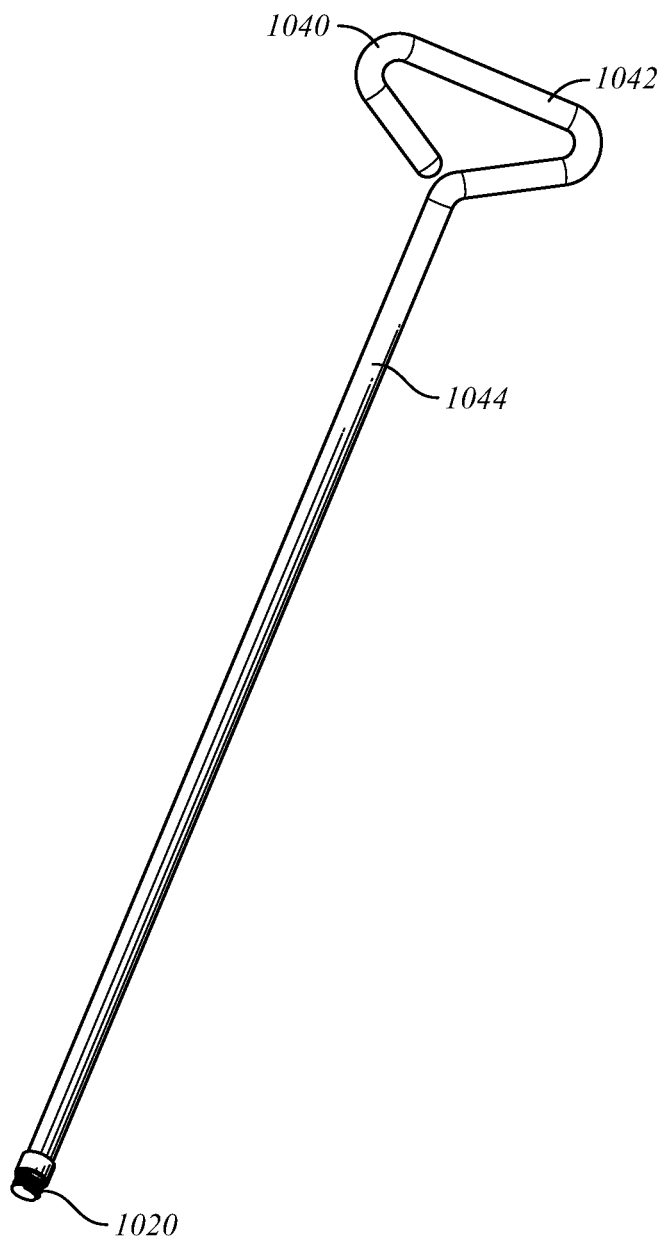

FIG. 44A depicts a perspective view of the device holder 1040 coupled to the plug assembly 1020.

Figure 44B:
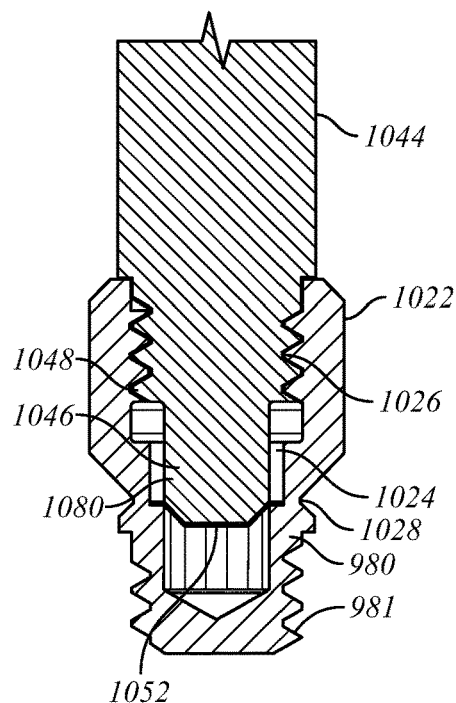

FIG. 44B depicts an enlarged cross-sectional view showing a portion of the device holder 1040 coupled to the plug assembly 1020.

Figure 44C:
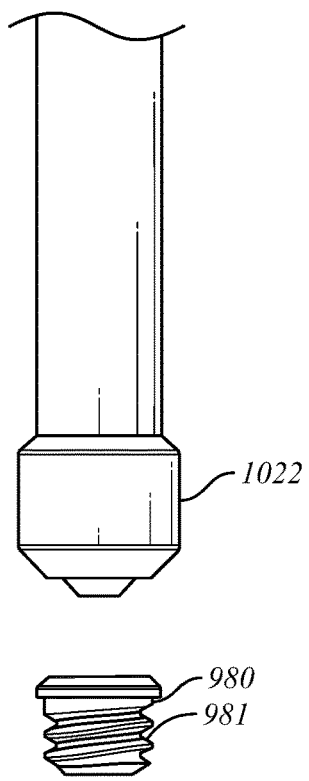

FIG. 44C is a front view showing the device holder 1040 coupled to a plug insertion section 1022 after separation of the plug insertion section 1022 from a plug 980.

Figure 45A:
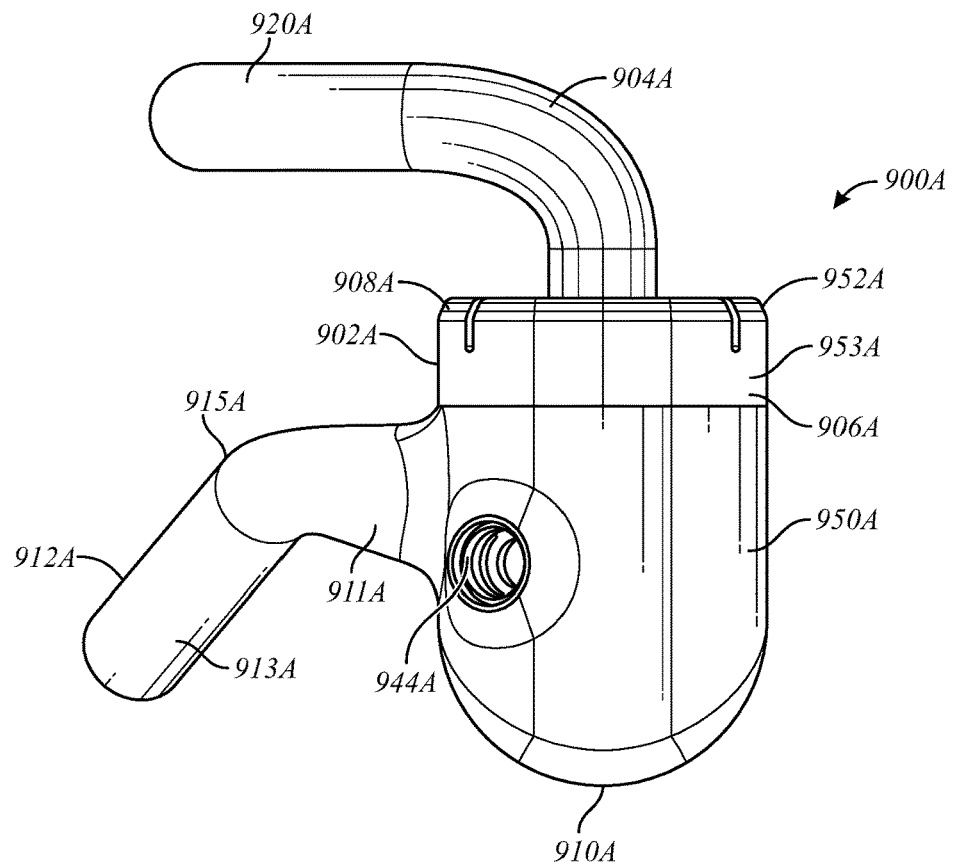

FIG. 45A depicts a posterior view of a facet joint replacement device 900A.

Figure 45B:
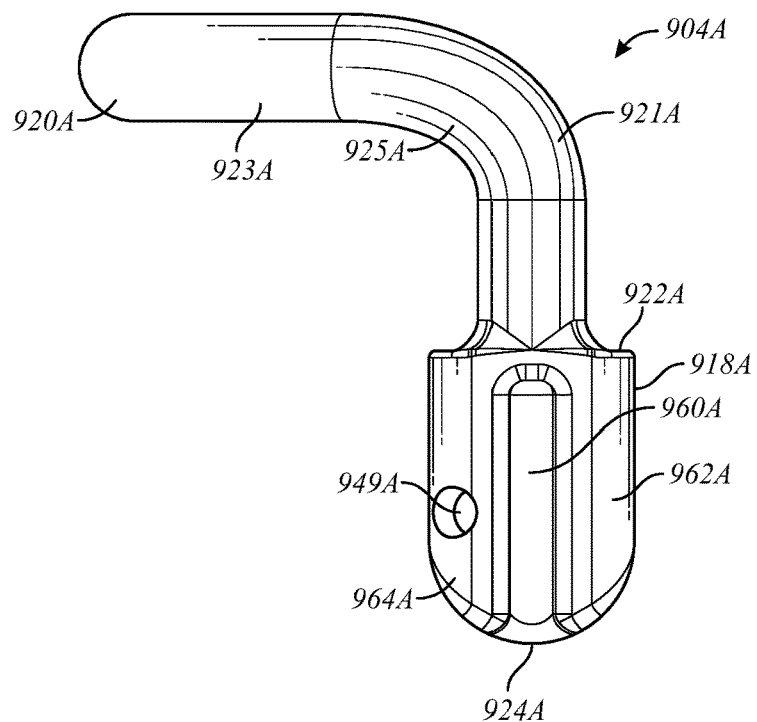

FIG. 45B depicts a posterior view of an articulating element 904A.

Figure 45C:
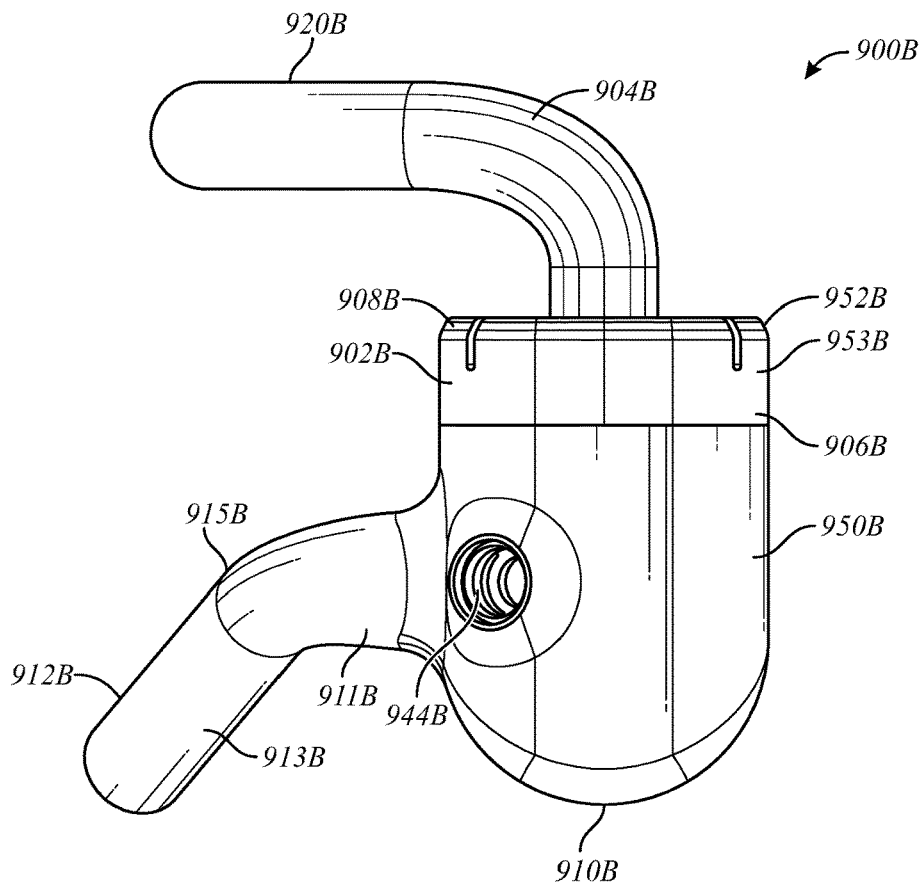

FIG. 45C depicts a posterior view of a facet joint replacement device 900B.

Figure 45D:
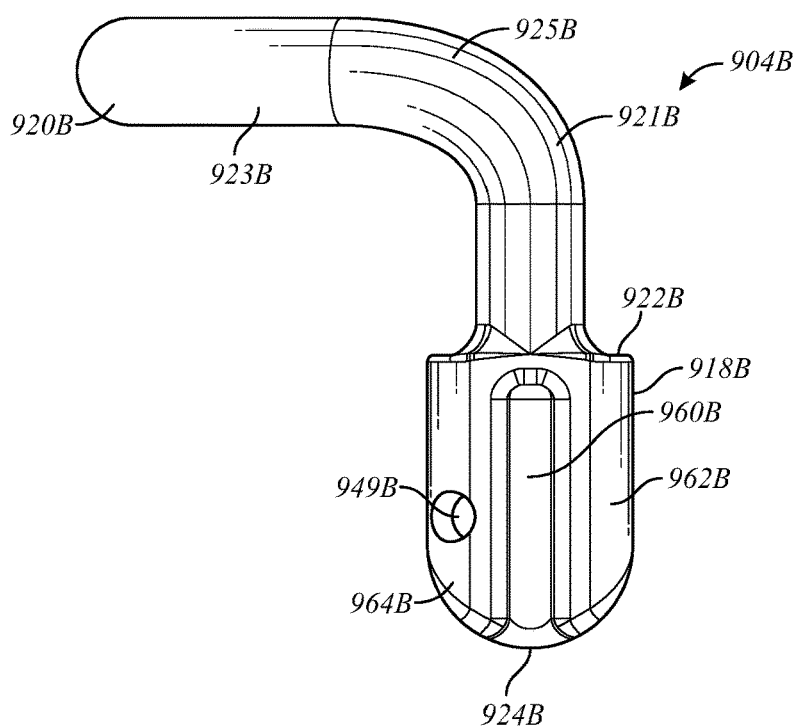

FIG. 45D depicts a posterior view of an articulating element 904B.

Figure 45E:
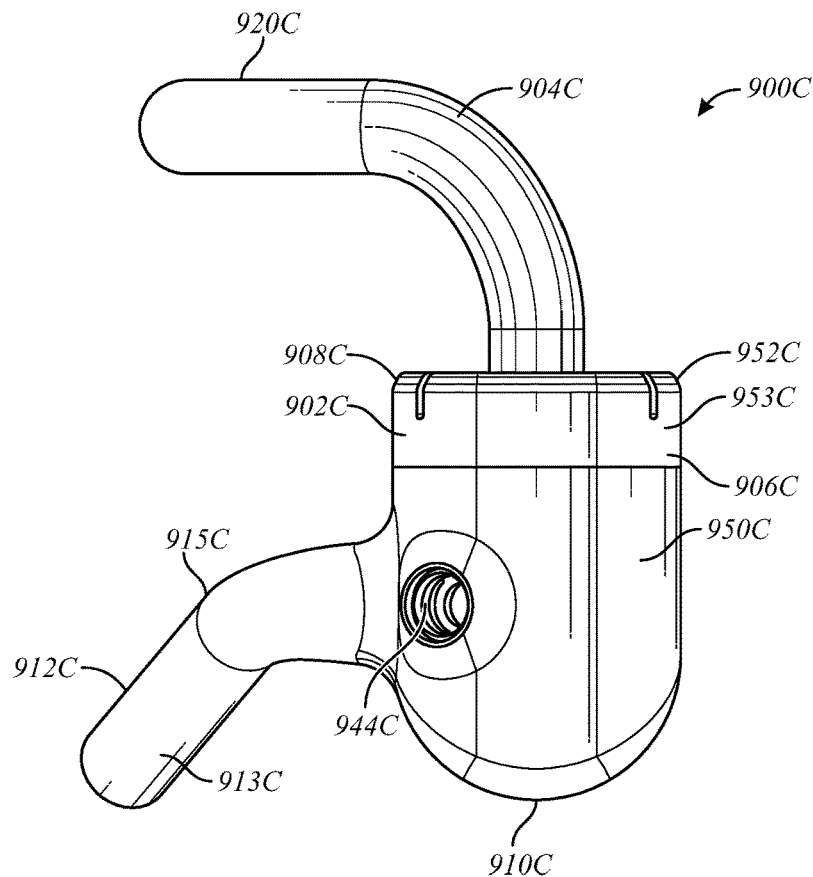

FIG. 45E depicts a posterior view of a facet joint replacement device 900C.

Figure 45F:
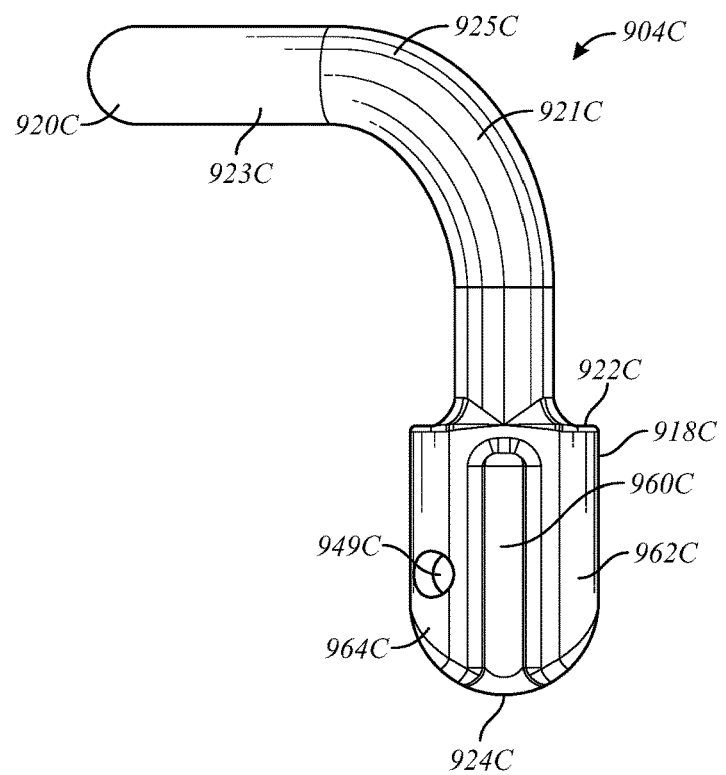

FIG. 45F depicts a posterior view of an articulating element 904C.

Figure 46:
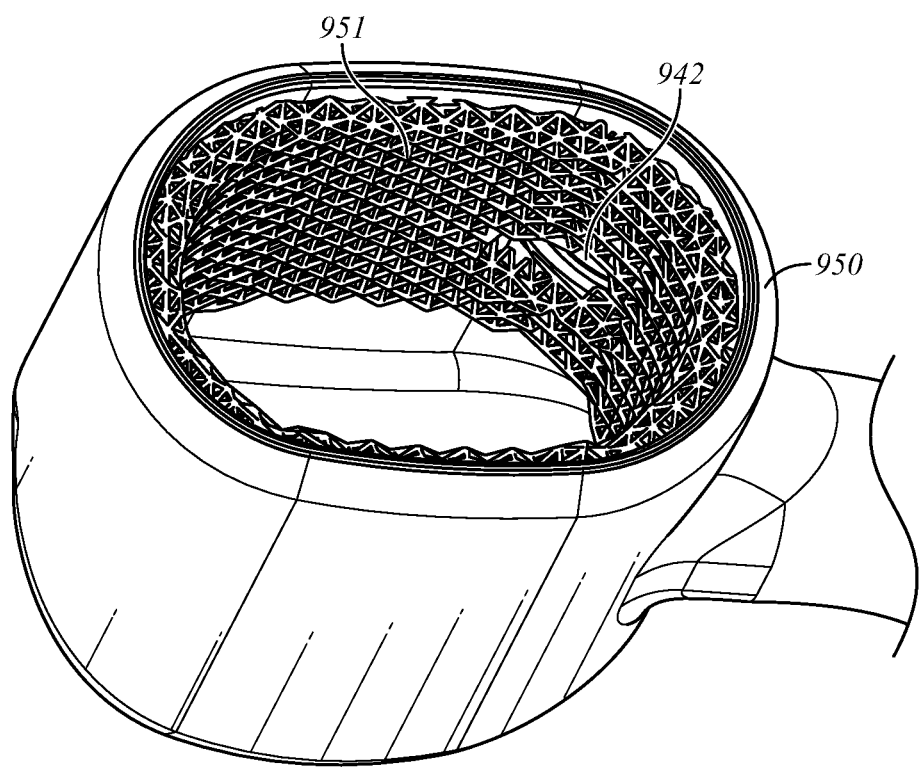

FIG. 46 depicts a perspective view of an embodiment of an outer shell 950.

DETAILED DESCRIPTION OF PREFERRED EMBODIMENTS

Methods, systems, and apparatuses are provided in certain embodiments of the present invention to replace a dysfunctional facet joint. In some embodiments a facet joint replacement device is provided. The facet joint replacement device can be configured to replace a facet joint that has been partially or fully resected. Following replacement, the facet joint replacement device can be configured to perform the function of a facet joint within a spinal motion segment. For example, the facet joint replacement device can include one or more components configured to perform the functions of a superior articular process, and inferior articular process, and/or a facet joint capsule. In some embodiments, the facet joint replacement device can include an enclosing element and one or more interior components positioned within an inner cavity of the enclosing element. The interior components can be configured to move within the enclosing element to facilitate movements of a spinal motion segment that simulate the movements allowed by a healthy facet joint in the human body. For example, the facet joint replacement device can allow for limited posterior/anterior motion, limited medial/lateral motion, and/or limited superior/inferior motion. The facet joint replacement device can also limit relative rotation and translation of adjacent vertebrae. For example, in some embodiments, the inner cavity of the enclosing element can be shaped and/or dimensioned to limit relative movement of the interior components within the enclosing element in at least one direction. In some embodiments, the enclosing element is shaped and/or dimensioned to limit relative movement in similar directions to a healthy facet joint capsule.

In some embodiments, the enclosing element can include a surface configured to simulate a superior articular surface of a healthy facet joint. In some embodiments, at least one of the internal components can include a surface configured to simulate an inferior articular surface that complements of a healthy facet joint. The enclosing body can be configured to provide resistance to or otherwise limit relative disassociation and/or rotation between the surfaces configured to simulate the superior articular surface and the inferior articular surface. The enclosing body can also maintain an intra-articular environment by encapsulating the surfaces configured to simulate the superior articular surface and the inferior articular surface. For example, the enclosing cylinder can act as a physical barrier to fibrosis at the surfaces configured to simulate the superior articular surface and the inferior articular surface. The enclosing cylinder can also act as a physical barrier to prevent friction wear to the adjacent anatomy due to relative movement between the surfaces configured to simulate the superior articular surface and the inferior articular surface.

In some embodiments, a body of the enclosing element can be shaped to conform to the shape of superior and inferior articular processes and a pars interarticularis of a healthy vertebral body. The shape of the enclosing element can be configured to support axial loading in a similar manner as healthy articular processes.

In some embodiments, at least some of the components of the facet joint replacement device can be designed such that assembly of the facet joint replacement device can be performed outside of the body. Such a facet joint replacement device can facilitate ease of implantation, as well as minimally invasive techniques.

Figure 1A:
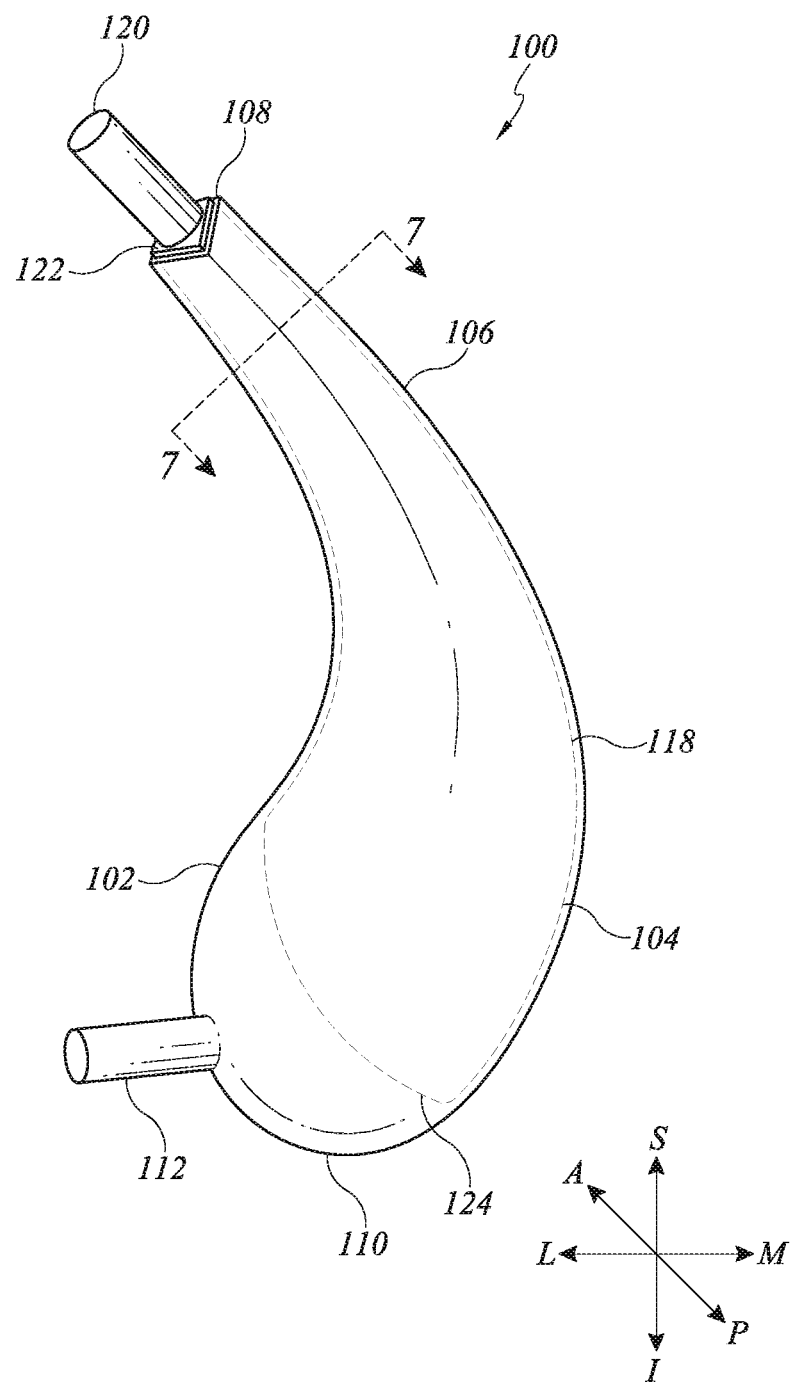
FIG. 1A depicts a posterior perspective view of the facet joint replacement device 100 showing interior components in dotted lines.

FIGS. 1A-7 depict a facet joint replacement device 100 according to one embodiment. The terms superior, inferior, anterior, posterior, medial, and lateral, when describing portions of the devices herein, refer to portions of the device as they are intended to be oriented with respect to the human spine. FIG. 1A depicts a posterior perspective view of the facet joint replacement device 100 showing interior components in dotted lines. FIG. 1A also includes three-dimensional coordinate axes indicating the superior ("S"), inferior ("I"), anterior ("A"), posterior ("P"), medial ("M"), and lateral ("L") directions. As shown in the three-dimensional coordinate axes in FIG. 1A, the posterior direction P is generally pointing out of the page and the anterior direction A is generally pointing into the page. The facet joint replacement device 100 includes an enclosing element 102 and an inferior articulating element 104 positioned at least partially within the enclosing element 102. The articulating element 104 is referred to as an inferior articulating element because it provides a generally inferiorly facing articulating surface to engage a corresponding generally superiorly facing articulating surface on the enclosing element 102, as described further below.

The enclosing element 102 includes an enclosing body 106 and an inferior attachment member 112. The enclosing body 106 can have a generally arcuate shape configured to correspond to the shape of a pars interarticularis of a vertebra. The enclosing body 106 includes a superior end 108 and an inferior end 110. The inferior attachment member 112 extends laterally from the enclosing body 106 at a segment of the enclosing body adjacent to the inferior end 110. The enclosing body 106 further include an inner cavity 114 (shown in FIG. 4) defined by an interior surface of the enclosing body 106 and an opening 116 (shown in FIG. 2A) at the superior end 108. A portion of the interior surface of the enclosing body 106 can be shaped to form a superior articulating surface 128 (shown in FIG. 4). In some embodiments, the enclosing body 106 is configured to protect the surrounding anatomy from friction, damage, or infection due to the movement of components, including the inferior articulating surface 126 and superior articulating surface 128 in the interior of the enclosing body 106, for example, by acting as a physical barrier. For example, the enclosing body 106 can protect an adjacent thecal sac and adjacent nerve roots from involvement with the articulating surfaces 126 and 128 during relative movement between the articulating surfaces 126 and 128. In some embodiments, the enclosing body 106 is configured to protect the components within the interior of the enclosing body 106 from damage, wear, or fibrosis due to the surrounding anatomy, for example, by acting as a physical barrier.

The inferior articulating element 104 includes an articulating body 118 and a superior attachment member 120. The articulating body 118 is at least partially positioned within and configured to move within the inner cavity 114 of the enclosing body 106. The inferior articulating body 118 has a superior end 122 and an inferior end 124. The superior attachment member 120 extends superior to the superior end 122 of the articulating body 118. In some embodiments, the superior attachment member 120 extends through the opening 116. In some embodiments, a portion of the articulating body 118 extends superior to or in alignment with the opening 116. The inferior end 124 of the articulating body 118 forms an inferior articulating surface 126.

The superior attachment member 120 and inferior attachment member 112 can be shaped and/or dimensioned to facilitate securement of the facet joint replacement device 100 to the spine. As shown in FIG. 1A, the superior attachment member 120 and inferior attachment member 112 can each be a rod. However, the superior attachment member 120 and inferior attachment member 112 can be any shape suitable for fixation directly or indirectly to a vertebral body.

In some embodiments, the enclosing element 102 and/or the inferior articulating element 104 can consist of or consist partially of one or more metals or metal alloys. For example, the enclosing element 102 and/or articulating element 104 can consist of cobalt-chromium, titanium, titanium-based alloys, or any other suitable metals or metal alloys. In some embodiments, the enclosing element 102 and/or inferior element 104 can be ceramic or partially ceramic. In some embodiments, the enclosing element 102 and/or inferior element 104 can include super-hard ceramics.

Figure 1B:
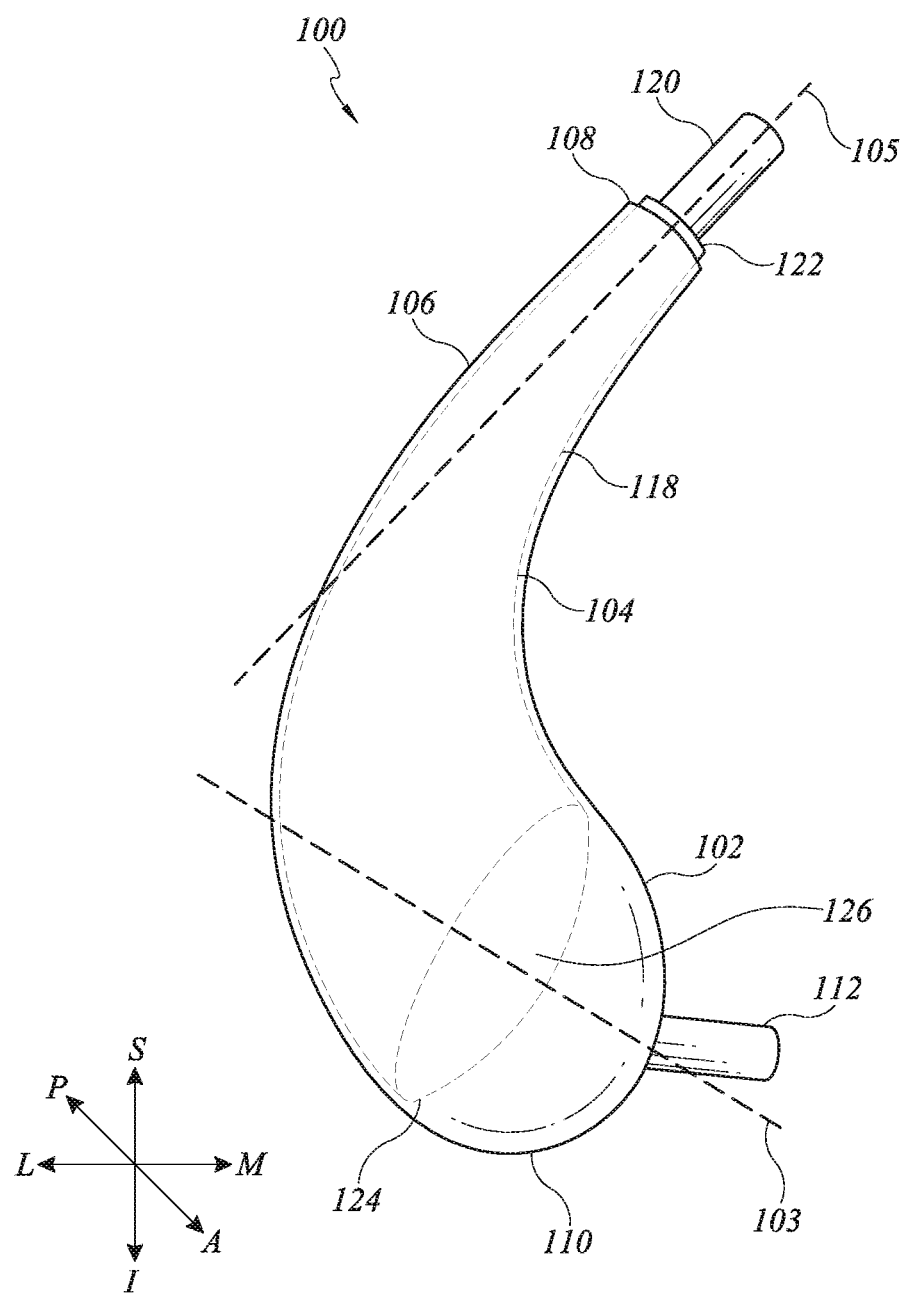
FIG. 1B depicts an anterior perspective view of the facet joint replacement device 100.

FIG. 1B depicts an anterior perspective view of the facet joint replacement device 100. FIG. 1B also includes three-dimensional coordinate axes indicating the superior ("S"), inferior ("I"), anterior ("A"), posterior ("P"), medial ("M"), and lateral ("L") directions. As shown in the three-dimensional coordinate axes of FIG. 1B, the anterior direction A is generally pointing out of the page and the posterior direction P is generally pointing into the page. As shown in FIG. 1B, the inferior articulating surface 124 can be configured to face at least partially in an anterior direction, as well as in a generally inferior direction and a generally lateral direction.

FIG. 1B also shows an axis 103 extending through a center point of the inferior articulating surface and an axis 105 extending through a long axis of the attachment member 120. Both the axis 105 and the axis 103 have superior-inferior, lateral-medial, and posterior-anterior components.

Figures 2A, 2B:
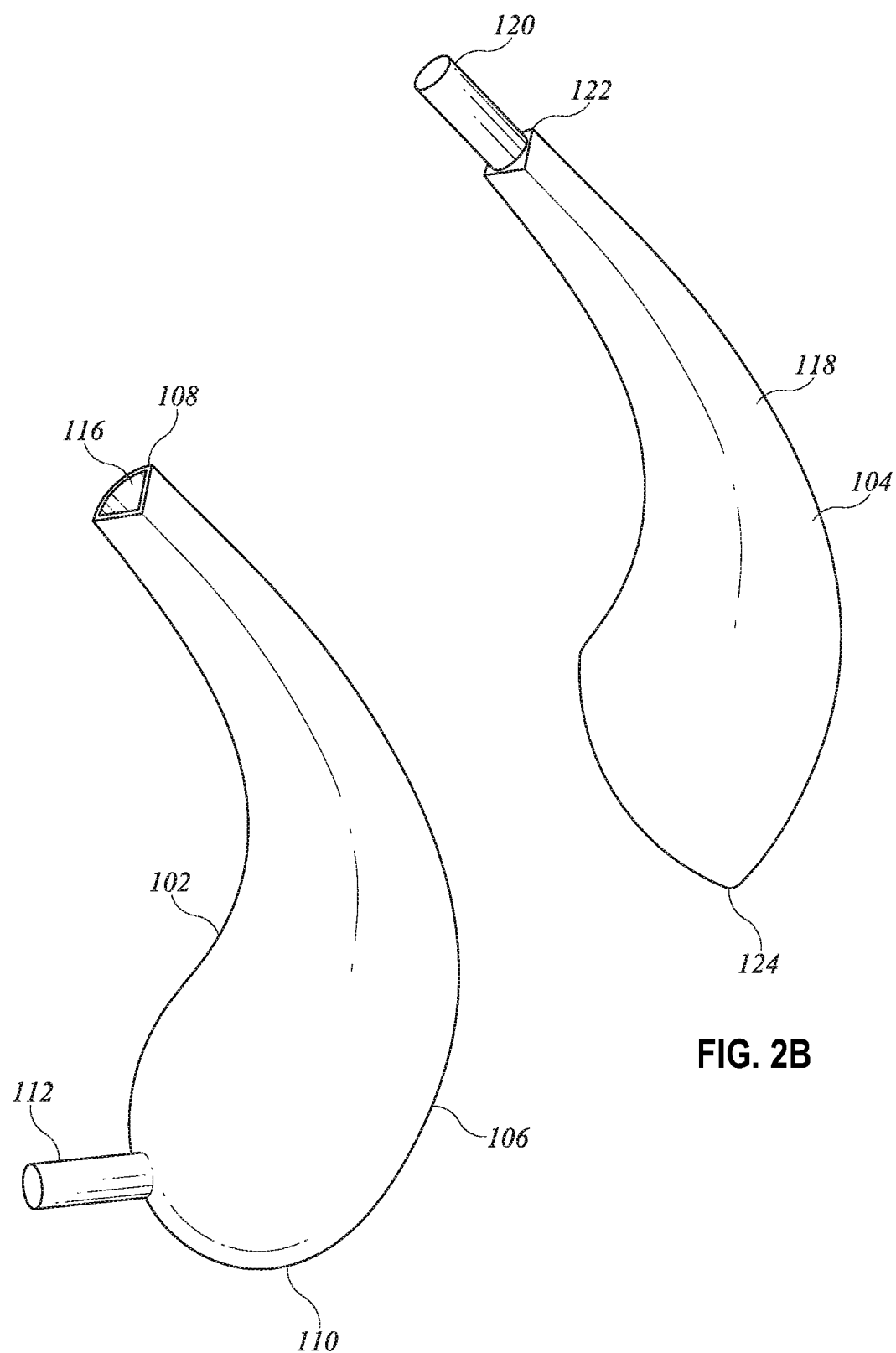
FIG. 2A depicts a posterior perspective view of an enclosing element 102.
FIG. 2B depicts a posterior perspective view of an inferior articulating element 104.

FIGS. 2A and 2B depicts a posterior perspective view of the enclosing element 102 and a posterior perspective view of the inferior articulating element 104, respectively. FIG. 2A shows the opening 116 through which a portion of the articulating body 118 can extend or align with when positioned within the enclosing body 106 of the enclosing element 102.

Figures 3A, 3B:
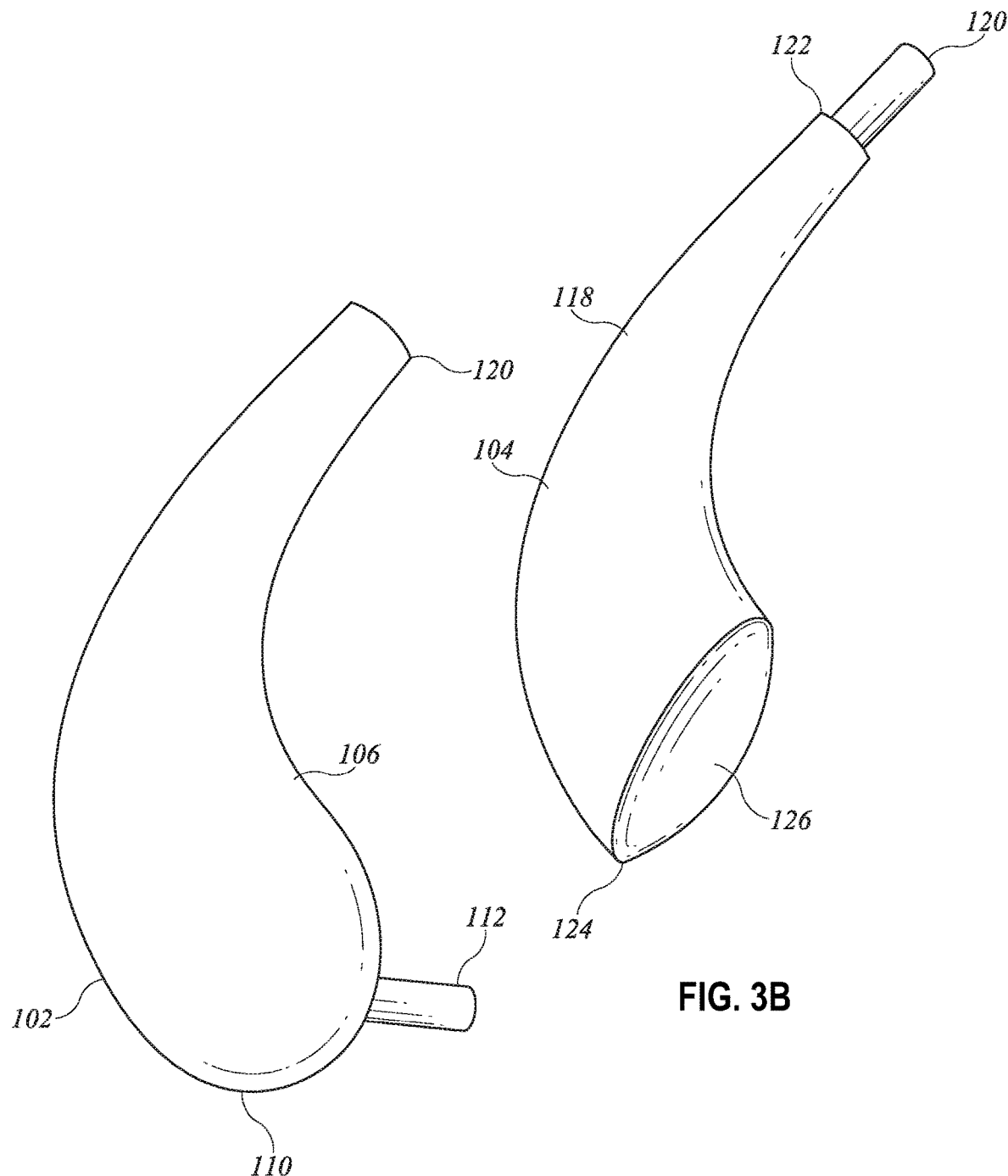
FIG. 3A depicts an anterior perspective view of the enclosing element 102.
FIG. 3B depicts an anterior perspective view of the inferior articulating element 104.

FIGS. 3A and 3B depict an anterior perspective view of the enclosing element 104 and an anterior perspective view of the inferior articulating element 104, respectively. As illustrated in FIG. 3B, the inferior articulating surface 126 can be ellipsoid or generally elliptical. The inferior articulating surface 126 can also be convex or at least partially convex. The inferior articulating surface 126 can be shaped and/or dimensioned to correspond to the shape, size, and/or convexity of an articular surface of a healthy inferior articular process.

Figure 4:
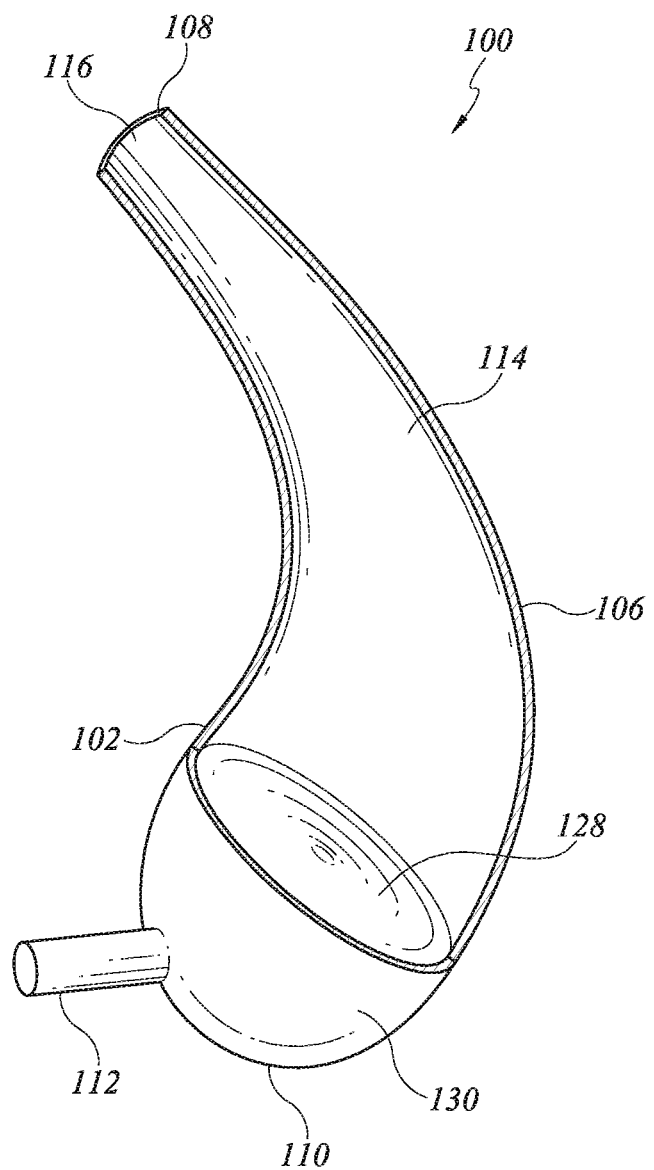
FIG. 4 depicts a partial cross-sectional view of the enclosing element 102 showing a cross-section superior to a superior articulating surface 128.

FIG. 4 depicts a partial cross-sectional view of the enclosing element 102 showing a cross-section superior to the superior articulating surface 128. FIG. 4 shows the inner cavity 114 defined by the interior surface of the enclosing body 106 and the superior articulating surface 128. As illustrated in FIG. 4, superior articulating surface 128 can be defined by a section of the interior surface of the enclosing body 106. The superior articulating surface 128 can be ellipsoid or generally elliptical. The superior articulating surface 128 can also be concave or at least partially concave. The superior articulating surface 128 can be shaped/and or dimensioned to correspond to the shape, size, and/or concavity of an articular surface of a healthy superior articular process.

While the inferior articulating surface 126 and superior articulating surface 128 are shown as elliptical in FIGS. 3B and 4, any suitable complementary surface shapes can be used. In some embodiments, the inferior articulating surface 126 and superior articulating surface 128 are circular or generally circular, oval or generally oval, rounded, polygonal, oblong, symmetric, asymmetric, or any other suitable shape. In some embodiments, the inferior articulating surface 126 and superior articulating surface 128 can be shaped such that force is applied symmetrically to the superior articulating 128 when the inferior articulating element 126 contacts or otherwise applies a force upon the superior articulating surface 126.

As described further herein, the articulating body 118 is configured to move within the enclosing body 106 in at least one direction. When the superior attachment member 120 is secured to a superior vertebral body and the inferior attachment member 112 is secured to an inferior vertebral body, movement between the superior and inferior vertebral bodies can cause movement of the superior attachment member 120 with respect to the position of the enclosing body 106 resulting from the inferior attachment member 112 being secured to the inferior vertebral body. Movement of the superior attachment member 120 with respect to the enclosing body 106 causes movement of the articulating body 118 within the enclosing body 106 generally along the inner wall of the enclosing body. Referring again to FIG. 1B, the superior attachment member 120 is configured to move along axis 105 towards and away from the enclosing body 106. When the superior attachment member 120 moves towards the enclosing body 106 along the axis 105, the superior attachment member 120 moves along the axis 105 in a medial, anterior, and inferior direction. When the superior attachment member 120 moves away from the enclosing body 106 along the axis 105, the superior attachment member 120 moves along the axis 105 in a lateral, posterior, and superior direction. The superior end 122 of the articulating body 118 moves along the axis 105 in the same manner when the superior attachment member 120 moves along the axis 105. Although relative movement of the superior attachment member 120 towards and away from the enclosing body 106 is discussed, one of skill in the art would understand that movement between the enclosing body 106 and superior attachment member 120 could be described as movement of the enclosing body 106 towards or away from the superior attachment member 120 or movement of the enclosing body 106 and superior attachment member 120 towards or away from each other.

Movement of the superior attachment member 120 with respect to the enclosing body 106 causes movement of the inferior articulating surface 126 along the axis 103 towards and away from the superior articulating surface 128. The inferior articulating surface 126 moves towards the superior articulating surface 128 along the axis 103 when the superior attachment member 120 moves towards the enclosing body 106, and the inferior articulating surface 126 moves away from the superior articulating surface 128 when the superior attachment member 120 moves away from the enclosing body 106. When the inferior articulating surface 126 moves away from the superior articulating surface 128 along the axis 103, the inferior articulating surface moves along the axis 103 in a superior, posterior, and medial direction. When the inferior articulating surface 126 moves towards the superior articulating surface 128 along the axis 103, the inferior articulating surface moves along the axis 103 in an inferior, anterior, and lateral direction. Although relative movement of the inferior articulating surface 126 towards and away from the superior articulating surface 128 is discussed, one of skill in the art would understand that movement between the inferior articulating surface 126 and the superior articulating surface 128 could be described as movement of the superior articulating surface 128 towards or away from the inferior articulating surface 126 or movement of the inferior articulating surface 126 and the superior articulating surface 128 towards or away from each other. In some embodiments, the axis 103 extends through a center point of the superior articulating surface 128. In some embodiments, the axis 103 extends transverse to a tangent of a center line of the inferior articulating surface 126. The axis 103 can represent the direction of relative movement between the articular surfaces of a healthy facet joint.

In some embodiments, the enclosing body 106 acts to limit relative movement between the inferior articulating surface 126 and the superior articulating surface 128 along the axis 103. In some embodiments, the enclosing body 106 acts to limit relative movement of the inferior articling surface 126 and superior articulating surface 128 perpendicular to the axis 103.

When the articulating body 118 moves within the enclosing body 106, the inferior articulating surface 126 can contact the superior articulating surface 128. In some embodiments, the enclosing body 106 and inferior articulating body 118 are configured such that a maximum distance between a center point of the inferior articulating surface 126 and the superior articulating surface 128 is 0.5 mm, 1.0 mm, 1.5 mm, 1.75 mm, 2.0 mm, 2.25 mm, 2.5 mm, 3.0 mm, 3.5 mm, 4.0 mm, 5.0 mm, less than 2.0 mm, less than 3.0 mm, less than 4.0 mm, between 1.0 mm and 3.0 mm, between 1.0 mm and 2.0 mm, between 2.0 mm and 3.0 mm, between 1.5 mm and 2.5 mm, or between 1.75 mm and 2.25 mm. In some embodiments, the superior articulating surface 128 is shaped and/or dimensioned to receive the inferior articulating surface 126. As shown in FIG. 4, the enclosing body 106 includes a solid portion 130 between the superior articulating surface 128 and the inferior attachment member 112. In some embodiments, the solid portion 130 of the enclosing body 106 can have a depth dimensioned for receiving an axial load supplied by the articulating body 118 to the inferior articulating surface 126 due to movement of the articulating body 118 within the enclosing body 106.

Figure 5:
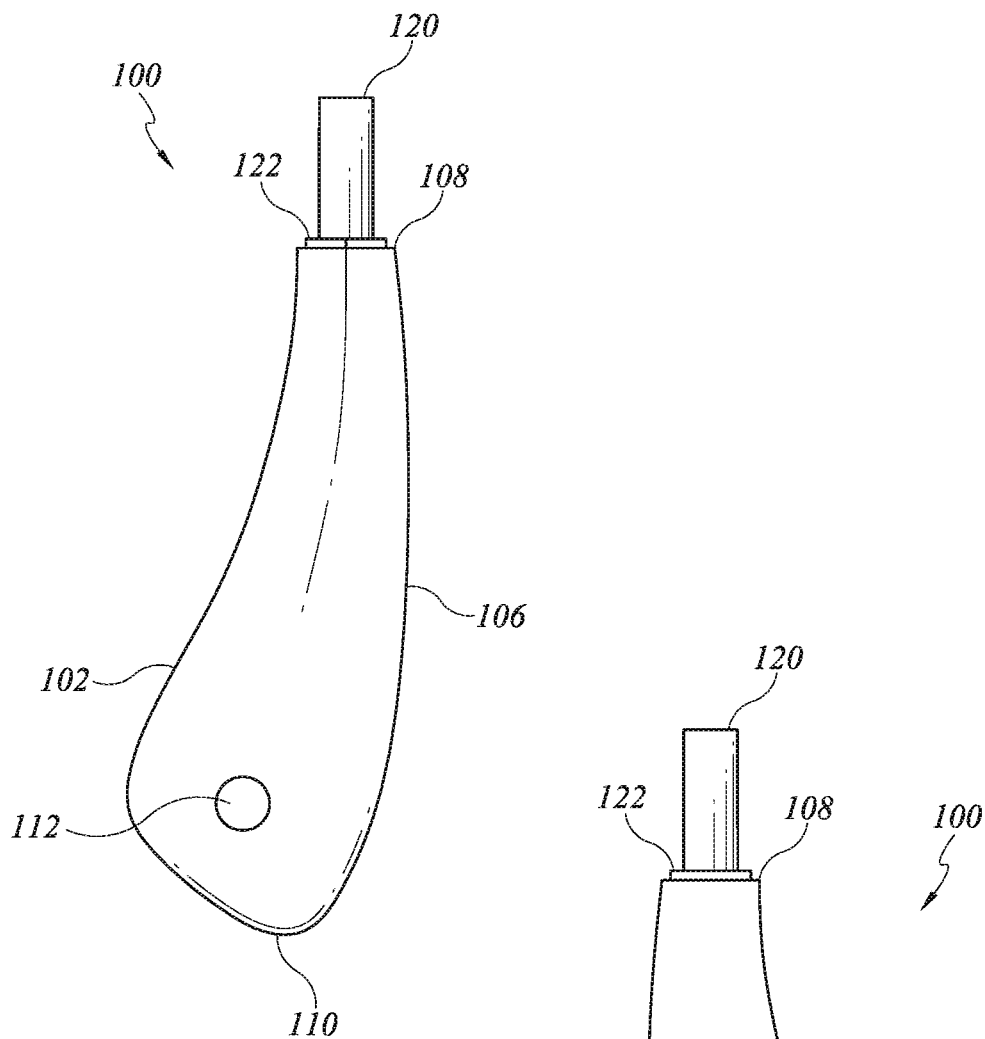
FIG. 5 depicts a first sagittal view of the facet joint replacement device 100.
Figure 6:
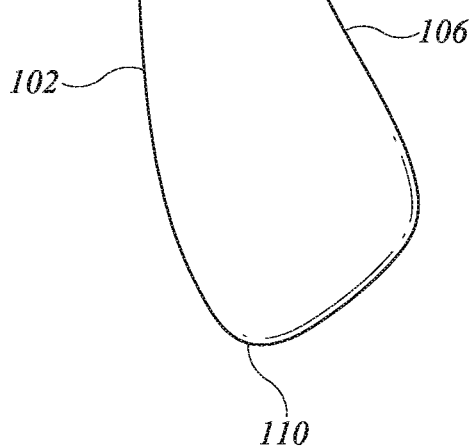
FIG. 6 depicts a second sagittal view of the facet joint replacement device 100.
Figure 7:
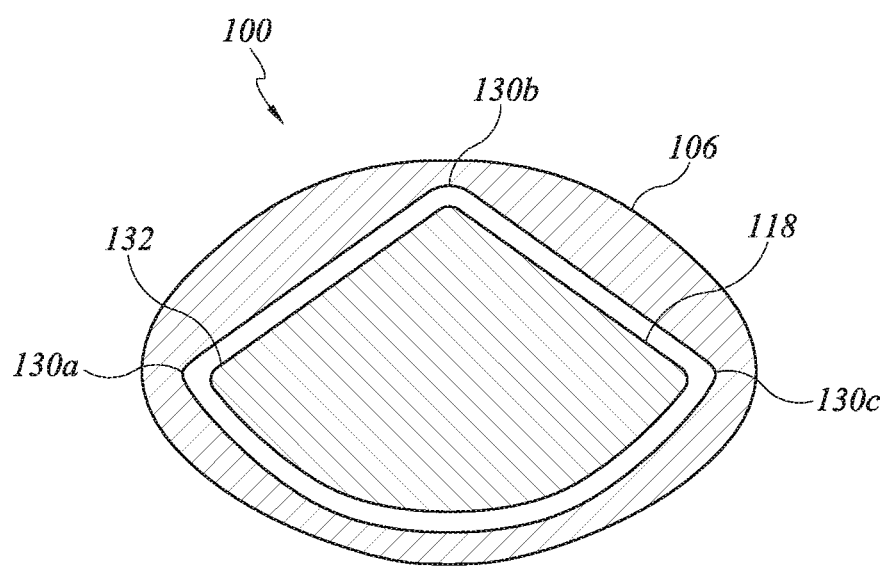
FIG. 7 depicts a cross-sectional view of the facet joint replacement device 100.

FIGS. 5 and 6 show a first sagittal view showing a lateral side of the facet joint replacement device 100 and a second sagittal view showing a medial side of the facet joint replacement device 100, respectively. FIG. 7 shows a cross-sectional view of the facet joint replacement device 100 taken along line 7-7 as show in FIG. 1A. As shown in FIG. 7, the interior surface of the enclosing body 106 includes a plurality of internal corners or grooves 130a, 130b, and 130b, each forming angle that corresponds to one of a plurality of external corners or edges 132 of the articulating body 118. Groove 130b is generally positioned within the posterior side of the facet joint replacement device 100. A linear portion extends between groove 130a and groove 130b. A second linear section extends between groove 130c and groove 130b. An arcuate section extends between groove 130a and groove 130c. The arcuate section between groove 130a and groove 130c is generally positioned within the anterior side of the facet joint replacement device 100. The grooves 130 can extend along one or more portions of the interior surface of the enclosing body 106. In some embodiments, the grooves 130 extend along a length of the interior surface of the enclosing body 106 from the superior end 108 to the superior articulating surface 128. The edges 132 can extend along one or more portions of the outer surface of the articulating body 118. In some embodiments, the edges 132 can extend along a length of the outer surface of the articulating body 118 between the superior end 122 to the inferior articulating surface 126. The grooves 130 of the enclosing body 106 can be configured to engage the edges 132 of the articulating body 118 to prevent relative rotation of the articulating body 118 within the enclosing body 106. The enclosing body 106 and articulating body 118 can be shaped and dimensioned to allow for relative axial movement between the inferior articulating surface 126 and the superior articulating surface 128 along the axis 103.

While three grooves 130 and three edges 132 are shown in FIG. 7, any number of grooves and edges may be utilized to prevent relative rotation of the articulating body 118 within the enclosing body 106. One of skill in the art would recognize that the cross-sections of the inner wall of the enclosing body 106 and the outer surface of the articulating body 118 could be any corresponding non-circular cross-sections suitable to prevent relative rotation and allow for relative translation along the length of the enclosing body 106. For example, in some embodiments, the inner wall of the enclosing body 106 and the outer surface of the articulating body 118 can each have an oval cross-section.

As described herein, the components of the facet joint replacement device 100 can be shaped and/or dimensioned to correspond to the anatomy of a healthy facet joint and related spinal motion segment. While lumbar facet joints are shown and described herein, applications of the facet joint replacement device 100 are not limited to the lumbar spine. In some embodiments, the facet joint replacement device 100 can be shaped and/or dimensioned to correspond to the anatomy of the thoracic spine. In some embodiments, a vertical distance between the superior end 108 of the enclosing body and the inferior end 110 of the enclosing body is between 20 mm to 44 mm, between 24 mm to 40 mm, between 28 mm and 36 mm, or between 30 mm and 34 mm. In some embodiments a vertical distance between the superior end 108 of the enclosing body and the inferior end 110 of the enclosing body is 28 mm, 29 mm, 30 mm, 31 mm, 32 mm, 33 mm, 34 mm, 35 mm, or 36 mm.

In some embodiments, one or both of the superior articular surface 128 and inferior articular surface 126 can have a major axis length of 10 mm, 11 mm, 12 mm, 13 mm, 14 mm, 15 mm, 16 mm, 17 mm, 18 mm, between 10 mm to 25 mm, between 9 to 14 mm, between 10 to 14 mm, or between 12 mm to 14 mm. In some embodiments, one or both of the superior articular surface 128 and inferior articular surface 126 can have a minor axis length of 8 mm, 9 mm, 10 mm, 11 mm, 12 mm, 13 mm, 14 mm, 15 mm, 16 mm, 17 mm, 18 mm, between 8 mm to 25 mm, between 8 mm to 14 mm, between 9 mm to 14 mm, or between 12 mm to 14 mm.

In some embodiments, the superior articulating surface 128 can be oriented at an angle of between 75° to 95° or between 55° to 85° from a transverse anatomic plane. In some embodiments, the superior articulating surface 128 can be oriented at an angle of between −100° to −150° or between −65° to −85° from a sagittal anatomic plane. In some embodiments, the inferior articulating surface 128 can be oriented at an angle of between 60° to 90° or between 55° to 85° from a transverse anatomic plane. In some embodiments, the superior articulating surface 128 can be oriented at an angle of between −65° to −165° or between −65° to −145° from a sagittal anatomic plane.

In some embodiments, an angle between the axis 103 and axis 105 can be 60°, 70°, 80°, 90°, 100°, 110°, 120°, 130°, between 60° and 130°, between 70° and 120°, between 80° and 110°, between 90° and 100°, between 60° and 80°, between 80° and 100°, or between 100°, and 120°.

In some embodiments, an angle between a plane extending through the center point of the inferior articulating surface 126 and a plane defined by the superior end 122 of the articulating body 118 can be 60°, 70°, 80°, 90°, 100°, 110°, 120°, 130°, between 60° and 130°, between 70° and 120°, between 80° and 110°, between 90° and 100°, between 60° and 80°, between 80° and 100°, or between 100°, and 120°.

In some embodiments, one or both of the superior attachment member 120 and the inferior attachment member 112 can have a diameter of 1 mm, 2 mm, 3 mm, 4 mm, 4.5 mm, 5 mm, 5.5 mm, 6 mm, 6.5 mm, 7 mm, 8 mm, 9 mm, 10 mm, between 2 mm to 8 mm, between 4 mm to 6 mm, between 5 mm to 7 mm, or between 5 mm to 6 mm. In some embodiments, one or both of the superior attachment member 120 and the inferior attachment member 112 can have a length of 1 mm, 2 mm, 3 mm, 4 mm, 5 mm, 6 mm, 7 mm, 8 mm, 9 mm, 10 mm, 15 mm, 20 mm, 25 mm, 30 mm, between 2 mm to 8 mm, between 4 mm to 6 mm, between 5 mm to 10 mm, between 10 mm to 15 mm, between 15 mm to 20 mm, between 20 mm to 25 mm, between 25 mm to 30 mm, between 15 mm to 30 mm, or less than 15 mm.

In some embodiments, a thickness of the solid portion 130 between the superior articulating surface 128 and an inferior most point of the enclosing body 106 along the axis 103 can be 6 mm, 7 mm, 8 mm, 9 mm, 10 mm, 11 mm, 12 mm, 13 mm, 14 mm between 8 mm to 25 mm, between 6 mm to 14 mm, or between 8 mm to 12 mm.

In some embodiments, the widest section of the enclosing body 106 is at the superior articulating surface 128. The enclosing body 106 can include an inflection point at the superior articulating surface 128. In some embodiments, the enclosing body 106 bows medially between the superior articulating surface 128 and the superior end 108 of the enclosing body 106. In some embodiments, the articulating body 118 bows medially between the inferior articulating surface 128 and the superior end 122 of the articulating body 118.

Figure 8:
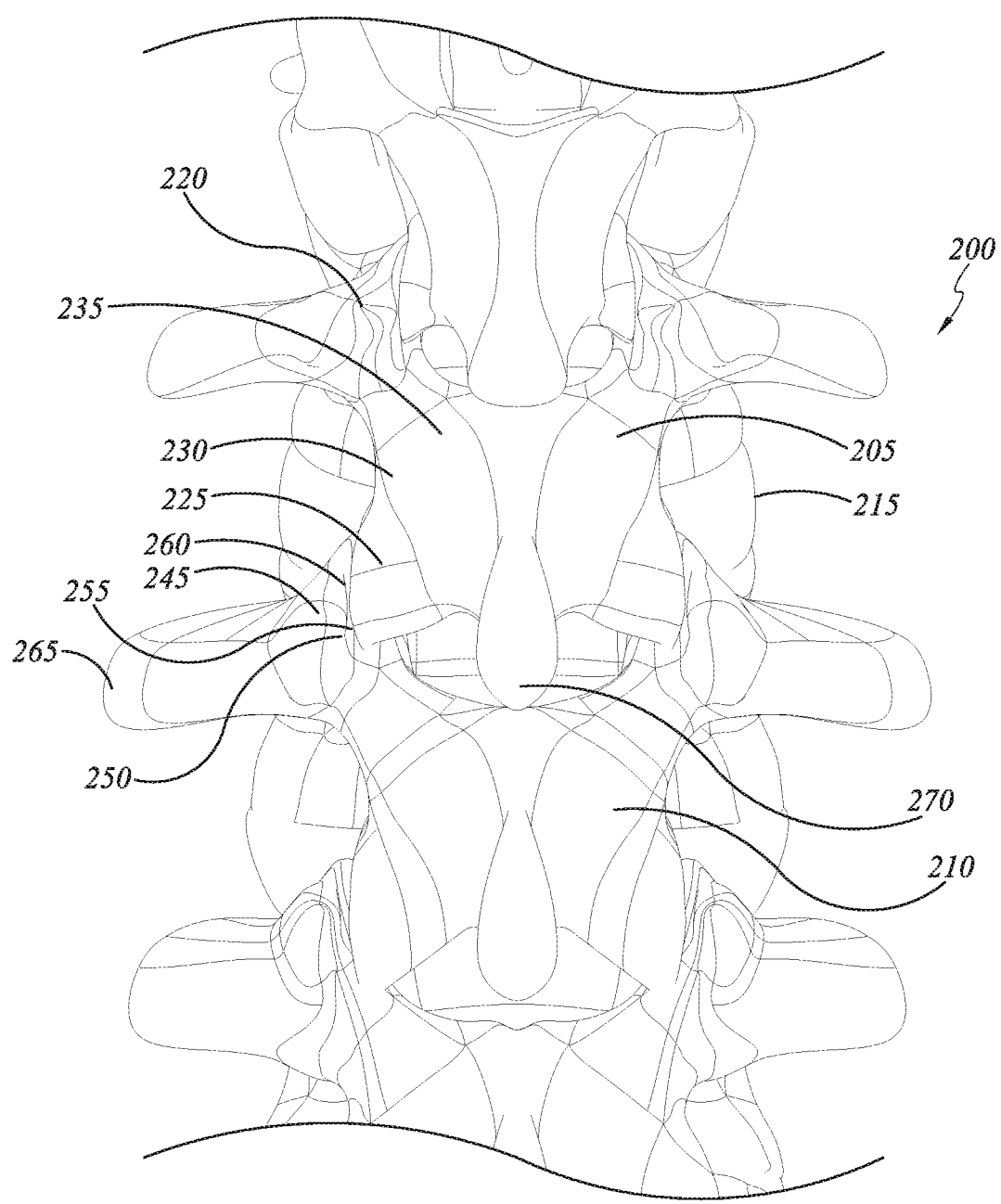
FIG. 8 depicts a posterior view of a lumbar motion segment 200.
Figure 9:
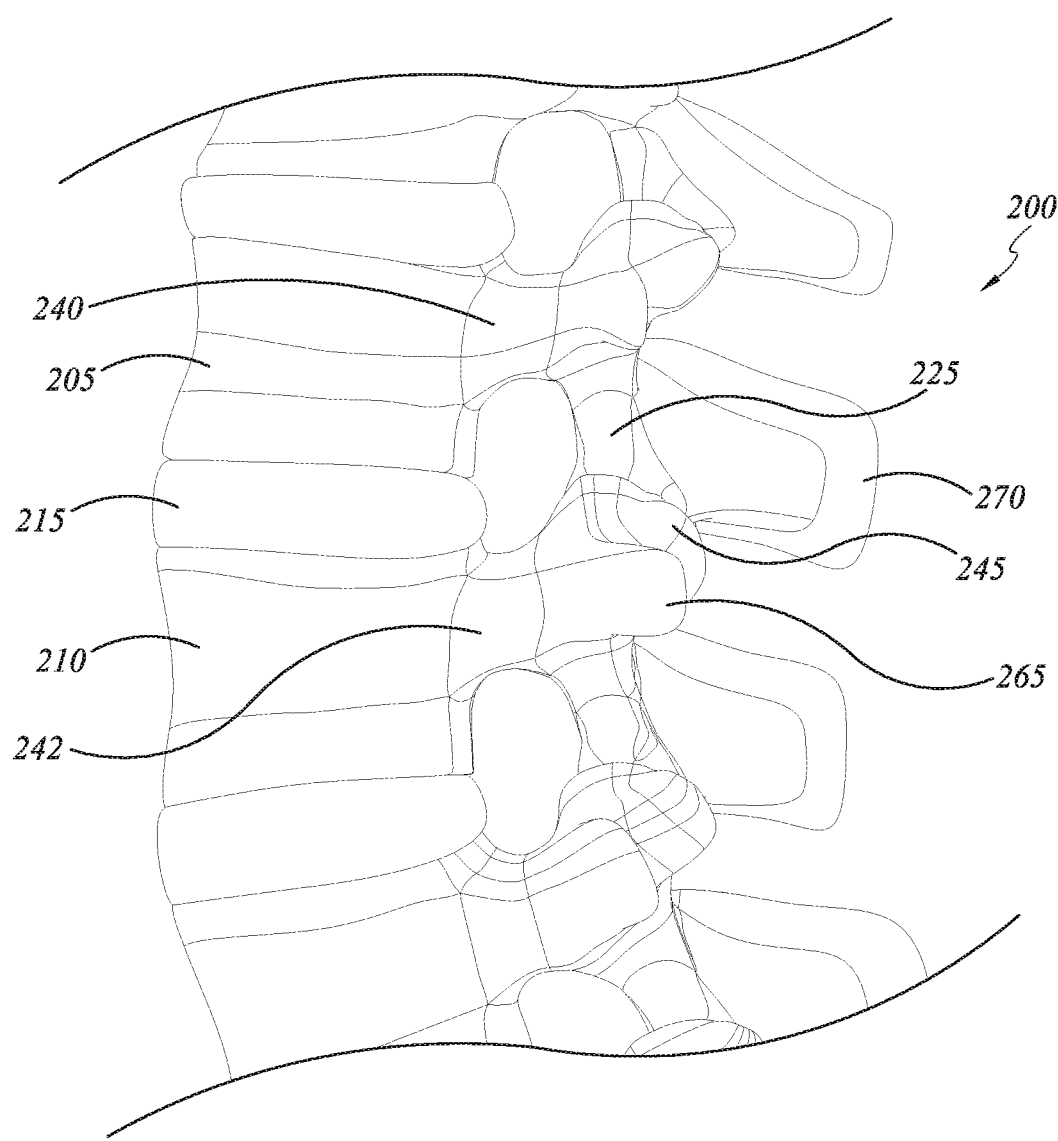
FIG. 9 depicts a sagittal view of the lumbar motion segment 200.

FIGS. 8 and 9 depict a posterior view and a sagittal view, respectively, of a lumbar motion segment 200 including a superior vertebra 205, an inferior vertebra 210, and an intervening disc 215. The superior vertebra 205 includes a superior articular process 220, an inferior articular process 225, and a pars interarticularis 230 extending between the superior articular process 220 and the inferior articular process 225. The pars interarticularis 230 is positioned between lamina 235 and pedicle 240. The pedicle 242 is also shown. A superior articular process 245 of the inferior vertebra 210 is also shown. An articular surface 250 of the superior articular process 245 and an articular surface 255 of the inferior articular process 225 align to form facet joint 260, which is encapsulated by a facet joint capsule (not shown). A sagittal inclination angle of the lumbar facet joint can range between 82° to 86°. As shown in FIG. 8, the facet joint 260 is located medial to transverse process 265 and lateral to spinous process 270. The facet joint is axially offset from the midline of the spine by between 15° to 70° degrees, dependent on the lumbar level, with more inferior lumbar segments have greater axial offset angles.

Figure 10:
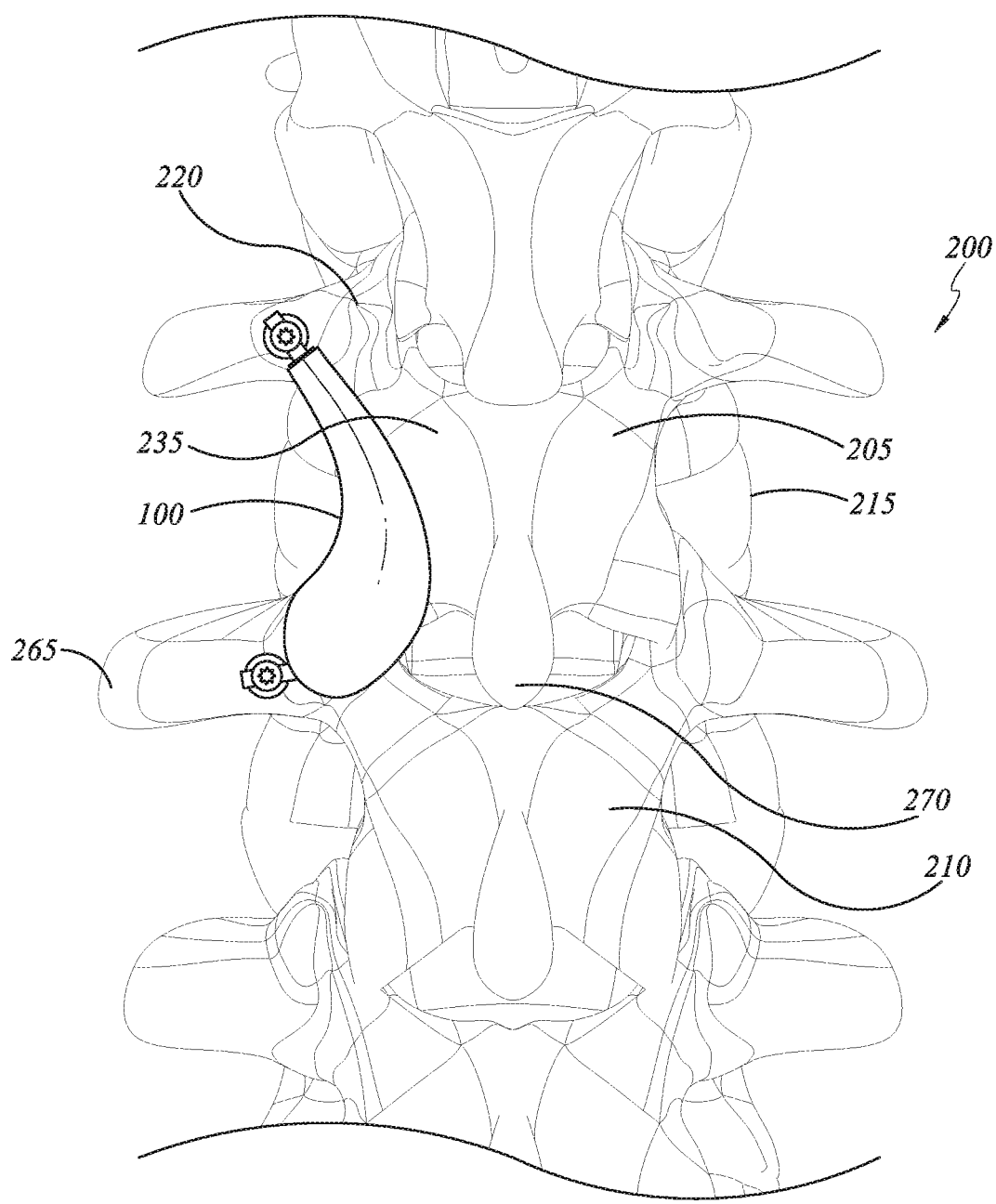
FIG. 10 depicts a posterior view of the lumbar motion segment 200 with the facet joint replacement device 100 implanted.
Figure 11A:
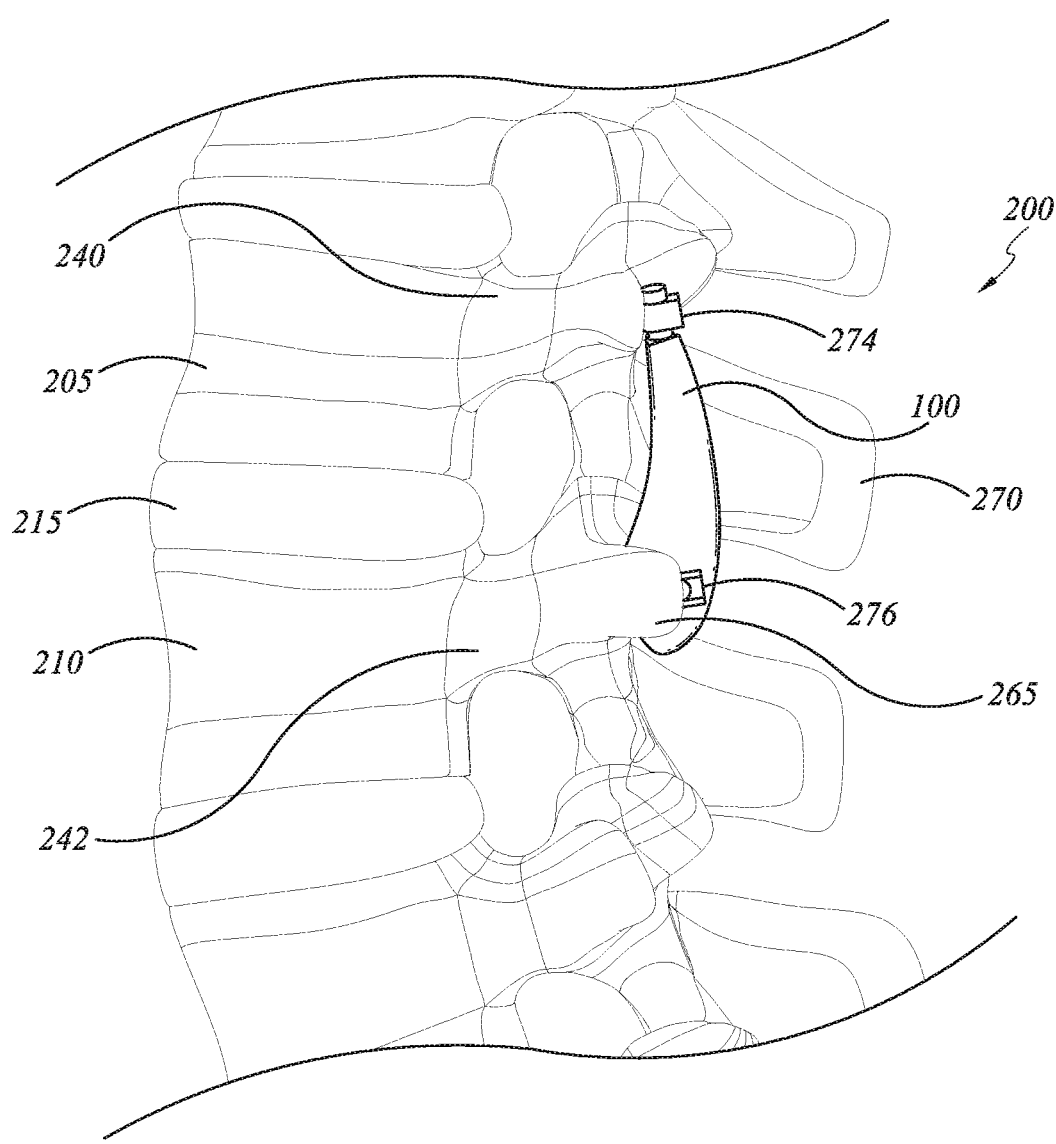
FIG. 11A depicts a sagittal view of the lumbar motion segment 200 with the facet joint replacement device 100 implanted.
Figure 11B:
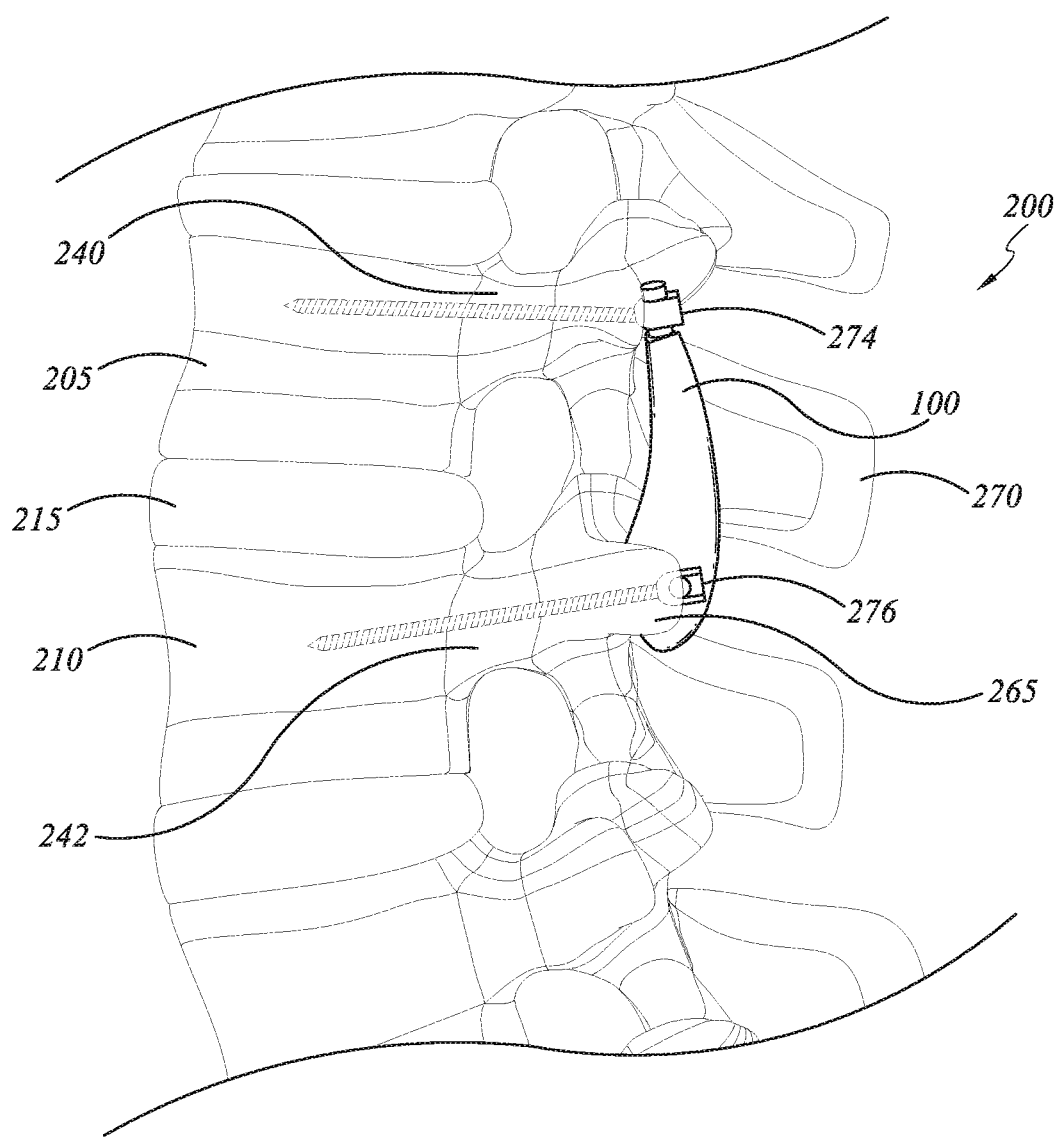
FIG. 11B depicts a sagittal view of the lumbar motion segment 200 with the facet joint replacement device 100 implanted showing components positioned within or obstructed by bone in dotted lines.

FIGS. 10 and 11A depict a posterior view and a sagittal view, respectively, of a lumbar motion segment 200 with the facet joint replacement device 100 implanted. The superior attachment member 120 is affixed to the pedicle 240 of a superior vertebra or superior vertebral body 205 by a fastener 274. The inferior attachment member 112 is affixed to the pedicle 242 of an interior vertebra or inferior vertebral body 210 by a fastener 276. As shown in FIGS. 10 and 11A, the fasteners 274 and 276 each include a tulip head bone screw and a top loading set screw. FIG. 11B shows the positioning of the tulip head bone screws of fasteners 274 and 276 within pedicles 240 and 242 in dotted lines.

Figure 12:
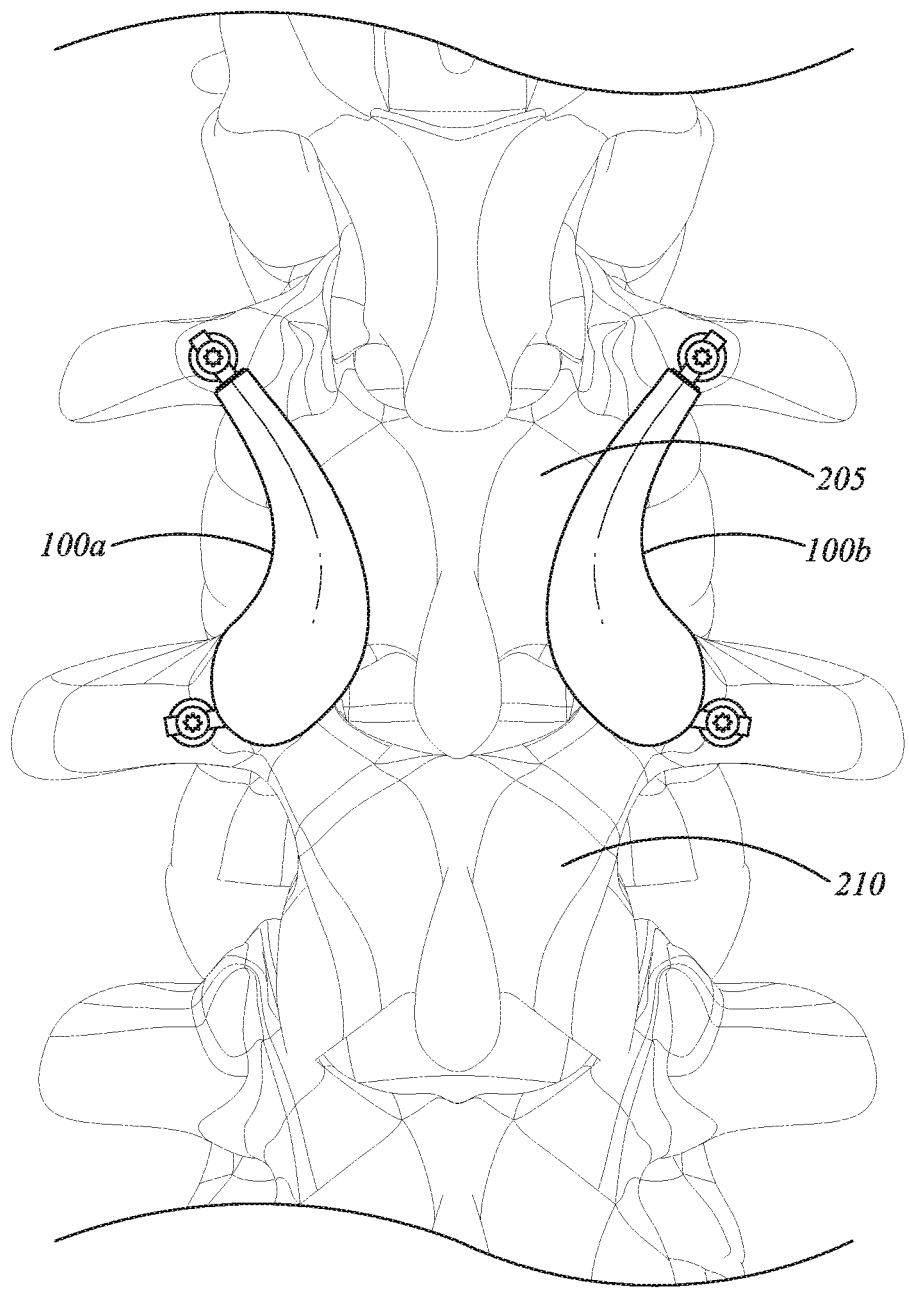
FIG. 12 depicts a posterior view of the lumbar motion segment 200 having a first facet joint replacement device 100A and a second facet joint replacement device 100B implanted bilaterally.

FIGS. 10 and 11A show a unilateral implantation of a facet joint replacement device 100. One of skill in the art would understand that a facet joint replacement device, such as facet joint replacement device 100, can be implanted on either lateral side of a motion segment, or two facet joint replacement devices can be implanted bilaterally, one on each side of a particular motion segment. FIG. 12 depicts a posterior view of the lumbar motion segment 200 having a first facet joint replacement device 100A positioned on a first lateral side of the lumbar motion segment 200 and a second facet joint replacement device 100B positioned on a second lateral side of the lumber motion segment 200.

In some embodiments, a method for implanting facet joint replacement device 100 into a patient begins with the administration of general endotracheal anesthesia. Following the administration of anesthesia, the patient is placed into a prone position and intraoperative fluoroscopy is used to identify a desired location for making a skin incision for implanting the facet joint replacement device 100. After the desired location is selected, a midline lumbar-sacral incision is made at the desired location, and subperiosteal dissection is utilized to expose a desired lamina, facet joint, and entry points to cannulate the ipsilateral pedicles of the superior and inferior vertebral bodies associated with the facet joint to be replaced. In some alternative embodiments, minimally invasive surgical techniques can be employed for exposure of the desired lamina, facet joint, and entry points to cannulate the ipsilateral pedicles. After exposure of the desired structures, intraoperative fluoroscopy is utilized to confirm desired levels of exposure. After the desired levels of exposure are confirmed, a self-retaining retractor system is placed to maintain the desired level of exposure.

After the retractor system is in place, removal of one or more sections of the facet joint and surrounding bone is performed. In some embodiments, the lamina or portion of the lamina in the motion region to be treated is removed. Removal can be performed using bone biters, angled curets, and/or bone punches. In some embodiments, a ligamentum flavum or a portion of the ligamentum flavum in the motion segment to be treated is removed. Removal of the ligamentum flavum can be performed using bone punches. The facet joint or a portion of the facet joint to be treated is also removed. Removal of the facet joint can be performed using a high speed drill, bone biters, and/or bone punches. After removal of the facet joint to be treated, further decompression of the lateral recess can be performed and adjacent nerve roots can be identified. Additional bone may be removed as necessary to prevent mechanical compression of the nerve roots.

Following removal of the desired bone, the pedicles of the superior vertebral body and inferior vertebral body of the motion segment to be treated and desired points of entry to cannulate the pedicles are identified, for example, using intraoperative fluoroscopy. A high speed drill or bone awl is then used to perforate the cortical bone overlying the optimal entry points to cannulate each of the pedicles. The pedicles are then probed and tapped under fluoroscopic guidance. Tulip head bone screws, such as the tulip head bone screws of fasteners 274 and 276, are then screwed into the previously tapped pedicles. Additional fixation augmentors, such as methylmethacrylate, can also be used. In some embodiments, a decision to use additional fixation augmentors is made based on apparent bone quality at the time of bone screw insertion. Methylmethacrylate or other fixation augmentors can be placed within the cannulated pedicle prior to placement of the bone screw, for example, to improve the fixation of the bone screw within the implanted pedicle bone.

After fixation of the bone screws to the superior and inferior vertebral bodies, the superior attachment member 120 can be placed within a receiving portion of the tulip head portion of the bone screw in the superior vertebral body, and the inferior attachment member 112 can be placed within a receiving portion of the tulip head portion of the bone screw in the inferior vertebral body. After the superior attachment member 120 and inferior attachment member 112 are received within the tulip head portions of the implanted bone screws, the superior attachment member 120 and inferior attachment member 112 can be secured to the bone screws by fixation of top loading set screws to each of the tulip head portions of the implanted bone screws.

In some embodiments, after ensuring that the implanted bone screws are in proper position and secure, but before the attachment members 120 and 112 are placed into the bone screws, distraction or compression can be applied between the implanted bone screws to address any asymmetric loss of the disc space height or malalignment.

In some embodiments, facet joint replacement devices may be available in a plurality of different sizes. In such embodiments, after implantation of the tulip head bone screws into the superior and inferior vertebral bodies, a distance is measured between the tulips head portions of the bone screws and a facet joint replacement device can be selected based on the distance measured between the tulip head portions of the bone screws, for example, so that the superior and inferior attachment members of the facet joint replacement device can be securely engaged with the tulip head portions of the implanted bone screws.

In some embodiments, facet joint replacement devices may be available with inferior articulating surfaces and superior articulating surfaces having a plurality of different angular orientations with respect to the sagittal and transverse anatomic planes, as described further herein. In such embodiments, after implantation of the tulip head bone screws into the superior and inferior vertebral body, a facet joint replacement device is selected based on the desired angular orientations of the superior articular surface and inferior articular surface. The desired angular orientations can be selected based on estimated angular orientations of the articular surfaces of a healthy facet joint in the treated motion segment.

Figure 13:
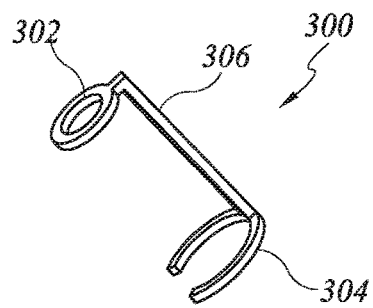
FIG. 13 depicts a perspective view of a removable clip 300.
Figure 14:
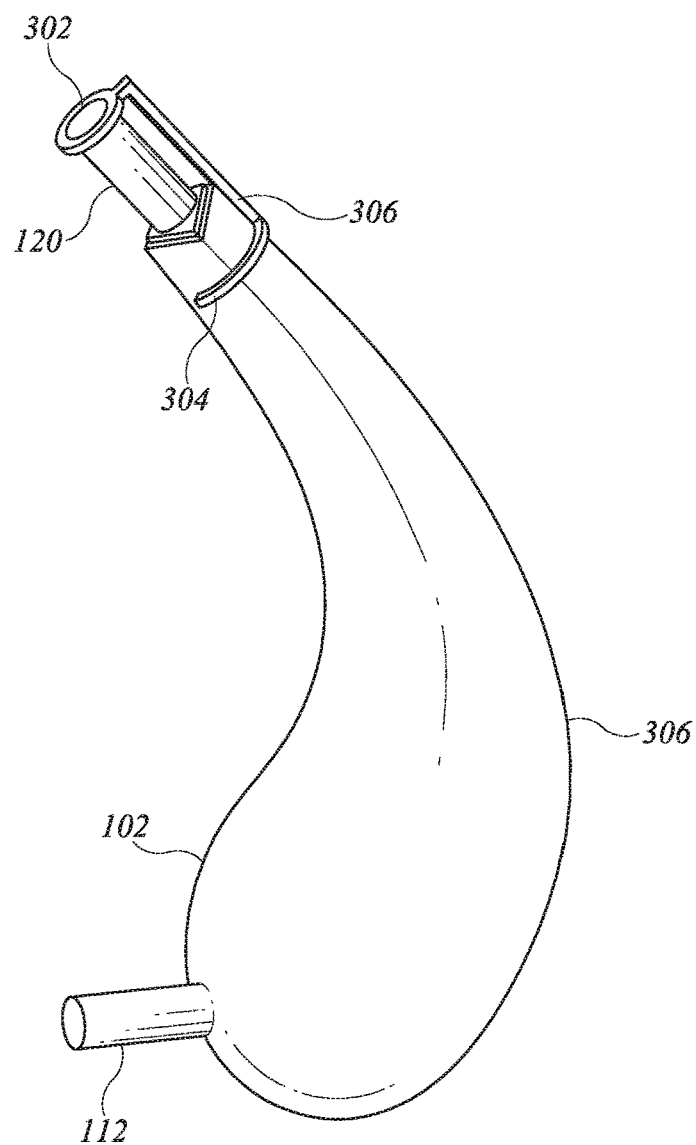
FIG. 14 depicts perspective view of the removable clip 300 secured to the facet joint replacement device 100.

In some embodiments, it may desirable for inferior articulating element 104 to reside in a particular position within the enclosing body 106 at the time of implantation into the body. For example, in some embodiments, it is desirable that the inferior articulating element is positioned within the enclosing body 106 so that the inferior articulating surface 126 is at its closest position with respect to the superior articulating surface 128. The position of the inferior articulating element 104 within the enclosing body 106 can be decided based on the position of the spine during implantation of the facet joint replacement device so that the inferior articulating surface 126 and superior articulating surface 128 conform to the natural position of the articular surfaces of the superior and inferior articular process of the spinal motion segment to be treated. FIG. 13 depicts a removable clip 300 according to one embodiment. The removable clip 300 includes a receiving member 302, a receiving member 304, and a connector 306 extending between the receiving member 302 and receiving member 304. The connector 306 prevents relative movement between the receiving member 302 and receiving member 304. The receiving member 302 can be configured to removably secure to the superior attachment member 120. The receiving member 304 can be configured to removably secure to a superior section of the exterior of the enclosing body 106. FIG. 14 depicts the removable clip 300 secured to the facet joint replacement device 100. When the receiving member 302 and receiving member 304 are secured to the facet joint replacement device, the removable clip 300 can constrain relative movement of the inferior articulating body 118 within the enclosing body 106. In some embodiments, the removable clip 300 is metallic.

Methods for implanting the facet joint replacement device 100 can optionally include securing the removable clip 300 to the facet joint replacement device 100 prior to implantation of the facet joint replacement device 100. After the facet joint replacement device 100 is secured to the spine, the removable clip 300 can be removed from the facet joint replacement device to allow for movement of the inferior articulating body 118 within the enclosing body 106.

Figures 15, 16:
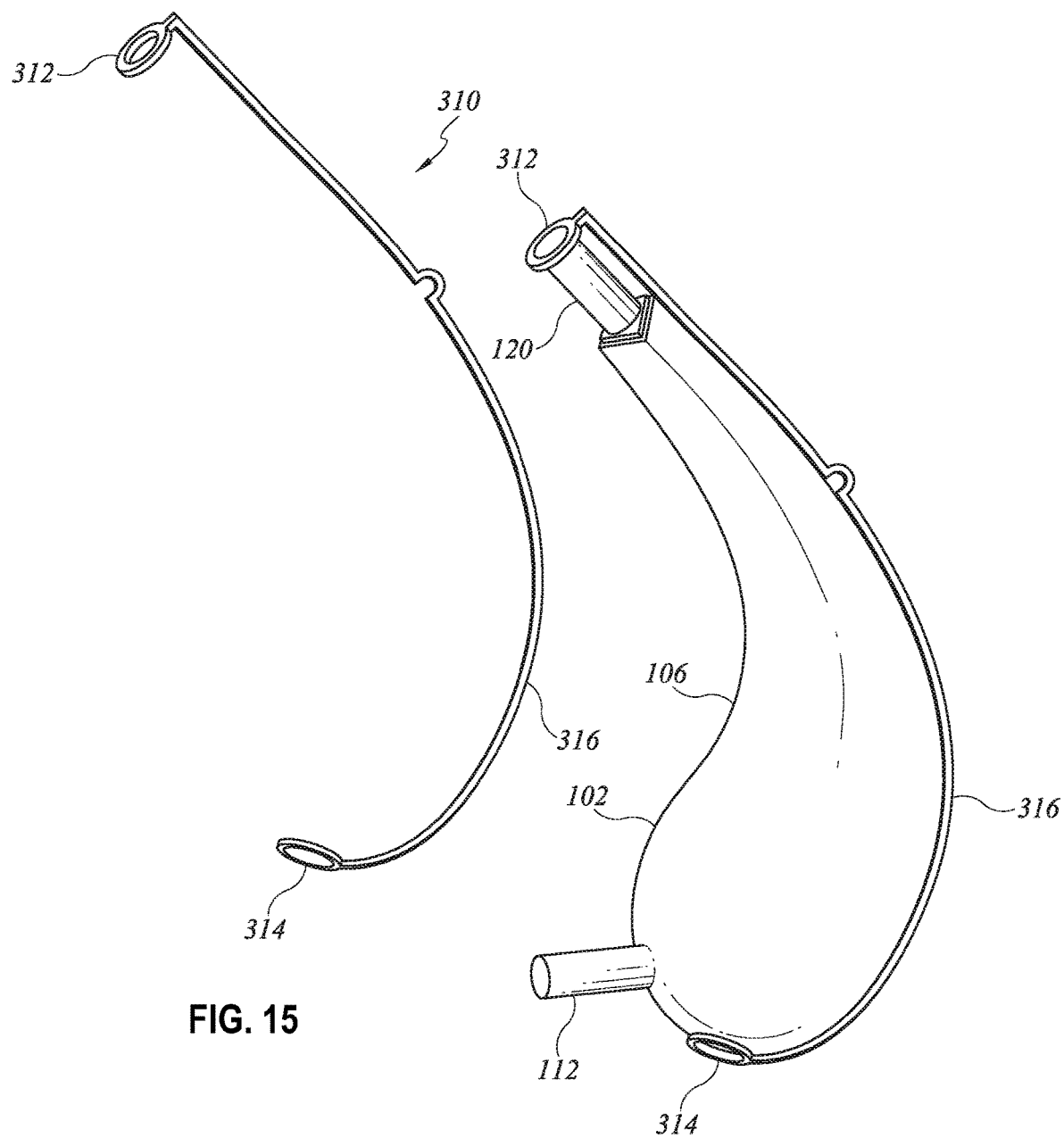
FIG. 15 depicts a perspective view of a removable clip 310.
FIG. 16 depicts a perspective view of the removable clip 310 secured to the facet joint replacement device 100.

FIG. 15 depicts a removable clip 310 according to another embodiment. The removable clip 310 includes a receiving member 312, a receiving member 314, and a connector 316 extending between the receiving member 312 and receiving member 314. The connector 316 prevents relative movement between the receiving member 312 and receiving member 314 and is shaped to correspond to the curvature of a side of the facet joint replacement device 100. The receiving member 312 can be configured to removably secure to the superior attachment member 120. The receiving member 314 can be configured to secure to a section of the exterior of the enclosing body 106 near the inferior end. FIG. 16 depicts the removable clip 310 secured to the facet joint replacement device 100. When the receiving member 312 is secured to the superior attachment member 120, the connector 316 extends along a medial side of the enclosing body 106 to the receiving member 314 at the inferior end of the enclosing body 106. The receiving member 314 can be positioned at the inferior end of the enclosing body 106 such that the removable clip 310 is secured to the facet joint replacement device 100. When the removable clip 310 is secured to the facet joint replacement device 100, the removable clip 310 can constrain relative movement of the inferior articulating body 118 within the enclosing body 106. In some embodiments, the removable clip 310 is metallic.

Methods for implanting the facet joint replacement device 100 can optionally include securing the removable clip 310 to the facet joint replacement device 100 prior to implantation of the facet joint replacement device 100. After the facet joint replacement device 100 is secured to the spine, the removable clip 310 can be removed from the facet joint replacement device to allow for movement of the inferior articulating body 118 within the enclosing body 106.

Figure 17:
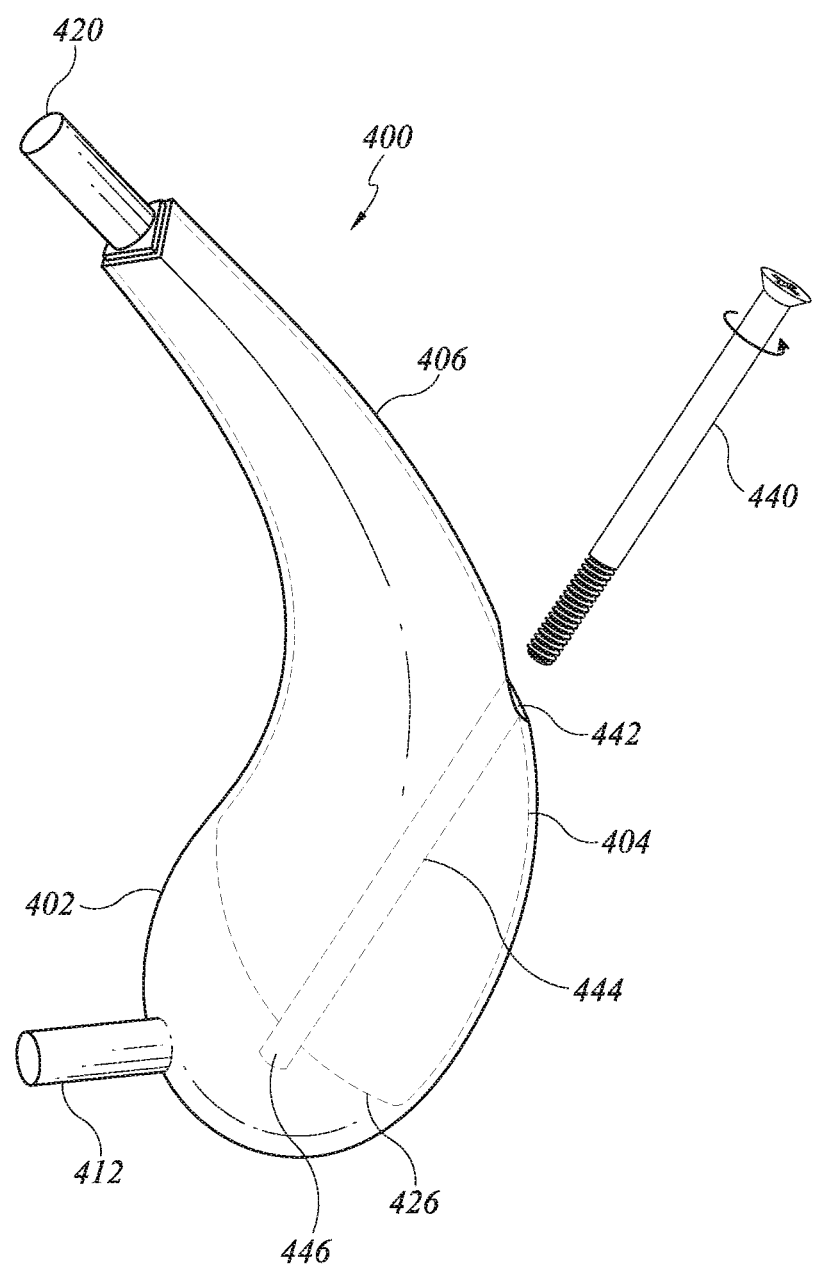
FIG. 17 depicts a posterior perspective view of a facet joint replacement device 400 and a fastener 440.

FIG. 17 depicts a posterior perspective view of a facet joint replacement device 400 and a fastener 440 according to another embodiment. The facet joint replacement device 400 includes many of the same or similar components as the facet joint replacement device 100 described with respect to FIGS. 1-7. The facet joint replacement device 400 includes an enclosing element 402 having an enclosing body 406 and an inferior attachment member 412. The facet joint replacement device 400 also includes an inferior articulating element 404 having an articulating body 418 and a superior attachment member 420. The articulating body 418 can include an articulating surface 426, similar to articulating surface 126. A portion of the interior surface of the enclosing body 406 can be shaped to form a superior articulating surface (not shown), similar to articulating surface 128. The enclosing body 406 can include an opening 442 configured to receive the fastener 440. The opening 442 is positioned on a medial section of the enclosing body 406. In some embodiments, the opening 442 is positioned on an inferior section of the enclosing body 406. In some embodiments, the opening 442 is positioned on a superior section of the enclosing body 406. In some embodiments, the opening 442 is positioned mid-position between a superior end of the enclosing body 406 and an inferior end of the enclosing body 406. The articulating body 418 can include a channel 444 configure to align with the opening 442 when in a particular position or range of particular positions within the enclosing body 406 and receive the fastener 440 when aligned with the opening 442. The enclosing body includes a channel 446 configured to align with the channel 444 of the articulating body 418 when the articulating body is aligned with the opening 442. The channel 444 can be configured to receive the fastener 440 when the fastener 440 passes through the opening 442 and channel 444. In some embodiments, the channels 444 and 446 extend along an axis that is the same as, similar to, or parallel to axis 103 as described with respect to FIG. 1B. When the fastener 440 is inserted into the opening 442, channel 444, and/or channel 446, the fastener 440 moves in an inferior, anterior, and lateral direction. If the fastener 440 is removed from the channel opening 442, channel 444, and/or channel 446, the fastener 440 moves in a superior, posterior, and medial direction.

The fastener 440 can include threads configured to be received by complementary threads within the channel 444 and channel 446. In some embodiments, the fastener 440 is a threaded screw. In some embodiments, the fastener 440 is a lag screw. When received within the channel 444 and the channel 446, the fastener 440 can secure the articulating body 418 in a particular position within the enclosing body 406. For example, the fastener 440 can secure the articulating body 418 within the enclosing body 406 so that the inferior articulating surface 426 is at its most proximal position with respect to the superior articulating surface of the enclosing body. By securing the articulating body 418 in a particular position within the enclosing body 406, the fastener 440 can perform a similar function to the removable clip 300.

In some embodiments, methods of implanting the facet joint replacement device 400 include securing the articulating body 418 in a desired position within the enclosing body 406 prior to implantation in the body using the fastener 440. The fastener 440 can be removed after the facet joint replacement device 400 is secured to the spine. In some embodiments, the fastener 440 can remain positioned within the facet joint replacement device 400 following implantation.

In some embodiments, the depth of the fastener 440 within the facet joint replacement device 400 can be altered by rotating the fastener 440. In some embodiments, changing the depth of the fastener 440 within the facet joint replacement device can change the distance between the inferior articulating surface 426 and the superior articulating surface of the enclosing body 406. In some embodiments, the depth of the fastener 440 can be changed after implantation to provide a different distance between the inferior articulating surface 426 and the superior articulating surface of the enclosing body 406. In some embodiments, the fastener 440 can allow for at least some movement between the inferior articulating surface 426 and superior articulating surface of the enclosing body at least some depths of the fastener 440.

Figure 18:
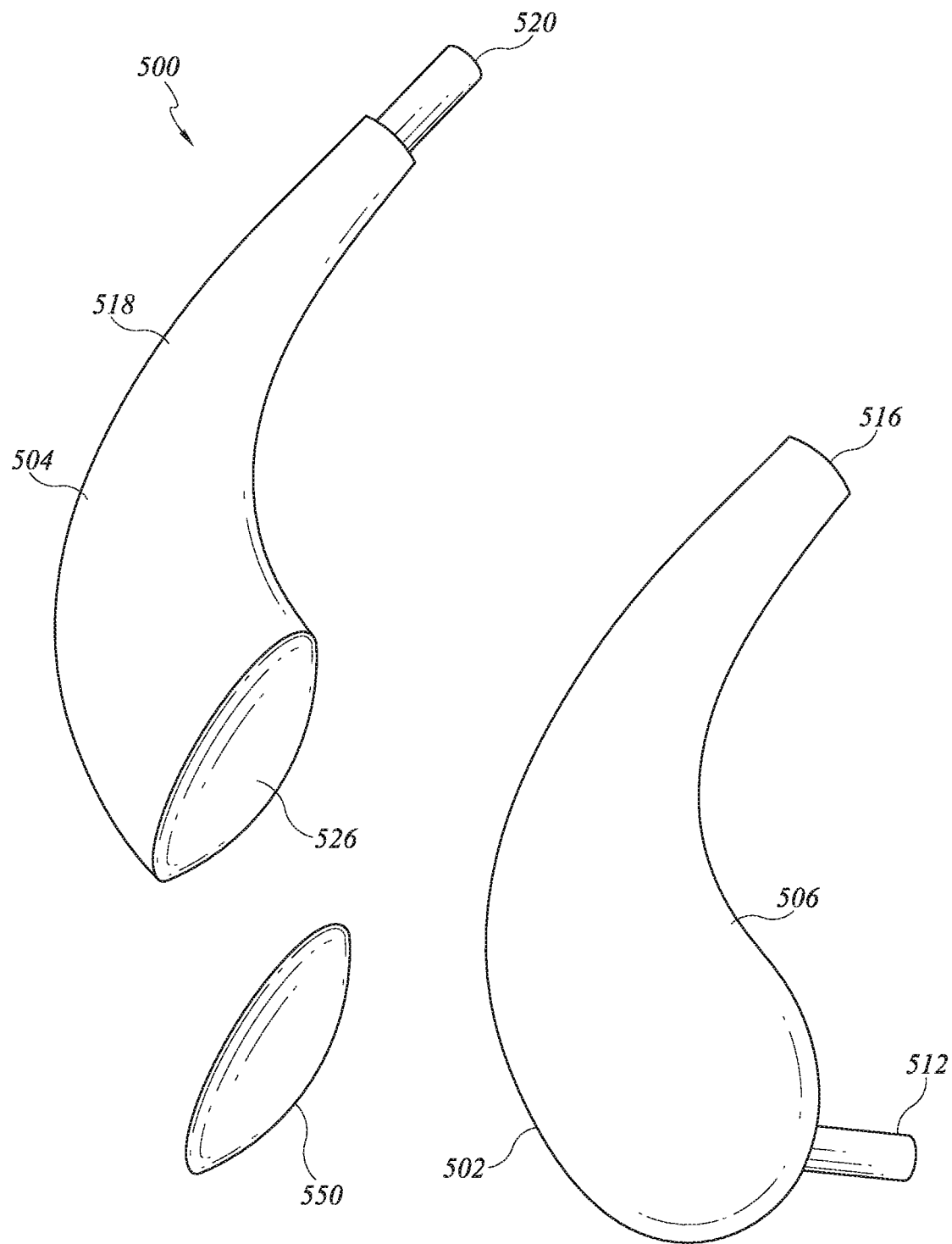
FIG. 18 depicts an exploded view of a facet joint replacement device 500.

FIG. 18 depicts an exploded view of a facet joint replacement device 500 in accordance with another embodiment. The facet joint replacement device 500 includes many of the same or similar components as the facet joint replacement device 100 described with respect to FIGS. 1A-7. The facet joint replacement device 500 includes an enclosing element 502 having an enclosing body 506, an inferior attachment member 512, and an opening 516. The facet joint replacement device 500 also includes an inferior articulating element 504 having an articulating body 518 and a superior attachment member 520. The articulating body 518 can include an inferior articulating surface 526, similar to inferior articulating surface 126. The inferior articulating surface 526 can be convex. A portion of the interior surface of the enclosing body 506 can be shaped to form a superior articulating surface (not shown), similar to articulating surface 128. The superior articulating surface of the facet joint replacement device 500 can be concave. The facet joint replacement device 500 further includes a veneer 550 configured to be positioned between the inferior articulating surface 526 and the superior articulating surface of the facet joint replacement device 500. In some embodiments, the veneer has a thickness of 1 mm, 2 mm, 3 mm, 4 mm, 5 mm, between 1 mm and 3 mm, between 1 mm and 2 mm, or between 2 mm and 3 mm. The veneer 550 can include a low friction material, such as high molecular weight polyethylene. In some embodiments, the veneer is formed of vitamin E impregnated polyethylene, which may function as a free radical scavenger. The veneer 550 can reduce friction and wear between the inferior articulating surface 526 and the superior articulating surface of the facet joint replacement device 500. In some embodiments, the veneer 550 includes a concave side configured to engage the inferior articulating surface 526. The veneer 550 can also include a convex side configured to engage the superior articulating surface of the facet joint replacement device 500. In some embodiments, the veneer 550 can be secured to the inferior articulating surface 526. In some embodiments, the veneer 550 can be secured to the inferior articulating surface 526 by a fastener, such as a screw. In an alternative embodiment, the veneer 550 can be formed as part of a sleeve configured to fit over at least a portion of the articulating body 518 including the inferior articulating surface 526.

Figure 19:
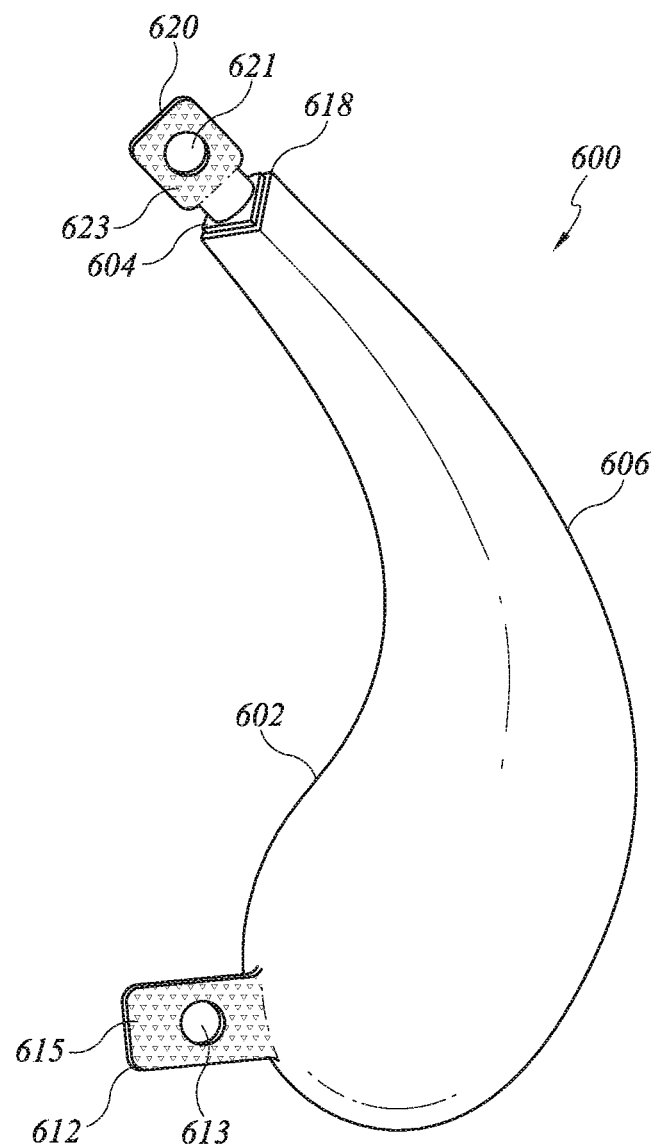
FIG. 19 depicts a posterior perspective view of a facet joint replacement device 600.

FIG. 19 depicts a posterior view of a facet joint replacement device 600 according to another embodiment. The facet joint replacement device 600 includes many of the same or similar components as the facet joint replacement device 100 described with respect to FIGS. 1A-7. The facet joint replacement device 600 includes an enclosing element 602 having an enclosing body 606 and an inferior attachment member 612. The facet joint replacement device 600 also includes an inferior articulating element 604 having an articulating body 618 and a superior attachment member 620. The articulating body 618 can include an articulating surface (not shown), similar to articulating surface 126. A portion of the interior surface of the enclosing body 606 can be shaped to form a superior articulating surface (not shown), similar to articulating surface 128. The inferior attachment member 612 includes a hole 613 and a textured surface 615. The superior attachment member 620 includes a hole 621 and a textured surface 623. The holes 613 and 621 can each receive a fastener, such as a threaded bone screw, to secure the facet joint replacement device 600 to the spine.

The shape of the inferior attachment member 612 allows for alignment of the inferior attachment member 612 with a superior attachment member of a facet joint replacement device positioned to replace a facet joint at an inferior contiguous vertebral body. The shape of the superior attachment member 620 allows for alignment of the superior attachment member 620 with an inferior attachment member of a facet joint replacement device positioned to replace a facet joint of a superior contiguous vertebral body.

Figure 20:
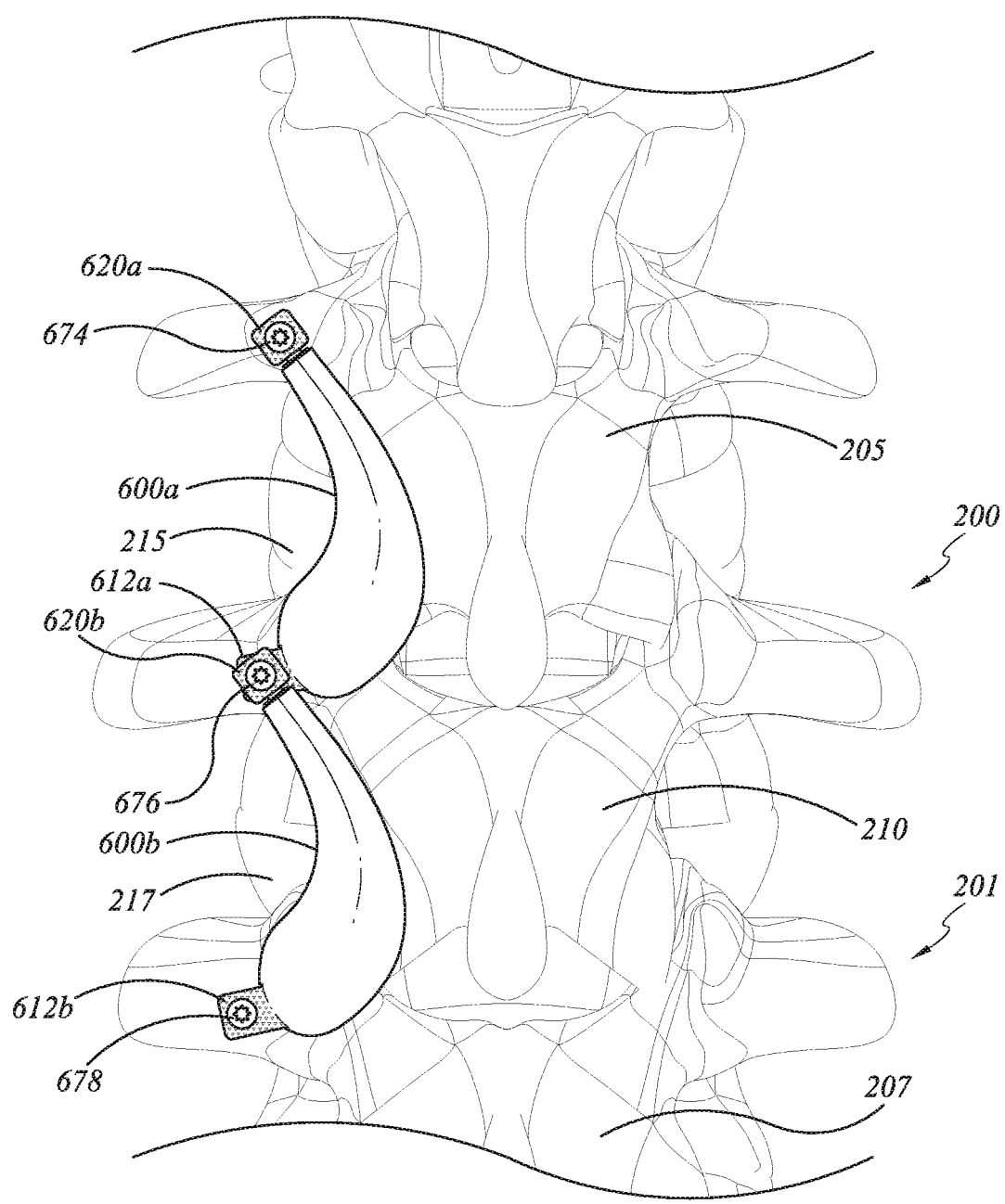
FIG. 20 depicts a posterior view of the motion segment 200 and a motion segment 201 with a first facet joint replacement device 600A and a second facet joint replacement device 600B implanted ipsilaterally.

FIG. 20 depicts a posterior view of the motion segment 200 and a motion segment 201 with a facet joint replacement device 600A and a facet joint replacement device 600B implanted ipsilaterally. The facet joint replacement device 600A is positioned to replace the facet joint 260 of the motion segment 200. The facet joint replacement device 600B is positioned to replace a facet joint of the motion segment 201, which is inferior to motion segment 200 and includes vertebral body 210, vertebral body 207, and intervertebral disc 217. The facet joint replacement devices 600A and 600B include the same components as the facet joint replacement device 600 described herein. The facet joint replacement device 600A includes a superior attachment member 620A and an inferior attachment member 612A, each having a hole and a textured surface. The facet joint replacement device 600B includes a superior attachment member 620B and an inferior attachment member 612B, each having a hole and a textured surface. The superior attachment member 620A is secured to the superior vertebral body 205 by a fastener 674 passing through the hole of the superior attachment member 620A. The inferior attachment member 612A is positioned so that the hole of the inferior attachment member 612A aligns with the hole of the superior attachment member 620B. The textured surfaces of the attachment members 612A and 620B can contact one another to provide friction or otherwise constrain movement of the attachment members 612A and 620B relative to one another once aligned. A fastener 676 extends through both the hole in the attachment member 612A and the hole in the attachment member 620B to secure the attachment members 612A and 620B to the inferior vertebral body 210. A fastener 678 extends through the hole of the inferior attachment member 612B to secure the attachment member 612B to vertebral body 207. In some embodiments, each of the fasteners 674, 676, and 678 can include a bone screw and/or a threaded locking nut.

Methods of implanting facet joint replacement devices 600A and 600B can include aligning the opening of the inferior attachment member 612A with the opening of the superior attachment member 620B and securing the inferior attachment member 612A and the superior attachment member 620B to the same vertebral body by extending a fastener through the opening of the inferior attachment member 612A device and the opening of the superior attachment member 620B.

Figure 21:
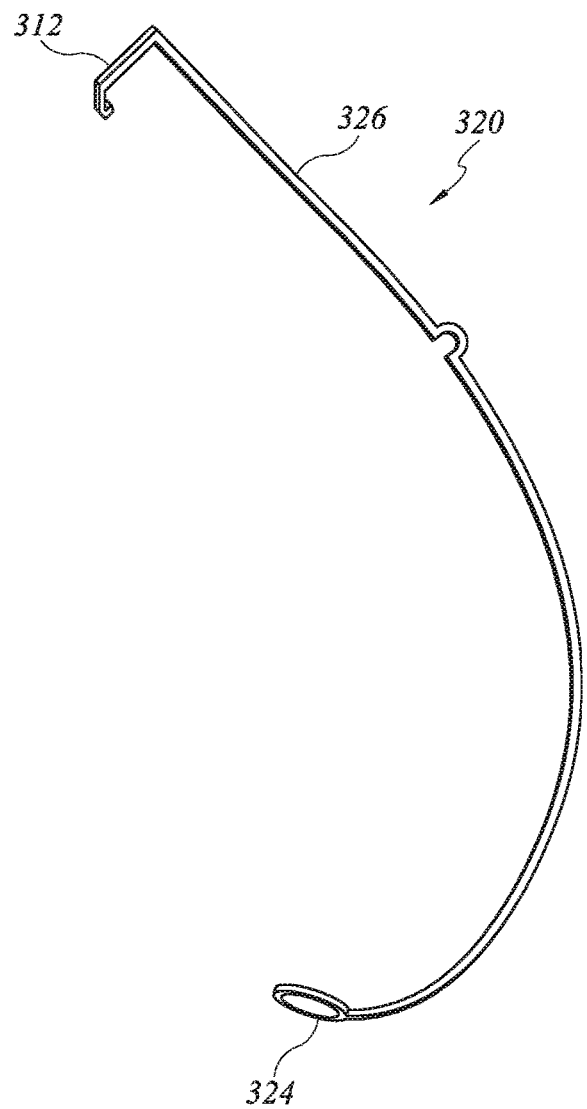
FIG. 21 depicts a perspective view of a removable clip 320.
Figure 22:
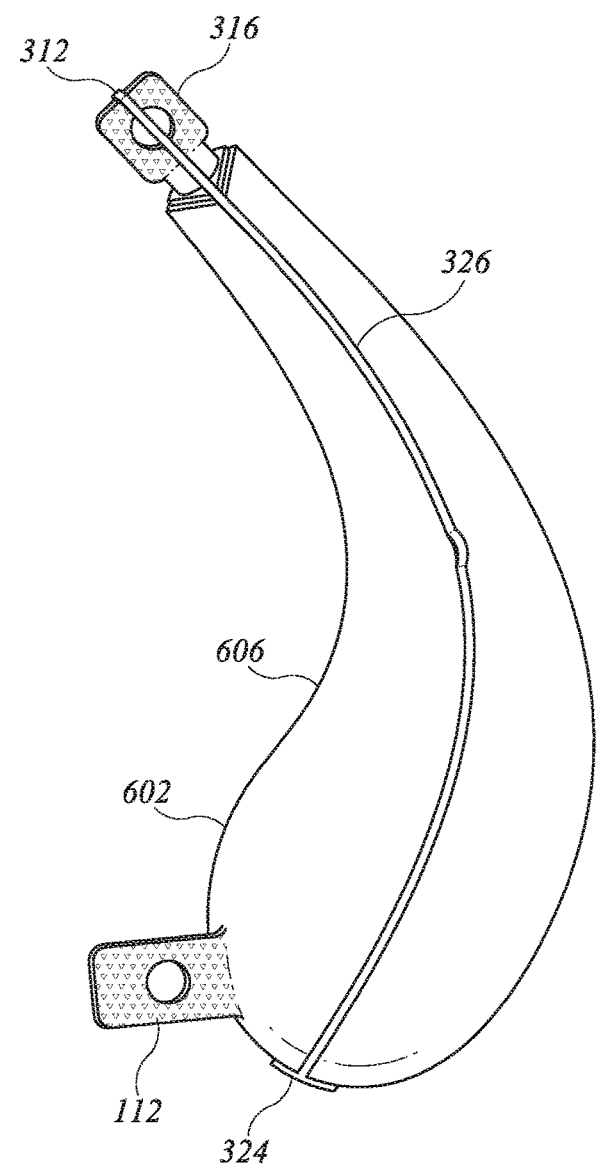
FIG. 22 depicts a perspective view the removable clip 320 secured to the facet joint replacement device 600.

FIG. 21 depicts a removable clip 320 according to another embodiment. The removable clip 320 includes a hook member 322, a receiving member 324, and a connector 326 extending between the hook member 322 and receiving member 324. The connector 326 prevents relative movement between the receiving member 322 and receiving member 324 and is shaped to correspond to the curvature of the posterior of the facet joint replacement device 600. The hook member 322 can be configured to removably secure to the superior attachment member 620. The receiving member 324 can be configured to secure to a section of the exterior of the enclosing body 606 near the inferior end. FIG. 22 depicts the removable clip 320 secured to the facet joint replacement device 600. When the hook member 322 is secured to the superior attachment member 620, the connector 326 extends along a posterior section of the enclosing body 606 to the receiving member 324 at the inferior end of the enclosing body 606. The receiving member 324 can be positioned at the inferior end of the enclosing body 606 such that the removable clip 320 is secured to the facet joint replacement device 600. When the removable clip 320 is secured to the facet joint replacement device 600, the removable clip 320 can constrain relative movement of the inferior articulating body 618 within the enclosing body 606. In some embodiments, the removable clip 320 is metallic.

Methods for implanting the facet joint replacement device 600 can optionally include securing the removable clip 320 to the facet joint replacement device 600 prior to implantation of the facet joint replacement device 600. After the facet joint replacement device 600 is secured to the spine, the removable clip 320 can be removed from the facet joint replacement device to allow for movement of the inferior articulating body 618 within the enclosing body 606.

Details regarding the facet joint replacement devices, methods, systems and other features and embodiments, as described above with respect to FIGS. 1-22 and as further described in U.S. Pat. No. 9,839,451, the entirety of which is hereby incorporated by reference, may be utilized in combination with, may be replaced by, or may be used in place of any of the features or embodiments described hereinbelow or elsewhere in the specification.

FIGS. 23A-J depict a facet joint replacement device 700 according to one embodiment. FIGS. 23A-D depict perspective views of the facet joint replacement device 700. FIGS. 23A-D also includes three-dimensional coordinate axes indicating the superior ("S"), inferior ("I"), anterior ("A"), posterior ("P"), medial ("M"), and lateral ("L") directions. As described herein, the terms superior, inferior, anterior, posterior, medial, and lateral, when describing portions of the devices herein, refer to portions of the device as they are intended to be oriented with respect to the human spine.

Figure 23A:
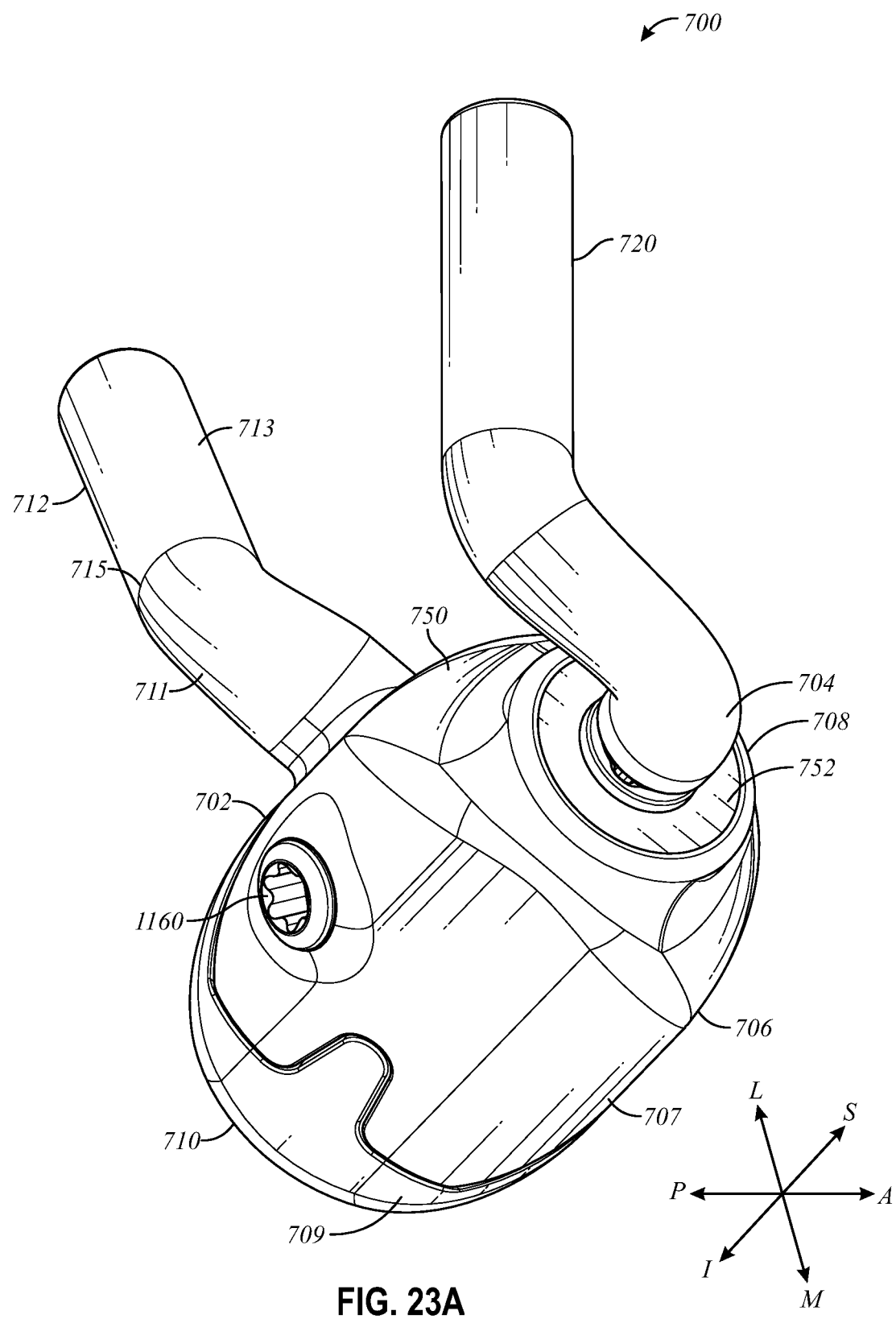
FIG. 23A depicts a top posterior perspective view of a facet joint replacement device 700.
Figure 23B:
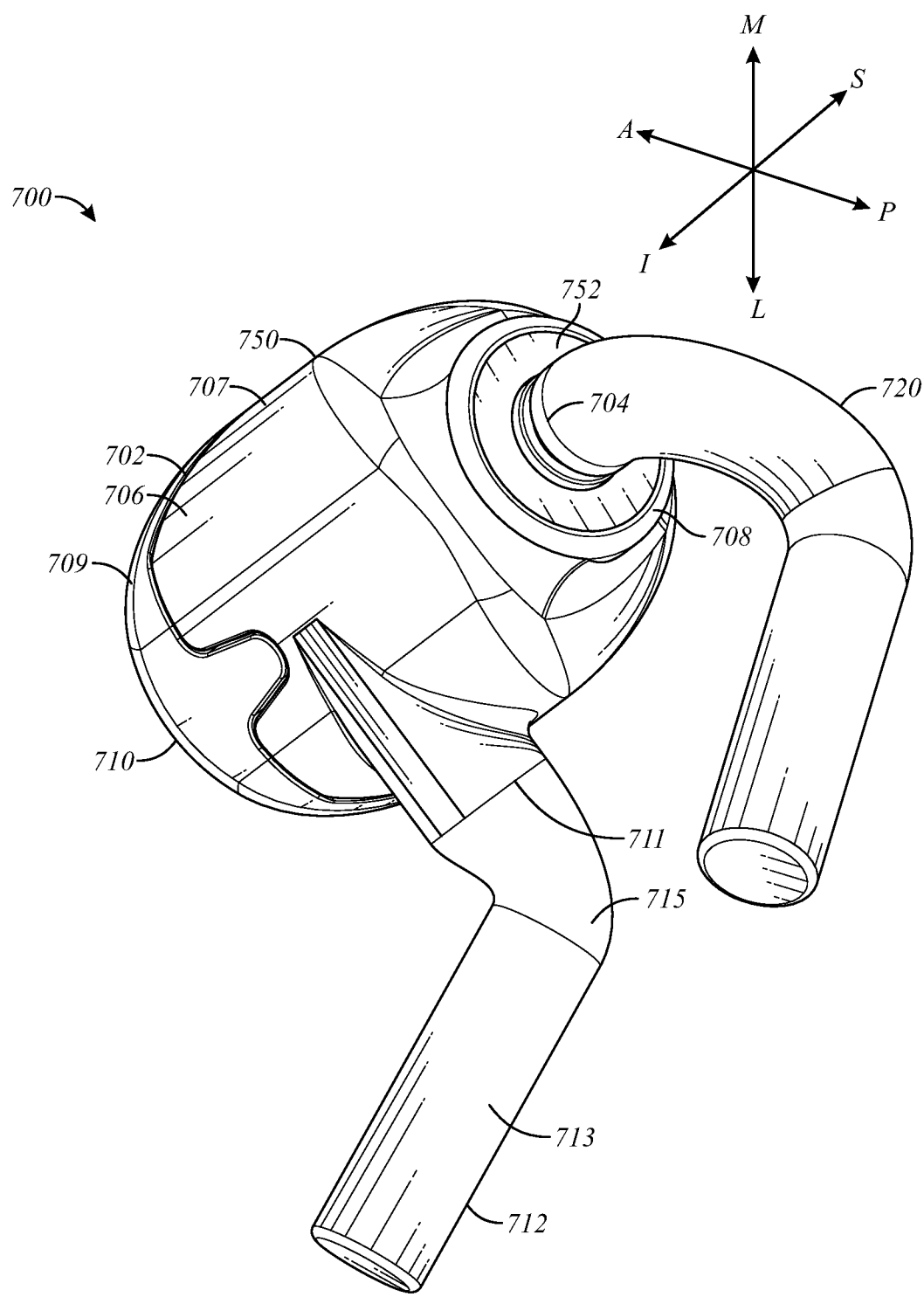
FIG. 23B depicts a top anterior perspective view of the facet joint replacement device 700.
Figure 23C:
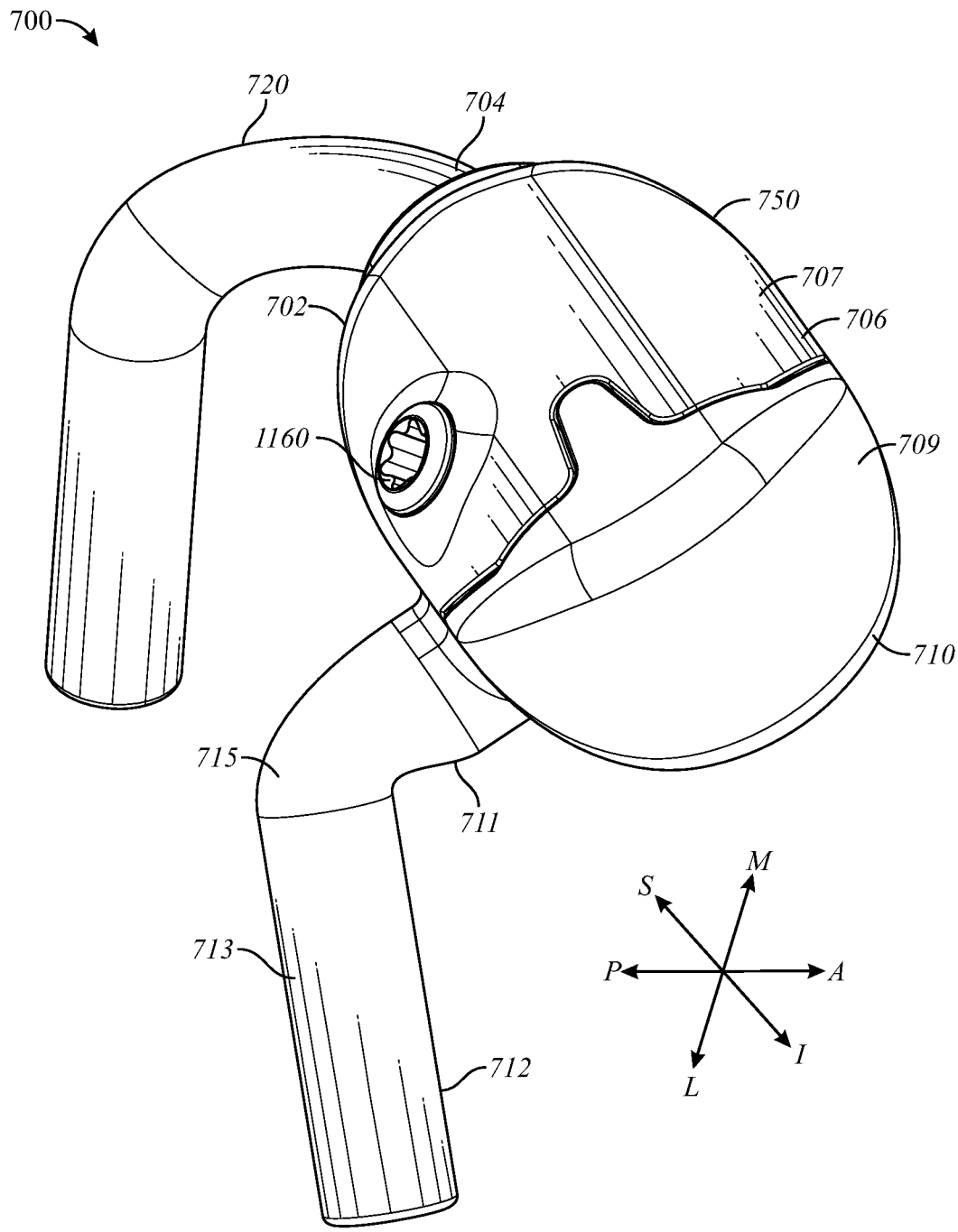
FIG. 23C depicts a bottom posterior perspective view of the facet joint replacement device 700.
Figure 23D:
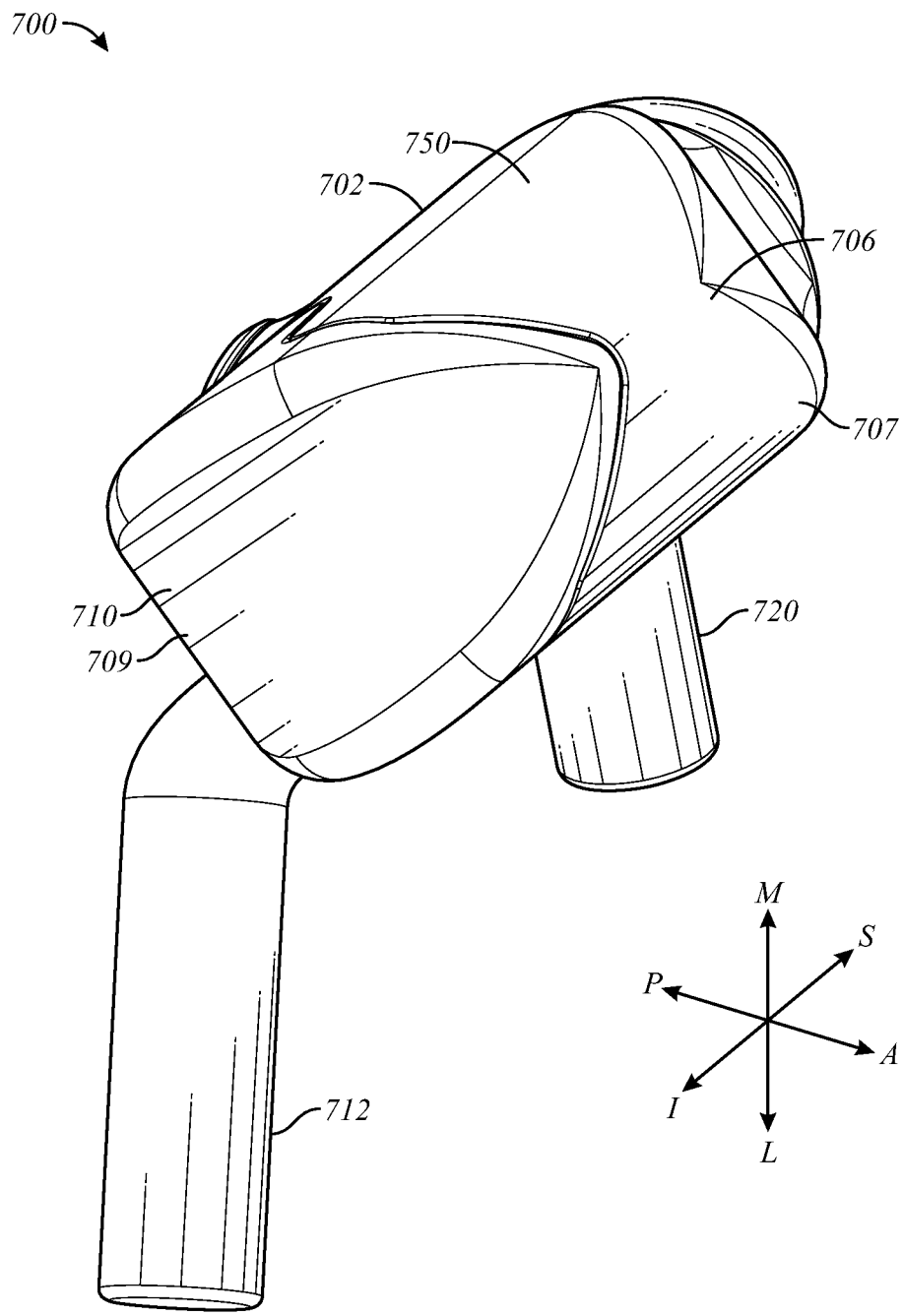
FIG. 23D depicts a bottom anterior perspective view of the facet joint replacement device 700.

FIG. 23A depicts a top posterior perspective view of the facet joint replacement device 700. FIG. 23B depicts a top anterior perspective view of the facet joint replacement device 700. FIG. 23C depicts a bottom posterior perspective view of the facet joint replacement device 700. FIG. 23D depicts a bottom anterior perspective view of the facet joint replacement device 700.

Figure 23E:
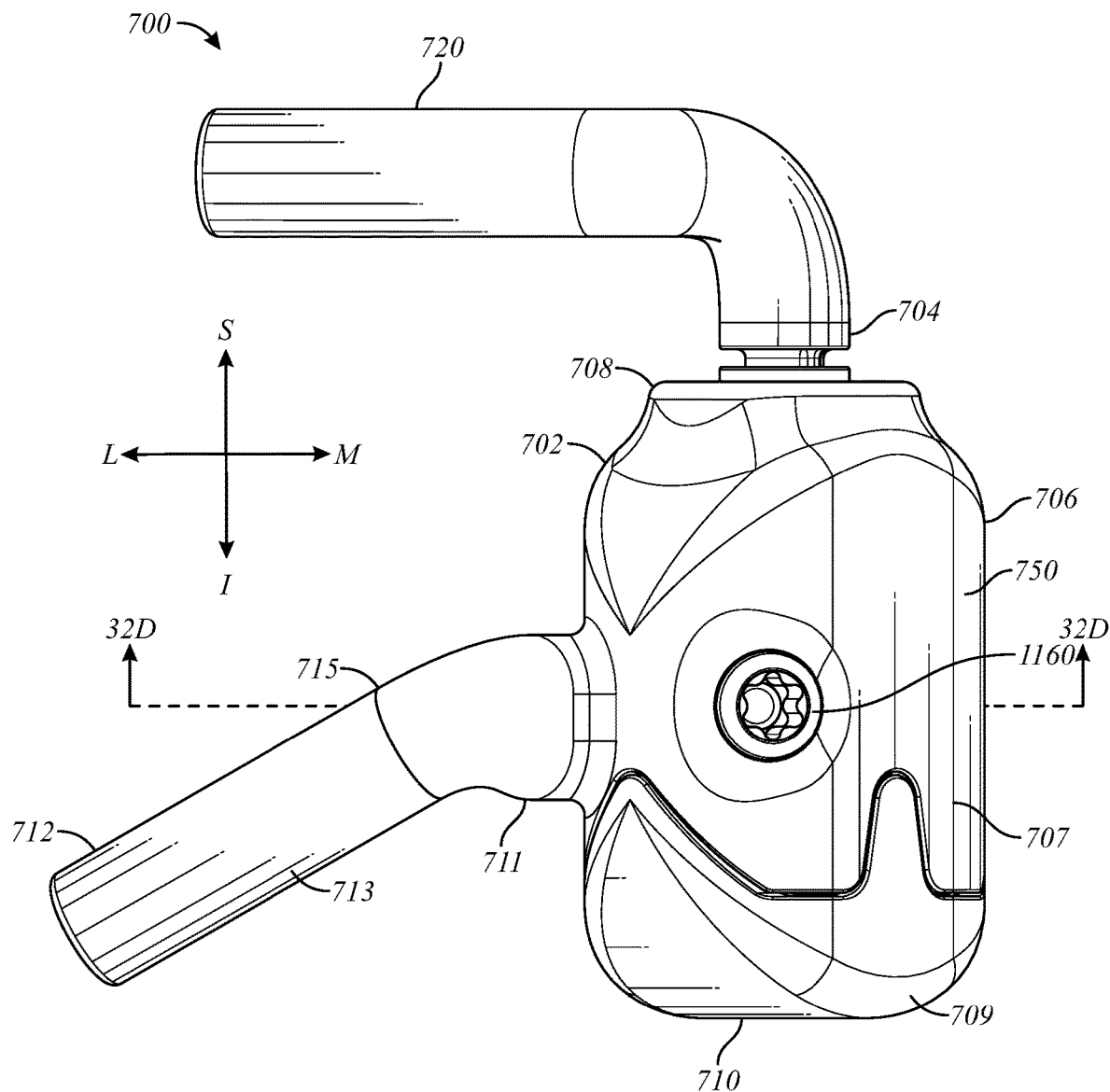
FIG. 23E depicts a posterior view of the facet joint replacement device 700.
Figure 23F:
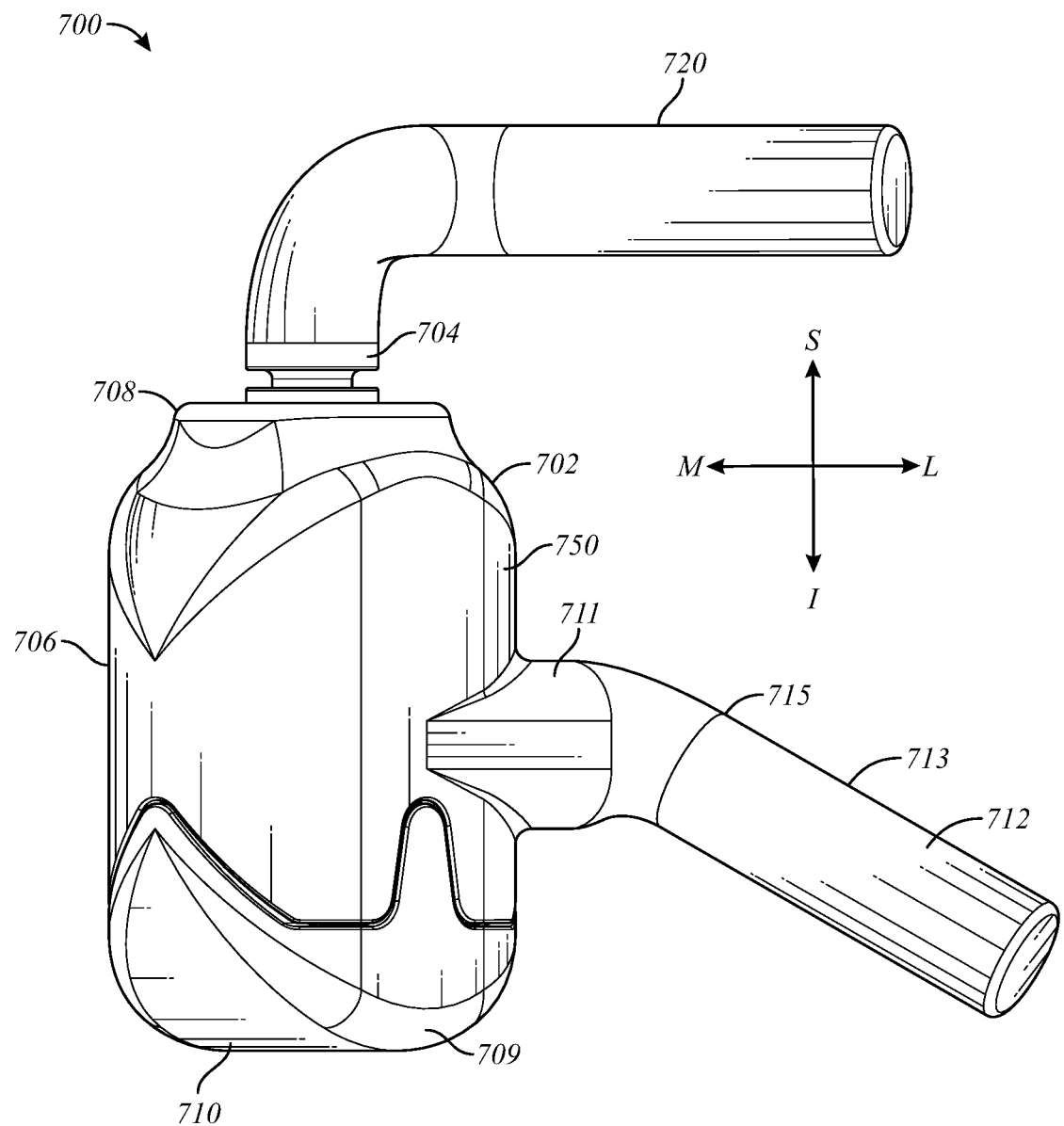
FIG. 23F depicts an anterior view of the facet joint replacement device 700.
Figure 23G:
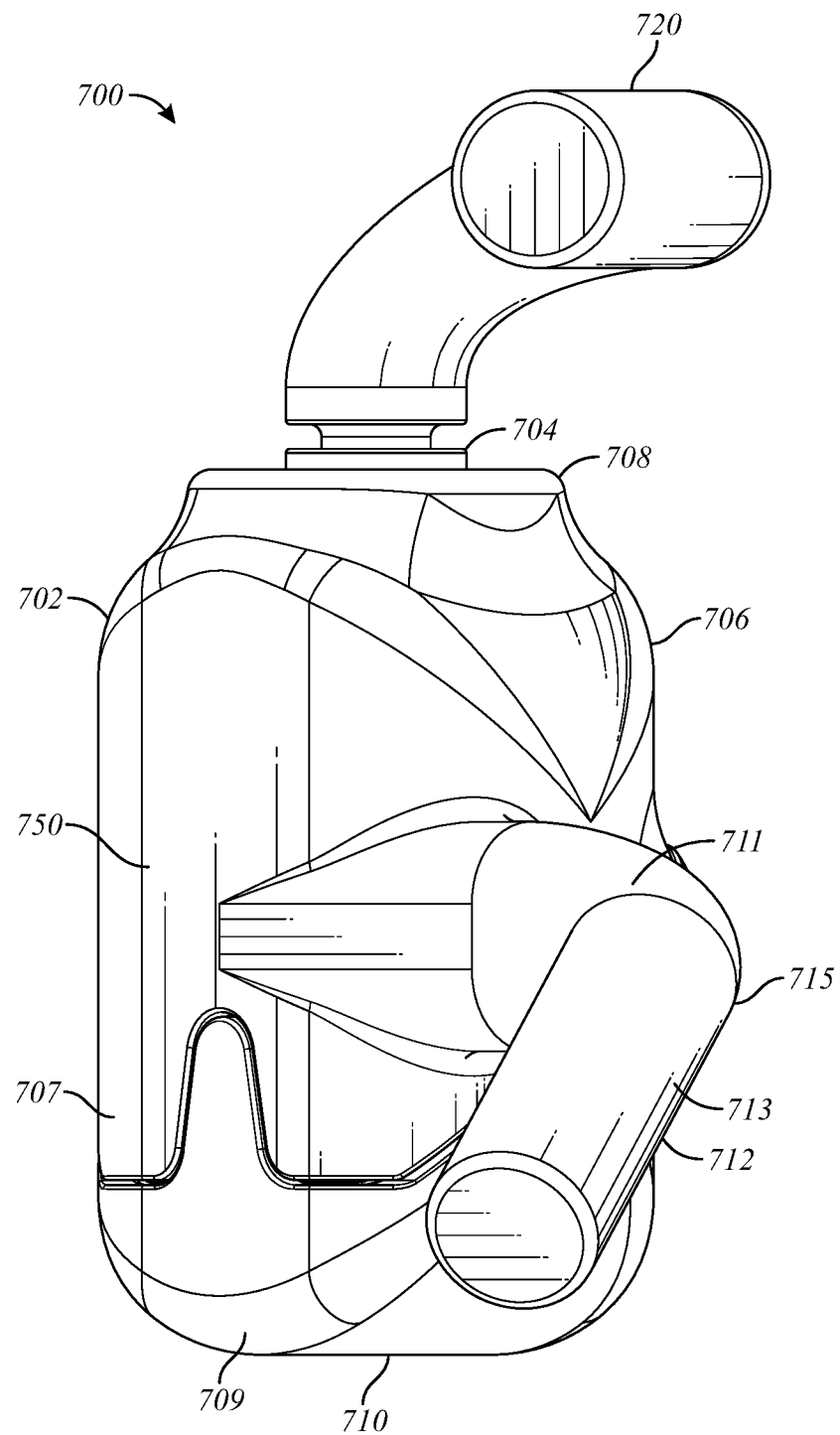
FIG. 23G depicts a first sagittal view of a lateral side of the facet joint replacement device 700.
Figure 23H:
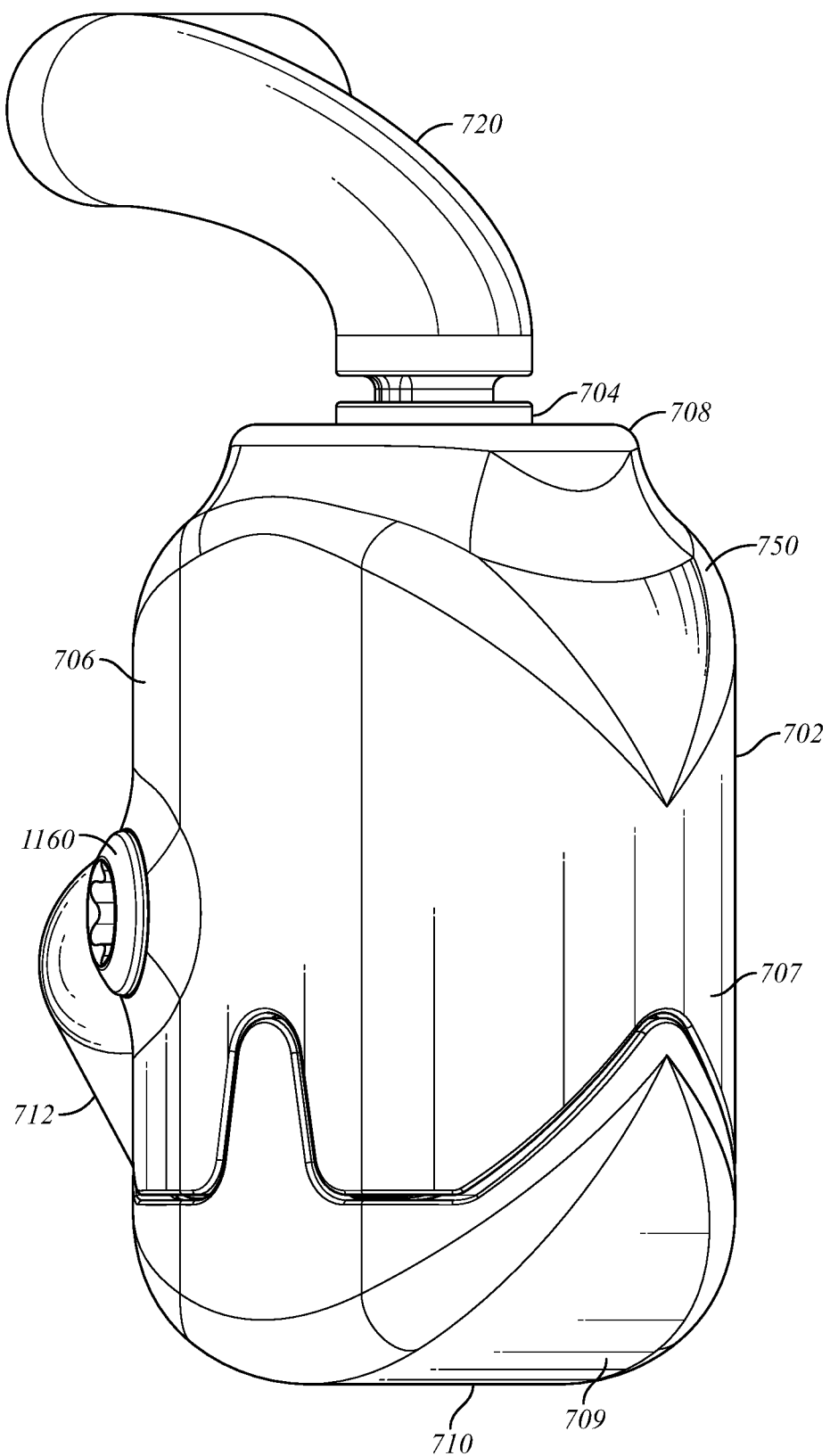
FIG. 23H depicts a second sagittal view of a medial side of the facet joint replacement device 700.
Figure 23I:
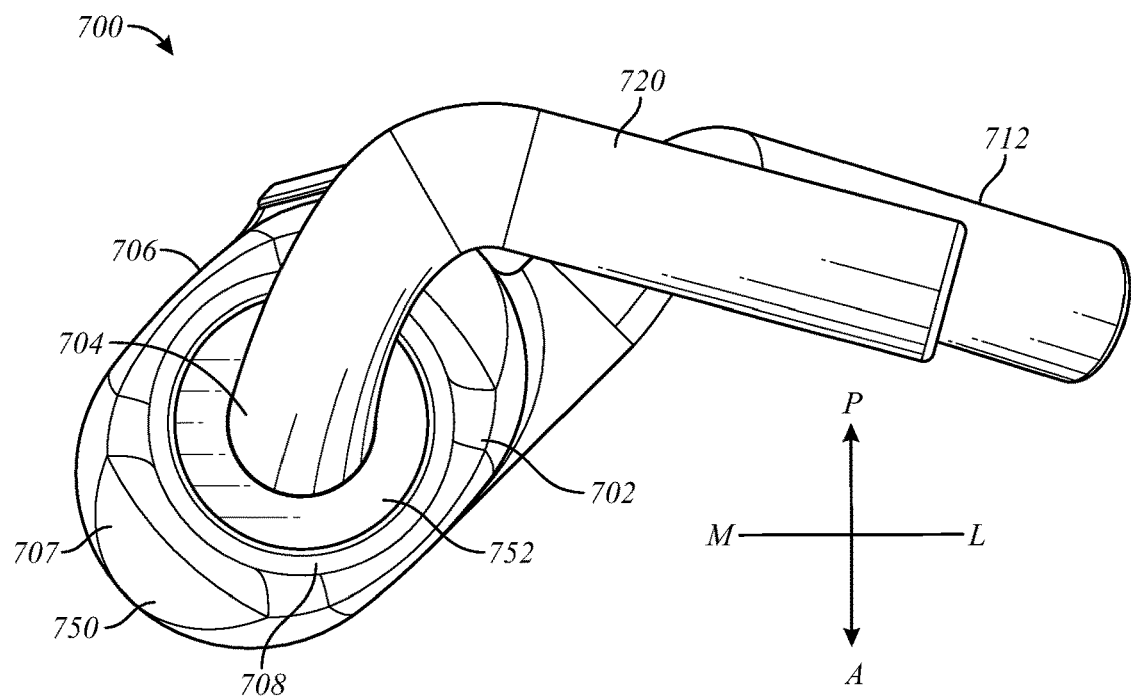
FIG. 23I depicts a top view of the facet joint replacement device 700.
Figure 23J:
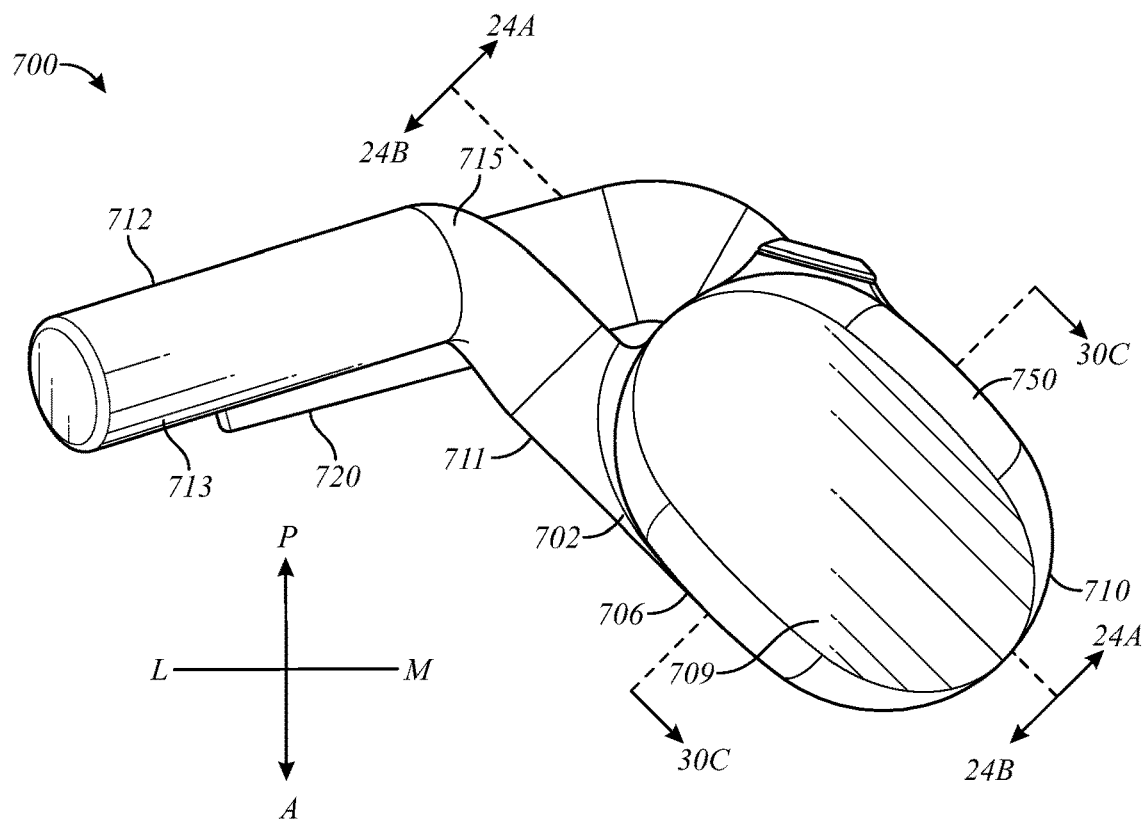
FIG. 23J depicts a bottom view of the facet joint replacement device 700.

FIG. 23E depicts a posterior view of the facet joint replacement device 700. FIG. 23F depicts an anterior view of the facet joint replacement device 700. FIG. 23G depicts a first sagittal view of a lateral side of the facet joint replacement device 700. FIG. 23H depicts a second sagittal view of a medial side of the facet joint replacement device 700. FIG. 23I depicts a top view of the facet joint replacement device 700. FIG. 23J depicts a bottom view of the facet joint replacement device 700.

As shown in FIG. 23A-J, the facet joint replacement device 700 includes an enclosing element 702 and an articulating element 704. The enclosing element 702 includes an enclosing body 706 and an attachment member 712. At least a portion of the enclosing body 706 can be dimensioned, shaped, or otherwise configured to correspond to the shape of a pars interarticularis of a vertebra. The enclosing element can include a superior end 708 and an inferior end 710.

The enclosing body 706 can be shaped, dimensioned, or otherwise configured to correspond to the shape and/or size of a facet joint capsule of a healthy facet joint. The enclosing body 706 can be configured to perform the functions of a facet joint capsule of a healthy facet joint.

The enclosing body 706 can include a main body 707 and a cap 709. In some embodiments, the cap 709 can be configured to secure to the main body 707. In some embodiments, the cap 709 can be can be configured to releasably secure to the main body 707. In some embodiments, the cap 709 can be configured to permanently secure to the main body 707.

As shown in FIG. 23A-J, the cap 709 is positioned at the inferior end 710 of the enclosing body 706. In some embodiments, the cap 709 can be positioned at the superior end 708 of the enclosing body 706.

As shown in FIGS. 23A-J, the attachment member 712 can extend from a lateral surface of the enclosing body 706. In some embodiments, the attachment member 712 can extend from a lateral surface of the main body 707. In some embodiments, the attachment member 712 can extend laterally from the enclosing body 706. In some embodiments, the attachment member 712 extends laterally from the main body 707 of the enclosing body 706. In some embodiments, the attachment member 712 can extend inferiorly from the enclosing body 706. In some embodiments, the attachment member 712 can extend inferiorly from the main body 707. In some embodiments, the attachment member 712 can extend posteriorly from the enclosing body 706. In some embodiments, the attachment member can extend posteriorly from the main body 707.

In some embodiments, the attachment member 712 can include a first section 711 and a second section 713. In some embodiments, the first section 711 can extend from the enclosing body 706 in lateral, posterior, and/or inferior directions. In some embodiments, the first section 711 can extend from the main body 707 in lateral, posterior, and/or inferior directions. In some embodiments, the second section 713 can extend from the first section 711 in lateral, anterior, and/or inferior directions. In some embodiments, the first section 711 and the second section 713 can connect at or form a bend 715. In some embodiments, the bend 715 can be positioned lateral to the enclosing body 706.

The attachment member 712 can be shaped and/or dimensioned to facilitate securement of the facet joint replacement device 700 to the spine. As shown in FIGS. 23A-J, the attachment member 712 can be a rod. However, the attachment member 712 can be any shape suitable for fixation directly or indirectly to a vertebral body. In some embodiments, the attachment member 712 can have a diameter of 5.5 mm. In some embodiments, the attachment member 712 can have a diameter of 1 mm, 2 mm, 3 mm, 4 mm, 4.5 mm, 5 mm, 5.5 mm, 6 mm, 6.5 mm, 7 mm, 8 mm, 9 mm, 10 mm, between 2 mm to 8 mm, between 4 mm to 6 mm, between 5 mm to 7 mm, or between 5 mm to 6 mm. In some embodiments, the attachment member 712 can have a length of 1 mm, 2 mm, 3 mm, 4 mm, 5 mm, 6 mm, 7 mm, 8 mm, 9 mm, 10 mm, 15 mm, 20 mm, 25 mm, 30 mm, between 2 mm to 8 mm, between 4 mm to 6 mm, between 5 mm to 10 mm, between 10 mm to 15 mm, between 15 mm to 20 mm, between 20 mm to 25 mm, between 25 mm to 30 mm, between 15 mm to 30 mm, or less than 15 mm.

As shown in FIGS. 23A-J, the enclosing body 706 can include an outer shell 750 and a liner 752. In some embodiments, the liner 752 covers an interior surface the outer shell 750.

In some embodiments, the outer shell 750 is formed of or formed partially of one or more metals or metal alloys. In some embodiments, the outer shell 750 is formed of cobalt-chrome. For example, the outer shell 750 can be formed of cobalt-chromium, titanium, titanium-based alloys, or any other suitable metals or metal alloys. In some embodiments, the outer shell 750 can be ceramic or partially ceramic. In some embodiments, the outer shell 750 can include superhard ceramics.

In some embodiments, the liner 752 is formed of a low friction material, such as high molecular weight polyethylene. In some embodiments, the liner 752 is formed of ultra-high molecular weight polyethylene. In some embodiments, the liner 752 is formed of vitamin E impregnated ultra-high molecular weight polyethylene, which may function as a free radical scavenger. In some embodiments, the material of the liner 752 can facilitate movement of the articulating element 704 within the enclosing body 706. In some embodiments, the material of the liner 752 can prevent or reduce wear from friction due to movement of the articulating element 704 within the enclosing body 706.

As shown in FIGS. 23A-J, in some embodiments, the facet joint replacement device 700 can include a plug 780. In some embodiments, the plug 780 can be removably received within an opening in an exterior surface of the enclosing body 706.

Figure 24A:
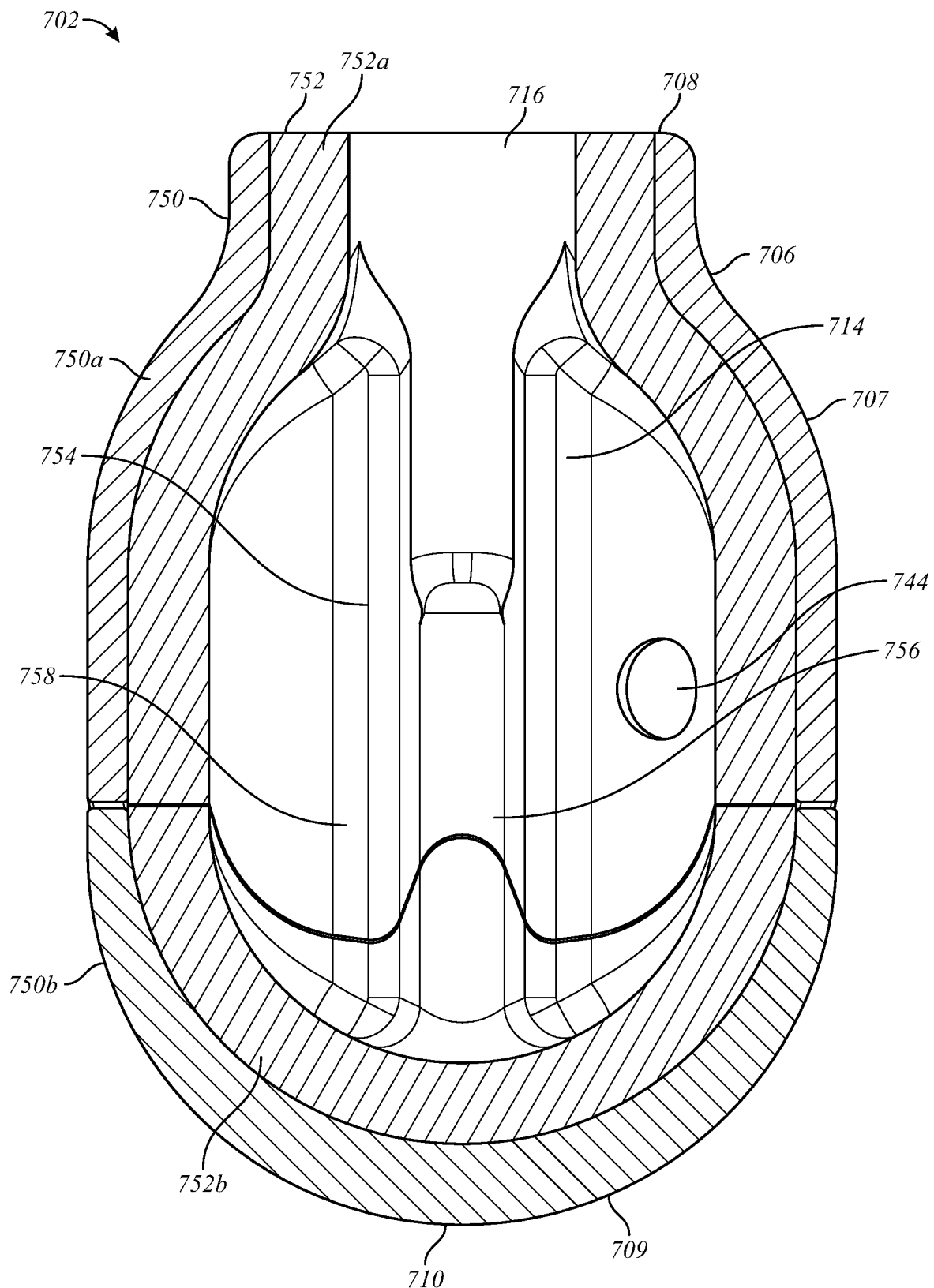
FIG. 24A depicts a first cross-sectional view of an enclosing element 702.
Figure 24B:
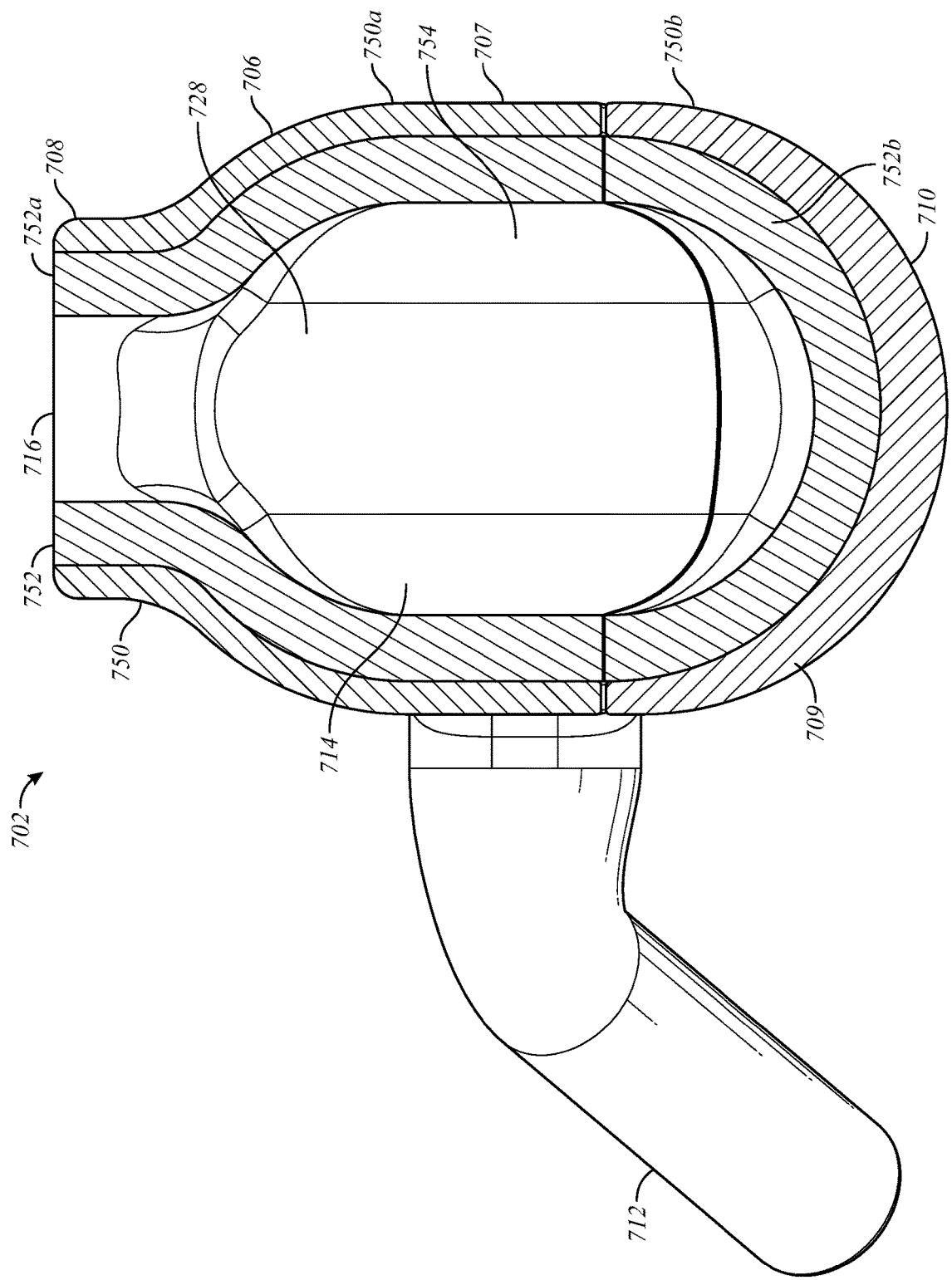
FIG. 24B depicts a second cross-sectional view of the enclosing element 702.

FIG. 24A depicts a first cross-sectional view of the enclosing element 702 taken along line 24A-24A as shown in FIG. 23J. FIG. 24B depicts a second cross-sectional view of the enclosing element 702 taken along line 24B-24B as shown in FIG. 23J. As shown in FIGS. 24A-B, the enclosing body 706 can include an inner cavity 714 defined by an interior surface 754 of the enclosing body 706. In some embodiments, the interior surface 754 can be an interior surface of the liner 752 of the enclosing body 706.

The inner cavity 714 can be further defined by an opening 716 of the enclosing body 706. In some embodiments, the opening 716 is positioned at the superior end 708 of the enclosing body.

As shown in FIGS. 24A-B, in some embodiments, the outer shell 750 can include an outer shell main body 750a and an outer shell cap 750b. In some embodiments, the liner 752 can include a liner main body 752a and a liner cap 752b. The outer shell main body 750a and liner main body 752a can for the main body 707. The outer shell cap 750b and liner cap 752b can form the cap 709.

In some embodiments, the enclosing body 706 can include a projection 756 extending inwardly relative to a surrounding area 758 of the interior surface 754. In some embodiments, the projection 756 can be formed by at least a portion of the main body 707 and at least a portion of the cap 709. In some embodiments, the projection 756 can be generally convex in shape. In some embodiments, the projection 756 is generally parabolic in shape. In some embodiments, the projection 756 can extend from an inferior portion of the enclosing body to a superior portion of the enclosing body 706.

As shown in FIGS. 24A-B, the enclosing body 706 can include a channel 744. The channel 744 can extend through the outer shell 750 and the liner 752. In some embodiments, the channel 744 can be configured to receive fastener or the plug 780.

As shown in FIG. 24B, In some embodiments, a portion of the interior surface 754 of the enclosing body 706 can be shaped to form an articulating surface 728. In some embodiments, the interior surface 754 can be an interior surface of the liner 752 and a portion of the interior surface 754 can be shaped to form the articulating surface 728. In some embodiments, the articulating surface 728 can be concave or at least partially concave. In some embodiments, the articulating surface 728 can be shaped/and or dimensioned to correspond to the shape, size, and/or concavity of an articular surface of a healthy superior articular process. In some embodiments, the articulating surface 728 can be positioned on a surface of the enclosing body 706 generally opposite the projection 756.

Figure 25A:
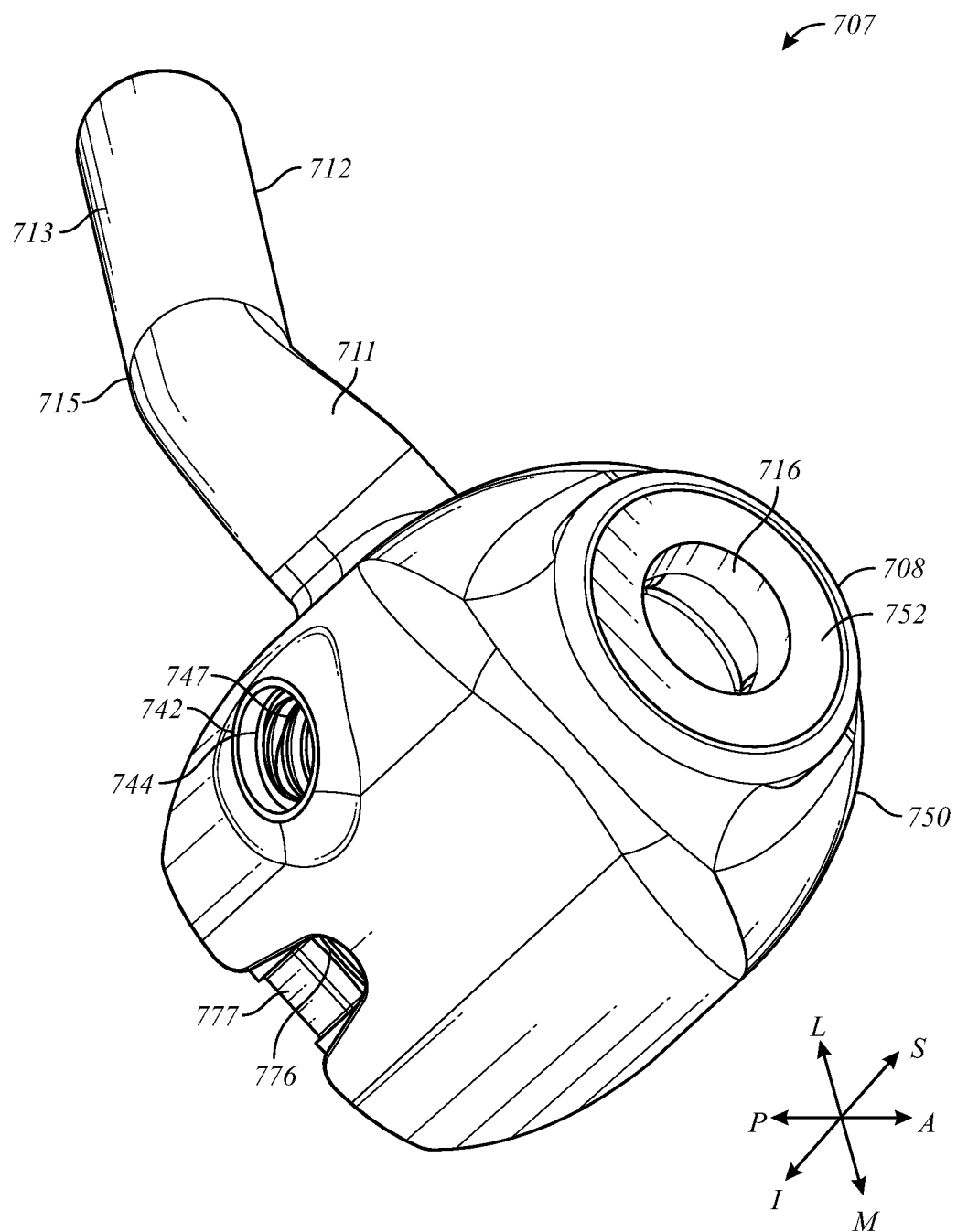
FIG. 25A depicts a top posterior perspective view of a main body 707.
Figure 25B:
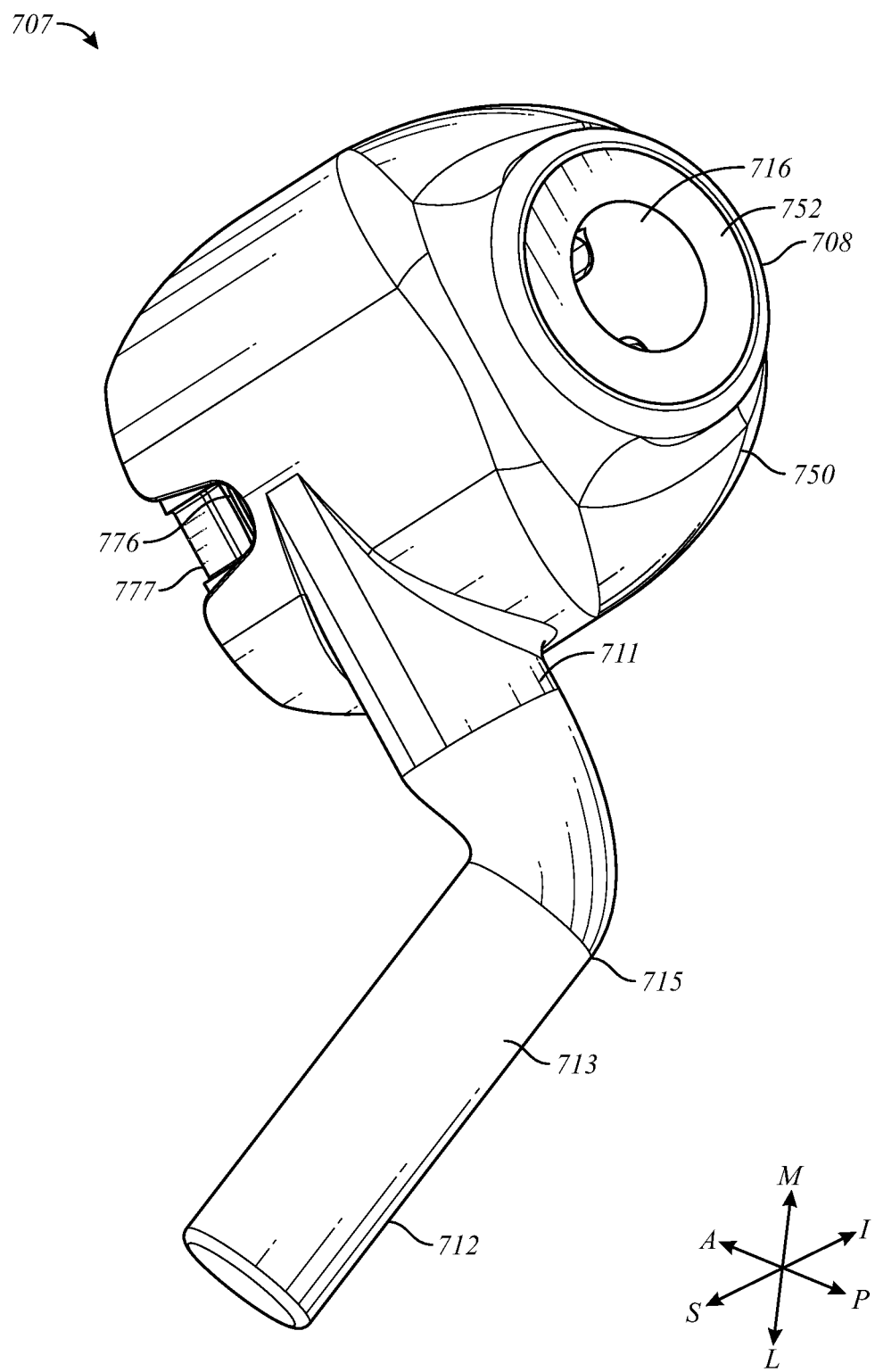
FIG. 25B depicts a top anterior perspective view of the main body 707.
Figure 25C:
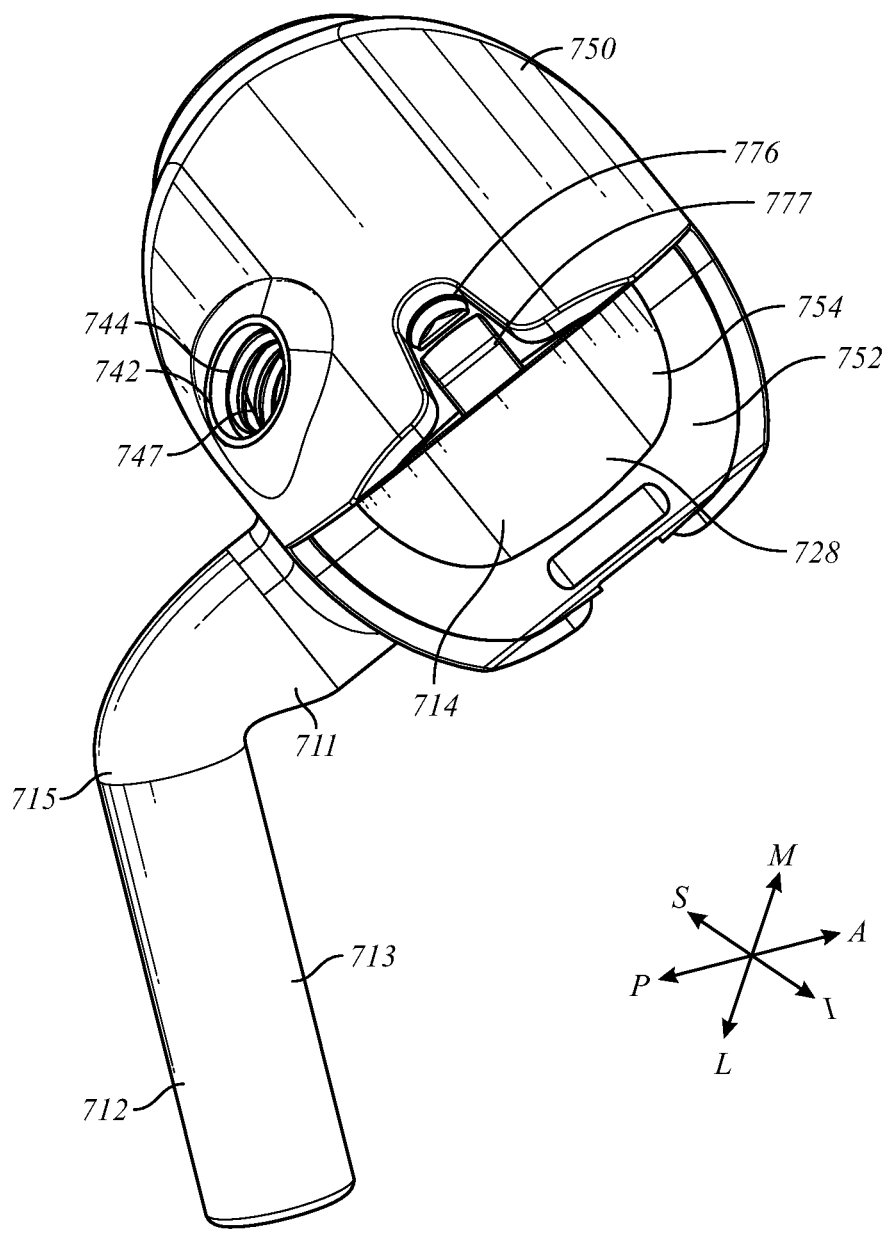
FIG. 25C depicts a bottom posterior perspective view of the main body 707.
Figure 25D:
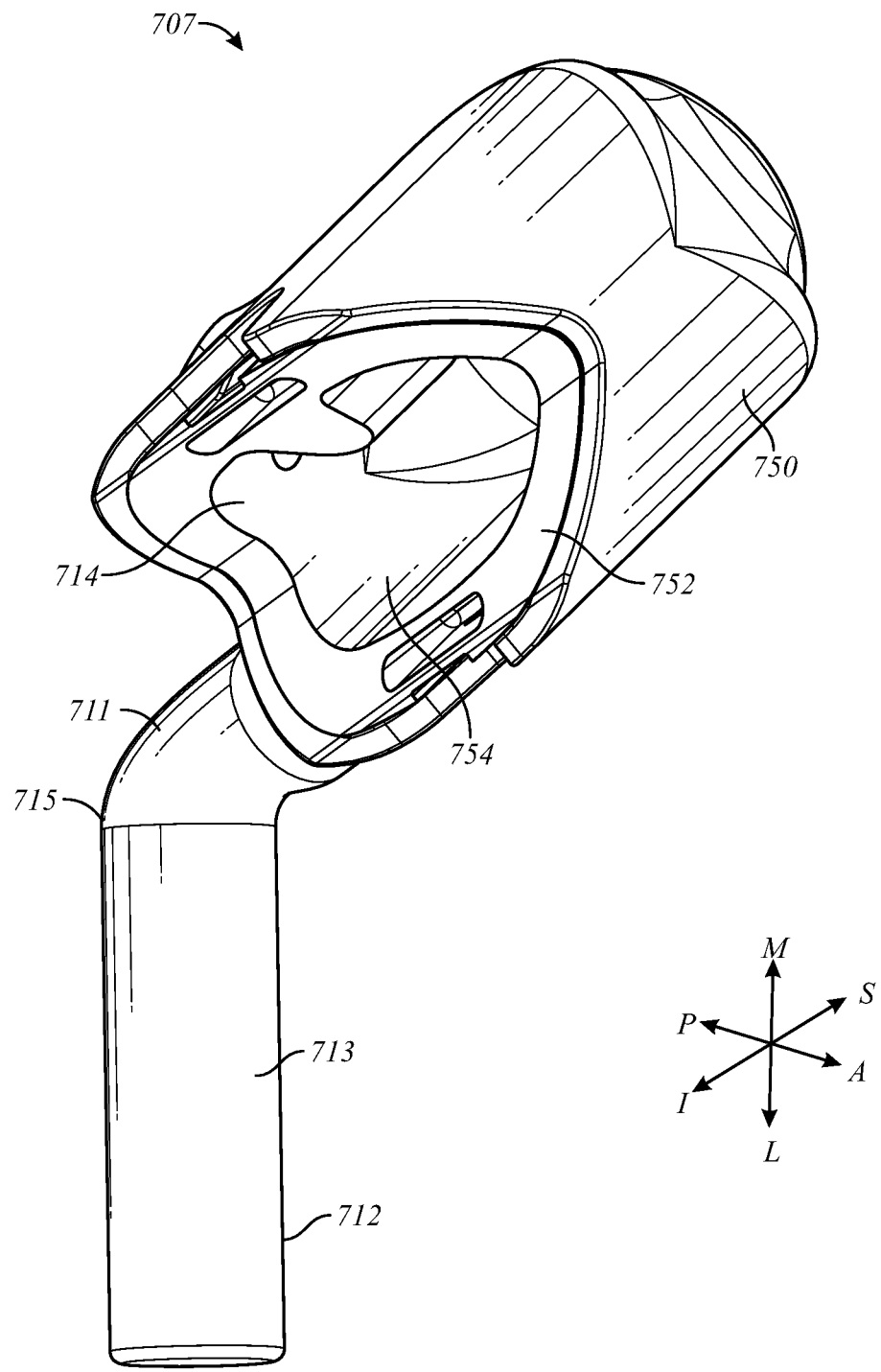
FIG. 25D depicts a bottom anterior perspective view of the main body 707.
Figure 25E:
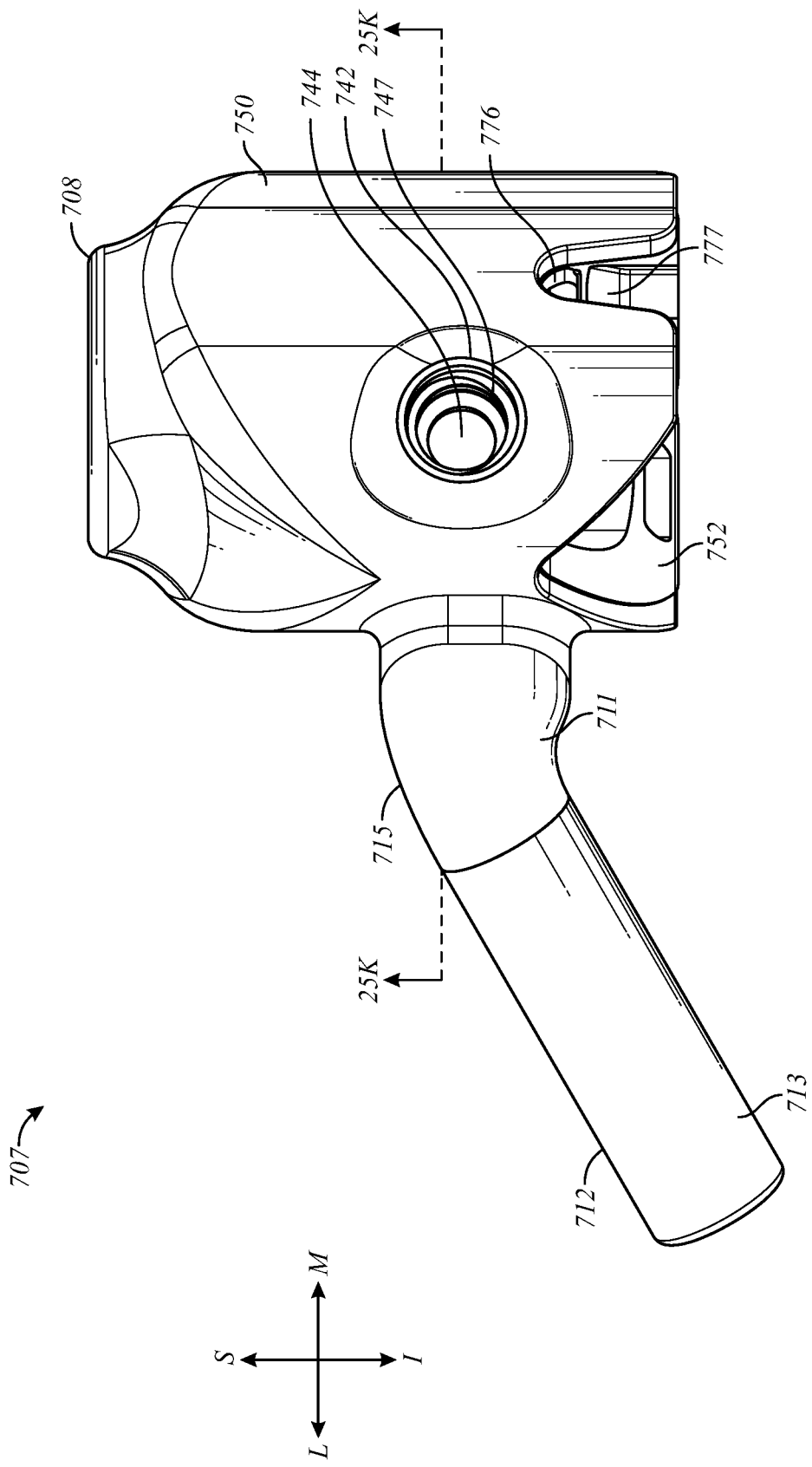
FIG. 25E depicts a posterior view of main body 707.
Figure 25F:
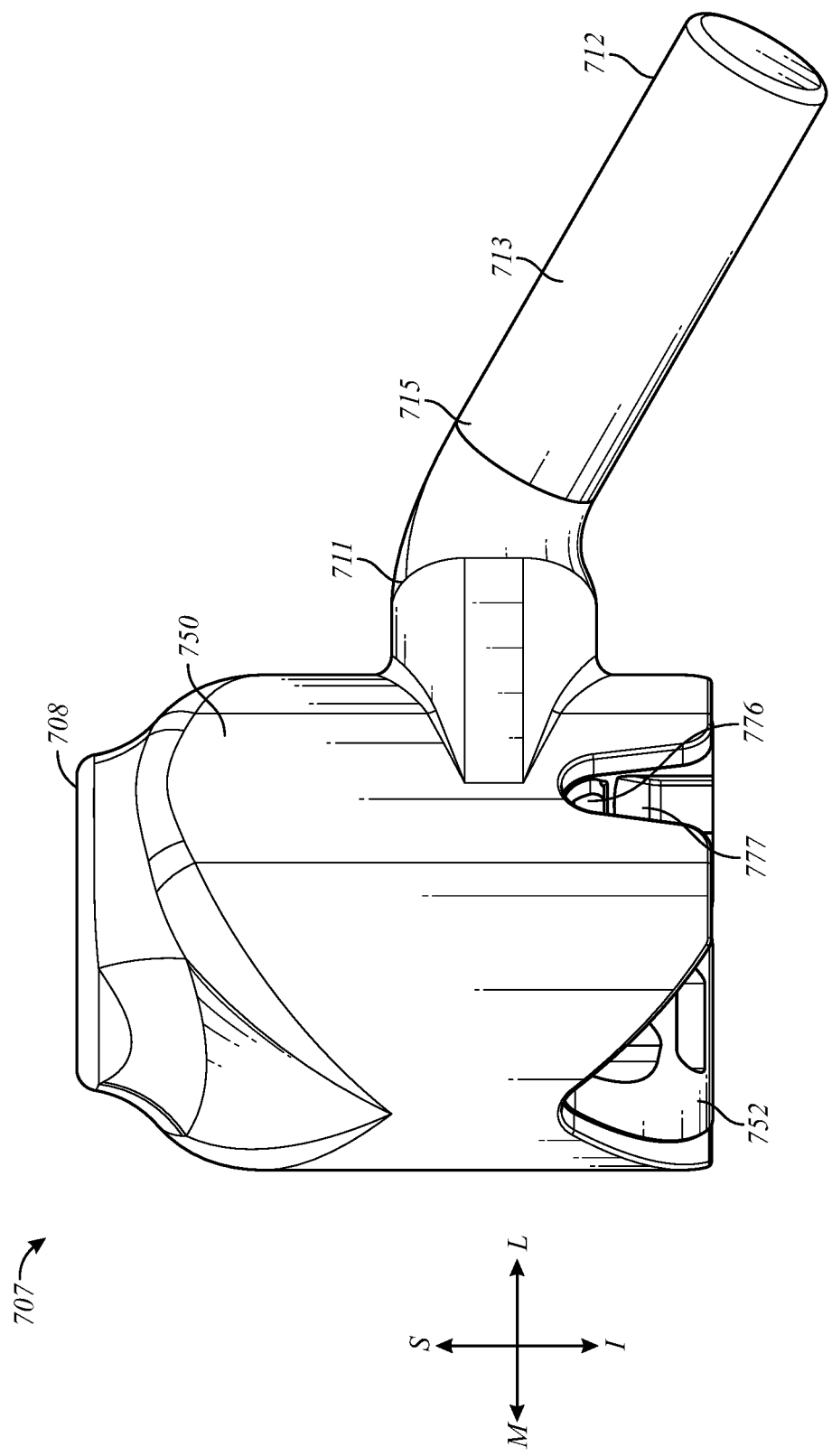
FIG. 25F depicts an anterior view of the main body 707.
Figure 25G:
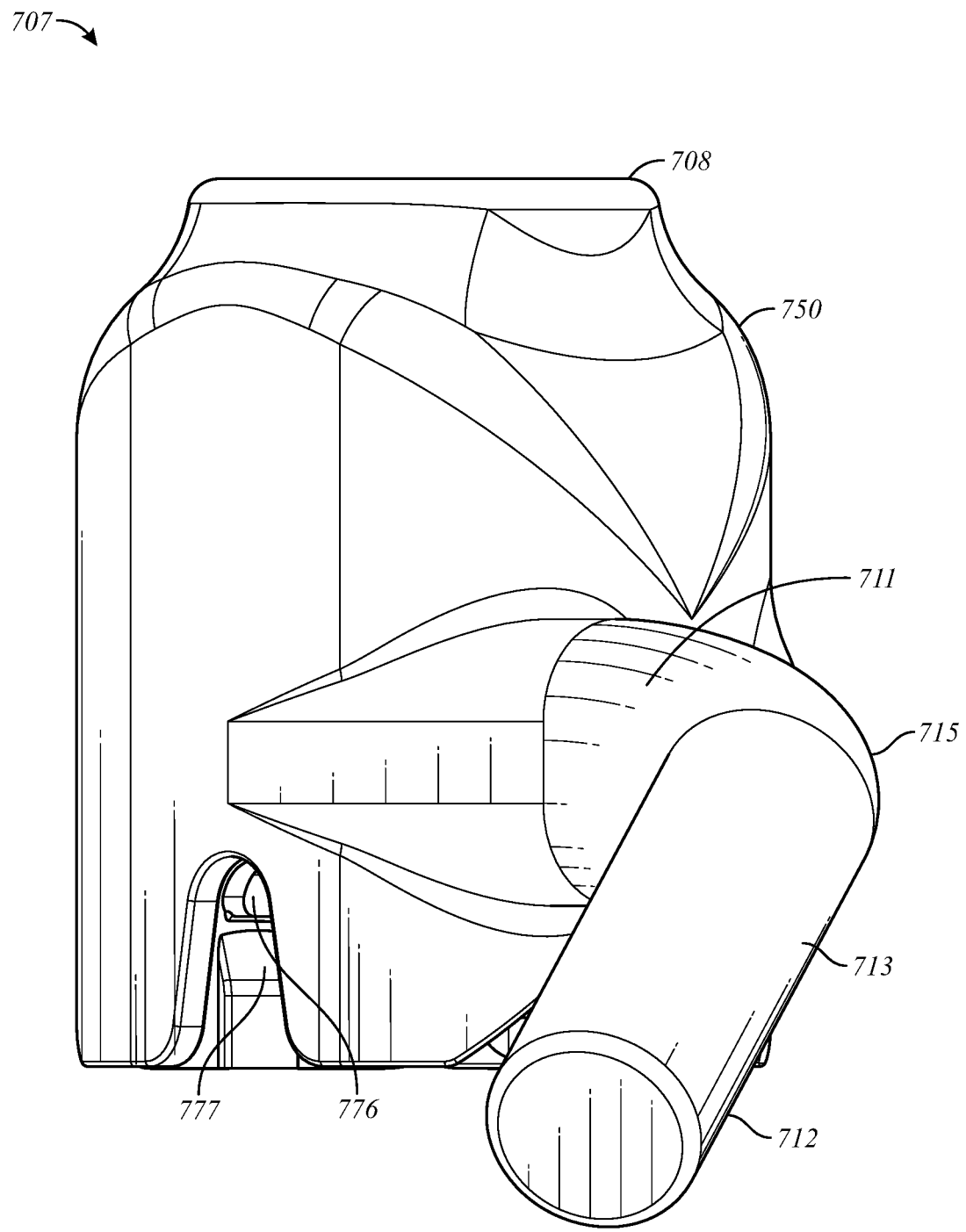
FIG. 25G depicts a first sagittal view of a lateral side of the main body 707.
Figure 25H:
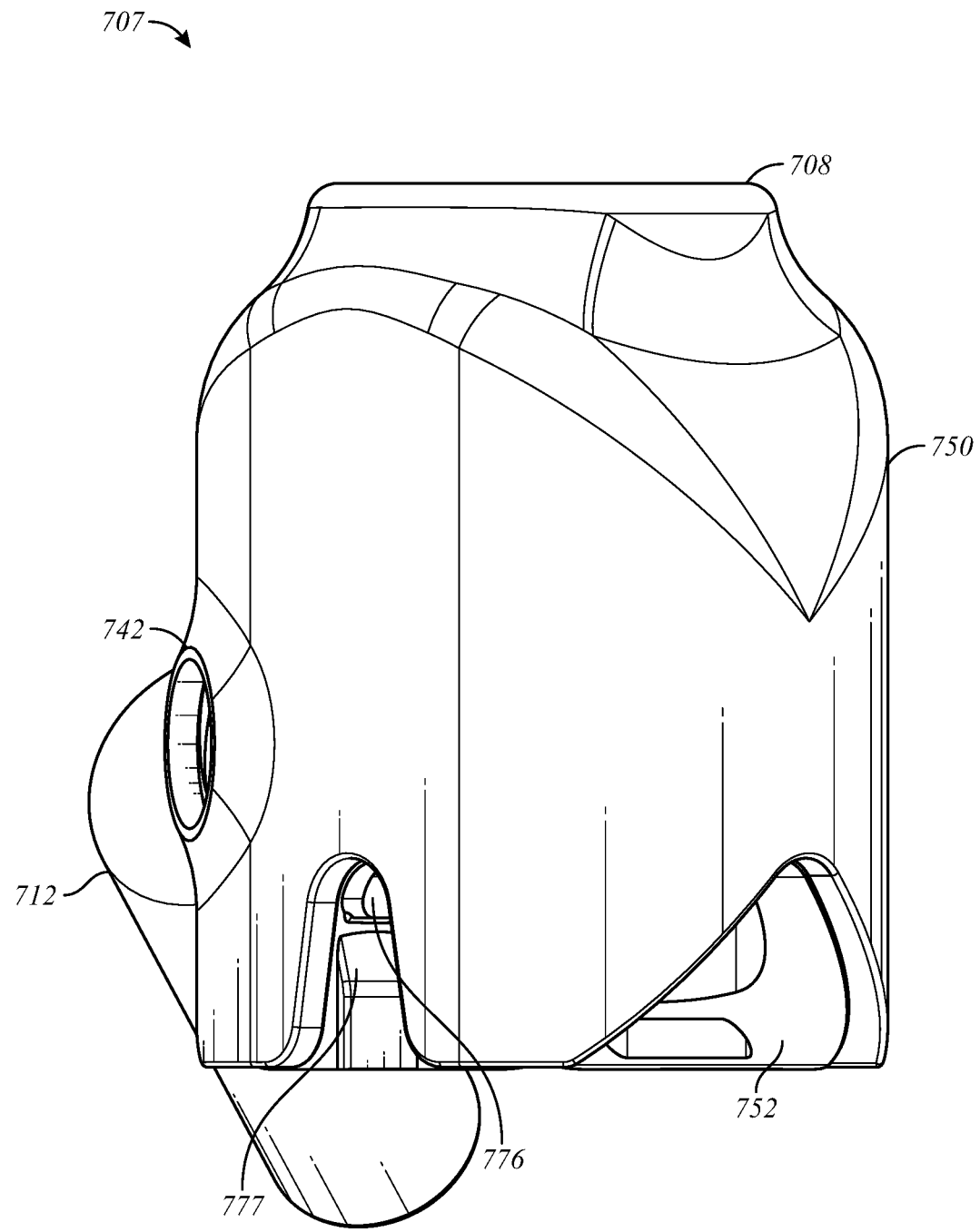
FIG. 25H depicts a second sagittal view of a medial side of the main body 707.
Figure 25I:
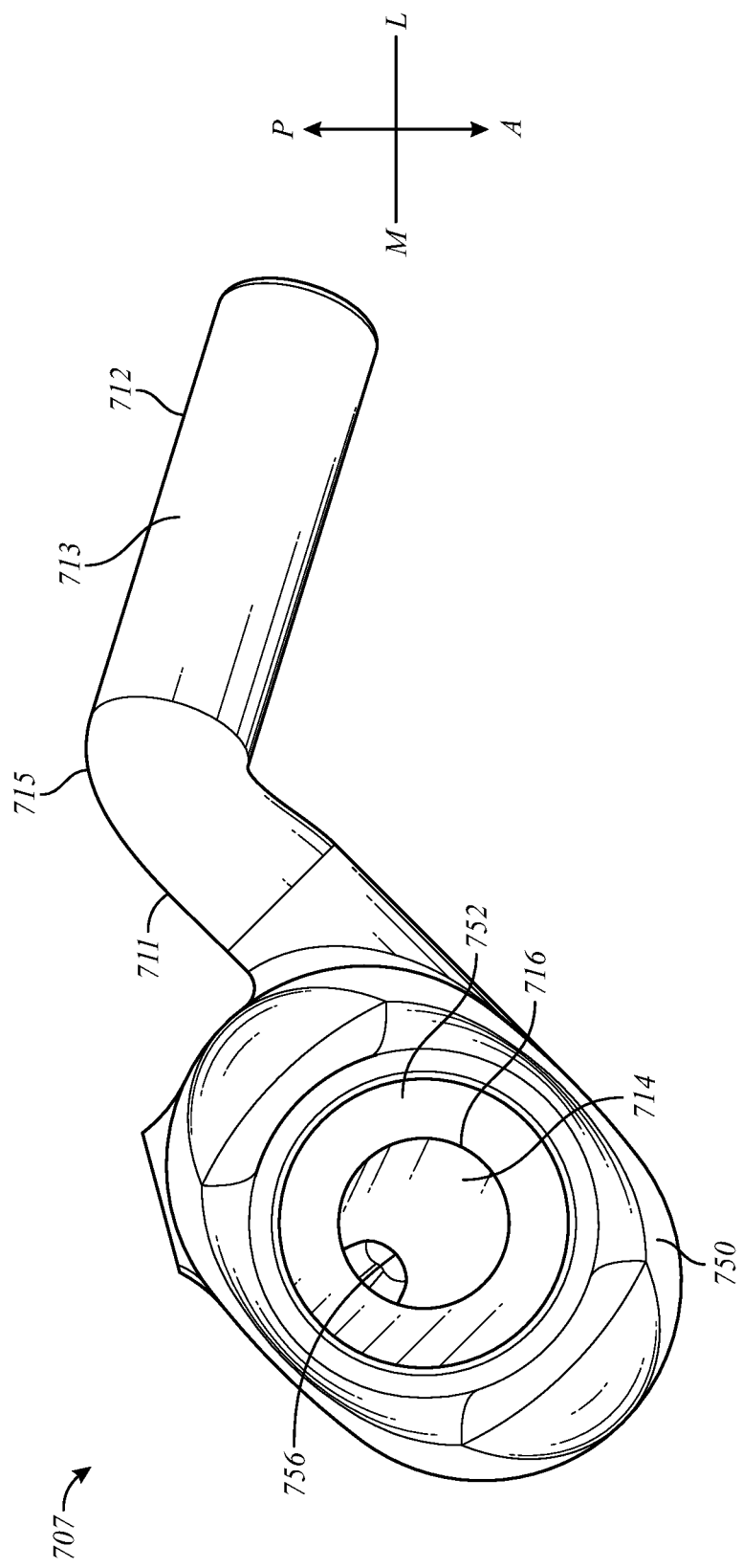
FIG. 25I depicts a top view of the main body 707.
Figure 25J:
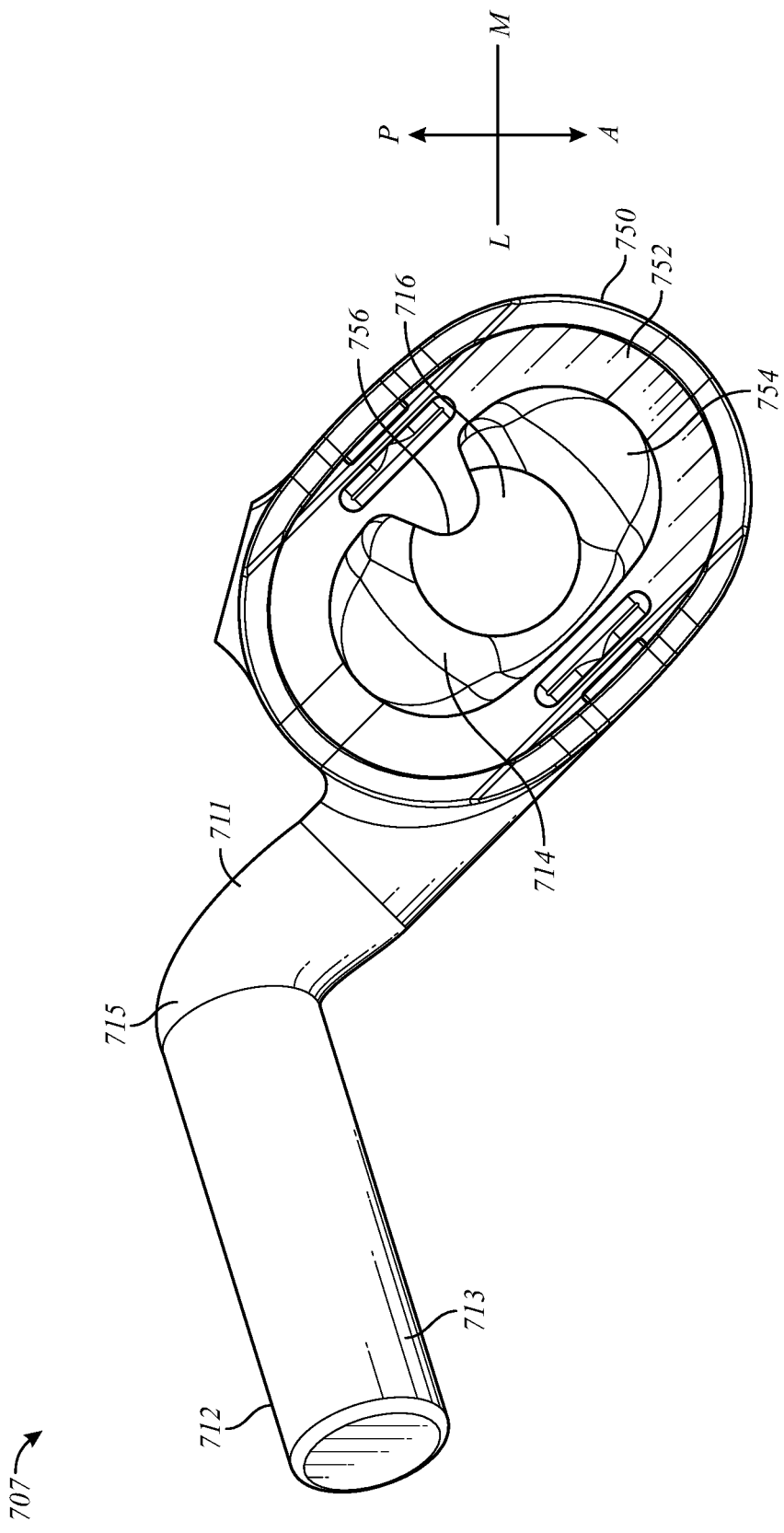
FIG. 25J depicts a bottom view of the main body 707.
Figure 25K:
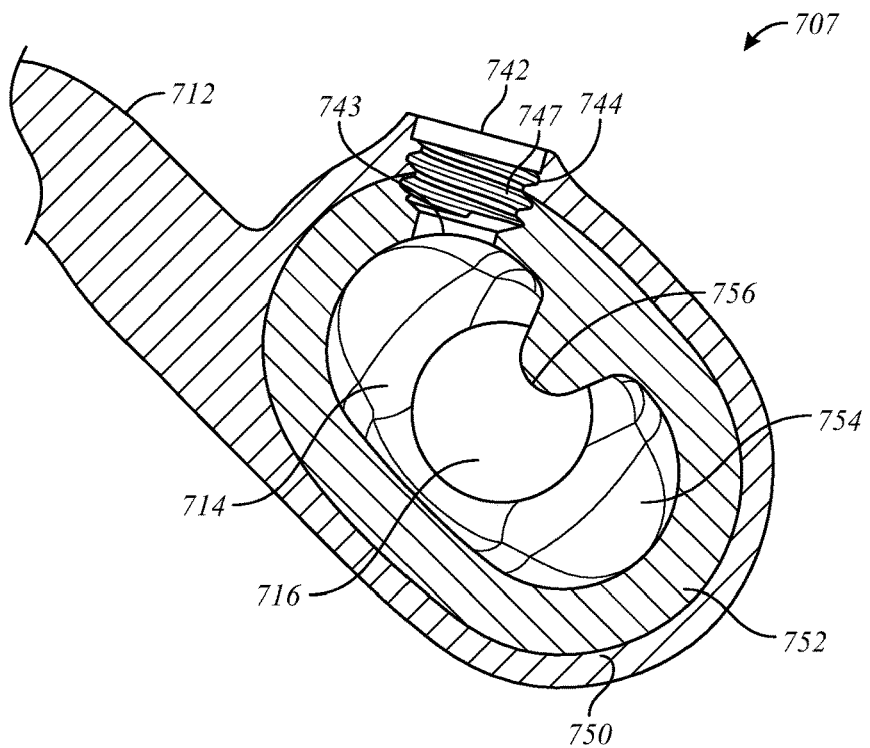
FIG. 25K depicts a cross-sectional view of the main body 707.
Figure 25L:
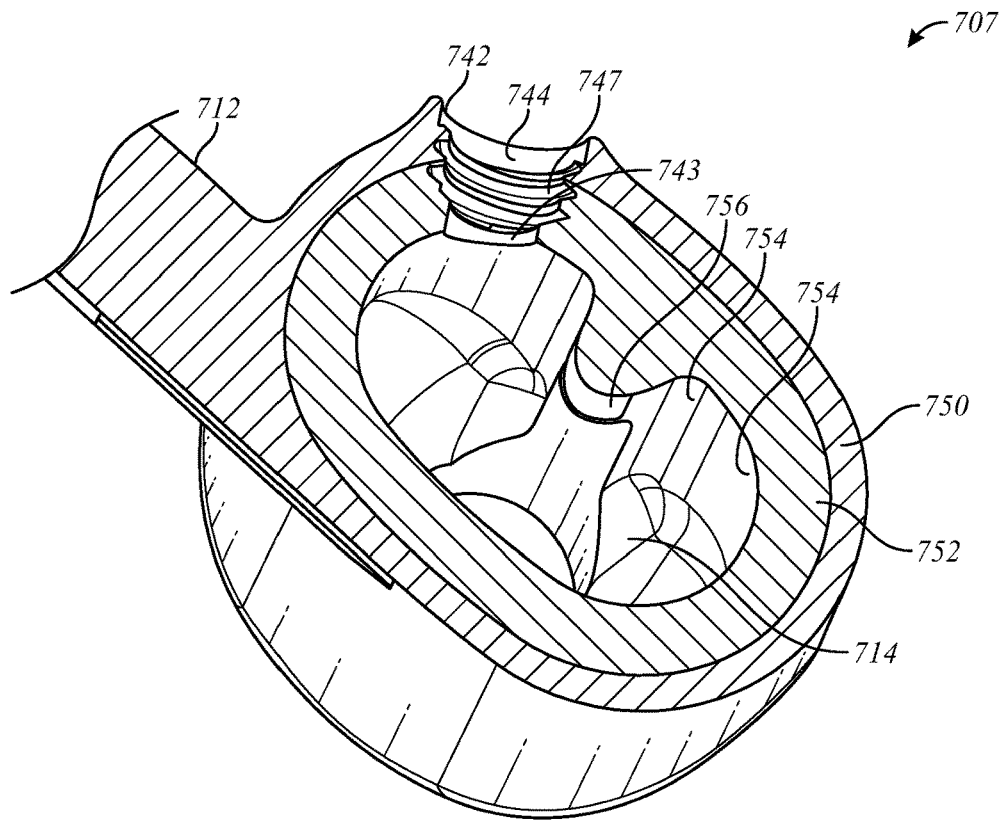
FIG. 25L depicts a first perspective view of a cross-section of the main body 707.
Figure 25M:
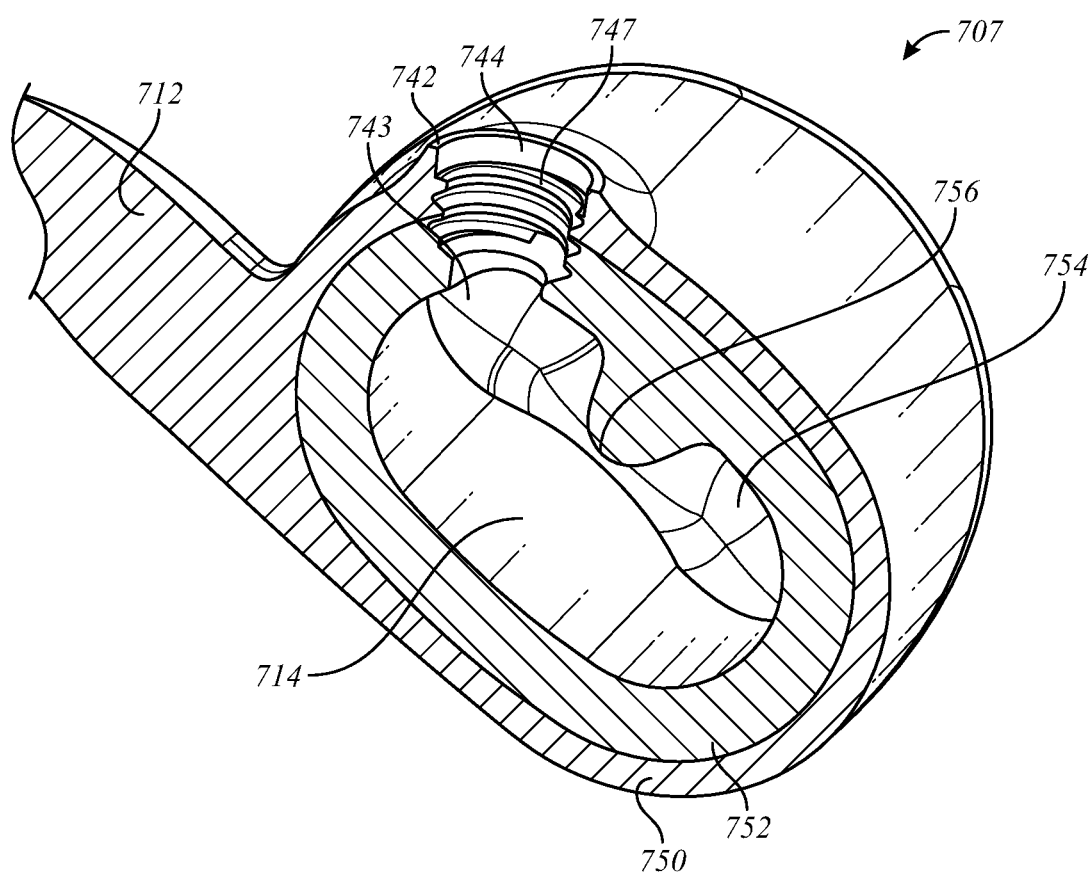
FIG. 25M depicts a second perspective view of a cross-section of the main body 707.

FIGS. 25A-M depict views of the main body 707 of the enclosing body 706. FIG. 25A depicts a top posterior perspective view of the main body 707. FIG. 25B depicts a top anterior perspective view of the main body 707. FIG. 25C depicts a bottom posterior perspective view of the main body 707. FIG. 25D depicts a bottom anterior perspective view of the main body 707. FIG. 25E depicts a posterior view of main body 707. FIG. 25F depicts an anterior view of the main body 707. FIG. 25G depicts a first sagittal view of a lateral side of the main body 707. FIG. 25H depicts a second sagittal view of a medial side of the main body 707. FIG. 25I depicts a top view of the main body 707. FIG. 25J depicts a bottom view of the main body 707. FIG. 25K depicts a cross-sectional view of the main body 707 taken along line 25K-25K as shown in FIG. 25E. FIG. 25L depicts a first perspective view of a cross-section of the main body 707. FIG. 25M depicts a second perspective view of a cross-section of the main body 707.

As shown in FIGS. 25A-M, the channel 744 can extend between an opening 742 on an exterior surface of the enclosing body 706 and an opening 743 on the interior surface 754 of the enclosing body 706. In some embodiments, the opening 742 is positioned on the exterior surface of the outer shell 750. In some embodiments, the interior surface 754 is an interior surface of the liner 752 and the opening 743 is positioned on the interior surface 754. The channel 744 can include a threaded section 747 configured to engage a threaded section of the plug 780 or a fastener. In some embodiments, at least a portion of the threaded section 747 is formed in the outer shell 750. In some embodiments, at least a portion of the threaded section 747 is formed in the liner 752.

As shown in FIG. 25A-M, the main body 707 can include one or more recesses 776. The recesses 776 can be dimensioned, shaped, or otherwise configured to engage coupling features of the cap 709 to releasably or permanently secure the cap 709 to the main body 707. The enclosing body 706 can further include one or more ramps 777. The ramps 777 can be dimensioned, shaped, or otherwise figures to direct the coupling features of the cap 709 towards the recesses 709.

Figure 26A:
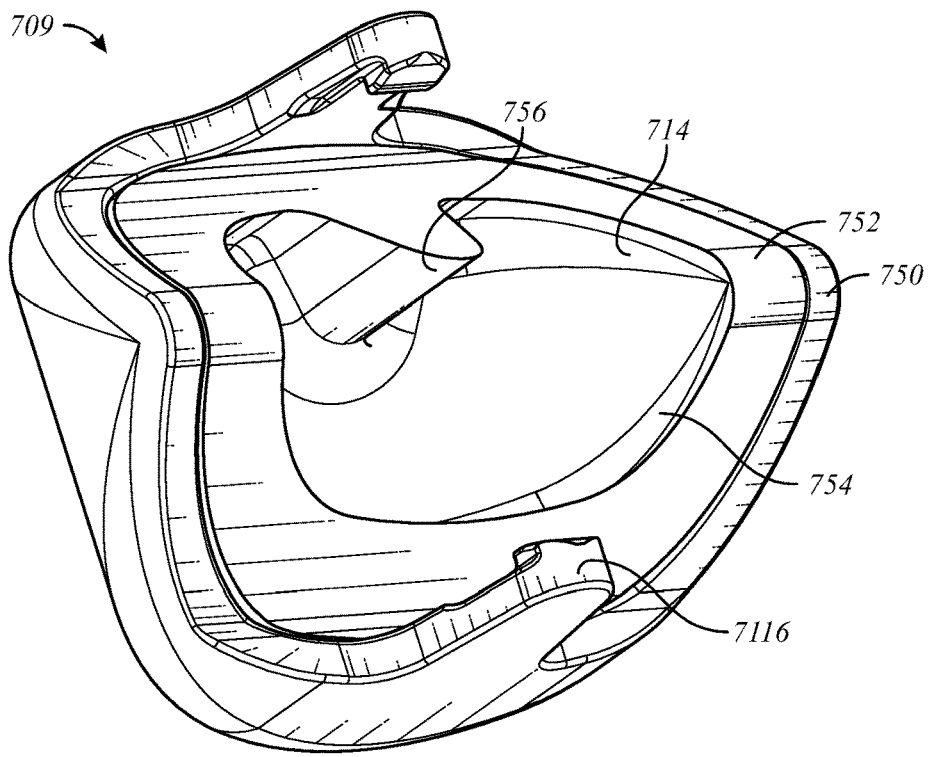
FIG. 26A depicts a first perspective view of a cap 709.
Figure 26B:
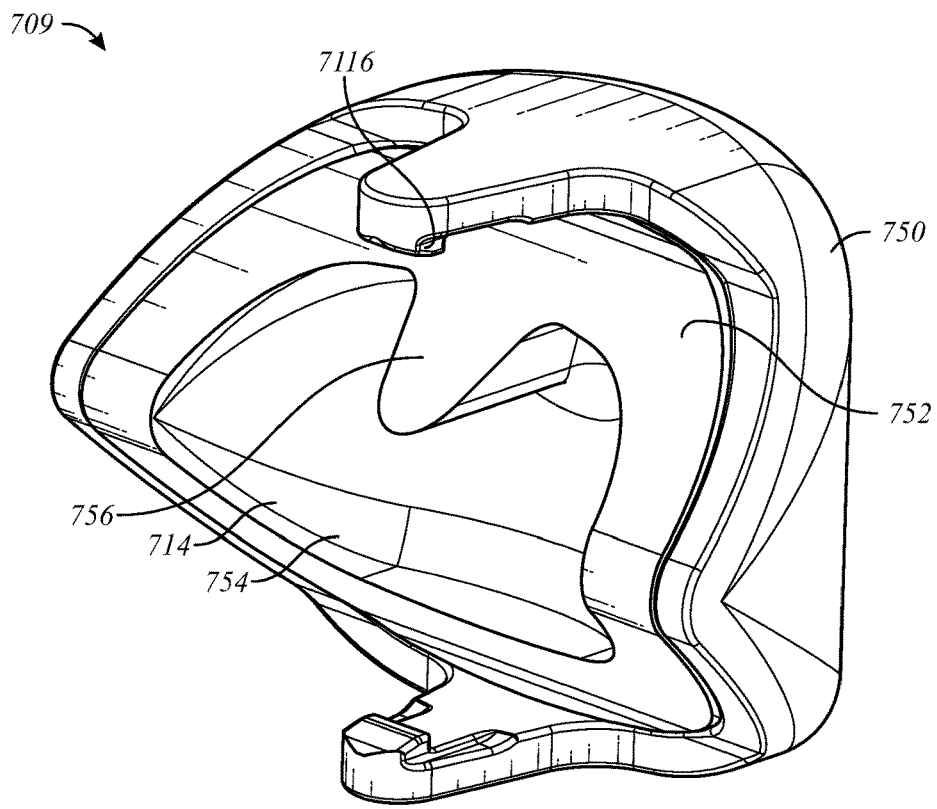
FIG. 26B depicts a second perspective view of the cap 709.

FIG. 26A depicts a first perspective view of the cap 709. FIG. 26B depicts a second perspective view of the cap 709. As shown in FIGS. 26A-B, the cap 709 can include one or more tabs 778. The one or more tabs 778 can be dimensioned, sized, or otherwise configured to be received within the recesses 776 of the main body 707. In some embodiments, the ramps 777 of the main body 707 can be dimensioned, shaped, or otherwise configured to guide the tabs 778 towards the recesses 776 during coupling of the cap 709 to the main body 707. In some embodiments, the tabs 778 can be configured to couple to the recesses 776 via a snap fit.

Figure 27A:
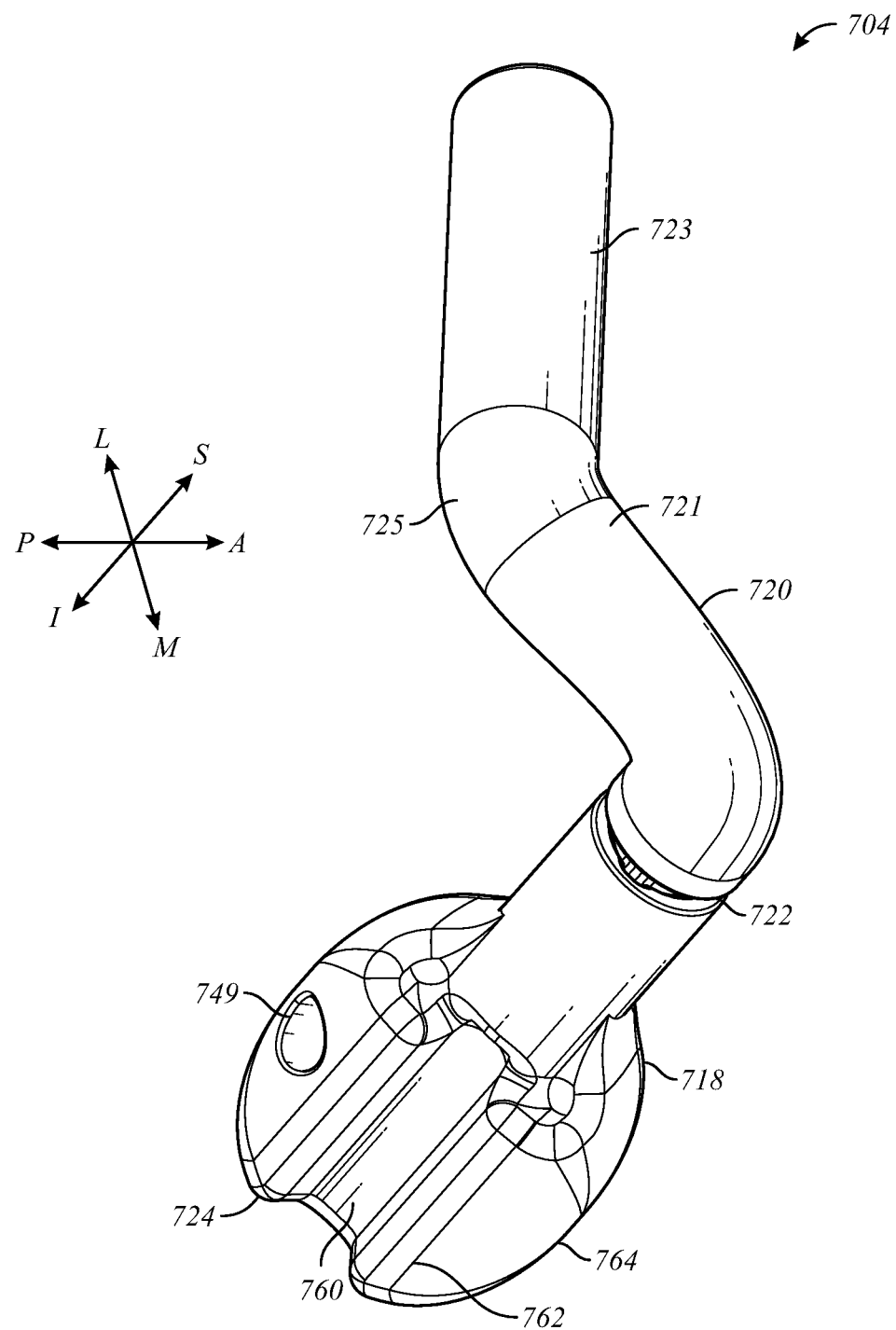
FIG. 27A depicts a top posterior perspective view of an articulating element 704.
Figure 27B:
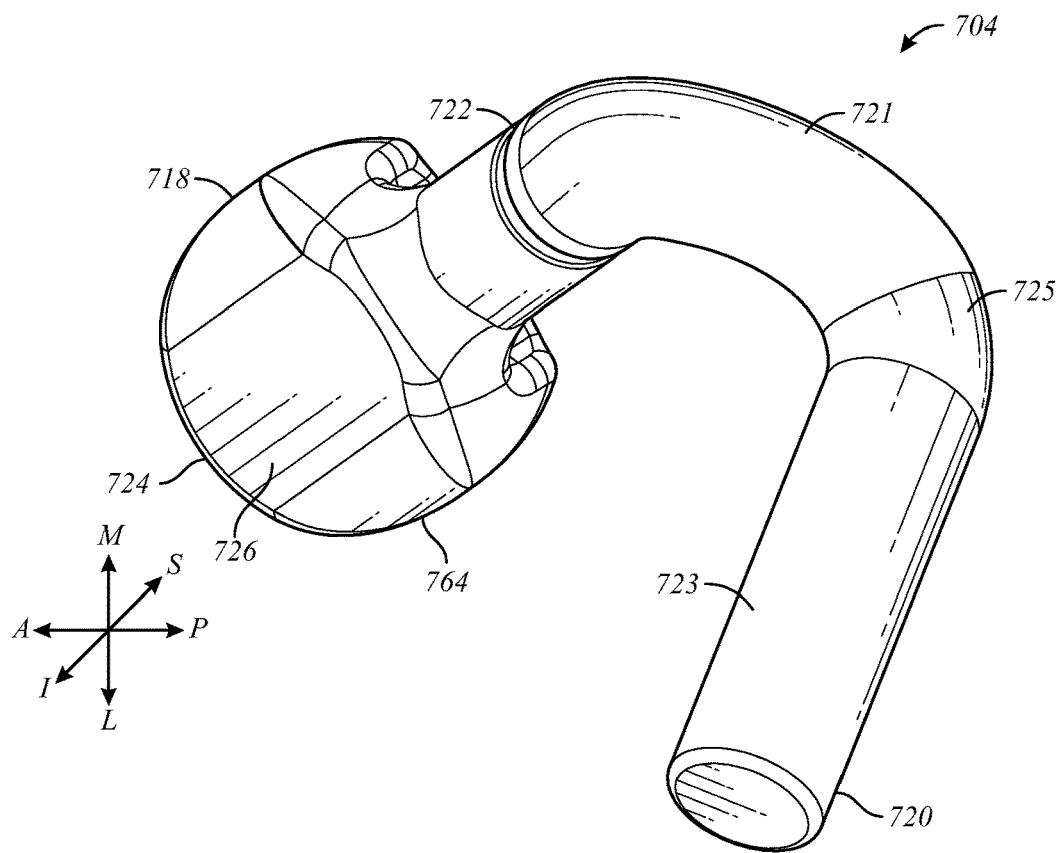
FIG. 27B depicts a top anterior perspective view of the articulating element 704.
Figure 27C:
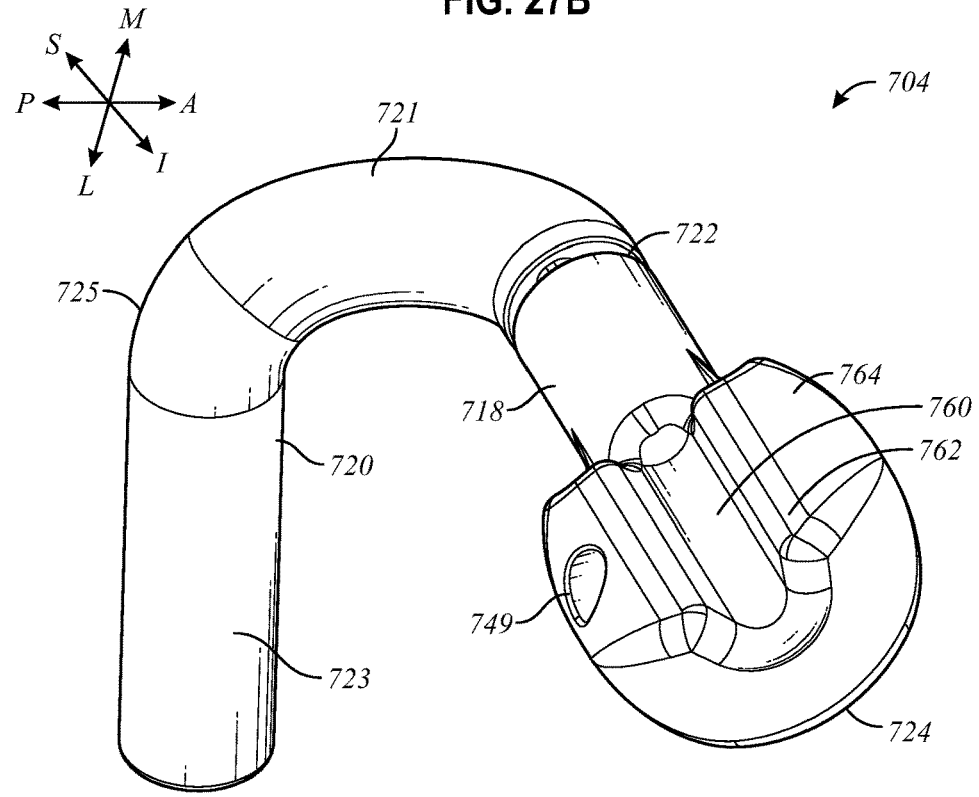
FIG. 27C depicts a bottom posterior perspective view of the articulating element 704.
Figure 27D:
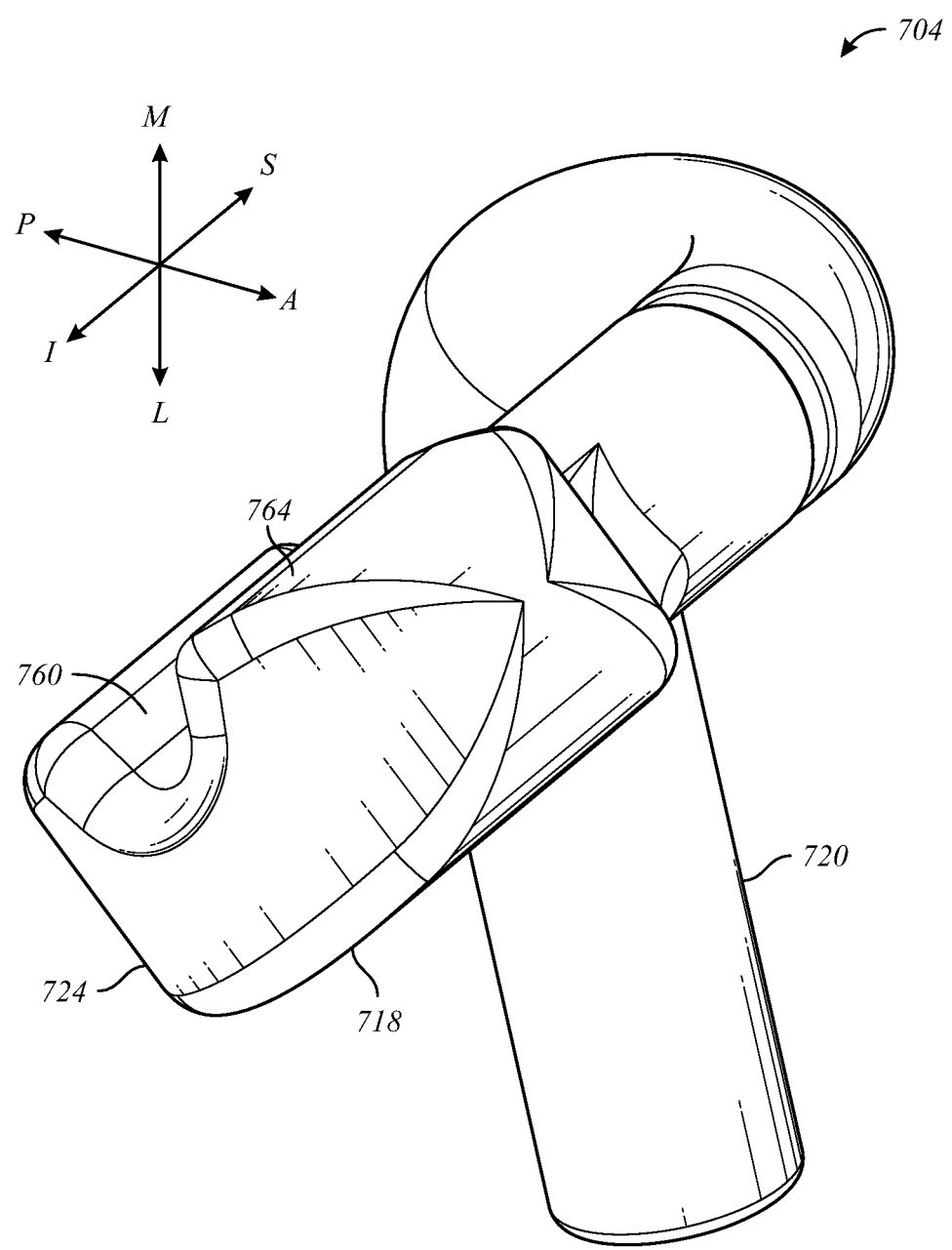
FIG. 27D depicts a bottom anterior perspective view of the articulating element 704.

FIGS. 27A-K depict views of the articulating element 704. FIG. 27A depicts a top posterior perspective view of the articulating element 704. FIG. 27B depicts a top anterior perspective view of the articulating element 704. FIG. 27C depicts a bottom posterior perspective view of the articulating element 704. FIG. 27D depicts a bottom anterior perspective view of the articulating element 704.

Figure 27E:
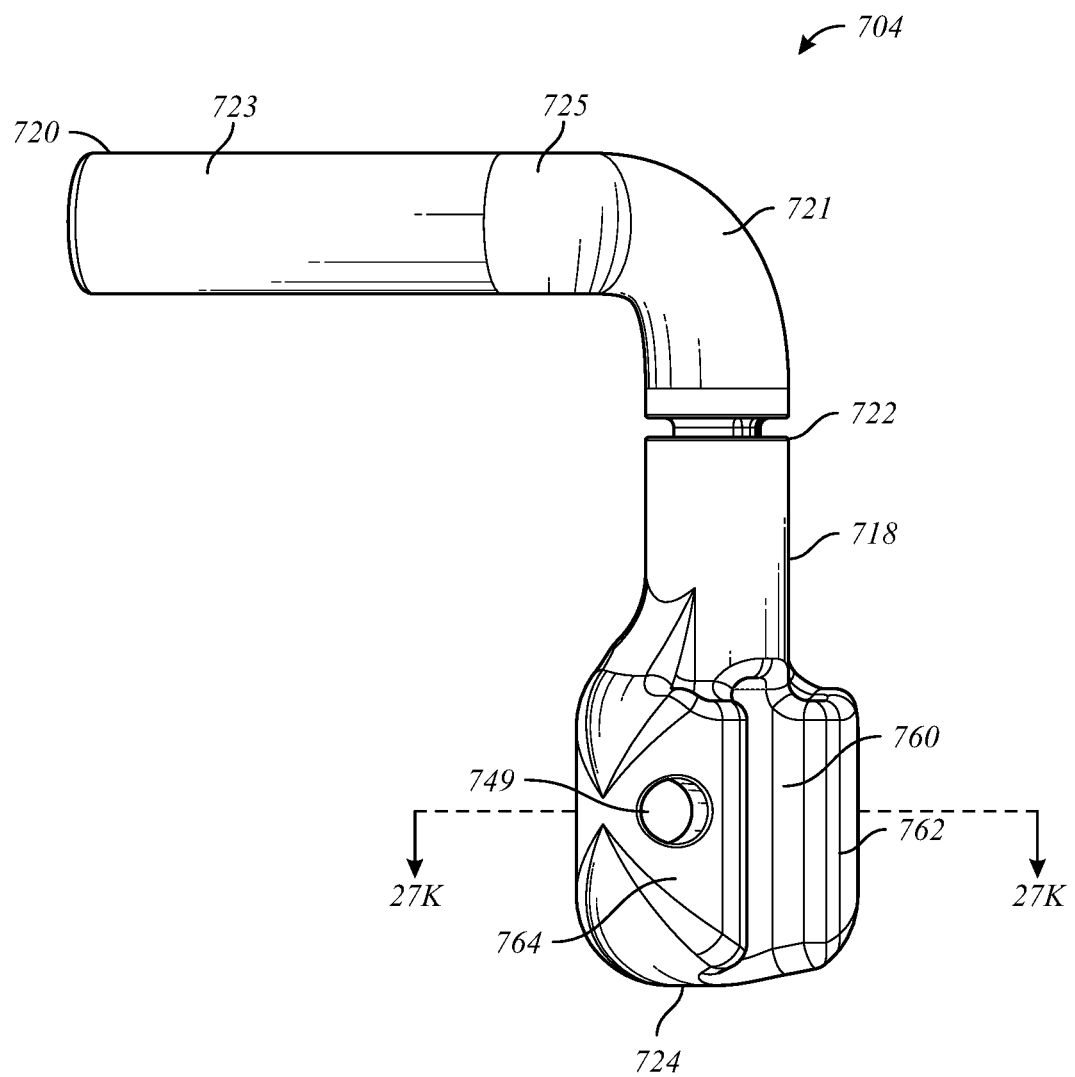
FIG. 27E depicts a posterior view of the articulating element 704.
Figure 27F:
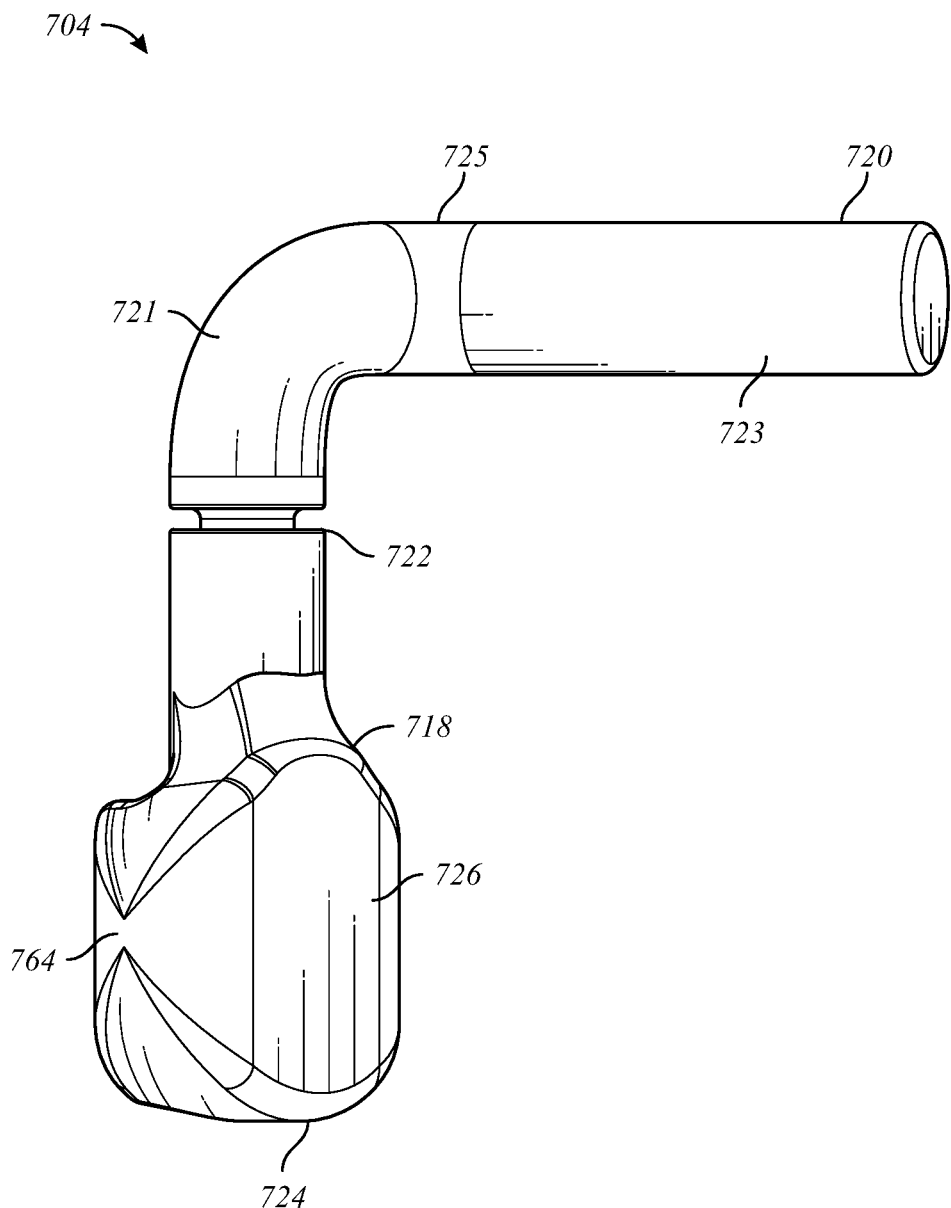
FIG. 27F depicts an anterior view of the articulating element 704.
Figure 27G:
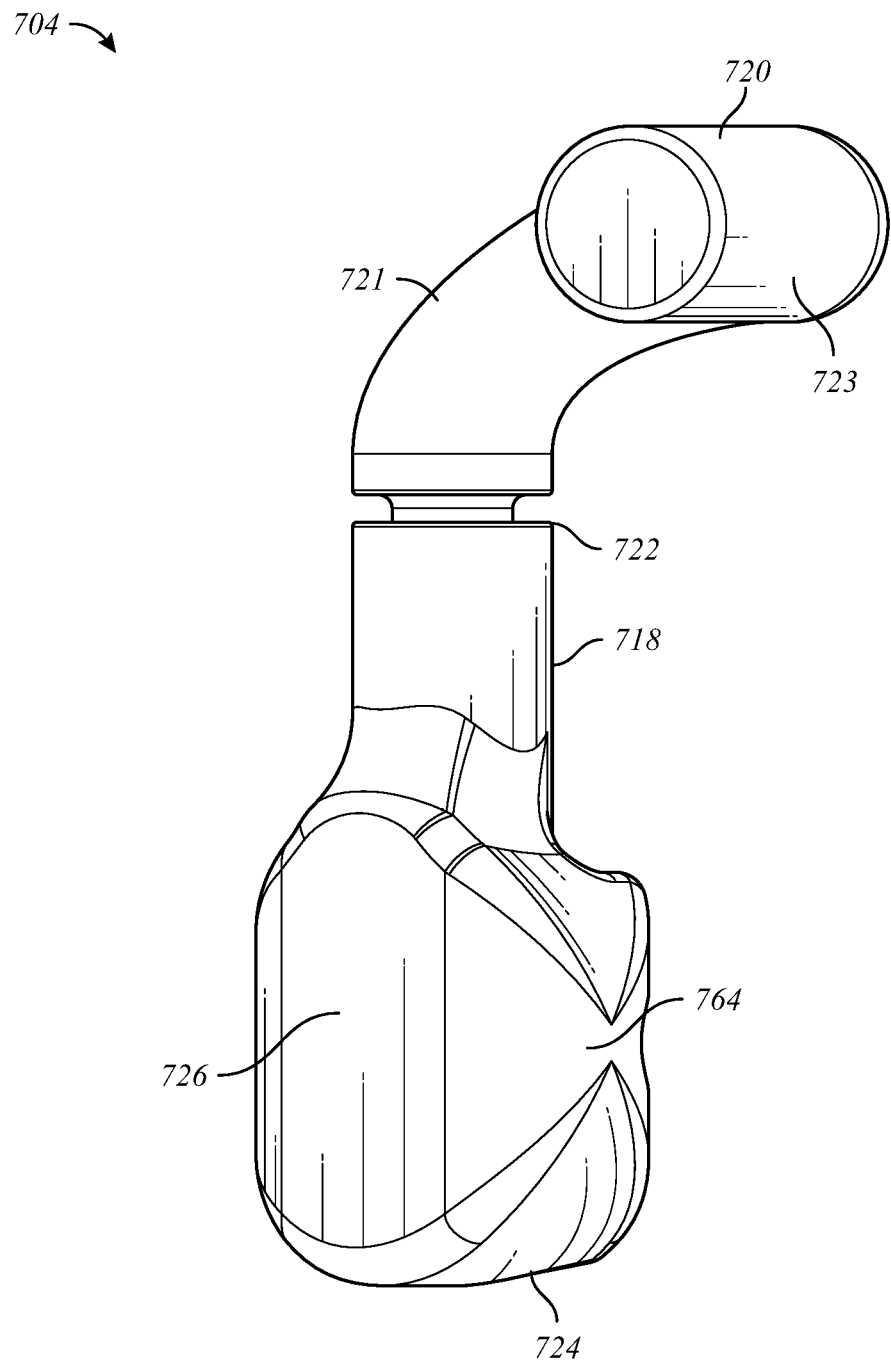
FIG. 27G depicts a first sagittal view of a lateral side of the articulating element 704.
Figure 27H:
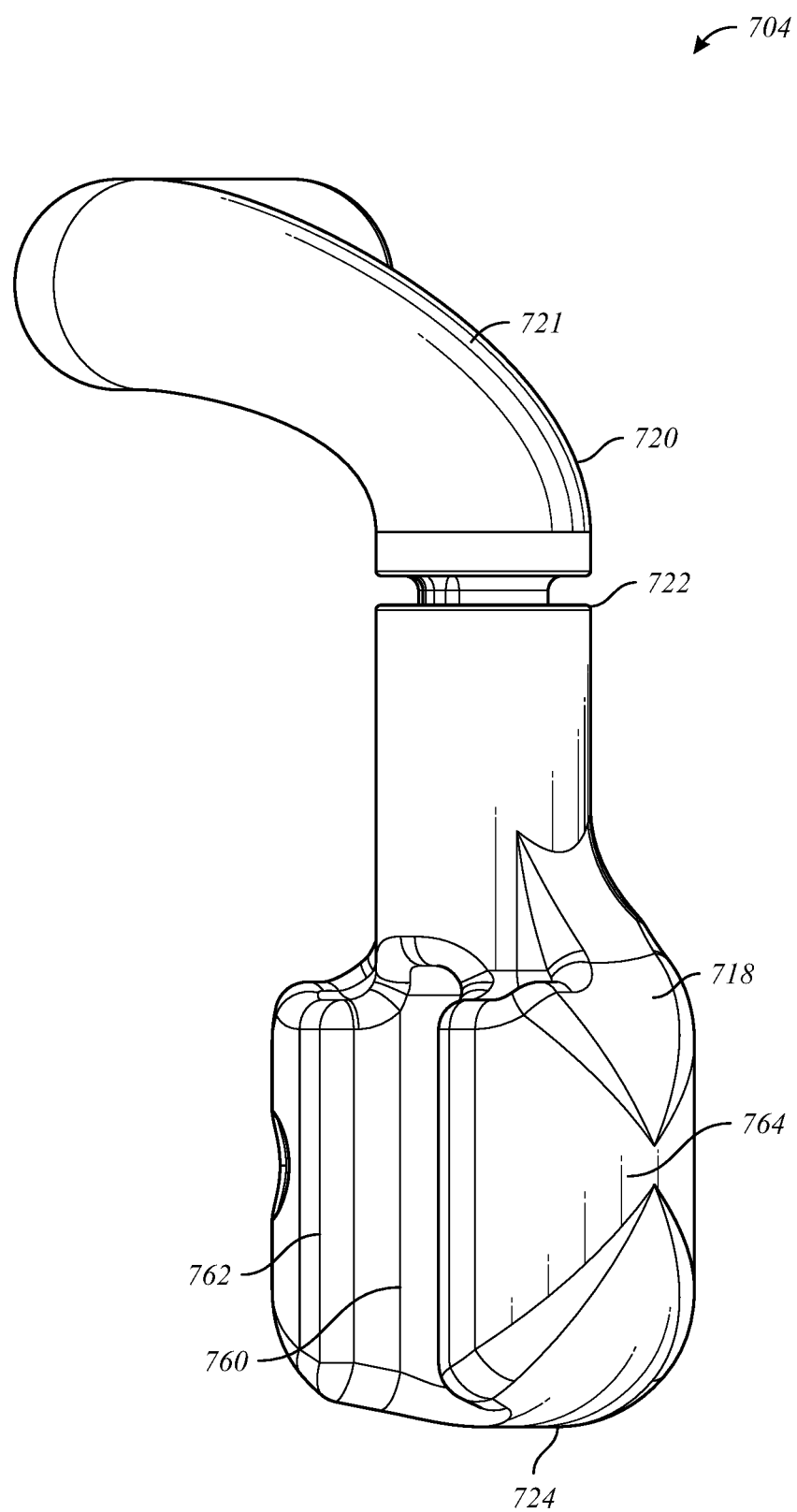
FIG. 27H depicts a second sagittal view of a medial side of the articulating element 704.
Figure 27I:
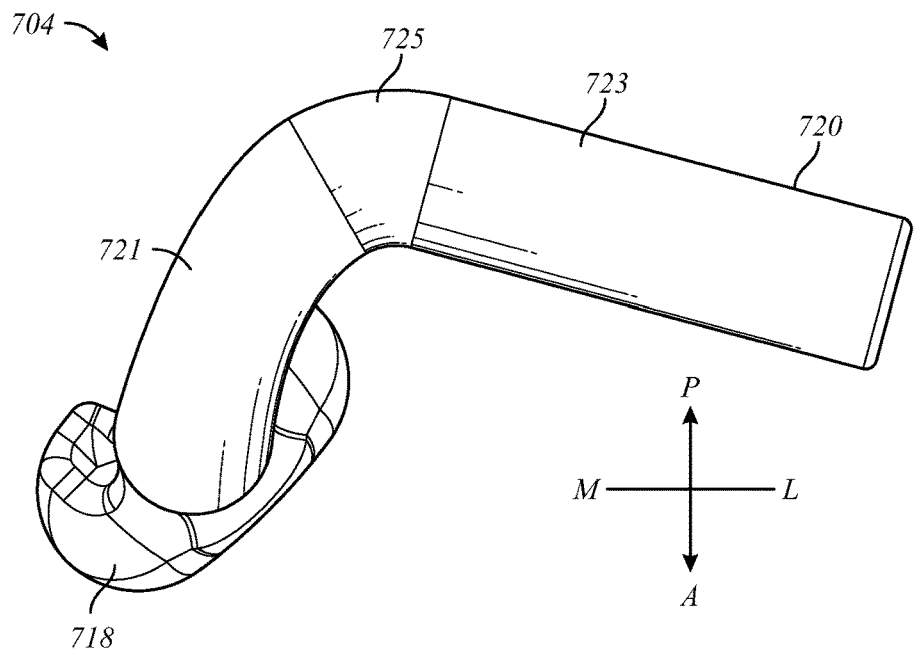
FIG. 27I depicts a top view of the articulating element 704.
Figure 27J:
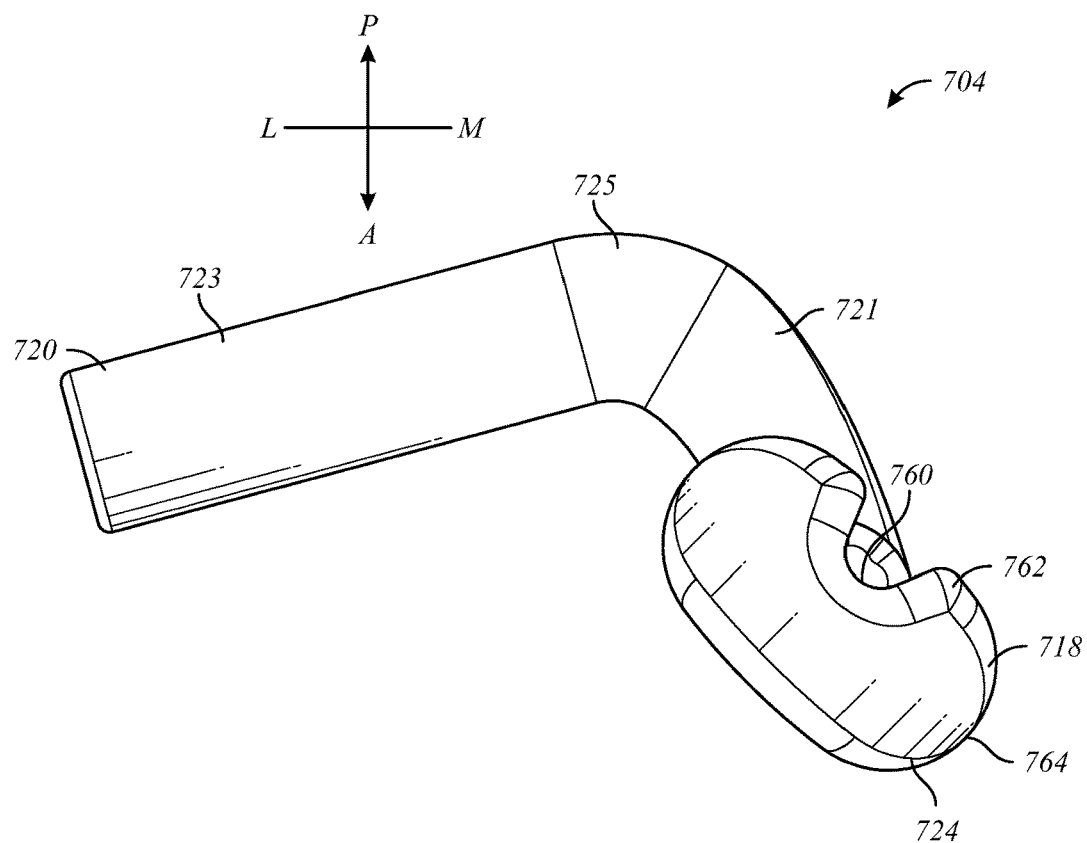
FIG. 27J depicts a bottom view of the articulating element 704.
Figure 27K:
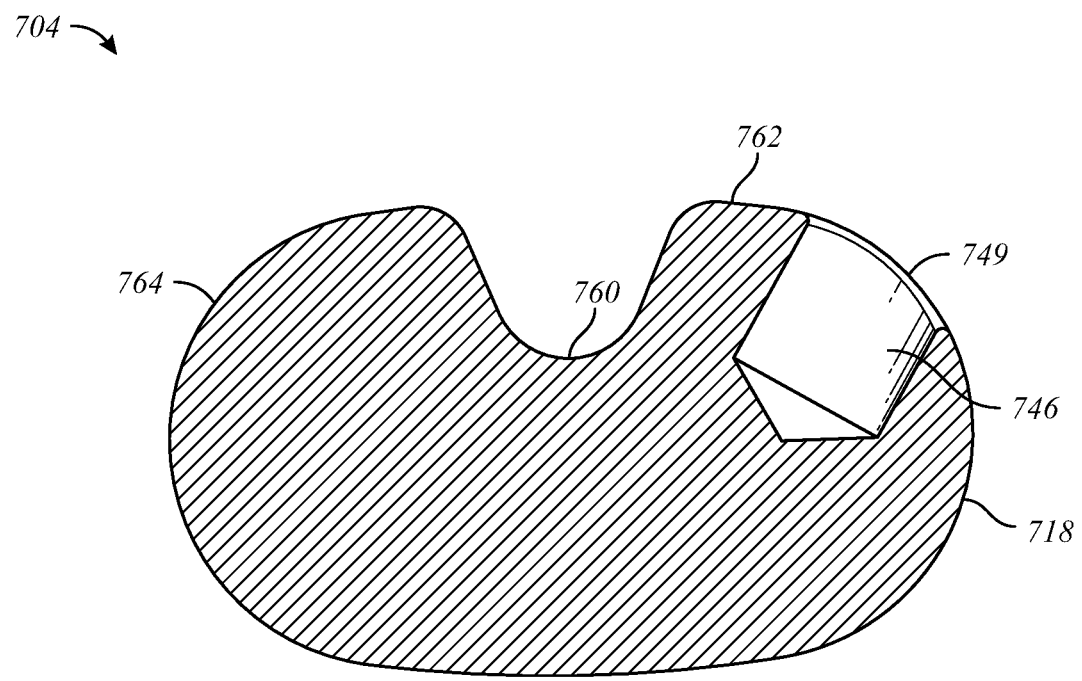
FIG. 27K depicts a cross-sectional view of the articulating element 704.

FIG. 27E depicts a posterior view of the articulating element 704. FIG. 27F depicts an anterior view of the articulating element 704. FIG. 27G depicts a first sagittal view of a lateral side of the articulating element 704. FIG. 27H depicts a second sagittal view of a medial side of the articulating element 704. FIG. 27I depicts a top view of the articulating element 704. FIG. 27J depicts a bottom view of the articulating element 704. FIG. 27K depicts a cross-sectional view of the articulating element 704 taken along line 27K-27K as shown in FIG. 27E.

As shown in FIGS. 27A-K, the articulating element 704 includes an articulating body 718 and an attachment member 720. As described herein, the articulating body 718 can be at least partially positioned within and configured to move within the inner cavity 714 of the enclosing body 706. The articulating body 718 has a superior end 722 and an inferior end 724.

As shown in FIGS. 27A-K, the attachment member 720 can extend from the superior end 722 of the articulating body 718. In some embodiments, the attachment member 720 can extend superiorly from the articulating body 718. In some embodiments, the attachment member 720 can extend laterally from the articulating body 718. In some embodiments, the attachment member 720 can extend posteriorly from the articulating body 718.

In some embodiments, the attachment member 720 can include a first section 721 and a second section 723. In some embodiments, the first section 721 can extend from the articulating body 718 in superior, lateral, and/or posterior directions. In some embodiments, the second section 723 can extend from the first section in lateral and/or anterior directions. In some embodiments, the first section 721 and the second section 723 can connect at or form a bend 725. In some embodiments, the bend 725 can be positioned lateral to the articulating body.

The attachment member 720 can be shaped and/or dimensioned to facilitate securement of the facet joint replacement device 700 to the spine. As shown in FIGS. 27A-J, the attachment member 720 can be a rod. However, the attachment member 720 can be any shape suitable for fixation directly or indirectly to a vertebral body. In some embodiments, the attachment member 720 can have a diameter of 5.5 mm. In some embodiments, the attachment member 720 can have a diameter of 1 mm, 2 mm, 3 mm, 4 mm, 4.5 mm, 5 mm, 5.5 mm, 6 mm, 6.5 mm, 7 mm, 8 mm, 9 mm, 10 mm, between 2 mm to 8 mm, between 4 mm to 6 mm, between 5 mm to 7 mm, or between 5 mm to 6 mm. In some embodiments, the attachment member 720 can have a length of 1 mm, 2 mm, 3 mm, 4 mm, 5 mm, 6 mm, 7 mm, 8 mm, 9 mm, 10 mm, 15 mm, 20 mm, 25 mm, 30 mm, between 2 mm to 8 mm, between 4 mm to 6 mm, between 5 mm to 10 mm, between 10 mm to 15 mm, between 15 mm to 20 mm, between 20 mm to 25 mm, between 25 mm to 30 mm, between 15 mm to 30 mm, or less than 15 mm.

As shown in FIGS. 27A-K, In some embodiments, a portion of an exterior surface 764 of the articulating body 718 can be shaped to form an articulating surface 726. In some embodiments, the articulating surface 726 can be convex or at least partially convex. In some embodiments, the articulating surface 726 can be shaped/and or dimensioned to correspond to the shape, size, and/or concavity of an articular surface of a healthy inferior articular process.

In some embodiments, the articulating surface 726 of the articulating body and the articulating surface 728 of the enclosing body have complementary surface shapes. In some embodiments, the articulating surface 726 and the articulating surface 728 are elliptical or generally elliptical, circular or generally circular, oval or generally oval, rounded, polygonal, oblong, symmetric, asymmetric, or any other suitable shape. In some embodiments, the articulating surface 726 and articulating surface 728 can be shaped such that force is applied symmetrically to the articulating 728 when the articulating element 726 contacts or otherwise applies a force upon the articulating surface 728.

As shown in FIGS. 27A-K, the articulating body 718 can include a slot, groove, or recess 760 extending inwardly relative to a surrounding area 762 of the exterior surface 764. In some embodiments, the projection 756 and recess 760 can be generally concave in shape. In some embodiments, the recess 760 can be generally parabolic in shape. In some embodiments, the recess 760 can extend from an inferior portion of the articulating body to a superior portion of the articulating body 718. In some embodiments, the articulating surface 726 can be positioned on a face of the articulating body 718 generally opposite the recess 760.

As shown in FIGS. 27A-K, the articulating body 718 can include an opening 749 on the exterior surface 764 of the articulating body 718. The opening 749 can be dimensioned, positioned, or otherwise configured to align with the opening 743 of the enclosing body 706 while the articulating body 718 is located at a particular position within the enclosing body 706. As shown in FIG. 27J, a channel 746 extends from the opening 749 into the interior of the articulating body 718. The channel 746 can be shaped, dimensioned, or otherwise configured to receive a fastener. In some embodiments, the channel 746 can include a threaded portion configured to couple with a threaded portion of a fastener.

In some embodiments, the articulating body 718 is formed of or formed partially of one or more metals or metal alloys. In some embodiments, the articulating body 718 is formed of cobalt-chrome. For example, the articulating body 718 can be formed of cobalt-chromium, titanium, titanium-based alloys, or any other suitable metals or metal alloys. In some embodiments, the articulating body 718 can be ceramic or partially ceramic. In some embodiments, the articulating body 718 can include super-hard ceramics.

Figure 28:
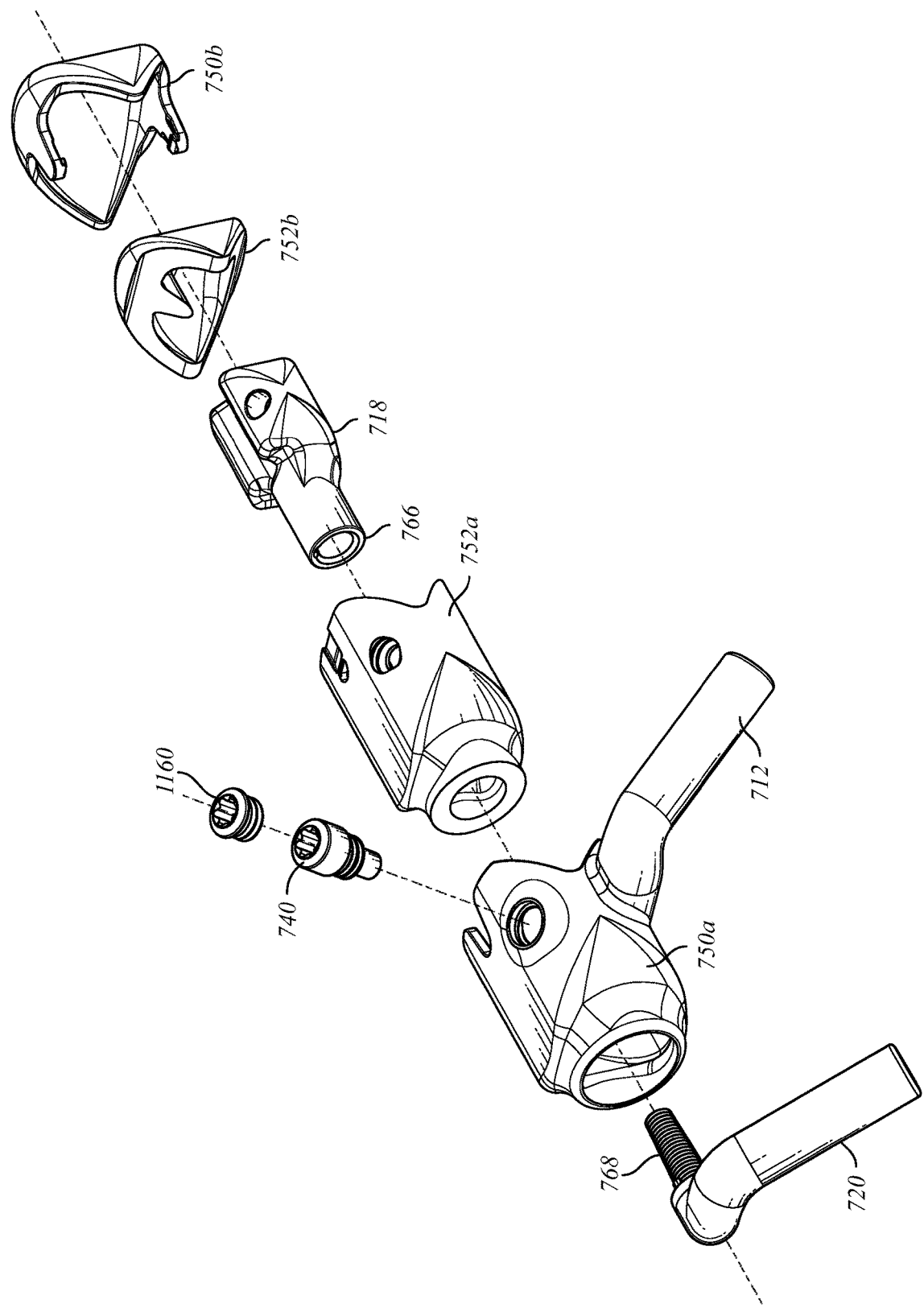
FIG. 28 is an exploded view of a facet joint replacement system including the facet joint replacement device 700 and a fastener 740.

FIG. 28 is an exploded view of a facet joint replacement system including the facet joint replacement device 700 and a fastener 740. As described further herein, in some embodiments, the fastener 740 can be used to restrict movement of the articulating body 718 within the enclosing body 706.

As shown in FIG. 28, in some embodiments, the attachment portion 720 can be releasably or permanently coupled to the articulating body 718. In some embodiments, the attachment portion 720 can be coupled to the articulating body 718 via a tapered connection. In some embodiments, the attachment portion 720 can be coupled to the articulating body 718 via a threaded connection.

In some embodiments, the articulating body 718 can include an opening 766 configured to receive a portion 768 of the attachment portion 720. In some embodiments, the portion 768 can be an end of the attachment portion 720. In some embodiments, the portion 768 can be a tapered end of the attachment portion 720. In some embodiments the portion 768 can be a keyed taper. In some embodiments, the portion 768 can be an externally threaded section and the opening 766 can include an internally threaded section configured to receive the externally threaded portion 768.

Figure 29A:
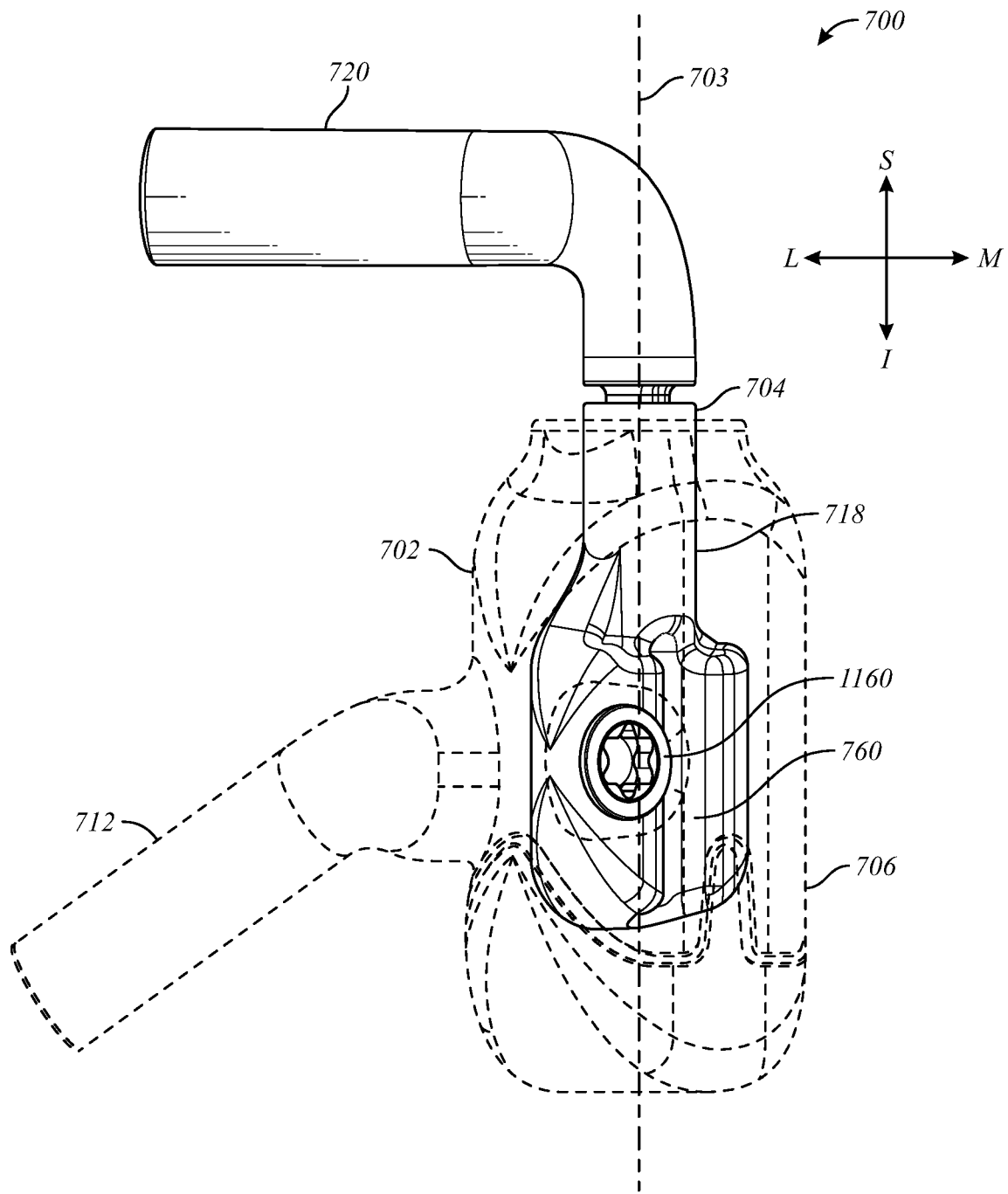
FIG. 29A depicts a posterior view of the facet joint replacement device 700.
Figure 29B:
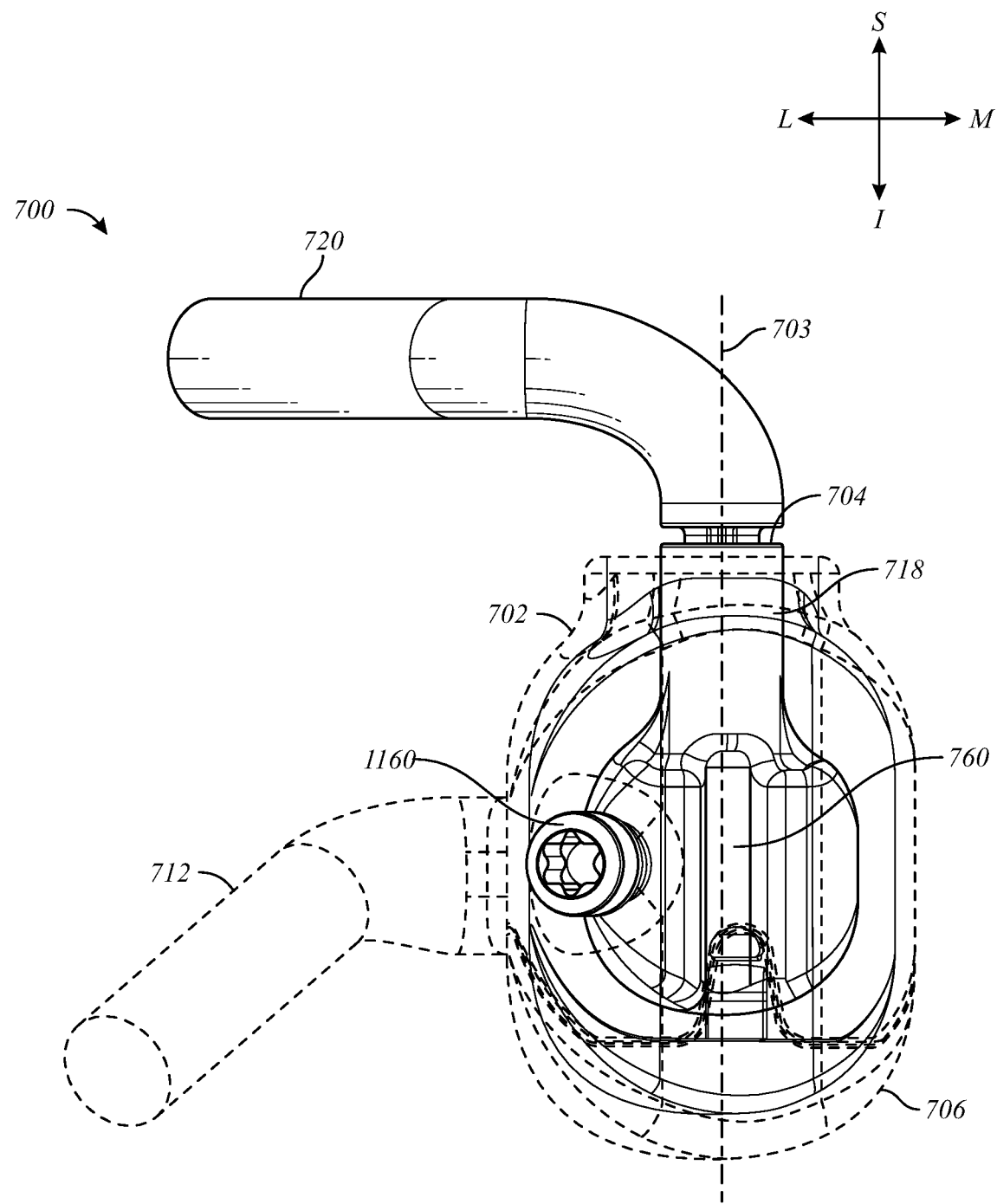
FIG. 29B depicts a posterior-medial view of the facet joint replacement device 700.
Figure 29C:
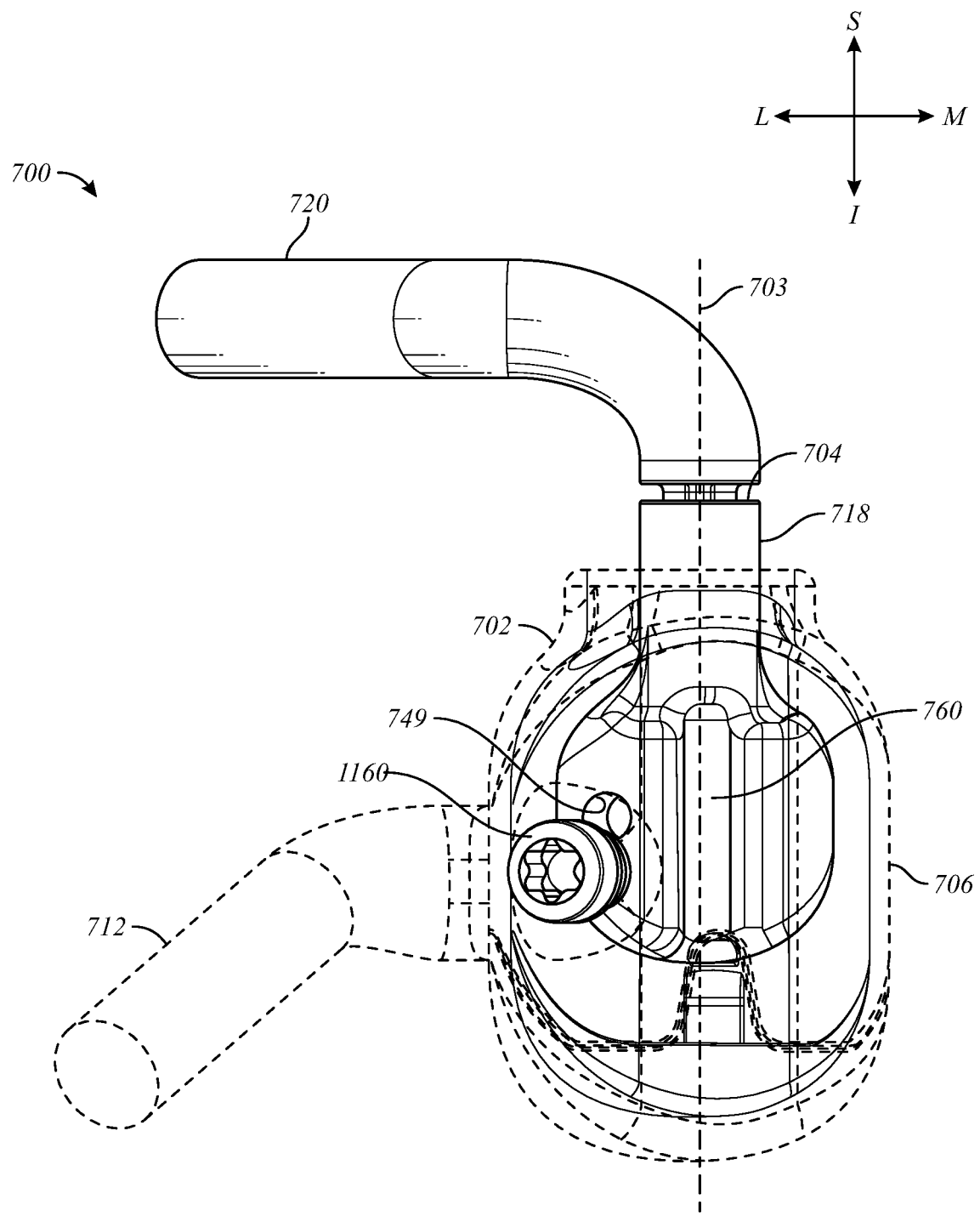
FIG. 29C depicts a posterior-medial view of the facet joint replacement device 700.
Figure 29D:
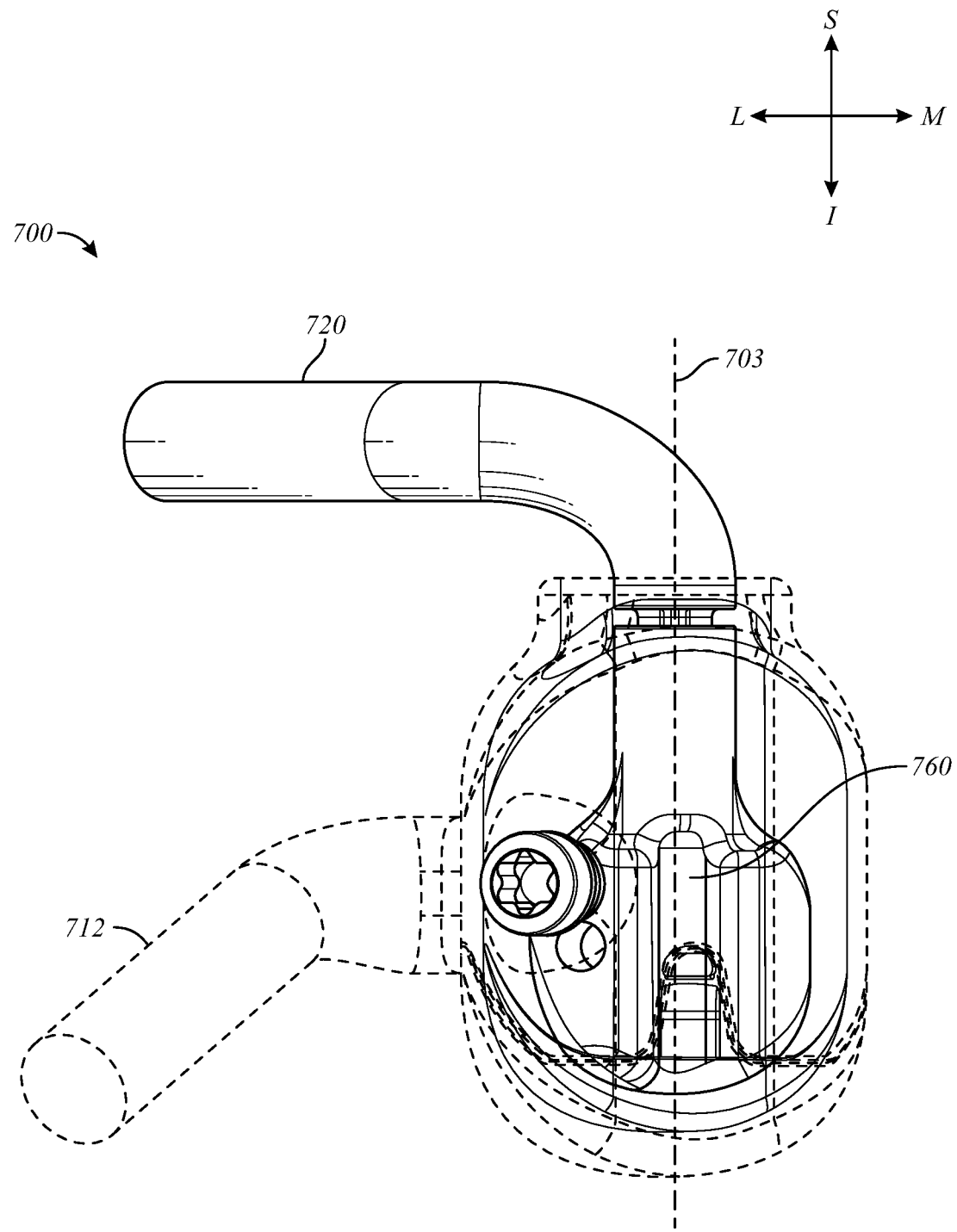
FIG. 29D depicts a posterior-medial view of the facet joint replacement device 700.
Figure 29E:
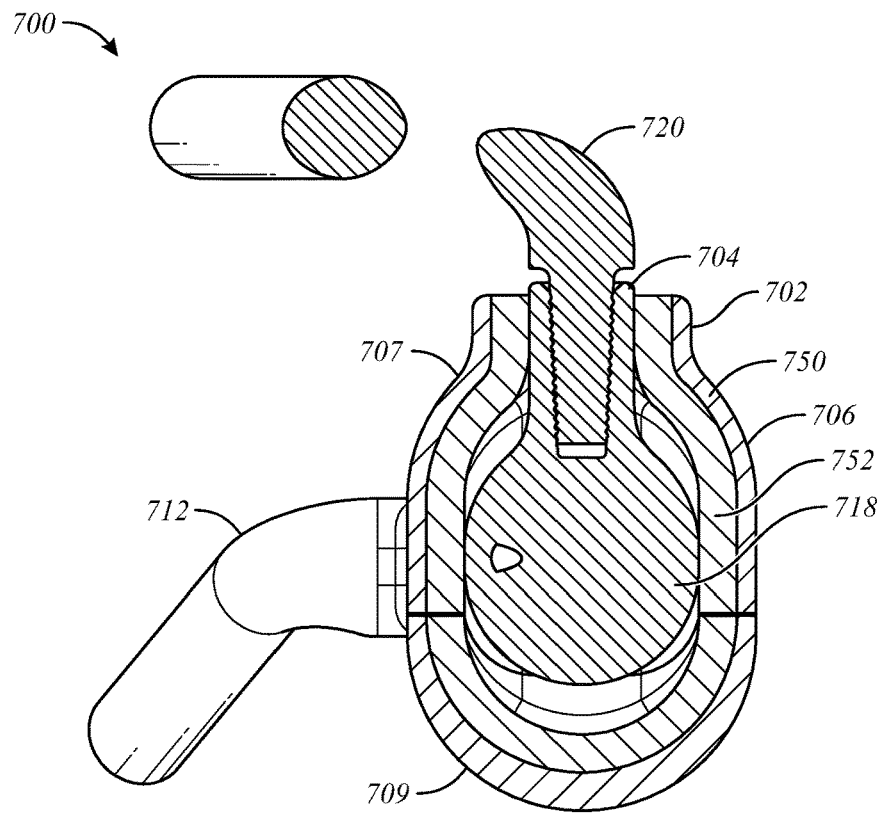
FIG. 29E depicts a posterior-medial cross-sectional view of the facet joint replacement device.
Figure 29F:
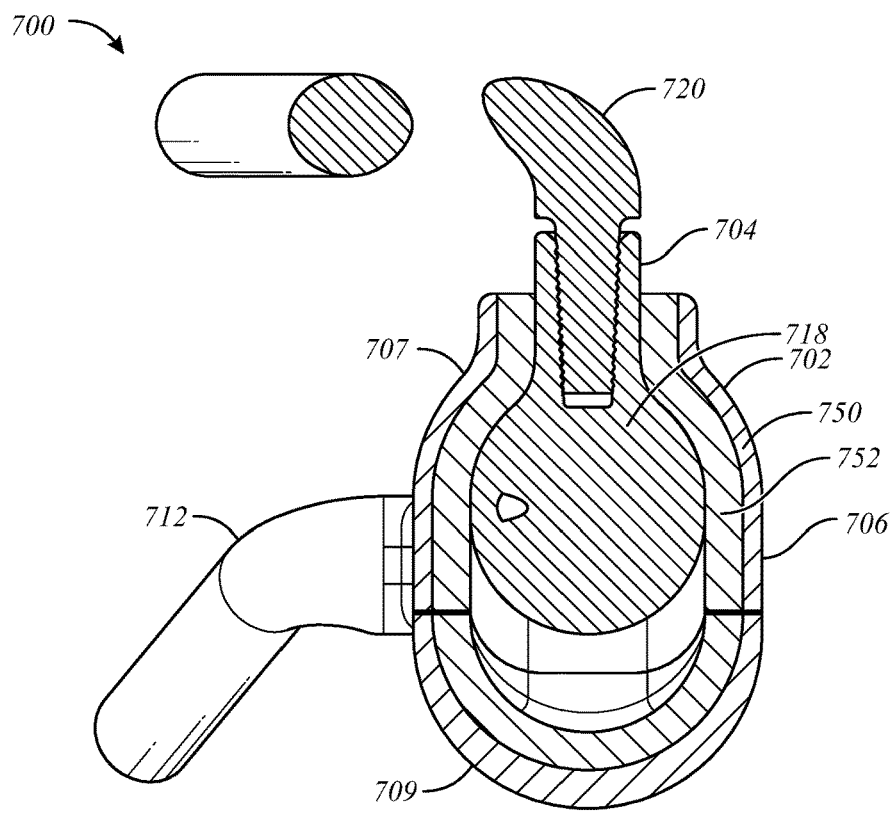
FIG. 29F depicts a posterior-medial cross-sectional view of the facet joint replacement device.
Figure 29G:
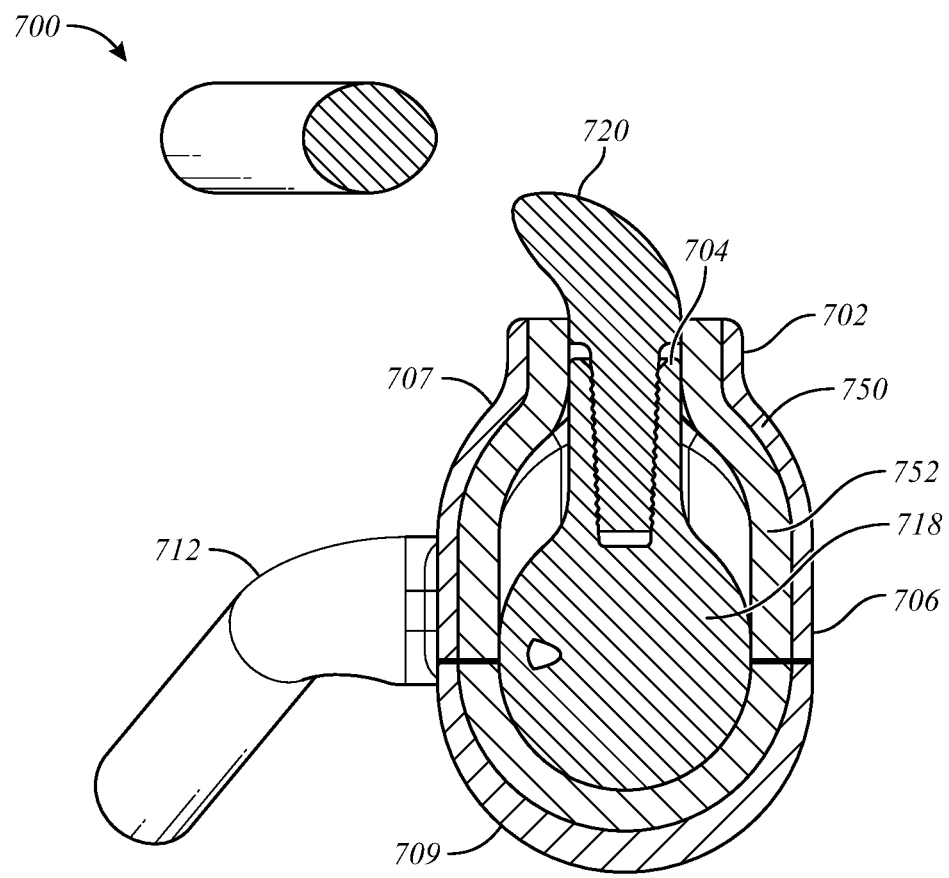
FIG. 29G depicts a posterior-medial cross-sectional view of the facet joint replacement device.

FIGS. 29A-D depict views of the facet joint replacement device 700 in which the enclosing element 702 is illustrated as transparent to show internal features of the facet joint replacement device 700. FIG. 29A depicts a posterior view of the facet joint replacement device 700. FIGS. 29B-D depict posterior-medial views of the facet joint replacement device 700. FIGS. 29E-G depict posterior-medial cross-sectional views of the facet joint replacement device 700 taken along lines 24B-24B as shown in FIG. 23J.

The articulating body 718 is configured to move within the enclosing body 706 in at least one direction. When the attachment member 720 is secured to a superior vertebral body and the attachment member 712 is secured to an inferior vertebral body, movement between the superior and inferior vertebral bodies can cause movement of the attachment member 720 with respect to the position of the enclosing body 706 resulting from the attachment member 712 being secured to the inferior vertebral body. Movement of the attachment member 720 with respect to the enclosing body 706 causes movement of the articulating body 718 within the enclosing body 706 generally along the interior surface 754 of the enclosing body 706.

FIGS. 29A-D further show an axis 703. The axis 703 represents an axis of articulation of the articulating body 718 within the enclosing body 706 and/or an axis of articulation of the articulating surfaces 726 and 728 relative to one another. The articulating body 718 can be configured to move along the axis 703 within the enclosing body. As shown in FIGS. 29A-D, the axis 703 can be parallel with a superior-inferior anatomical axis when the facet joint replacement device 700 is implanted within a patient. In some embodiments, the axis 703 can be parallel with an angle formed between the articulating surfaces 726 and 728.

Figure 30A:
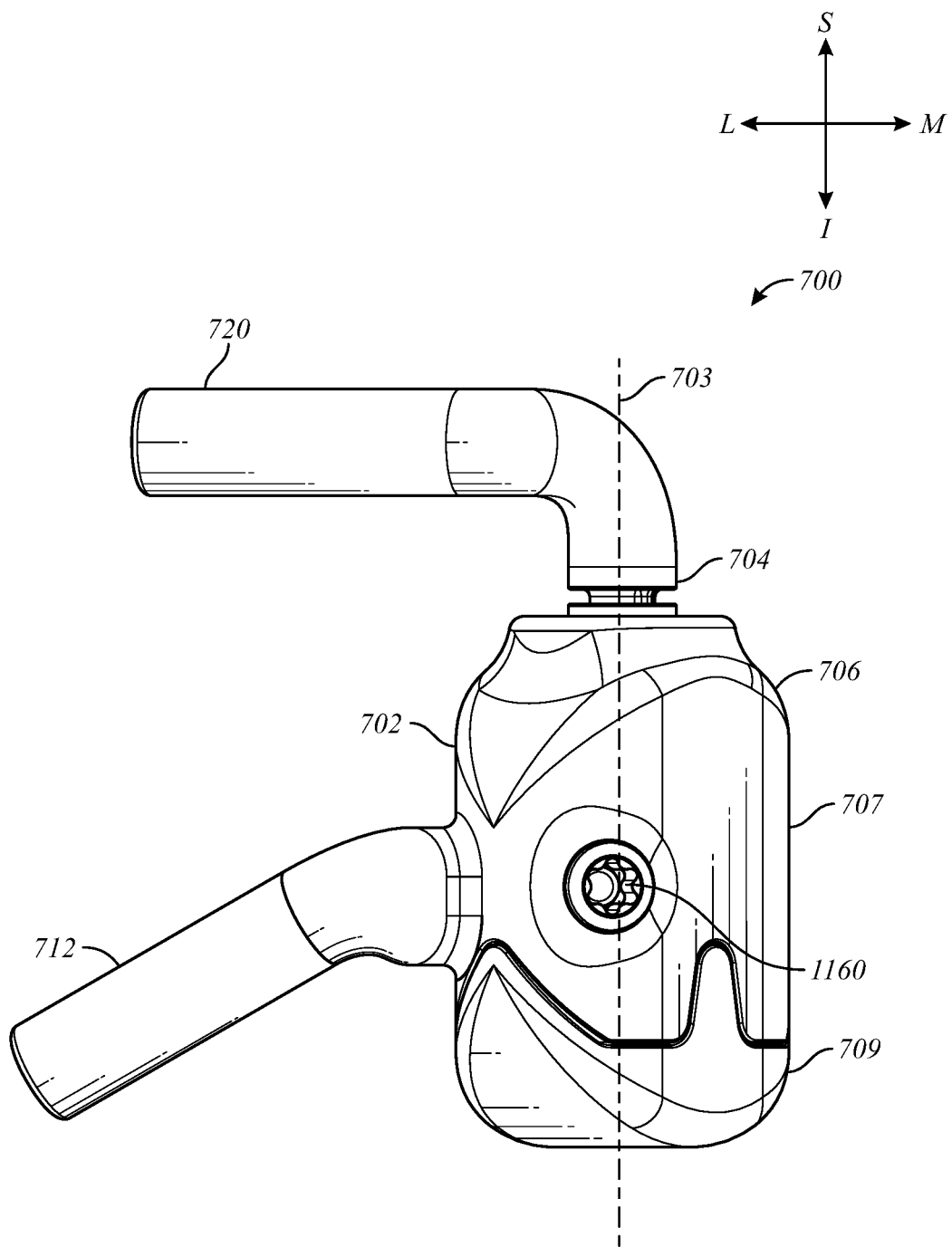
FIG. 30A depicts a posterior view of the facet joint replacement device 700.
Figure 30B:
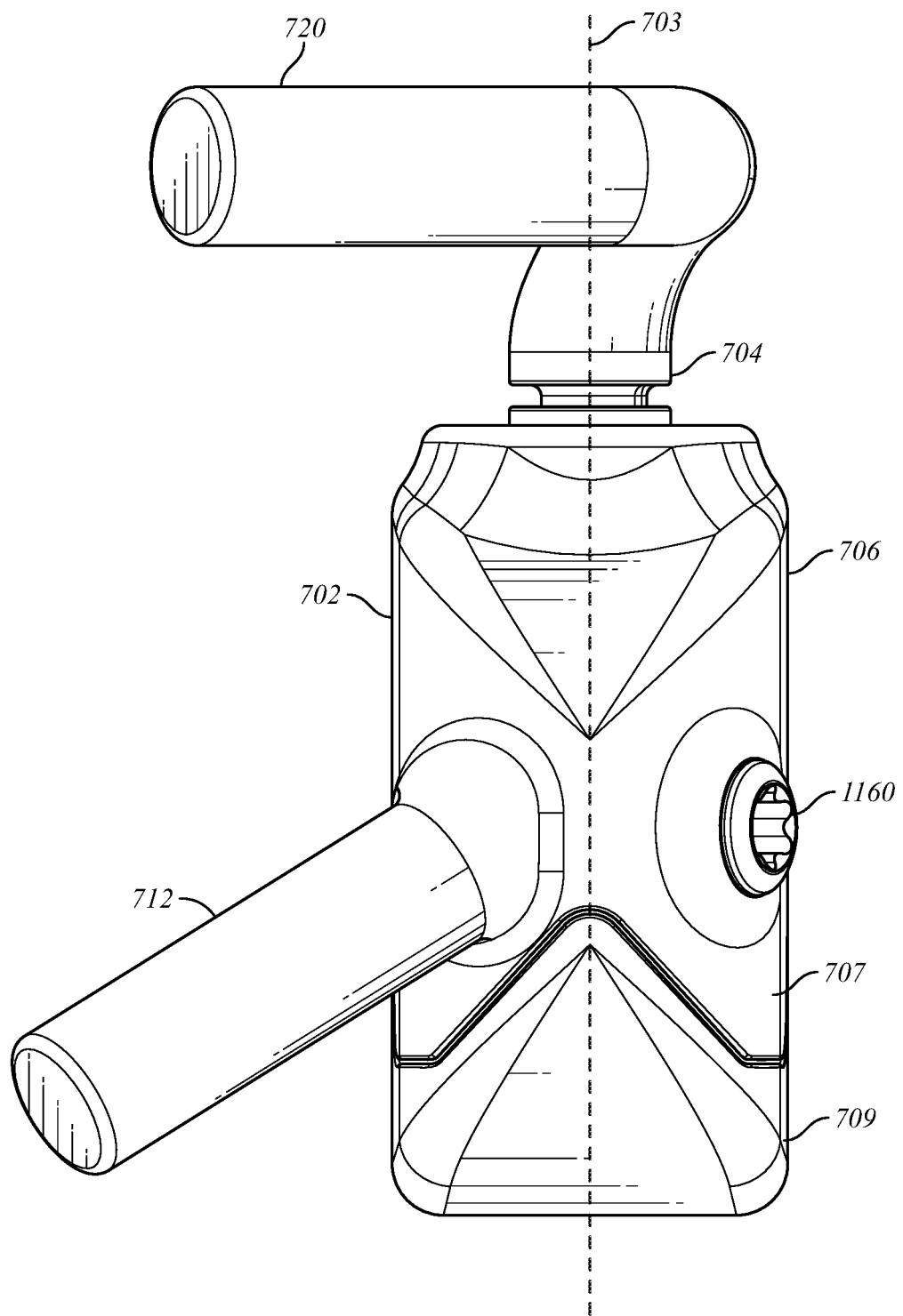
FIG. 30B depicts a sagittal view showing a lateral side of the facet joint replacement device 700.
Figure 30C:
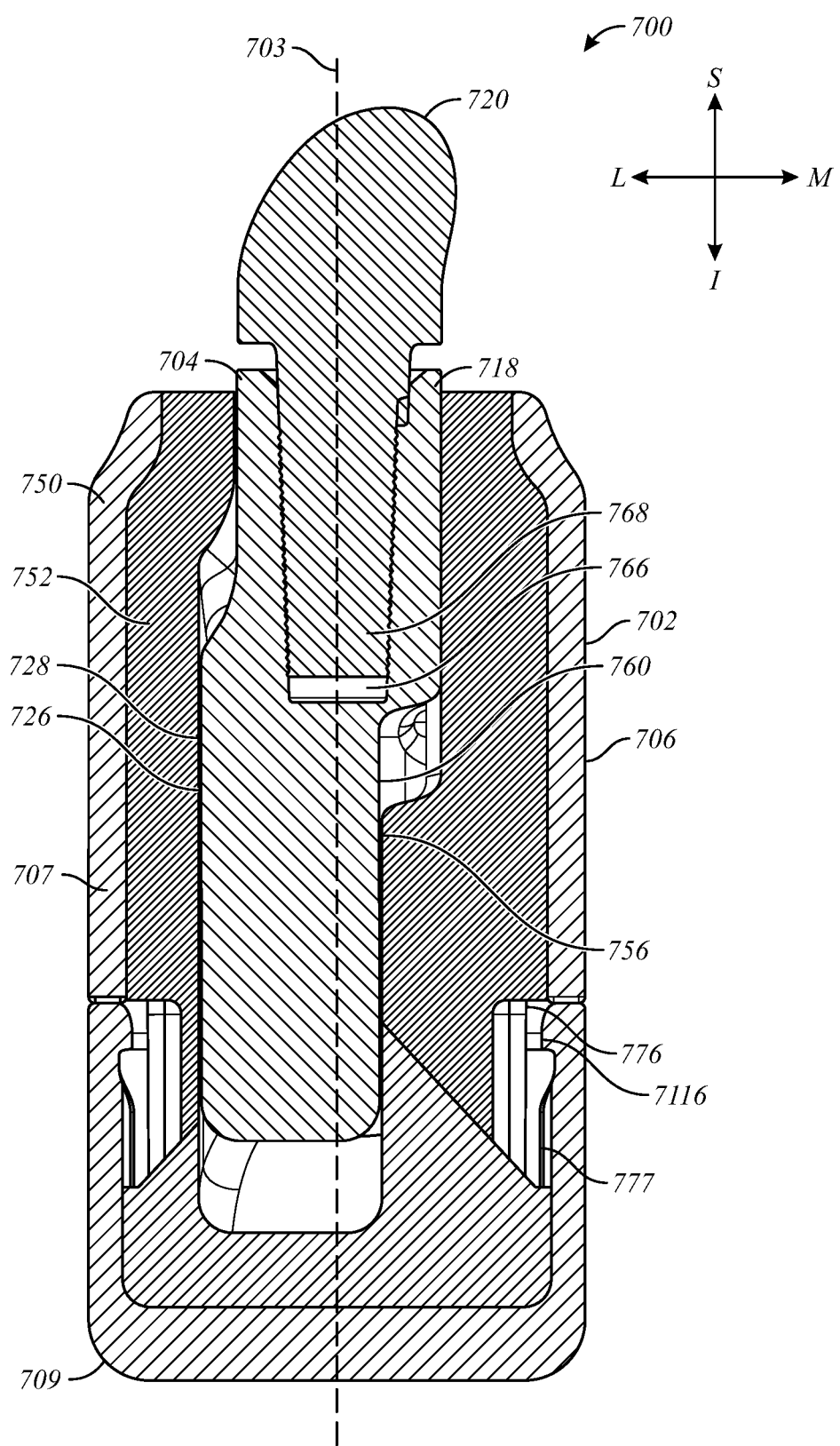
FIG. 30C shows a cross-sectional view of the facet joint replacement device 700.

FIG. 30A depicts a posterior view of the facet joint replacement device 700 showing the axis 703. FIG. 30B depicts a sagittal view showing a lateral side of the facet joint replacement device 700 showing the axis 703. FIG. 30C shows a cross-sectional view of the facet joint replacement device 700 taken along line 30C-30C as shown in FIG. 23J and showing the axis 703.

The attachment member 720 is configured to move along axis 703 towards and away from the enclosing body 706. When the attachment member 720 moves towards the enclosing body 106 along the axis 703, the attachment member 720 moves along the axis 703 in an inferior direction. When the attachment member 720 moves away from the enclosing body 706 along the axis 703, the attachment member 720 moves along the axis 703 in a superior direction. The articulating body 718 moves along the axis 703 in the same manner when the attachment member 720 moves along the axis 703. Although relative movement of the attachment member 720 towards and away from the enclosing body 706 is discussed, one of skill in the art would understand that movement between the enclosing body 706 and attachment member 720 could be described as movement of the enclosing body 706 towards or away from the attachment member 720 or movement of the enclosing body 706 and attachment member 720 towards or away from each other.

Movement of the attachment member 720 with respect to the enclosing body 706 causes movement of the articulating surface 726 relative to the articulating surface 728. In some embodiments, movement of the attachment member 720 with respect to the enclosing body 706 causes movement of the articulating surface 726 along the axis 703 relative to the articulating surface 728. In some embodiments, the articulating surface 726 can be configured to articulate relative to the articulating surface 728 by moving substantially only parallel to an angle formed by the two juxtaposed articulating surfaces 726 and 778. Although relative movement of the articulating surface 726 relative to the articulating surface 728 is discussed, one of skill in the art would understand that movement between the articulating surface 726 and the articulating surface 728 could be described as movement of the articulating surface 728 relative to the articulating surface 728 or movement of the articulating surfaces 726 and 728 relative to each other. The axis 703 can represent the direction of relative movement between the articular surfaces of a healthy facet joint. In some embodiments, the articulating surfaces 726 and 728 can be configured to articulate relative each other by moving substantially only parallel to an angle formed by the two juxtaposed articulating surfaces 726 and 778.

In some embodiments, the enclosing body 706 acts to limit relative movement between the articulating surface 726 and the articulating surface 728 along the axis 703. In some embodiments, the enclosing body 706 acts to limit relative movement of the articling surface 726 and articulating surface 728 perpendicular to the axis 703. In some embodiments, the enclosing body 706 can act to limit relative movement between the articulating surfaces 726 and 728 to correspond to the limitations of movement of the articular surfaces of a healthy facet joint. In some embodiments, the enclosing body 706 can act to limit movement between the articulating surfaces 726 and 728 to correspond to the limitations of movement provided by the facet joint capsule of a healthy facet joint. In any of the embodiments described above or elsewhere in this specification, the enclosing body can be configured to restrict movement of the articulating body within the enclosing body such that the articulating surface 726 moves only along an axis parallel with the superior/inferior axis of the patient. In some embodiments, the enclosing body 706 can be configured to restrict movement of the articulating body 718 within the enclosing body such that the articulating body 718 moves only along an axis parallel with an angle formed by the juxtaposed articulating surface 726 and articulating surface 728. In some embodiments, the enclosing body 706 can be configured to restrict movement of the articulating body 718 within the enclosing body 706 such that the articulating surface 726 moves only along an axis parallel with an angle formed by the juxtaposed articulating surfaces 726 and 728.

When the articulating body 718 moves within the enclosing body 706, the articulating surface 726 can contact the articulating surface 728. The articulating surface 726 can articulate against the articulating surface 728. In some embodiments, the articulating surfaces 726 and 728 may apply an axial load to one another during articulation. In some embodiments, the outer shell 750 and/or liner 752 may have a sufficient thickness at articulating surface 728 to receive an axial load supplied by the articulating body 718 to the articulating surface 728 due to movement of the articulating body 718 within the enclosing body 706. In some embodiments, the articulating body 718 may have a sufficient thickness at articulating surface 726 to receive an axial load supplied by the enclosing body 706 to the articulating surface 728 due to movement of the articulating body 718 within the enclosing body 706.

Although articulation between the articulating surface 726 and the articulating surface 728 is discussed herein, it is contemplated that articulation between any or all of the exterior surfaces of the articulating body 718 and any or all of the interior surfaces of the enclosing body 706 could occur alternatively or in addition to articulating between the articulating surface 726 and the articulating surface 728.

In some embodiments, the enclosing body 706 and articulating body 718 are configured such that a maximum distance between a center point of the articulating surface 726 and the articulating surface 728 is 0.5 mm, 1.0 mm, 1.5 mm, 1.75 mm, 2.0 mm, 2.25 mm, 2.5 mm, 3.0 mm, 3.5 mm, 4.0 mm, 5.0 mm, less than 2.0 mm, less than 3.0 mm, less than 4.0 mm, between 1.0 mm and 3.0 mm, between 1.0 mm and 2.0 mm, between 2.0 mm and 3.0 mm, between 1.5 mm and 2.5 mm, or between 1.75 mm and 2.25 mm.

As shown in FIGS. 29A-D, in some embodiments, a portion of the articulating body 718 can extend or align with the opening 716 of the enclosing body. In some embodiments, the opening 716 is dimensioned, shaped, or otherwise configured to prevent removal of the articulating body 718 through the opening 716. For example, in some embodiments, at least some sections of the articulating body 718 are wider than the opening 716. In some embodiments, the superior end 708 can be shaped, dimensioned, or otherwise configured to prevent removal of the articulating body 718 from the enclosing body 706. For example, in some embodiments, a cross-section of the enclosing body 706 at or near the superior end 708 is narrower than a cross-section of at least a portion of the articulating body 718. In some embodiments, the enclosing body 706 can taper such that a cross-section of the enclosing body 706 is narrower at the superior end 708 or near the superior end 708 than at a more inferior segment of the enclosing body 706.

In some embodiments, the enclosing body 706 is shaped, dimensioned, or otherwise configured to circumferentially enclose the articulating surface 726 and the articulating surface 728. In some embodiments, the enclosing body 706 encloses an entire circumferential portion of the articulating body 718 that includes the articulating surface 726. In some embodiments, the liner 752 is shaped, dimensioned, or otherwise configured to circumferentially enclose the articulating surface 726 and the articulating surface 728. In some embodiments, the liner 752 encloses an entire circumferential portion of the articulating body 718 that includes the articulating surface 726.

FIGS. 29A, 29B, and 29E depict the articulating body 718 at a neutral position within the enclosing body 706. The neutral position can refer to a position in which the opening 749 and/or channel 746 of the articulating body 718 is aligned with the opening 743 and/or channel 744 of the enclosing body 706. In some embodiments, the neutral position is a mid-position between a superior-most articulating position and an inferior-most articulating position over which the articulating body 718 can move within the enclosing body 706. FIGS. 29C and 29F show the articulating body 718 at a position superior to the neutral position within the enclosing body 706. FIGS. 29D and 29G show the articulating body 718 at a position inferior to the neutral position within the enclosing body 706. As shown in FIG. 29A-D, the articulating body 718 can move along the axis 703 within the enclosing body while the plug 780 is positioned within the channel 744 of the enclosing body.

When the articulating body 718 is positioned within the enclosing body 706, the recess 760 receives the projection 756. In other words, the projection 756 is positioned within the recess 760. In some embodiments, the recess 760 and the projection 756 can have complementary shapes and/or dimensions. The recess 760 and/or projection 756 can be shaped, dimensioned, or otherwise configured to prevent relative rotation of the articulating body 718 within the enclosing body 706 when the projection 756 is received within the recess 760. The recess 760 and/or projection 756 can be shaped, dimensioned, or otherwise configured to allow relative movement between the articulating surface 726 and the articulating surface 728 along the axis 703. As shown in FIGS. 29A-C, the axis 703 can be generally aligned with a longitudinal axis of the recess 760. The recess 760 can be configured to move superiorly and inferiorly relative to the projection 756, and/or the projection 756 can be configured to move superiorly and inferiorly within the recess 760.

Although a single projection 756 and a single recess 760 are shown, any number of projections and recesses may be utilized to prevent relative rotation of the articulating body 718 within the enclosing body 706.

In some embodiments, the enclosing body 706 is configured to protect the surrounding anatomy from friction, damage, or infection due to the movement of components, including the articulating surface 726 and articulating surface 728 in the interior of the enclosing body 706, for example, by acting as a physical barrier. For example, the enclosing body 706 can protect an adjacent thecal sac and adjacent nerve roots from involvement with the articulating surfaces 726 and 728 during relative movement between the articulating surfaces 726 and 728. In some embodiments, the enclosing body 706 is configured to protect the components within the interior of the enclosing body 706 from damage, wear, or fibrosis due to the surrounding anatomy, for example, by acting as a physical barrier.

As shown in FIG. 30C, the articulating body 718 can include a tapered channel 770. The tapered channel 770 can be configured to receive the portion 768 of the attachment portion 720 to releasably or permanently couple the attachment portion 720 to the articulating body 718.

Figure 31A:
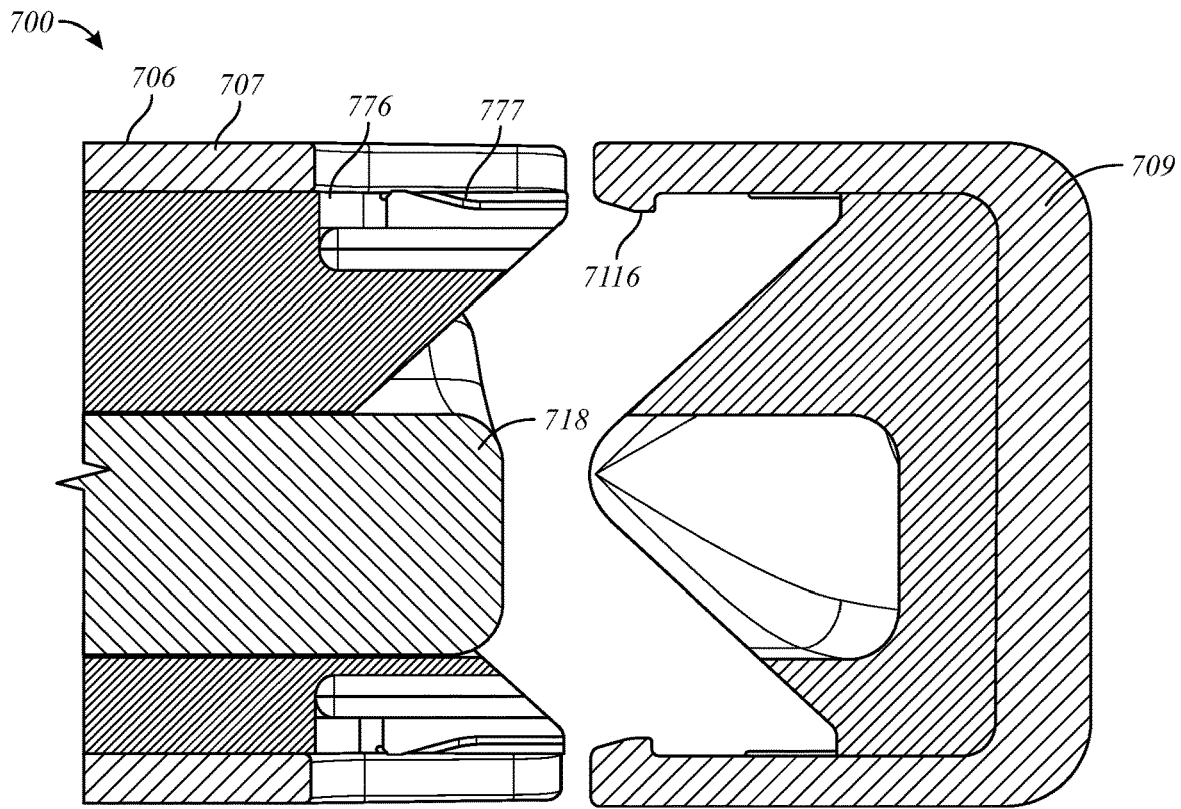
FIG. 31A depicts a cross-sectional view of the facet joint replacement device 700 showing the cap 709 separated from the main body 707.
Figure 31B:
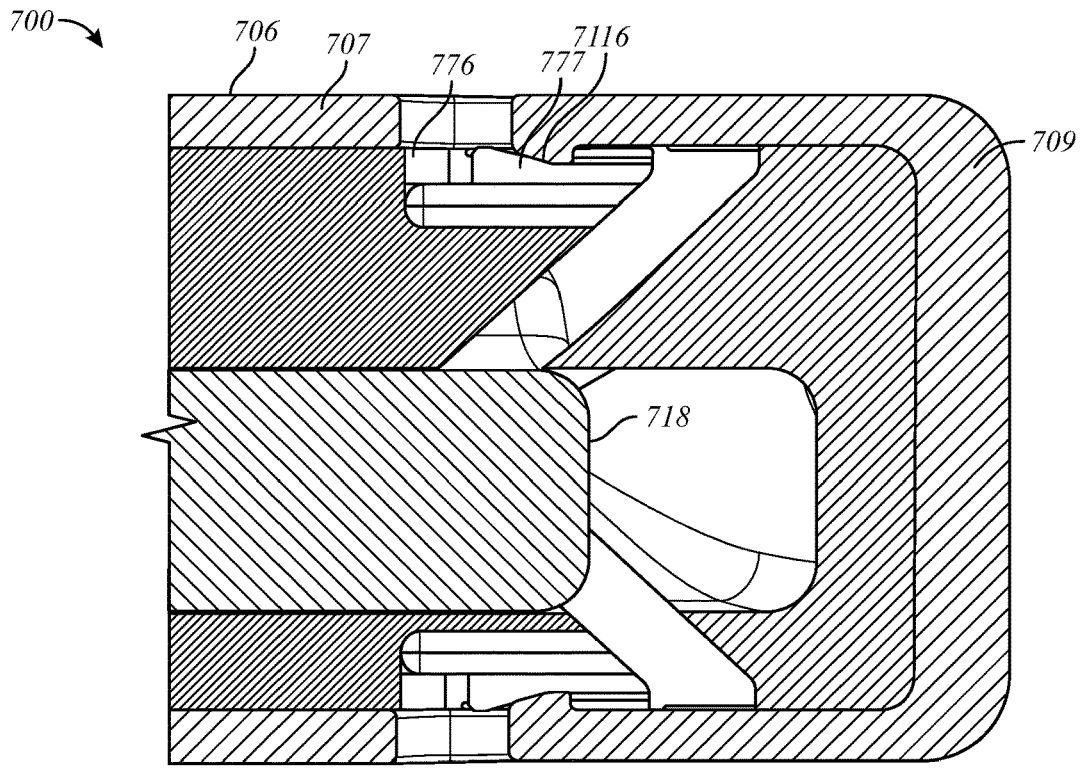
FIG. 31B depicts a cross-sectional view showing the cap 709 partially engaging the main body 707.
Figure 31C:
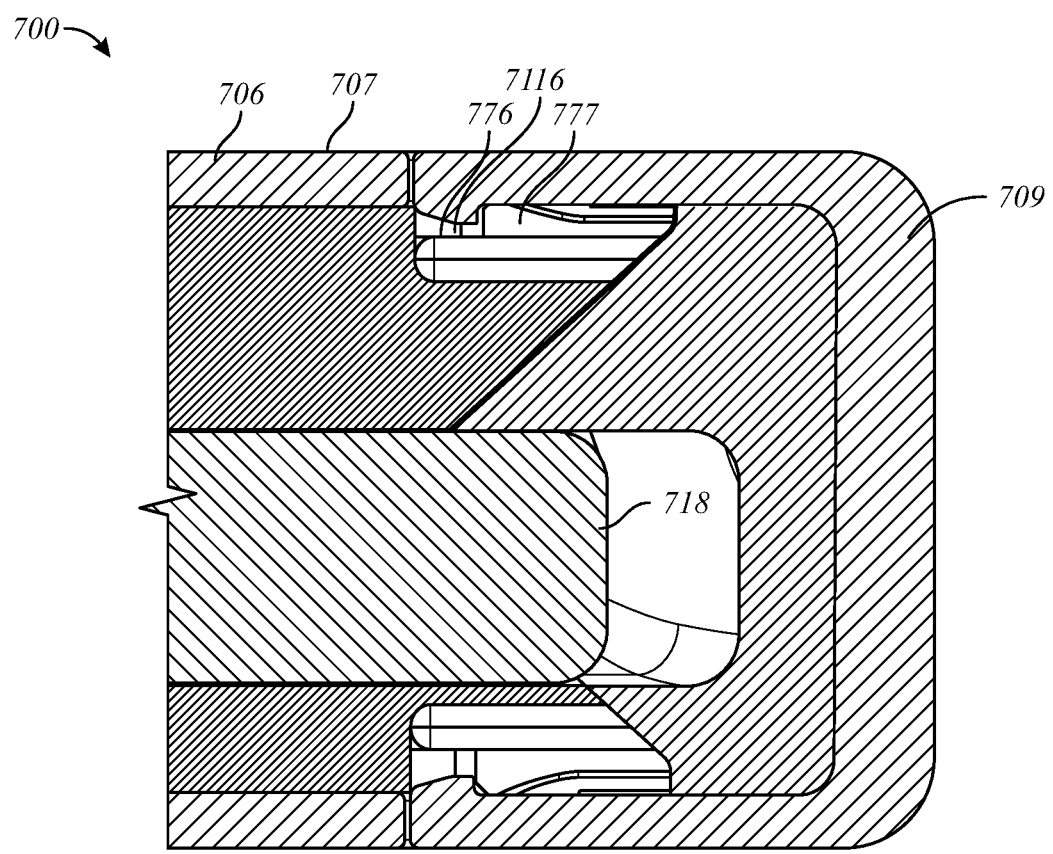
FIG. 31C depicts a cross-sectional view of the facet joint replacement device 700 showing the cap 709 coupled to the main body 707.

FIGS. 31A-C depict an example of stages of coupling the cap 709 to the main body 707 of the facet joint replacement device 700. FIG. 31A depicts a cross-sectional view of the facet joint replacement device 700 showing the cap 709 separated from the main body 707. FIG. 31B depicts a cross-sectional view showing the cap 709 partially engaging the main body 707. In FIG. 31B, the tabs 778 of the cap 709 are positioned in engagement with the ramps 777 of the main body 707. When the tabs 778 are engaged with the ramps 777, the cap 709 can be moved towards the main body 707 to cause the tabs 778 to engage the recesses 776. FIG. 31C depicts a cross-sectional view of the facet joint replacement device 700 showing the cap 709 coupled to the main body 707. As shown in FIG. 31C, the tabs 778 are engaged with the recesses 776.

Figure 31D:
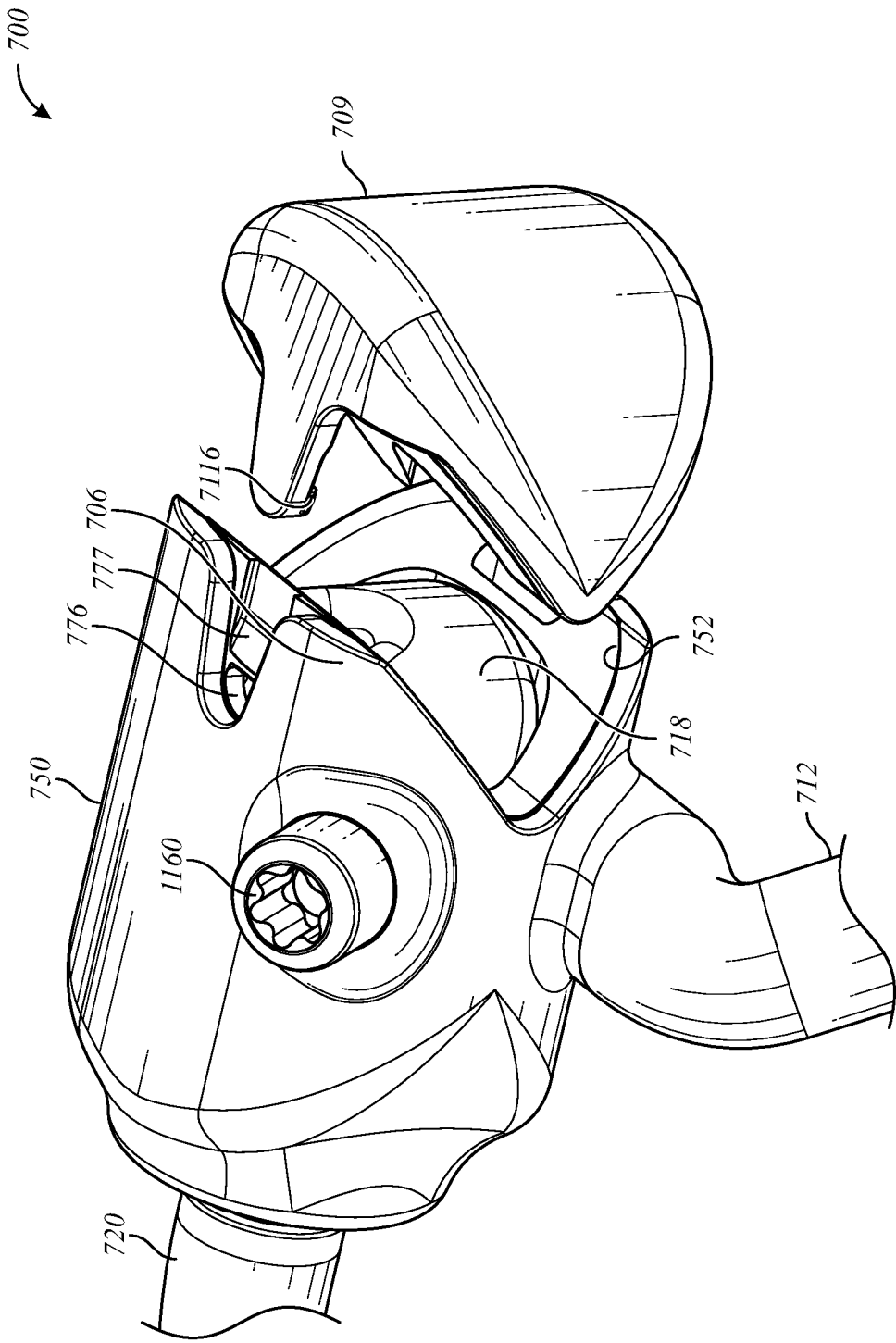
FIG. 31D depicts an exploded perspective view of the facet joint replacement device 700 showing the cap 709 separated from the main body 707.
Figure 31E:
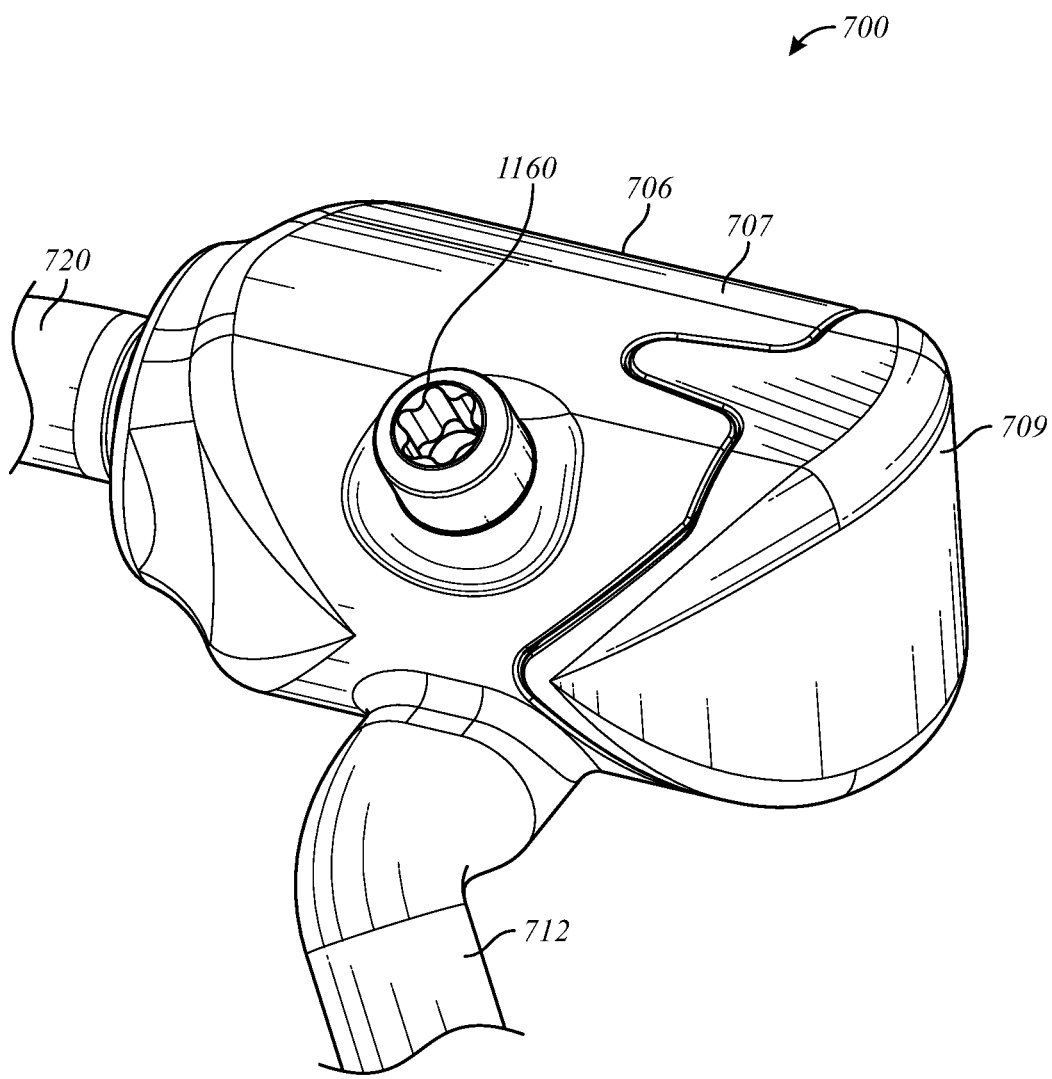
FIG. 31E depicts a perspective view of the facet joint replacement device 700 showing the cap 709 coupled to the main body 707.
Figure 31F:
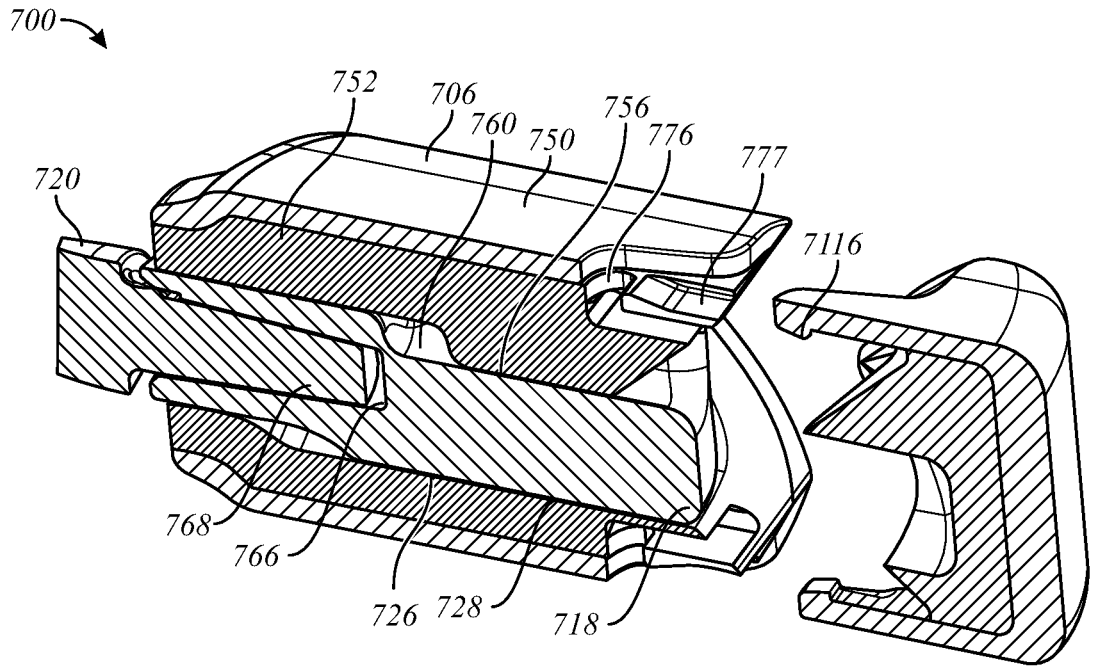
FIG. 31F depicts a cross-sectional perspective view of the facet joint replacement device 700 showing the cap 709 separated from the main body 707.
Figure 31G:
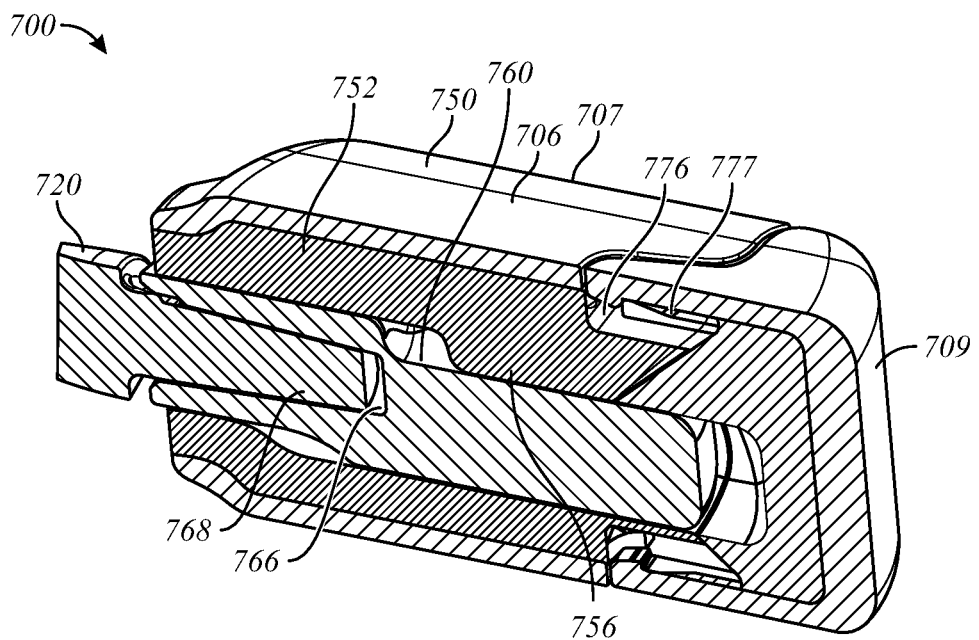
FIG. 31G depicts a cross-sectional perspective view of the facet joint replacement device 700 showing the cap 709 coupled to the main body 707.

FIG. 31D depicts an exploded perspective view of the facet joint replacement device 700 showing the cap 709 separated from the main body 707. FIG. 31E depicts a perspective view of the facet joint replacement device 700 showing the cap 709 coupled to the main body 707. FIG. 31F depicts a cross-sectional perspective view of the facet joint replacement device 700 showing the cap 709 separated from the main body 707. FIG. 31G depicts a cross-sectional perspective view of the facet joint replacement device 700 showing the cap 709 coupled to the main body 707.

FIGS. 32A-C depict a top perspective, bottom perspective, and front view of the fastener 740. As shown in FIGS. 32A-C, the fastener 740 can include an externally threaded portion 737, a generally cylindrical portion 739, and a tip 741.

In some embodiments, the fastener 740 is formed of or formed partially of one or more metals or metal alloys. For example, the fastener 740 can be formed of cobalt-chromium, titanium, titanium-based alloys, or any other suitable metals or metal alloys. In some embodiments, the fastener 740 can be ceramic or partially ceramic. In some embodiments, the fastener 740 can include super-hard ceramics.

Figure 32D:
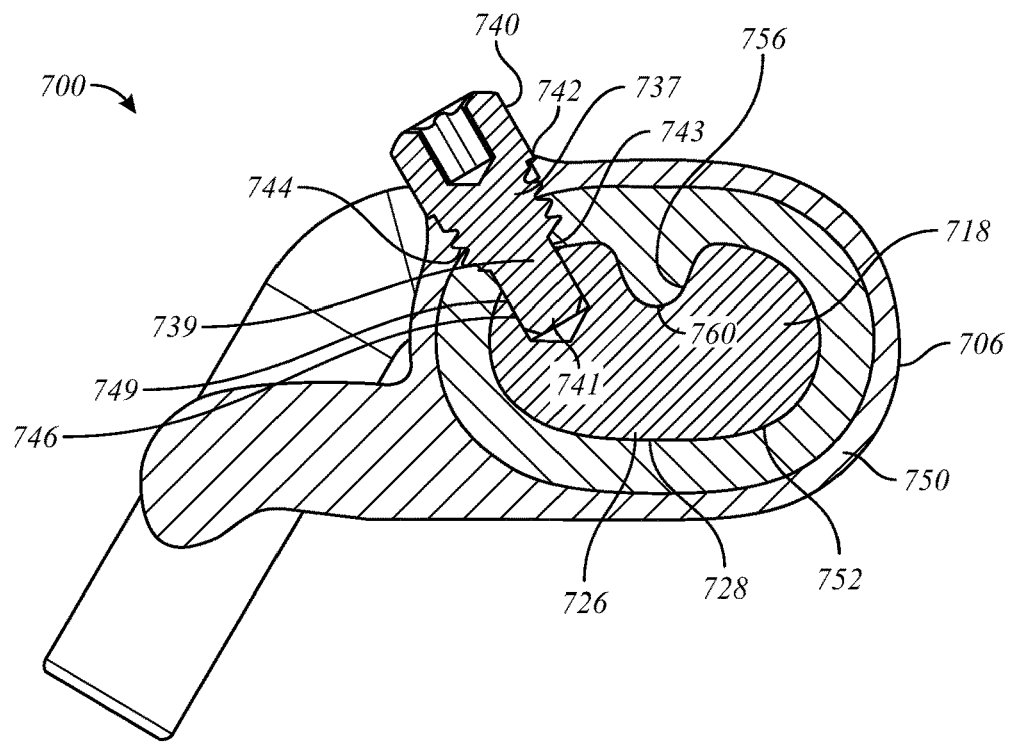
FIG. 32D depicts a cross-sectional view showing the fastener 740 positioned within the channels 744 and 746 of the enclosing body 706 and articulating element 718.
Figure 32E:
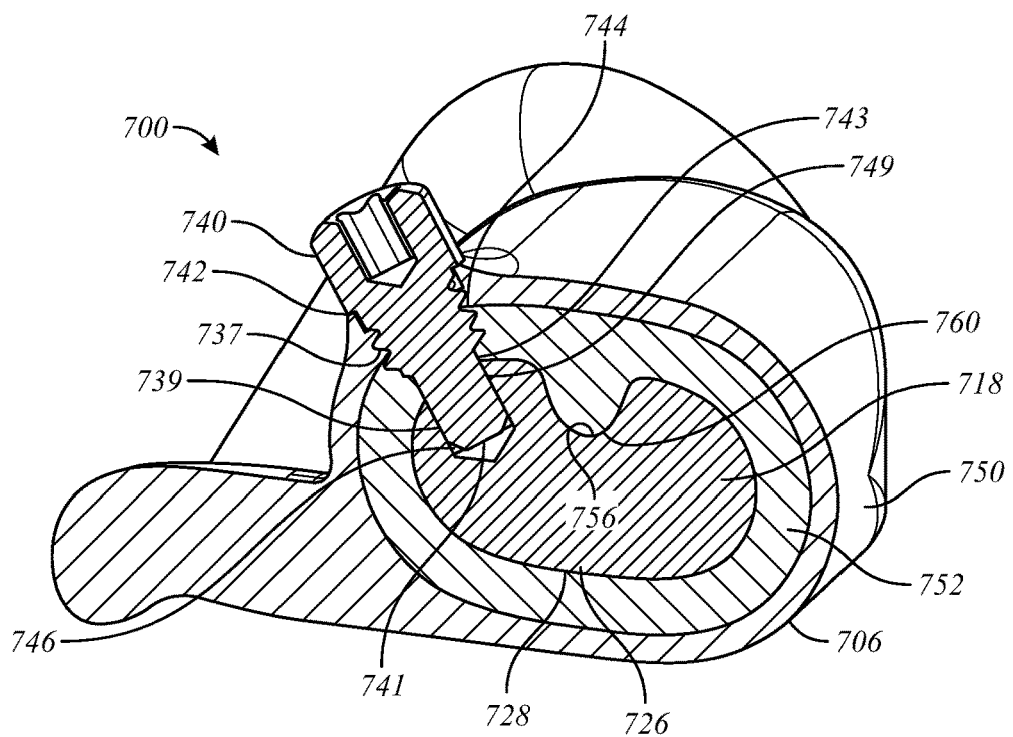
FIG. 32E depicts a perspective cross-sectional view showing the fastener 740 positioned within the channels 744 and 746 of the enclosing body 706 and articulating element 718.

FIGS. 32D and 32E illustrate a cross-sectional view and a perspective cross-sectional view, respectively, showing the fastener 740 positioned within the channels 744 and 746 of the enclosing body 706 and articulating element 718. As shown in FIGS. 32D and 32E, the externally threaded section 737 of the fastener 740 can removably secure to the internally threaded section 747 of the channel 744. In some embodiments, the externally threaded section 737 of the fastener 740 can removably secure to an internally threaded section of the channel 746. When positioned within the channels 744 and 746, the fastener 704 can prevent movement of the articulating body 718 relative to the enclosing body 706. When positioned within the channels 744 and 746, the fastener 744 can maintain the articulating body 718 at the neutral position within the channels 744 and 746.

Figure 33A:
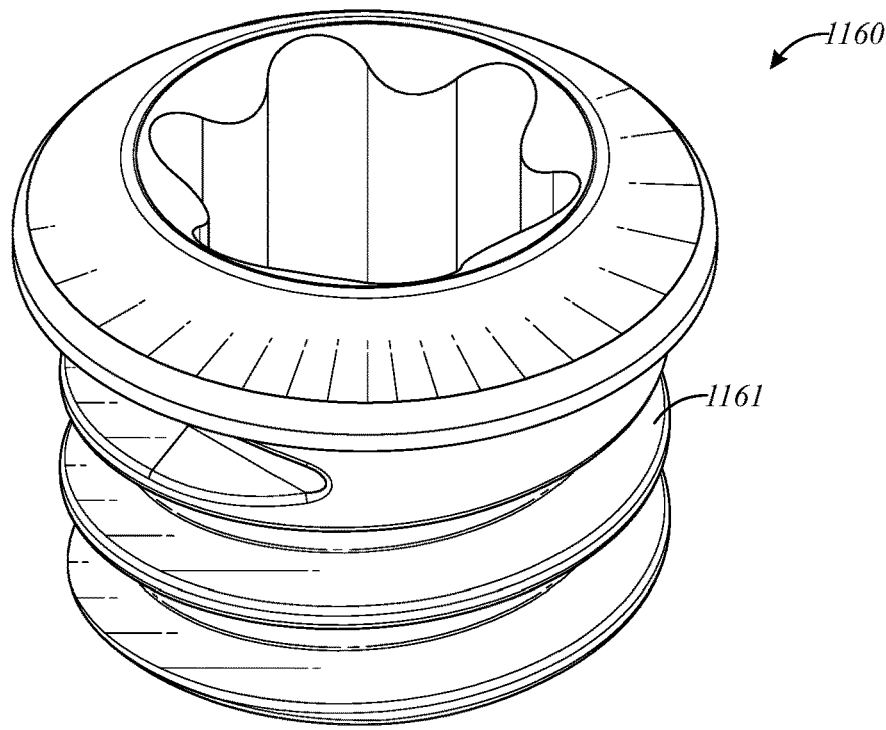
FIG. 33A depicts a top perspective view of the plug 780.
Figure 33B:
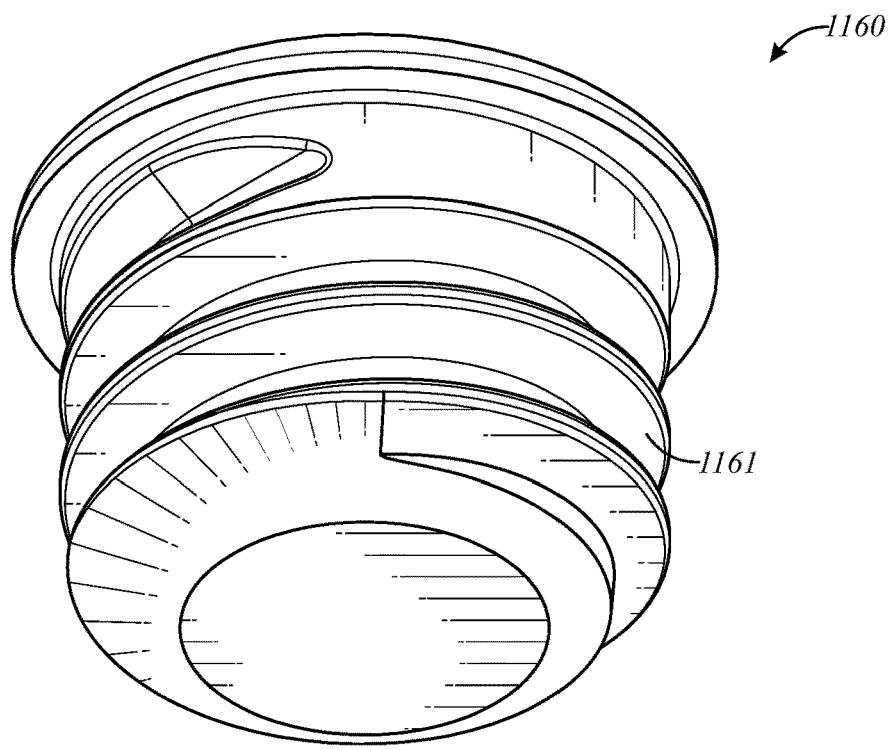
FIG. 33B depicts a bottom perspective view of the plug 780.

FIGS. 33A and 33B illustrate a top perspective view and a bottom perspective view, respectively of the plug 780. As shown in FIGS. 33A and 32B, the plug 780 can include an externally threaded section 781.

In some embodiments, the plug 780 is formed of or formed partially of one or more metals or metal alloys. For example, the plug 780 can be formed of cobalt-chromium, titanium, titanium-based alloys, or any other suitable metals or metal alloys. In some embodiments, the plug 780 can be ceramic or partially ceramic. In some embodiments, the plug 780 can include super-hard ceramics.

Figure 33C:
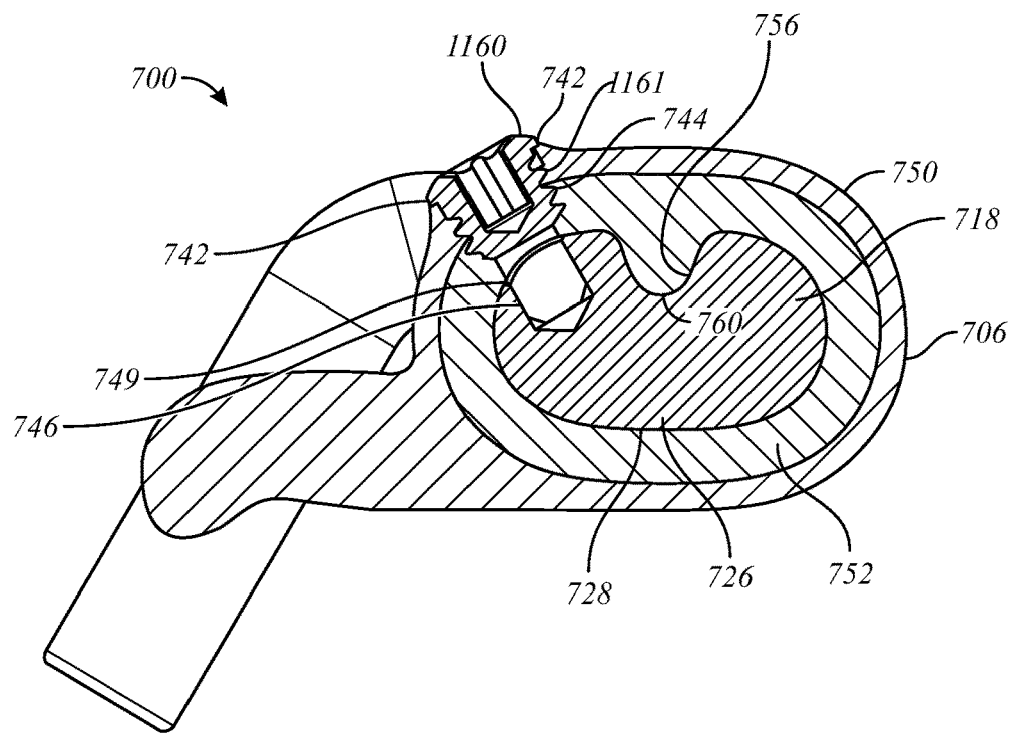
FIG. 33C depicts a cross-sectional view showing the plug 780 positioned within the channel 744.
Figure 33D:
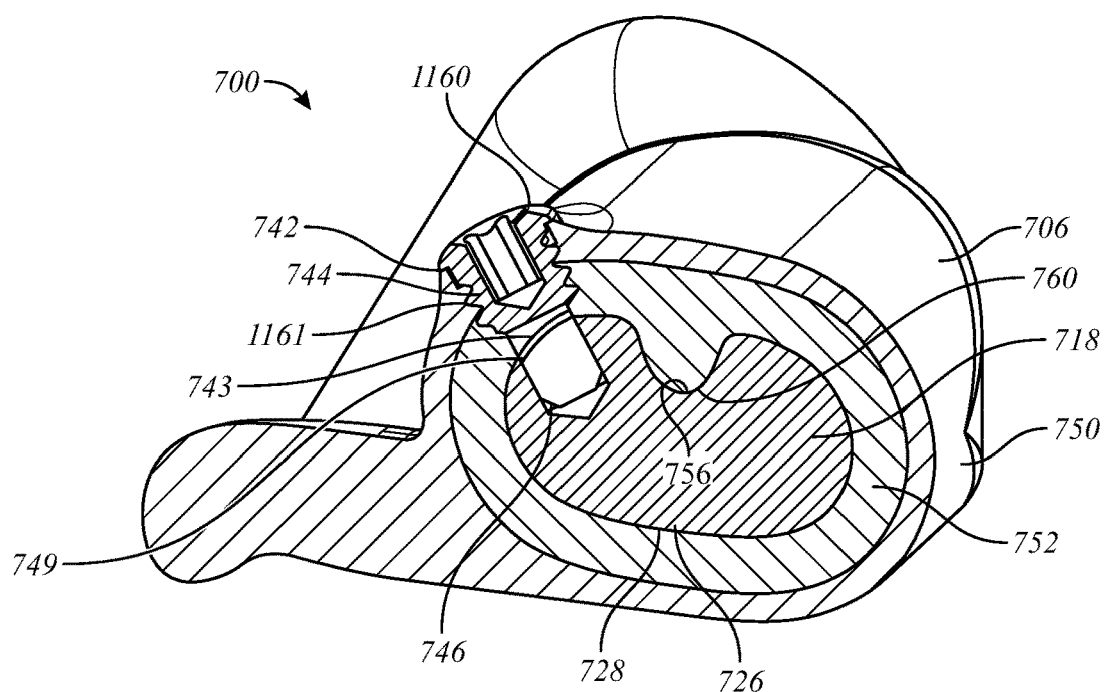
FIG. 33D depicts a perspective cross-sectional view showing the plug 780 positioned within the channel 744.

FIGS. 33C and 33D illustrate a cross-sectional view and a perspective cross-sectional view, respectively, showing the plug 780 positioned within the channel 744. As shown in FIGS. 33C and 33D, the externally threaded section 781 of the plug 780 can removably secure to the internally threaded section 747 of the channel 744. In some embodiments, the plug is shaped, dimensioned, or otherwise configured to extend through only a portion of the channel 744. The plug 780 can be dimensioned, shaped, or otherwise configured such that when the plug 780 is positioned within the facet joint replacement device 700, the plug 780 does not extend into the channel 746. When the plug 780 is positioned within the facet joint replacement device 700, the plug 780 does not restrict movement of the articulating body 718 within the enclosing body 706. In some embodiments, the plug 780 is shaped, dimensioned, or otherwise configured to fit flush with an exterior surface of the enclosing body 706.

When positioned within the enclosing body 706, the plug 780 can seal the opening 742 and/or channel 744 relative to the surrounding anatomy. By sealing the opening 742 and/or channel 744, the plug 780 can act as a physical barrier along with enclosing body 706 to protect the surrounding anatomy from friction, damage, or infection due to the movement of components, including the articulating surface 726 and articulating surface 728 in the interior of the enclosing body 706. For example, the enclosing body 706 and plug 780 can protect an adjacent thecal sac and adjacent nerve roots from involvement with the articulating surfaces 726 and 728 during relative movement between the articulating surfaces 726 and 728. In some embodiments, the plug 780 and enclosing body 706 are configured to protect the components within the interior of the enclosing body 706 from damage, wear, or fibrosis due to the surrounding anatomy, for example, by acting as a physical barrier.

FIGS. 34A-D depict a posterior view, a sagittal view, a bottom view, and a perspective view, respectively of a lumbar motion segment 200 with the facet joint replacement device 700 implanted. FIGS. 34A-D also depict a sagittal plane 802, a transverse plane 804, and a frontal plan 806.

The attachment member 720 is affixed to the pedicle 240 of the superior vertebra or superior vertebral body 205 by a fastener 874. The attachment member 712 is affixed to the pedicle 242 of the interior vertebra or inferior vertebral body 210 by a fastener 876. In alternative embodiments, an attachment member of an enclosing element 702, such as attachment member 712, can be secured to the superior vertebral body 205 and an attachment member of an articulating element 704, such as attachment member 720 can be secured to the inferior vertebral body 210. While the attachment member 720 of the articulating body 718 is shown extending superiorly from the opening 716 of the enclosing body 706 herein, in some embodiments the attachment member 720 can extend inferiorly from an opening at the inferior end 710 of the enclosing body 706.

Figure 34A:
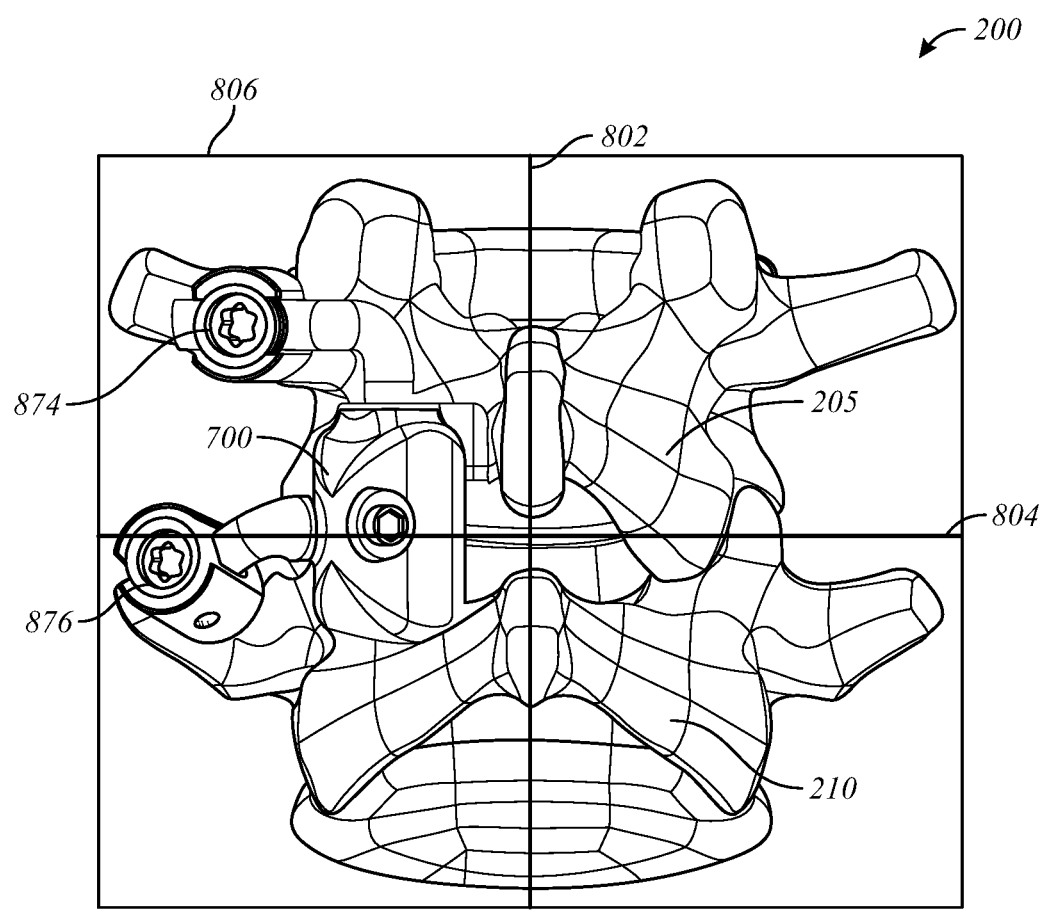
FIG. 34A depicts a posterior view of the lumbar motion segment 200 with the facet joint replacement device 700 implanted.
Figure 34B:
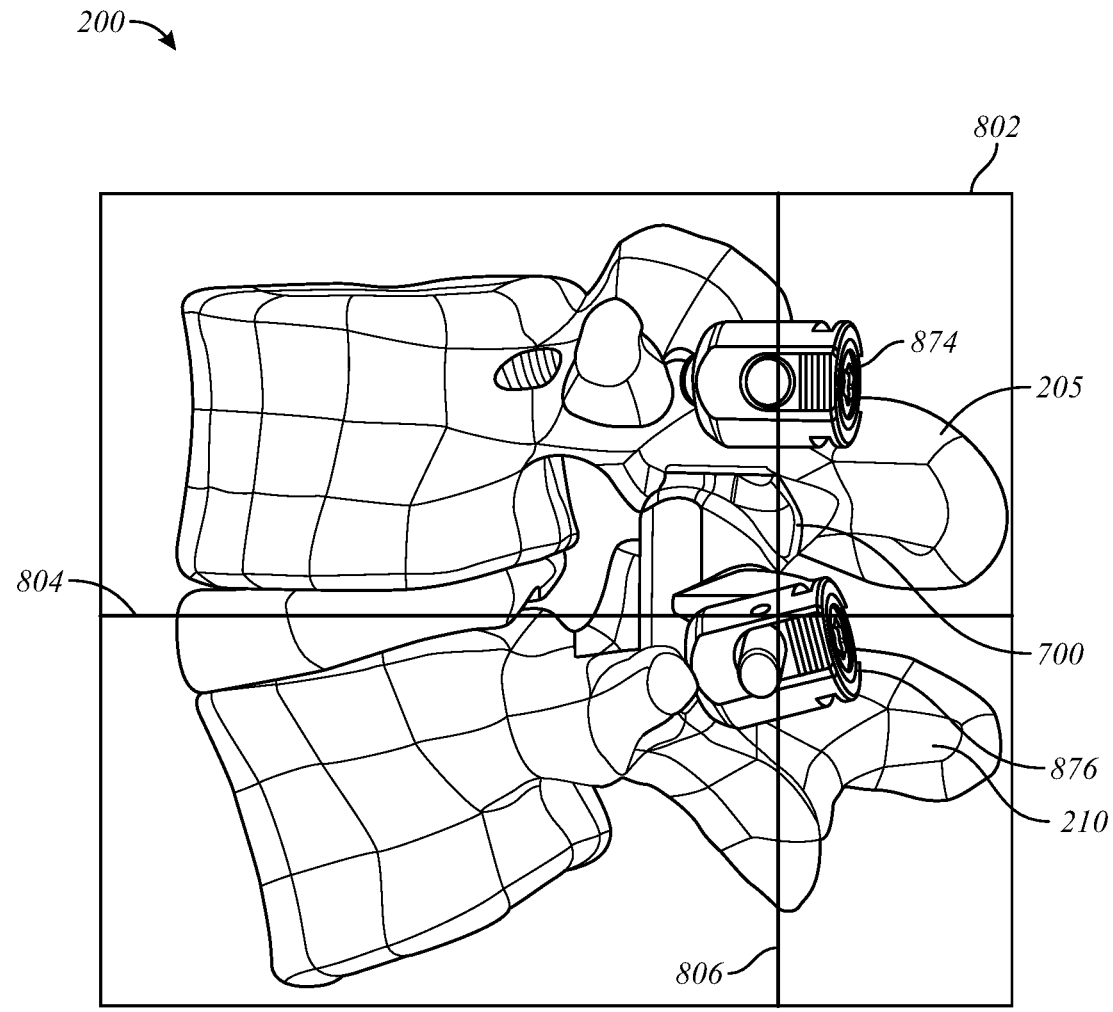
FIG. 34B depicts a sagittal view of the lumbar motion segment 200 with the facet joint replacement device 700 implanted.
Figure 34C:
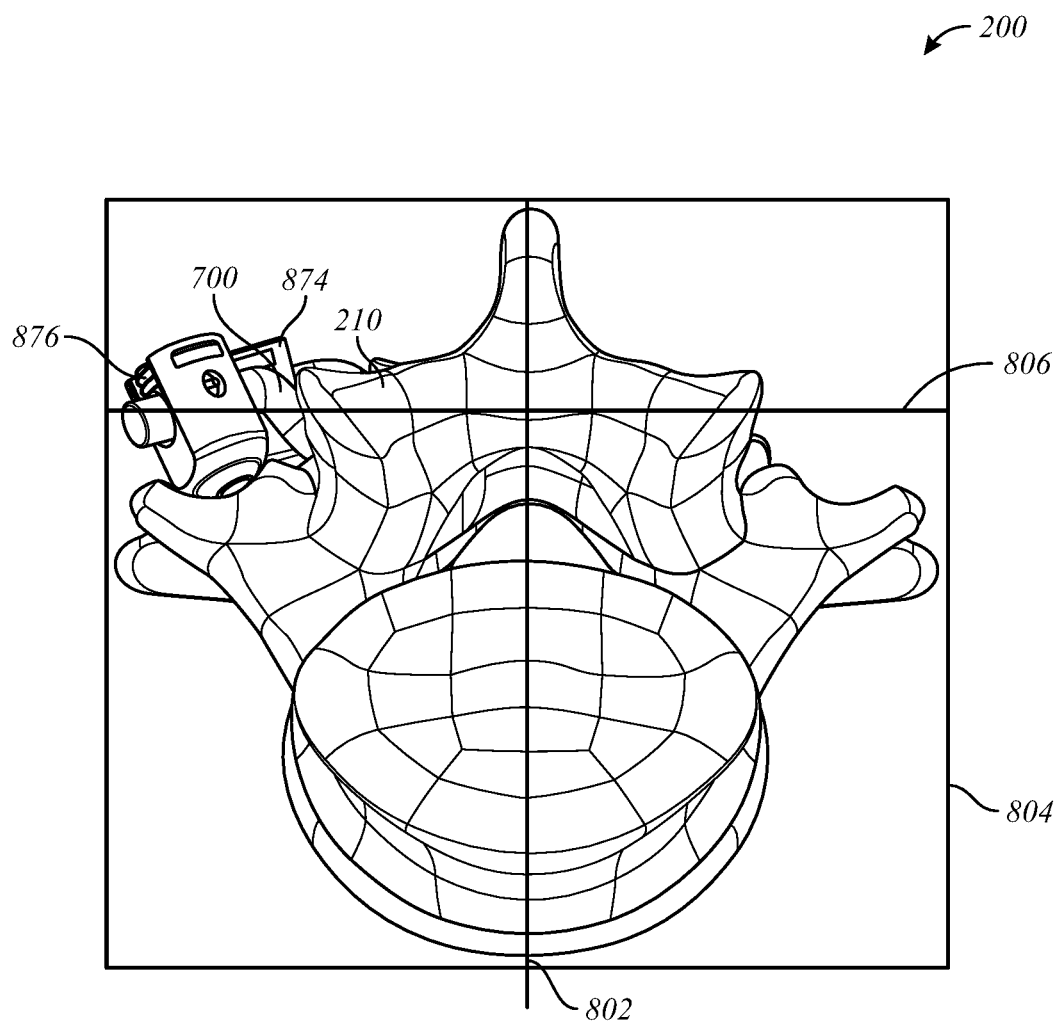
FIG. 34C depicts a bottom view of the lumbar motion segment 200 with the facet joint replacement device 700 implanted.
Figure 34D:
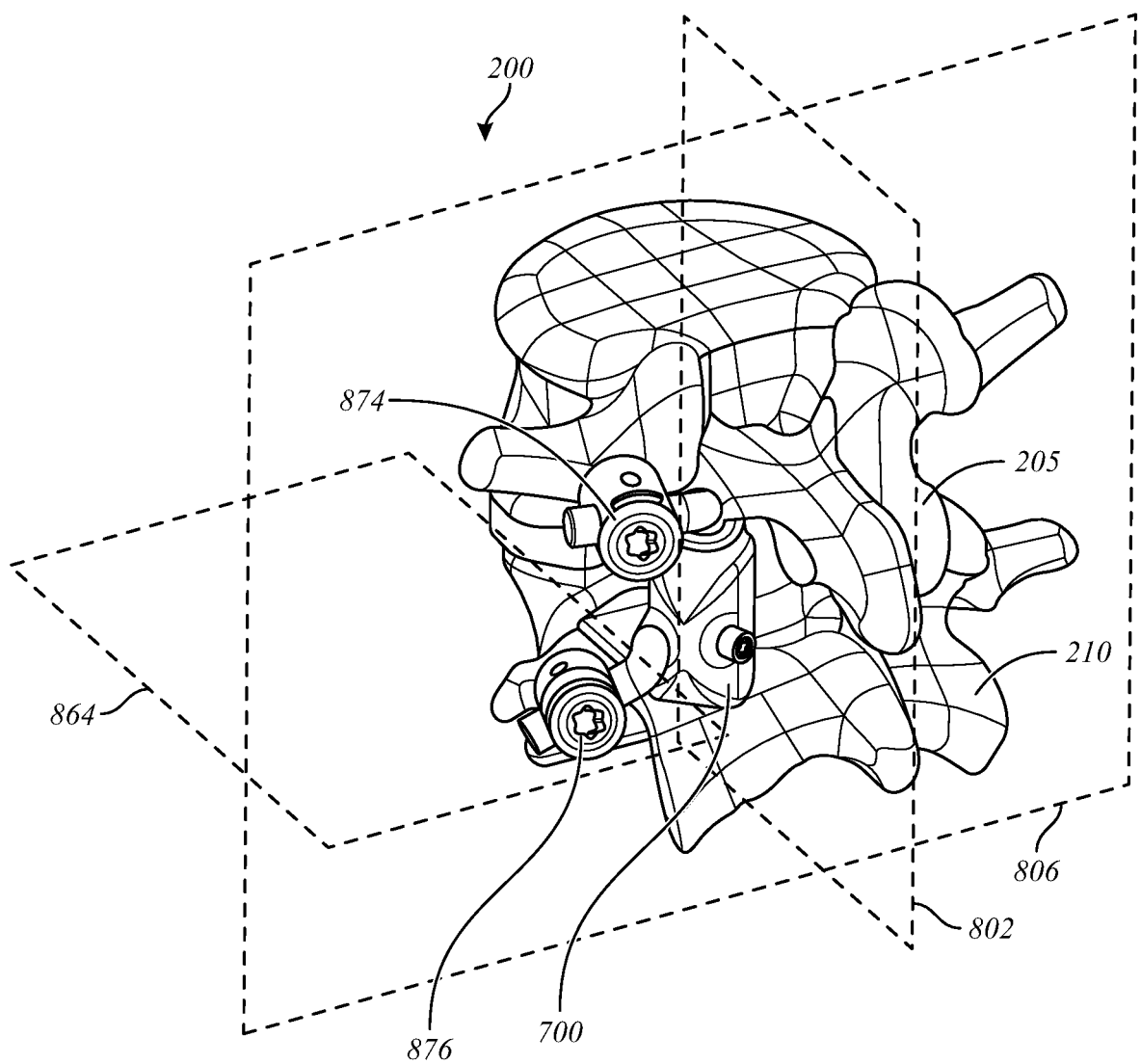
FIG. 34D depicts a perspective view of the lumbar motion segment 200 with the facet joint replacement device 700 implanted.
Figure 34E:
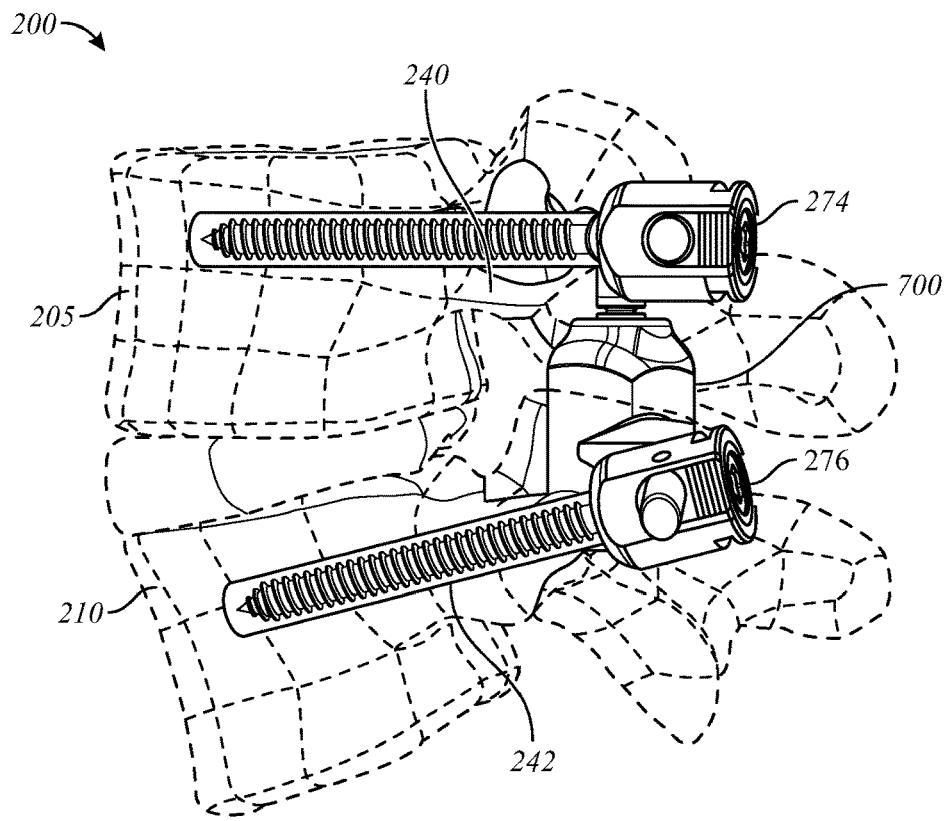
FIG. 34E depicts a sagittal view of the lumbar motion segment 200 with the facet joint replacement device 700 implanted showing the bone as transparent to illustrate components positioned within or obstructed by bone.
Figure 34F:
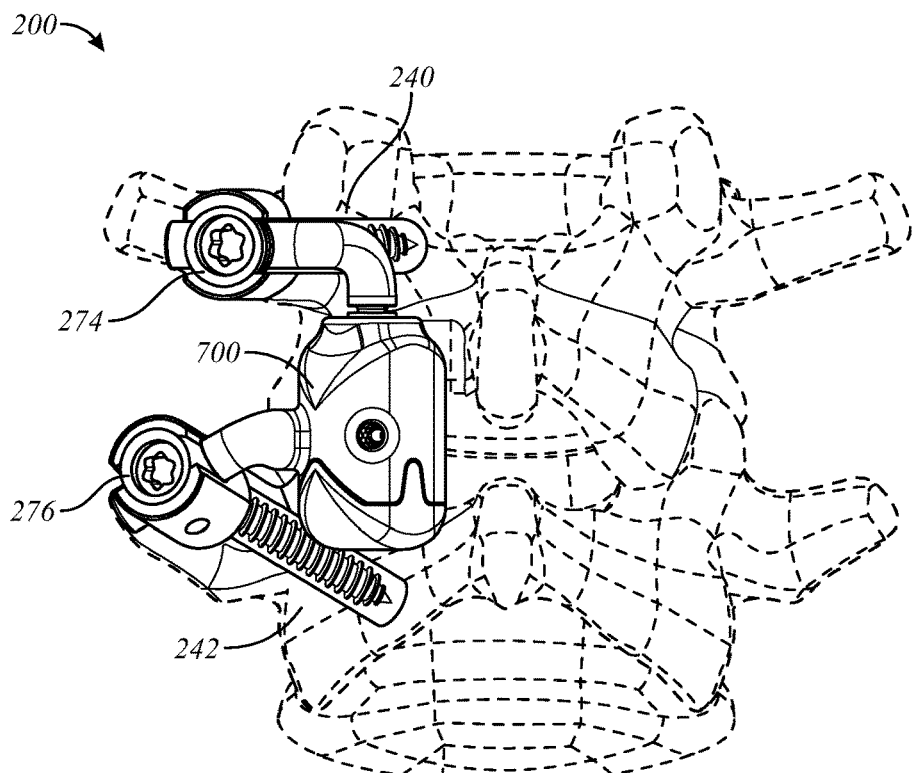
FIG. 34F depicts a posterior view of the lumbar motion segment 200 with the facet joint replacement device 700 implanted showing the bone as transparent to illustrate components positioned within or obstructed by bone.
Figure 34G:
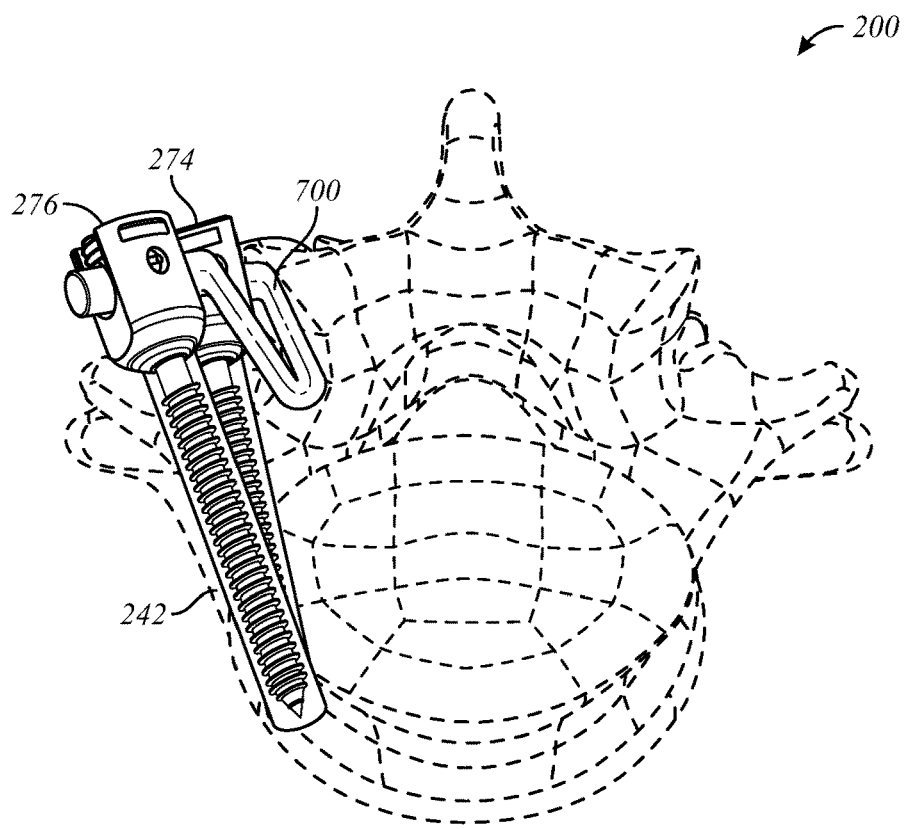
FIG. 34G depicts a bottom view of the lumbar motion segment 200 with the facet joint replacement device 700 implanted showing the bone as transparent to illustrate components positioned within or obstructed by bone.

As shown in FIGS. 34A-D, the fasteners 874 and 876 each include a tulip head bone screw and a top loading set screw. FIGS. 34E-G show the positioning of the tulip head bone screws of fasteners 874 and 876 within pedicles 240 and 242.

When the facet joint replacement device 700 is implanted, the articulating surface 726 can be shaped, dimensioned, or otherwise configured to face at least partially in an anterior and lateral direction. When the facet joint replacement device 700 is implanted, the articulating surface 726 can be shaped, dimensioned, or otherwise configured to face in a direction that corresponds to that of an inferior articular surface of a healthy facet joint. When the facet joint replacement device 700 is implanted, the articulating surface 728 can be shaped, dimensioned, or otherwise configured to face at least partially in a posterior and medial direction. When the facet joint replacement device 700 is implanted, the articulating surface 728 can be shaped, dimensioned, or otherwise configured to face in a direction that corresponds to that of a superior articular surface of a healthy facet joint. In some embodiments, when the facet joint replacement device 700 is implanted, the enclosing body 706 can be located at an anatomical location corresponding to that of a healthy facet joint. In some embodiments, when the attachment member 712 is fixed relative to the inferior vertebral body and the attachment member 720 is fixed relative to the superior vertebral body, the attachment member 712 and/or the attachment member 720 can be shaped, dimensioned, or otherwise configured to locate the articulating surfaces 726 and 728 at a location corresponding to the location of the articular surfaces within the a healthy facet joint.

FIGS. 34A-G show a unilateral implantation of a facet joint replacement device 700. One of skill in the art would understand that a facet joint replacement device, such as facet joint replacement device 700, can be implanted on either lateral side of a motion segment, or two facet joint replacement devices can be implanted bilaterally, one on each side of a particular motion segment, for example, as described with respect to FIG. 12. One of skill in the art would further understand that two facet joint replacement devices, such as facet joint replacement device 700, can be implanted ipsilaterally, as described with respect to FIG. 20.

As described herein, the components of the facet joint replacement device 700 can be shaped and/or dimensioned to correspond to the anatomy of a healthy facet joint and related spinal motion segment. While lumbar facet joints are shown and described herein, applications of the facet joint replacement device 700 are not limited to the lumbar spine. In some embodiments, the facet joint replacement device 700 can be shaped and/or dimensioned to correspond to the anatomy of the thoracic spine. In some embodiments, a vertical distance between the superior end 708 of the enclosing body and the inferior end 710 of the enclosing body is between 20 mm to 44 mm, between 24 mm to 40 mm, between 28 mm and 36 mm, or between 30 mm and 34 mm. In some embodiments a vertical distance between the superior end 708 of the enclosing body and the inferior end 710 of the enclosing body is 28 mm, 29 mm, 30 mm, 31 mm, 32 mm, 33 mm, 34 mm, 35 mm, or 36 mm. In some embodiments, the facet joint replacement device 700 can be shaped and/or dimensioned to correspond to the anatomy of the cervical spine.

In some embodiments, one or both of the articulating surface 728 and articulating surface 726 can have a major axis length of 10 mm, 11 mm, 12 mm, 13 mm, 14 mm, 15 mm, 16 mm, 17 mm, 18 mm, between 10 mm to 25 mm, between 9 to 14 mm, between 10 to 14 mm, or between 12 mm to 14 mm. In some embodiments, one or both of the articulating surface 128 and articulating surface 126 can have a minor axis length of 8 mm, 9 mm, 10 mm, 11 mm, 12 mm, 13 mm, 14 mm, 15 mm, 16 mm, 17 mm, 18 mm, between 8 mm to 25 mm, between 8 mm to 14 mm, between 9 mm to 14 mm, or between 12 mm to 14 mm.

Figure 35:
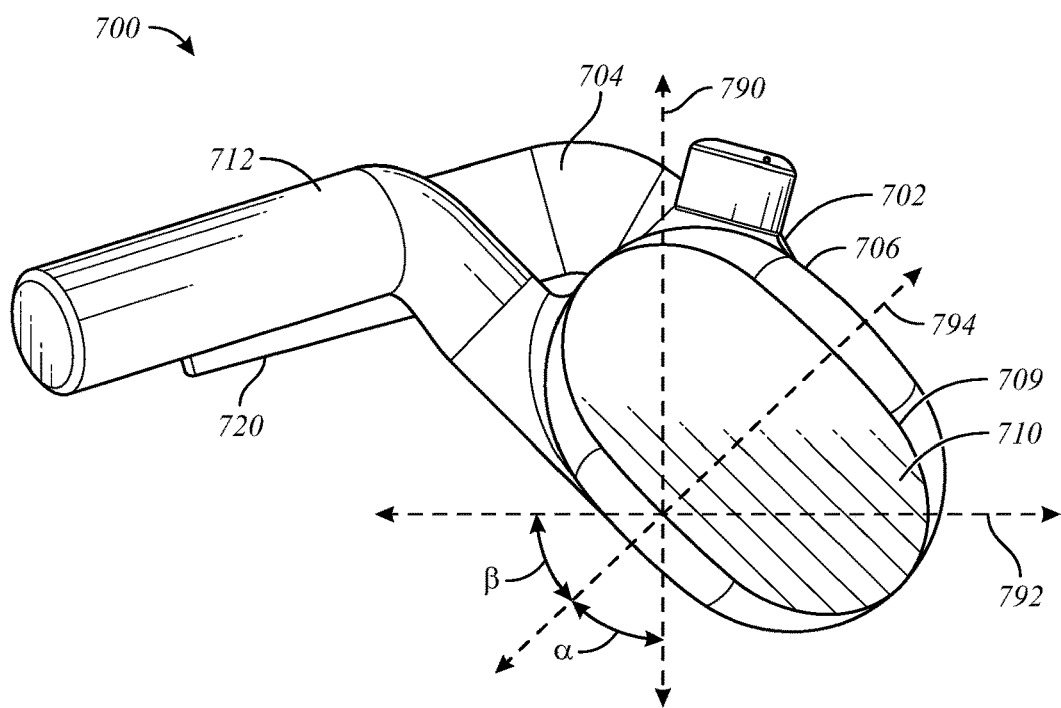
FIG. 35 depicts a bottom view of the facet joint replacement device 700.

FIG. 35 depicts a bottom view of the facet joint replacement device 700 showing an axis 790 parallel to a sagittal anatomic plane extending through a center point of the articulating surface 726, and axis 792 parallel to a frontal anatomic plane and extending through a center point of the articulating surface 726, and an axis 794 extending through the center point of the articulating surface 726 and perpendicular to a tangent of the articulating surface 726 at the center point. As shown in FIG. 35, an angle α extends between the axis 790 and the axis 794. An angle β extends between the axis 792 and 794. In some embodiments, the angle α can be between 30° and 60°, between 35° and 55°, between 40° and 50°, or any other suitable range. In some embodiments, the angle α can be 30°, 35°, 40°, 45°, 50°, 55°, 60°, or any other suitable angle. In some embodiments, the angle β can be between 30° and 60°, between 35° and 55°, between 40° and 50°, or any other suitable range. In some embodiments, the angle β can be 30°, 35°, 40°, 45°, 50°, 55°, 60°, or any other suitable angle. In some embodiments, an angle between an axis extending through the center point of the articulating surface 726 parallel to a transverse anatomic plane and the axis 794 can be between 75° and 105°, between 80° to 100°, between 85° to 95° or any other suitable angle. In some embodiments, an angle between an axis extending through the center point of the articulating surface 726 parallel to a transverse anatomic plane and the axis 794 can be 75°, 80°, 85°, 90°, 95°, 100°, 105° or any other suitable angle.

Similarly, in some embodiments, an angle between an axis parallel to a frontal anatomic plane and extending through a center point of the articulating surface 728 and an axis extending through the center point of the articulating surface 728 and perpendicular to a tangent of the articulating surface 728 at the center point can be between 30° and 60°, between 35° and 55°, between 40° and 50°, or any other suitable range. In some embodiments, an angle between an axis parallel to a frontal anatomic plane and extending through a center point of the articulating surface 728 and an axis extending through the center point of the articulating surface 728 and perpendicular to a tangent of the articulating surface 728 at the center point can be 30°, 35°, 40°, 45°, 50°, 55°, 60°, or any other suitable angle. In some embodiments, an angle between an axis parallel to a sagittal anatomic plane and extending through a center point of the articulating surface 728 and an axis extending through the center point of the articulating surface 728 and perpendicular to a tangent of the articulating surface 728 at the center point can be between 30° and 60°, between 35° and 55°, between 40° and 50°, or any other suitable range. In some embodiments, an angle between an axis parallel to a sagittal anatomic plane and extending through a center point of the articulating surface 728 and an axis extending through the center point of the articulating surface 728 and perpendicular to a tangent of the articulating surface 728 at the center point can be 30°, 35°, 40°, 45°, 50°, 55°, 60°, or any other suitable angle. In some embodiments, an angle between an axis parallel to a transverse anatomic plane and extending through a center point of the articulating surface 728 and an axis extending through the center point of the articulating surface 728 and perpendicular to a tangent of the articulating surface 728 at the center point can be between 75° and 105°, between 80° to 100°, between 85° to 95° or any other suitable angle. In some embodiments, an angle between an axis parallel to a transverse anatomic plane and extending through a center point of the articulating surface 728 and an axis extending through the center point of the articulating surface 728 and perpendicular to a tangent of the articulating surface 728 at the center point can be 75°, 80°, 85°, 90°, 95°, 100°, 105°, or any other suitable angle.

In some embodiments, the axis 703 can be perpendicular to a transverse anatomic plane. In some embodiments, the axis 703 can be parallel to a sagittal anatomic plane. In some embodiments, the axis 703 can be parallel to a frontal anatomic plane.

As described herein, in some embodiments, the implant 700 can be shaped and/or dimensioned to correspond to the anatomy of the lumbar spine, thoracic spine, or cervical spine.

In some embodiments, an angle between the transverse anatomic plane and a mean orientation of the articulating surface 726 can be between 0° and 98°, between 10° and 88°, between 20° and 78°, or any other suitable angle for a facet joint replacement device 700 implanted within the cervical spine. In some embodiments, an angle between the transverse anatomic plane and a mean orientation of the articulating surface 726 can be between 35° and 100°, between 45° and 90°, between 55° and 80°, or any other suitable angle for a facet joint replacement device 700 implanted within the thoracic spine. In some embodiments, an angle between the transverse anatomic plane and a mean orientation of the articulating surface 726 can be between 62° and 106°, between 72° and 96°, between 82° and 86°, or any other suitable angle for a facet joint replacement device 700 implanted within the lumbar spine. In some embodiments, the transverse anatomic plane may be referred to as the 0° transverse plane. In some embodiments, the foregoing angles between the transverse anatomic plane and a mean orientation of the articulating surface 726 may be referred to as inclination angles of the articulating surface 726 within the sagittal anatomic plane.

In some embodiments, an angle between the sagittal anatomic plane and a mean orientation of the articulating surface 726 can be between 50° and 116°, between 60° and 106°, between 70° and 96°, or any other suitable angle for a facet joint replacement device 700 implanted within the cervical spine. In some embodiments, an angle between the sagittal anatomic plane and a mean orientation of the articulating surface 726 can be between 65° and 140°, between 75° and 130°, between 85° and 120°, or any other suitable angle for a facet joint replacement device 700 implanted within the thoracic spine. In some embodiments, an angle between the sagittal anatomic plane and a mean orientation of the articulating surface 726 can be between 0° and ° 90, between 5° and 80°, between 15° and 70°, or any other suitable angle for a facet joint replacement device 700 implanted within the lumbar spine. In some embodiments, the sagittal anatomic plane may be referred to as the 0° sagittal plane. In some embodiments, the foregoing angles between the sagittal anatomic plane and a mean orientation of the articulating surface 726 may be referred to as inclination angles of the articulating surface 726 within the transverse anatomic plane.

In some embodiments, the articulating surface 726 can be configured to articulate relative to the articulating surface 728 by moving substantially only parallel to an axis defined by the inclination angles of the articulating surface 726 within the sagittal and transverse anatomic planes.

In some embodiments, an angle between the transverse anatomic plane and a mean orientation of the articulating surface 728 can be between 0° and 98°, between 10° and 88°, between 20° and 78°, or any other suitable angle for a facet joint replacement device 700 implanted within the cervical spine. In some embodiments, an angle between the transverse anatomic plane and a mean orientation of the articulating surface 728 can be between 35° and 100°, between 45° and 90°, between 55° and 80°, or any other suitable angle for a facet joint replacement device 700 implanted within the thoracic spine. In some embodiments, an angle between the transverse anatomic plane and a mean orientation of the articulating surface 728 can be between 62° and 106°, between 72° and 96°, between 82° and 86°, or any other suitable angle for a facet joint replacement device 700 implanted within the lumbar spine. In some embodiments, the transverse anatomic plane may be referred to as the 0° transverse plane. In some embodiments, the foregoing angles between the transverse anatomic plane and a mean orientation of the articulating surface 728 may be referred to as inclination angles of the articulating surface 728 within the sagittal anatomic plane.

In some embodiments, an angle between the sagittal anatomic plane and a mean orientation of the articulating surface 728 can be between 50° and 116°, between 60° and 106°, between 70° and 96°, or any other suitable angle for a facet joint replacement device 700 implanted within the cervical spine. In some embodiments, an angle between the sagittal anatomic plane and a mean orientation of the articulating surface 728 can be between 65° and 140°, between 75° and 130°, between 85° and 120°, or any other suitable angle for a facet joint replacement device 700 implanted within the thoracic spine. In some embodiments, an angle between the sagittal anatomic plane and a mean orientation of the articulating surface 728 can be between 0° and ° 90, between 5° and 80°, between 15° and 70°, or any other suitable angle for a facet joint replacement device 700 implanted within the lumbar spine. In some embodiments, the sagittal anatomic plane may be referred to as the 0° sagittal plane. In some embodiments, the foregoing angles between the sagittal anatomic plane and a mean orientation of the articulating surface 728 may be referred to as inclination angles of the articulating surface 728 within the transverse anatomic plane.

In some embodiments, the articulating surface 728 can be configured to articulate relative to the articulating surface 726 by moving substantially only parallel to an axis defined by the inclination angles of the articulating surface 728 within the sagittal and transverse anatomic planes.

FIGS. 36A-J depict a facet joint replacement device 900 according to one embodiment. With the exception of the differences described herein, the facet joint replacement device 900 and the components thereof can have any of the same or similar features or functions as the facet joint replacement device 700.

FIGS. 36A-D depict perspective views of the facet joint replacement device 900. FIGS. 36A-D also includes three-dimensional coordinate axes indicating the superior ("S"), inferior ("I"), anterior ("A"), posterior ("P"), medial ("M"), and lateral ("L") directions. As described herein, the terms superior, inferior, anterior, posterior, medial, and lateral, when describing portions of the devices herein, refer to portions of the device as they are intended to be oriented with respect to the human spine.

Figure 36A:
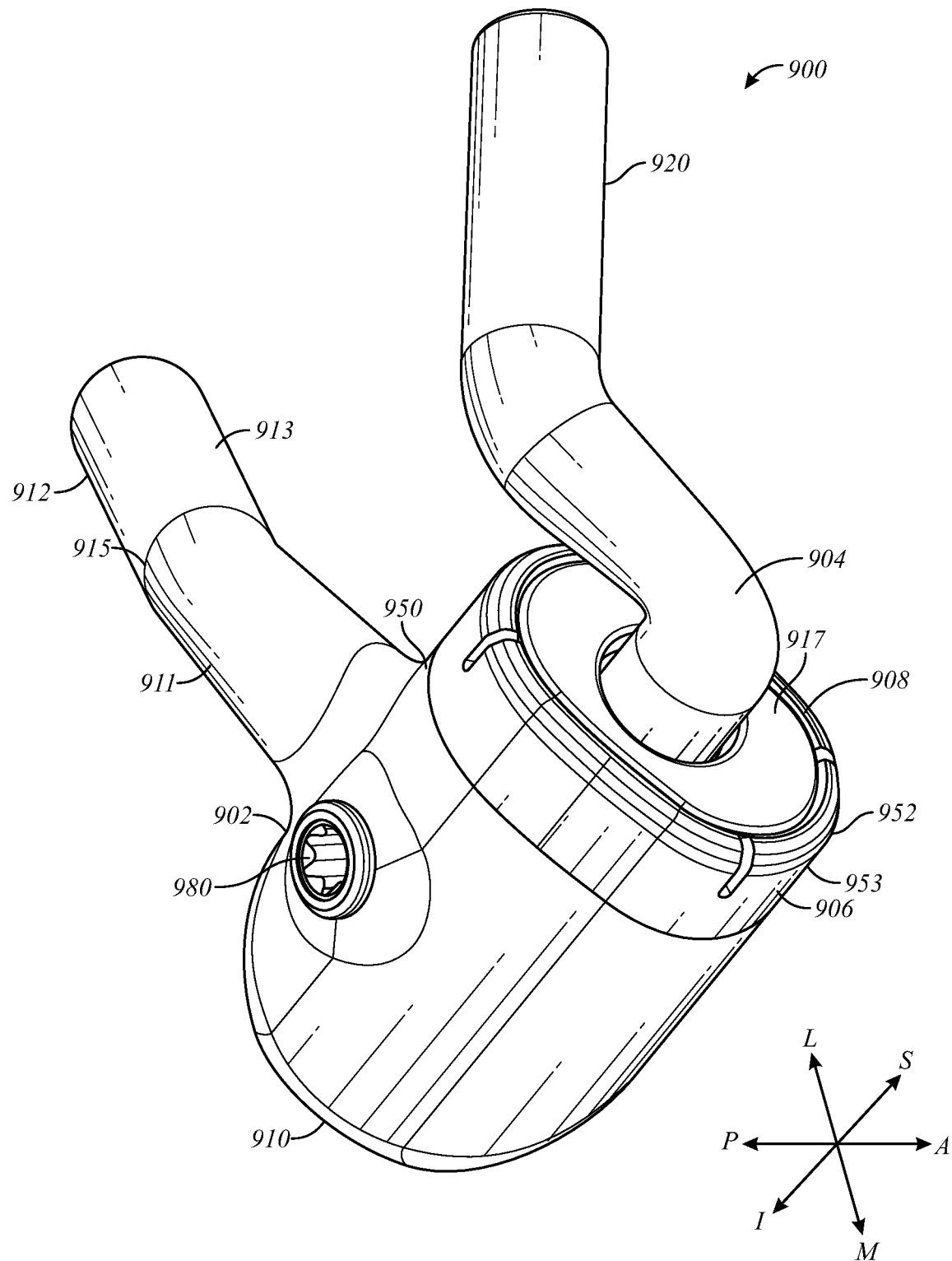
FIG. 36A depicts a top posterior perspective view of a facet joint replacement device 900.
Figure 36B:
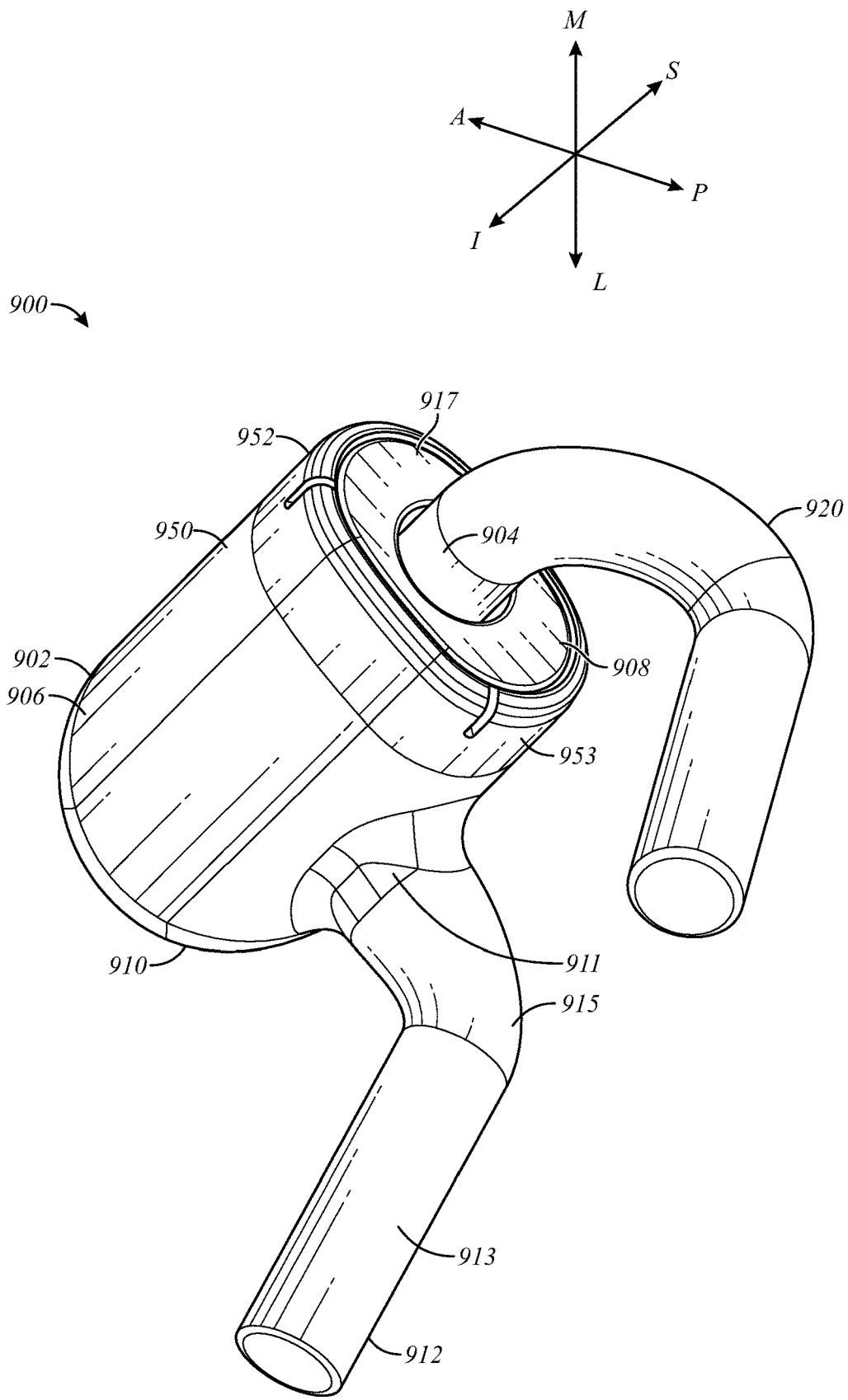
FIG. 36B depicts a top anterior perspective view of the facet joint replacement device 900.
Figure 36C:
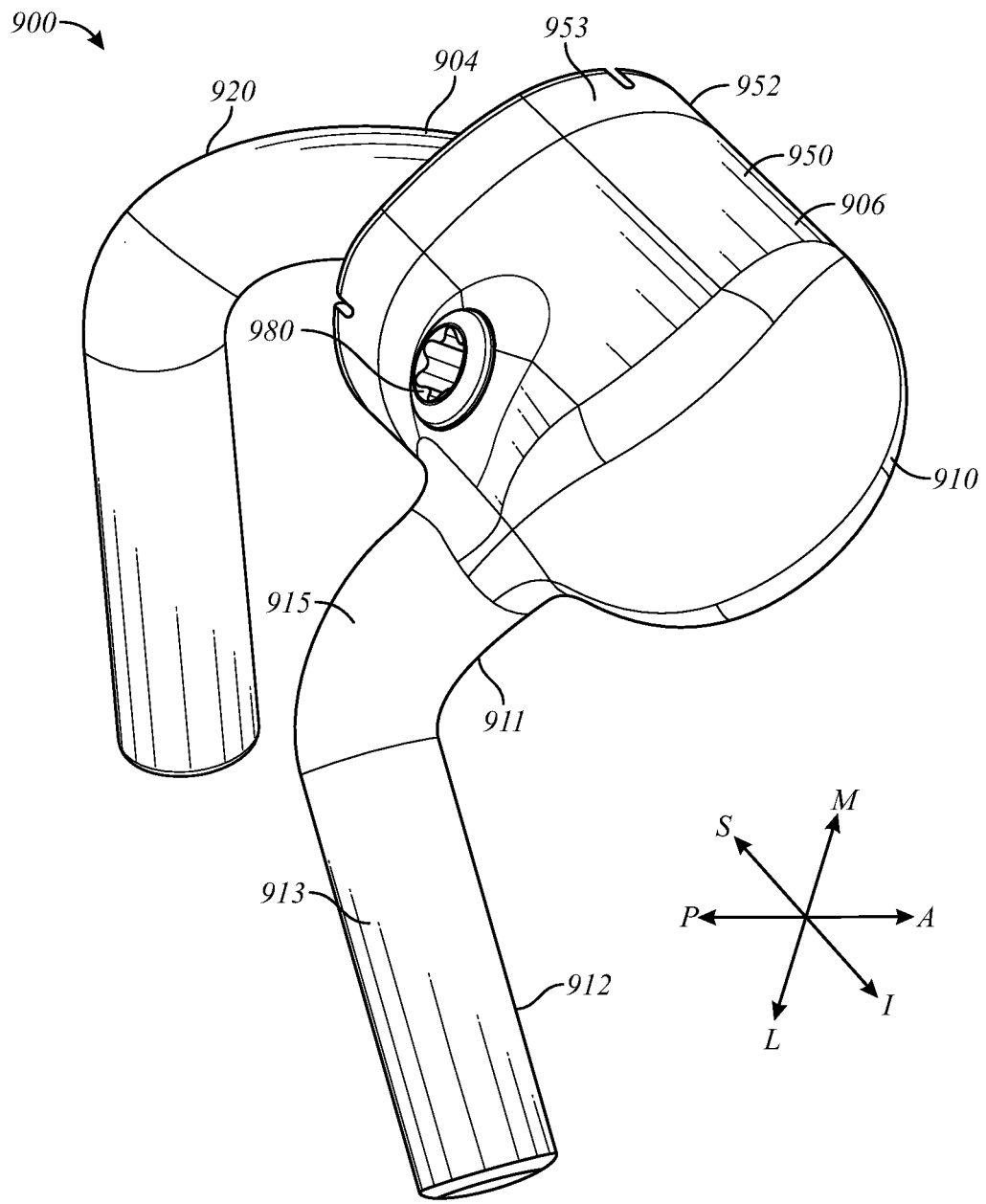
FIG. 36C depicts a bottom posterior perspective view of the facet joint replacement device 900.
Figure 36D:
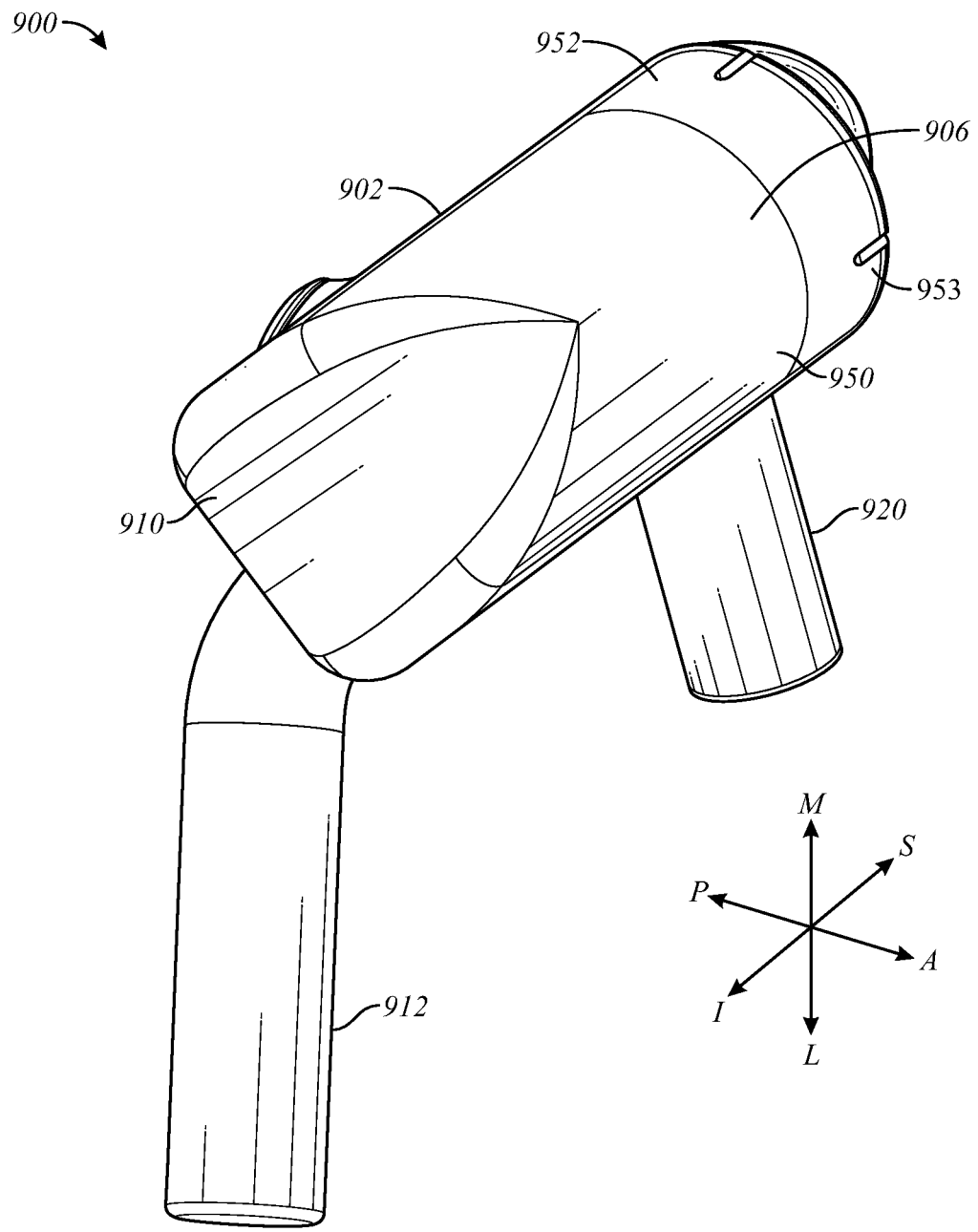
FIG. 36D depicts a bottom medial perspective view of the facet joint replacement device 900.

FIG. 36A depicts a top posterior perspective view of the facet joint replacement device 900. FIG. 36B depicts a top anterior perspective view of the facet joint replacement device 900. FIG. 36C depicts a bottom posterior perspective view of the facet joint replacement device 900. FIG. 36D depicts a bottom anterior perspective view of the facet joint replacement device 900.

Figure 36E:
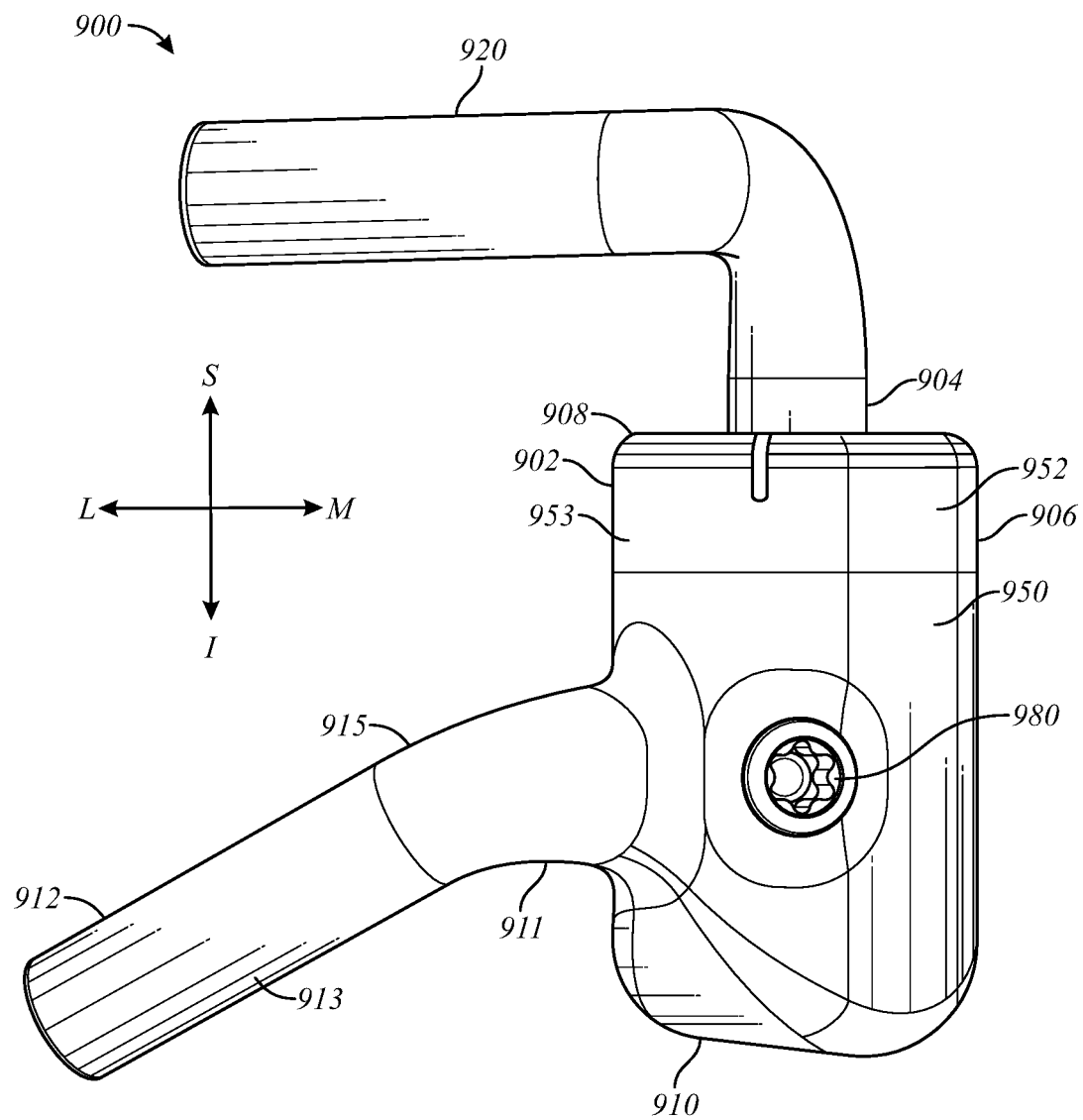
FIG. 36E depicts a posterior view of the facet joint replacement device 900.
Figure 36F:
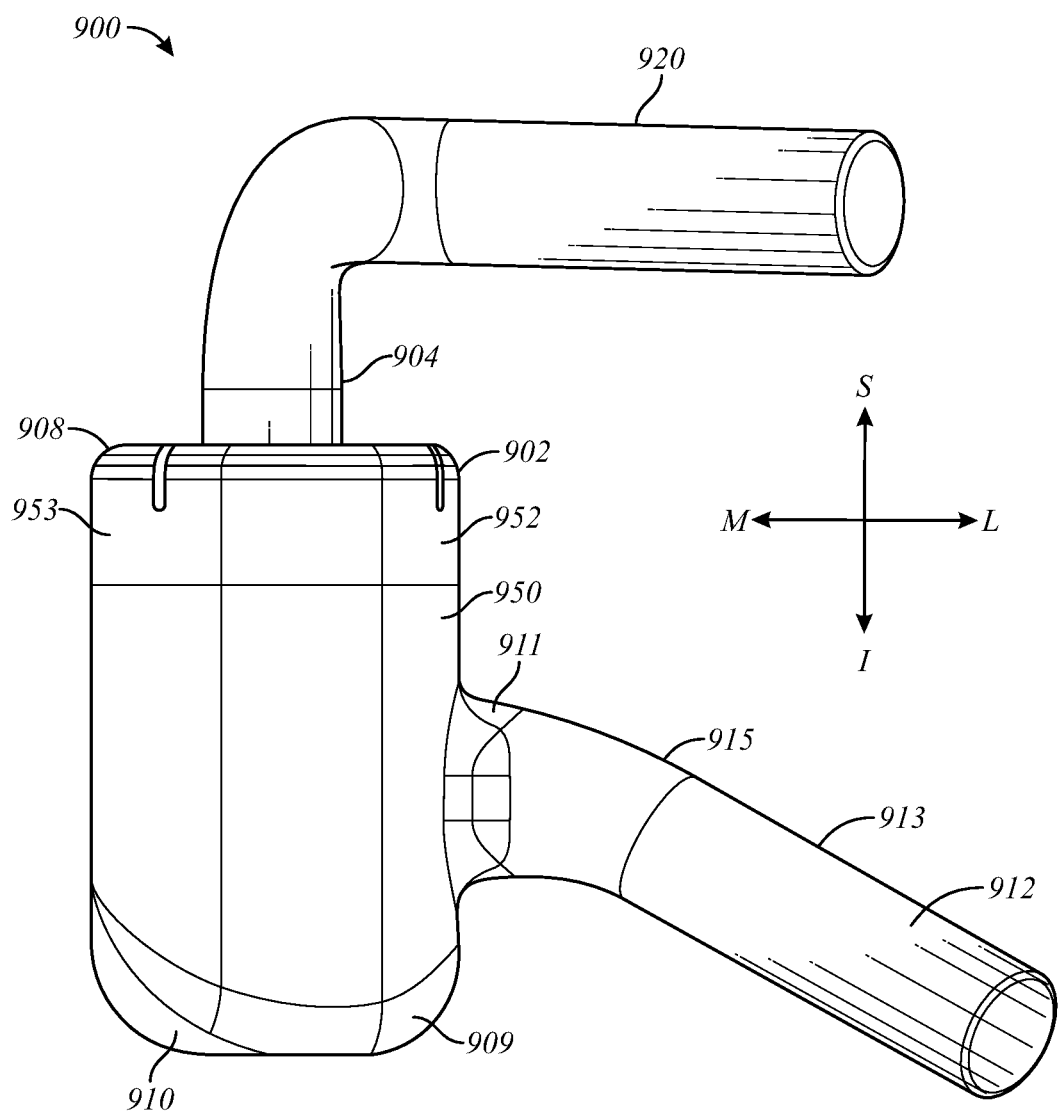
FIG. 36F depicts an anterior view of the facet joint replacement device 900.
Figure 36G:
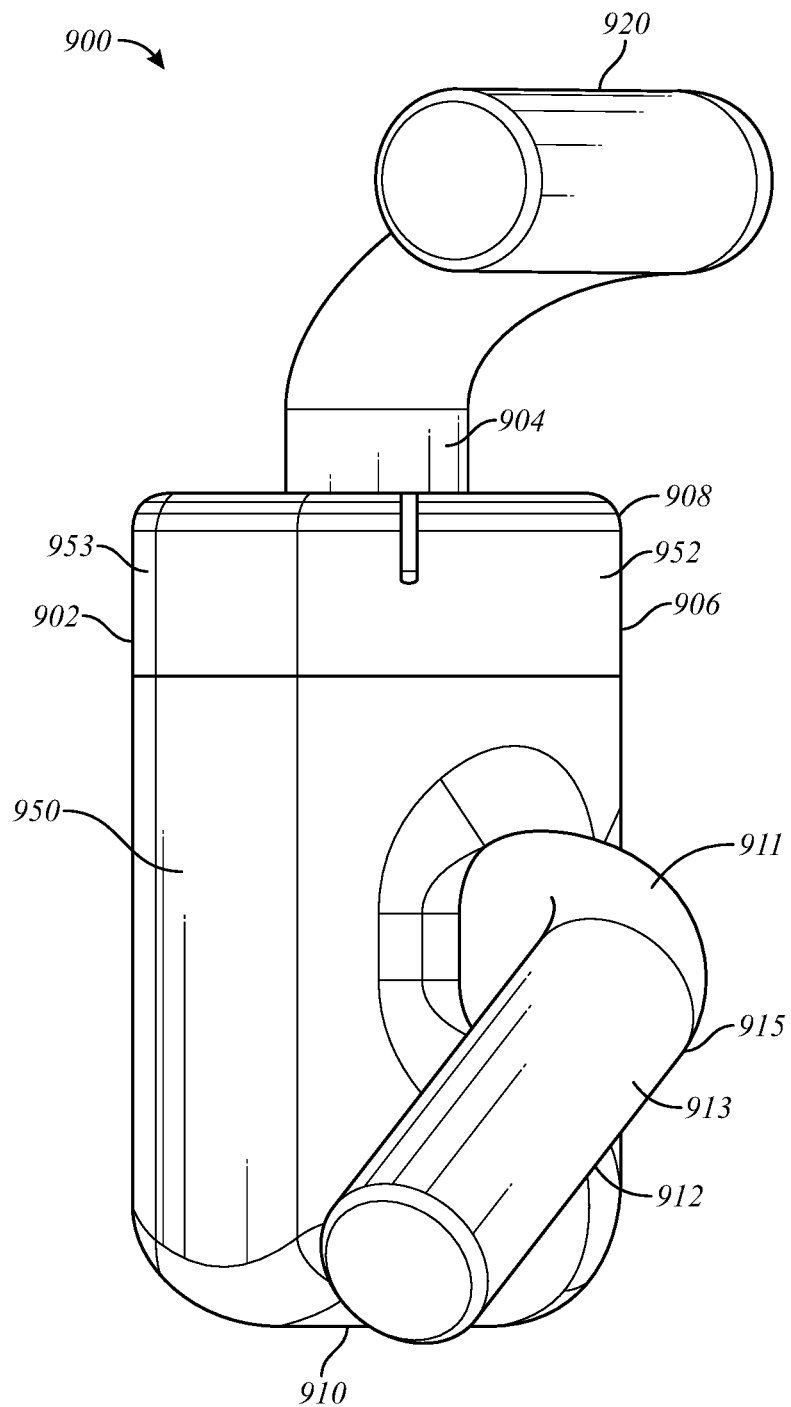
FIG. 36G depicts a first sagittal view of a lateral side of the facet joint replacement device 900.
Figure 36H:
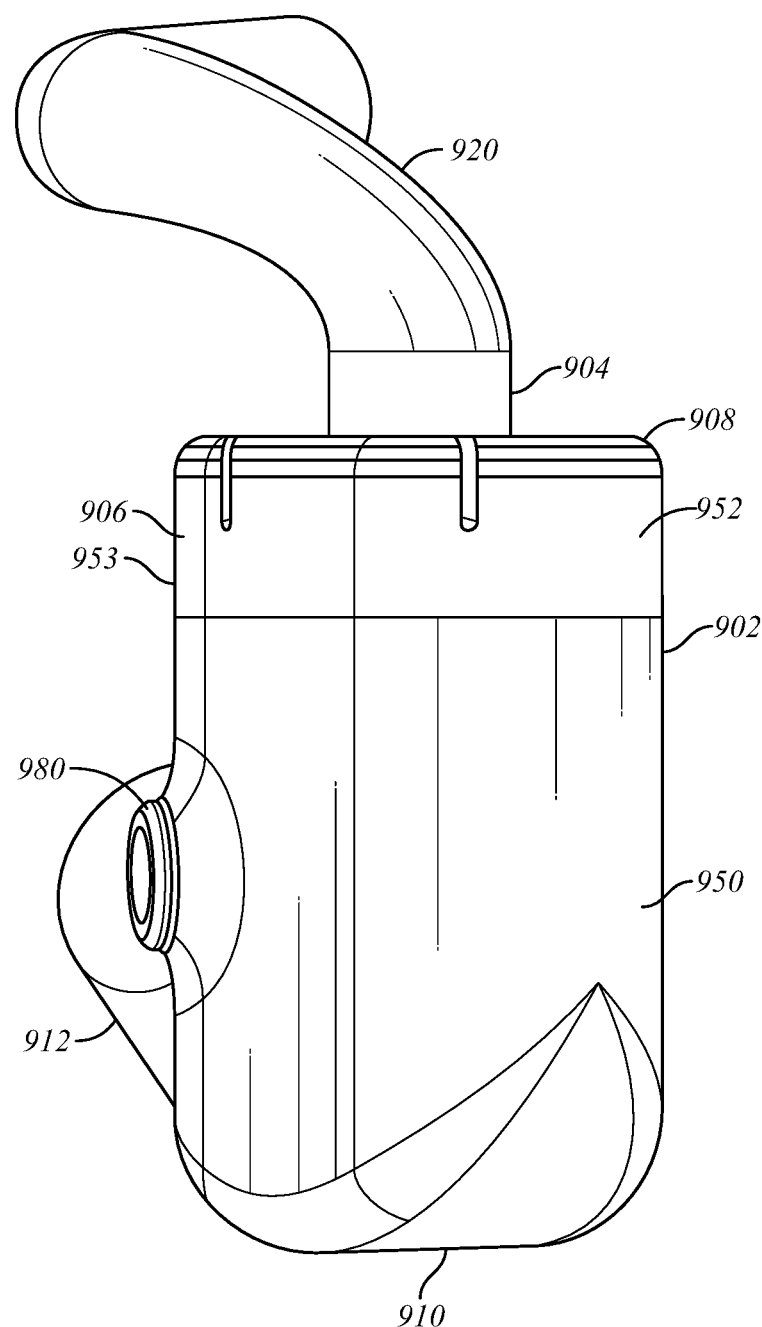
FIG. 36H depicts a second sagittal view of a medial side of the facet joint replacement device 900.
Figure 36I:
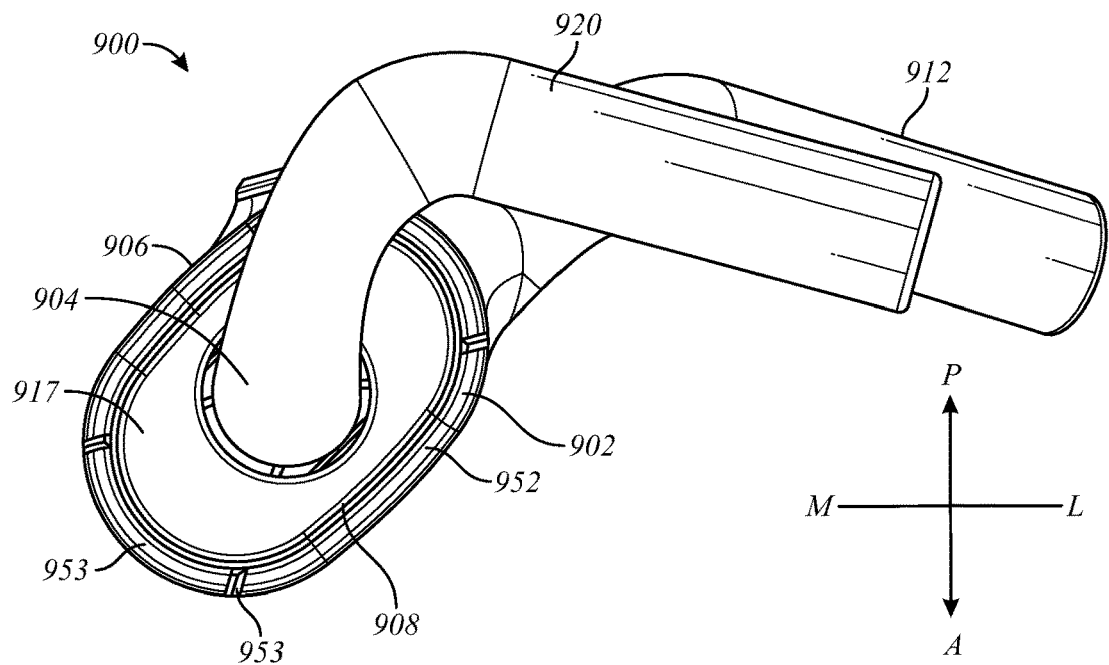
FIG. 36I depicts a top view of the facet joint replacement device 900.
Figure 36J:
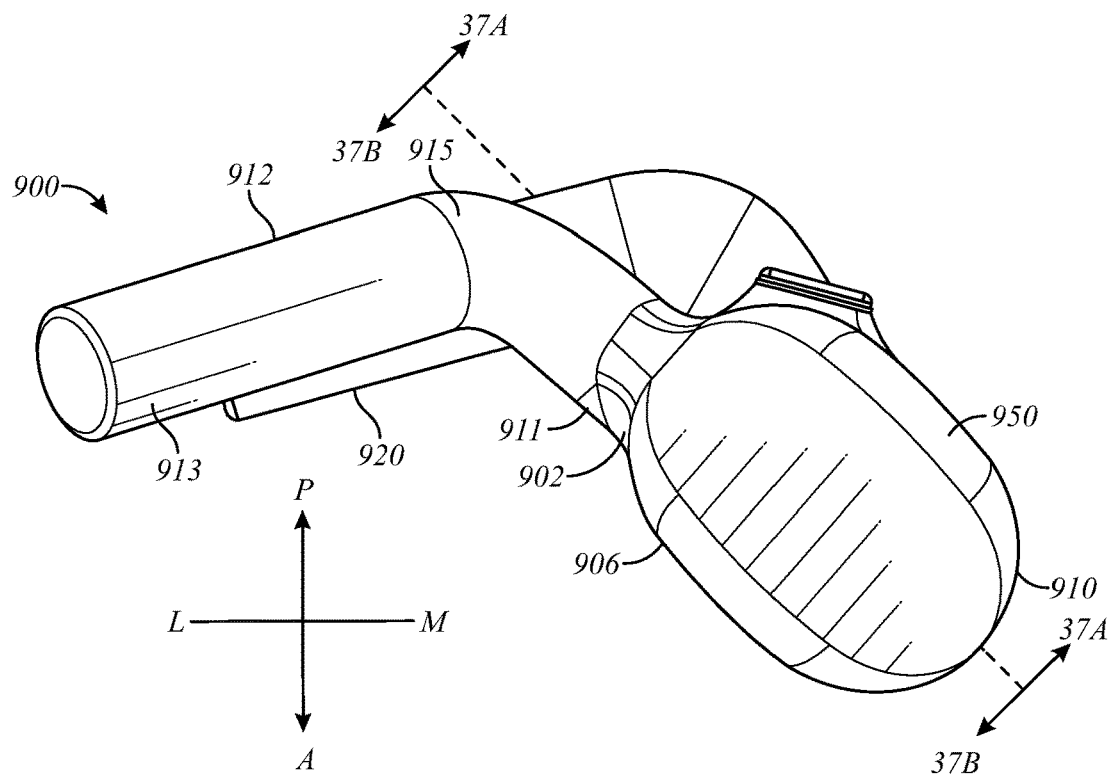
FIG. 36J depicts a bottom view of the facet joint replacement device 900.

FIG. 36E depicts a posterior view of the facet joint replacement device 900. FIG. 36F depicts an anterior view of the facet joint replacement device 900. FIG. 36G depicts a first sagittal view of a lateral side of the facet joint replacement device 900. FIG. 36H depicts a second sagittal view of a medial side of the facet joint replacement device 900. FIG. 36I depicts a top view of the facet joint replacement device 900. FIG. 36J depicts a bottom view of the facet joint replacement device 900.

As shown in FIG. 36A-J, the facet joint replacement device 900 includes an enclosing element 902 and an articulating element 904. The enclosing element 902 includes an enclosing body 906 and an attachment member 912. At least a portion of the enclosing body 906 can be dimensioned, shaped, or otherwise configured to correspond to the shape of a pars interarticularis of a vertebra. The enclosing element can include a superior end 908 and an inferior end 910.

The enclosing body 906 can be shaped, dimensioned, or otherwise configured to correspond to the shape and/or size of a facet joint capsule of a healthy facet joint. The enclosing body 906 can be configured to perform the functions of a facet joint capsule of a healthy facet joint.

The enclosing body 906 differs from the enclosing body 706 in that the enclosing body 906 does not include a separate main body and cap. Instead, portions of the enclosing body 906 similar to the main body 707 and cap 709 of the enclosing body 706 can be integrally or monolithically formed.

As shown in FIGS. 36A-J, the attachment member 912 can extend from a lateral surface of the enclosing body 906. In some embodiments, the attachment member 912 can extend laterally from the enclosing body 906. In some embodiments, the attachment member 912 can extend inferiorly from the enclosing body 906. In some embodiments, the attachment member 912 can extend posteriorly from the enclosing body 906.

In some embodiments, the attachment member 912 can include a first section 911 and a second section 913. In some embodiments, the first section 911 can extend from the enclosing body 906 in lateral, posterior, and/or inferior directions. In some embodiments, the second section 913 can extend from the first section 911 in lateral, anterior, and/or inferior directions. In some embodiments, the first section 911 and the second section 913 can connect at or form a bend 915. In some embodiments, the bend 915 can be positioned lateral to the enclosing body 906.

The attachment member 912 can be shaped and/or dimensioned to facilitate securement of the facet joint replacement device 900 to the spine. As shown in FIGS. 36A-J, the attachment member 912 can be a rod. However, the attachment member 912 can be any shape suitable for fixation directly or indirectly to a vertebral body. In some embodiments, the attachment member 912 can have a diameter of 5.5 mm. In some embodiments, the attachment member 912 can have a diameter of 1 mm, 2 mm, 3 mm, 4 mm, 4.5 mm, 5 mm, 5.5 mm, 6 mm, 6.5 mm, 7 mm, 8 mm, 9 mm, 10 mm, between 2 mm to 8 mm, between 4 mm to 6 mm, between 5 mm to 7 mm, or between 5 mm to 6 mm. In some embodiments, the attachment member 912 can have a length of 1 mm, 2 mm, 3 mm, 4 mm, 5 mm, 6 mm, 7 mm, 8 mm, 9 mm, 10 mm, 15 mm, 20 mm, 25 mm, 30 mm, between 2 mm to 8 mm, between 4 mm to 6 mm, between 5 mm to 10 mm, between 10 mm to 15 mm, between 15 mm to 20 mm, between 20 mm to 25 mm, between 25 mm to 30 mm, between 15 mm to 30 mm, or less than 15 mm.

As shown in FIGS. 36A-J, the enclosing body 906 can include an outer shell 950 and a liner 952. In some embodiments, the liner 952 covers an interior surface the outer shell 950. In some embodiments, a portion 953 of the liner 952 extends superiorly beyond a superior end of the outer shell 950.

In some embodiments, the outer shell 950 is formed of or formed partially of one or more metals or metal alloys. In some embodiments, the outer shell 950 is formed of cobalt-chrome. For example, the outer shell 950 can be formed of cobalt-chromium, titanium, titanium-based alloys, or any other suitable metals or metal alloys. In some embodiments, the outer shell 950 can be ceramic or partially ceramic. In some embodiments, the outer shell 950 can include super-hard ceramics.

In some embodiments, the liner 952 is formed of a low friction material, such as high molecular weight polyethylene. In some embodiments, the liner 952 is formed of ultra-high molecular weight polyethylene. In some embodiments, the liner 952 is formed of vitamin E impregnated ultra-high molecular weight polyethylene, which may function as a free radical scavenger. In some embodiments, the material of the liner 952 can facilitate movement of the articulating element 904 within the enclosing body 906. In some embodiments, the material of the liner 952 can prevent or reduce wear from friction due to movement of the articulating element 904 within the enclosing body 906.

In some embodiments, the liner 952 and/or the outer shell 950 can include one or surface features to provide a connection between the liner 952 and outer shell 950 and/or to prevent or restrict relative motion between the liner 952 and the outer shell 950. For example, one of the liner 952 and the outer shell 950 can include a plurality of protrusions and the other of the liner 952 and shell 950 can include a plurality of corresponding recesses or openings configured to receive the protrusions. In some embodiments, the liner 952 can be molded into the outer shell 950. In some embodiments, the outer shell 950 and/or liner 952 can include one or more surface features configured to facilitate coupling between the outer shell 950 and the liner 952 during the molding process. For example, FIG. 46 depicts an embodiment of the outer shell 950 having a scaffold 951 extending from an inner surface of the outer shell 950. In some embodiments, the scaffold 951 can be integrally formed with the inner surface of the outer shell 950. In some embodiments, during the molding process, the scaffolding 951 can form a connection with the liner 952. For example, in some embodiments, the scaffolding 951 may be embedded within the scaffolding 952 during the molding process. In some embodiments, the scaffolding 951 can form a porous and/or textured surface to which the liner 952 can interdigitate for form connection. In some embodiments, the scaffolding 951 can form a porous and/or textured surface to which the liner 952 can interdigitate for form a durable and permanent connection.

As shown in FIGS. 36A-J, in some embodiments, the facet joint replacement device 900 can include a plug 980. In some embodiments, the plug 980 can be removably received within an opening in an exterior surface of the enclosing body 906.

As shown in FIGS. 36A-J, the enclosing element 902 can include a retention plate 917. The retention plate 917 can be configured to couple to the liner 952 and/or the shell 950 to form the enclosing body 906. In some embodiments, the retention plate 917 is positioned at the superior end 908 of the enclosing body. In some embodiments, the retention plate can couple to the portion 953 of the liner 952. In some embodiments, the retention plate 917 can be releasably or permanently secured to the liner 952 and/or the shell 950. For example, in some embodiments, the liner 952 can be molded around at least a portion of the retention plate 917.

In some embodiments, the retention plate 917 can at least partially form a barrier to restrict movement of the articulating element 904 in a superior direction relative to the enclosing body 906.

Figure 37A:
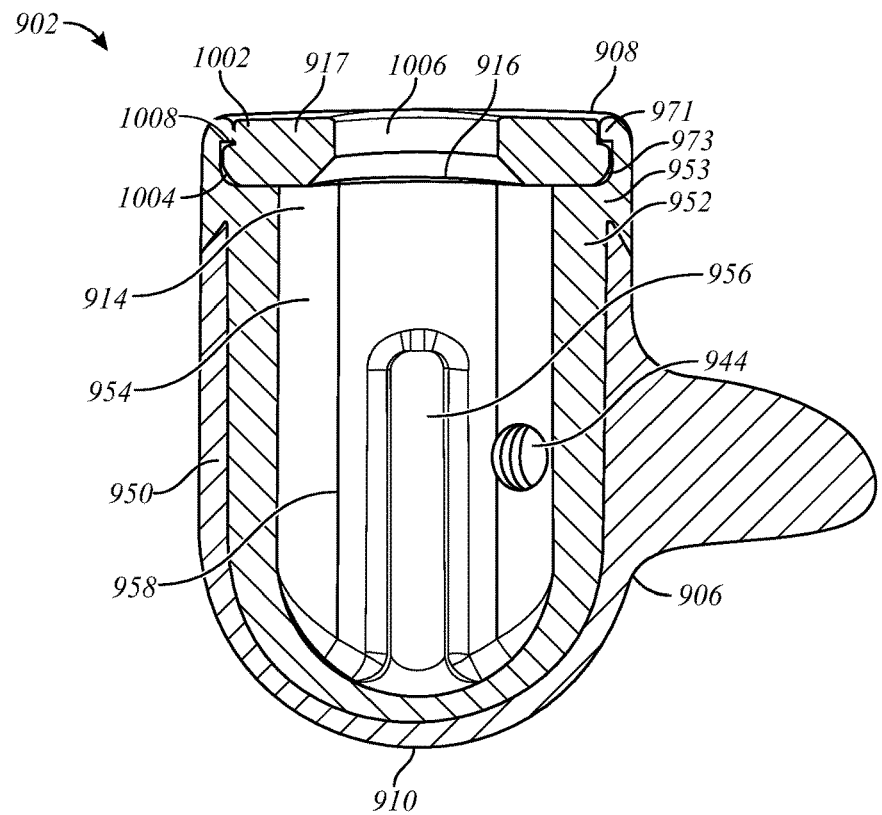
FIG. 37A depicts a posterior longitudinal cross-sectional view of an enclosing element 902.
Figure 37B:
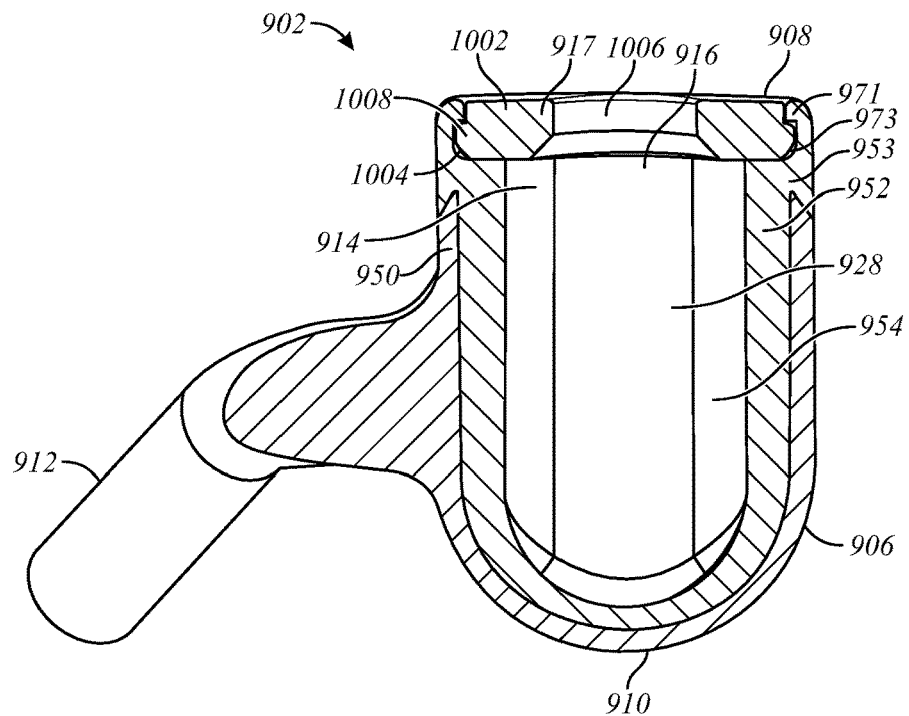
FIG. 37B depicts an anterior, longitudinal cross-sectional view of the enclosing element 902.
Figure 37C:
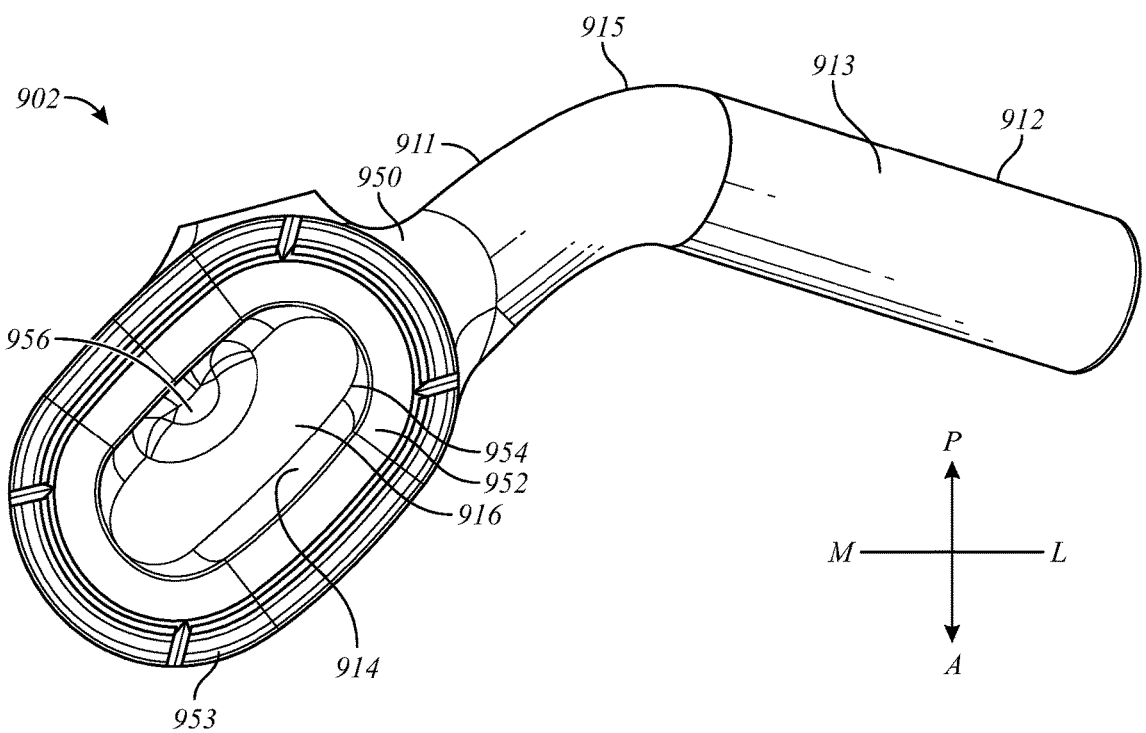
FIG. 37C depicts a top view of the enclosing element 902.
Figure 37D:
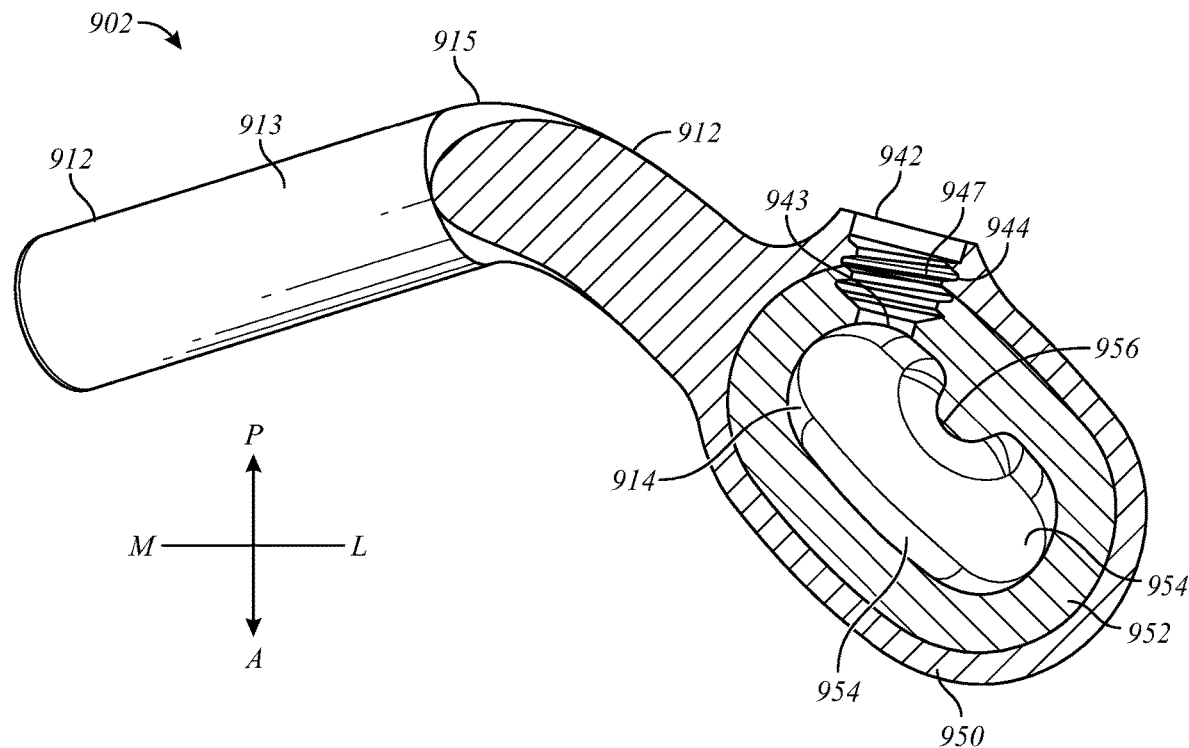
FIG. 37D depicts a bottom cross-sectional view of the enclosing element 902.
Figure 37E:
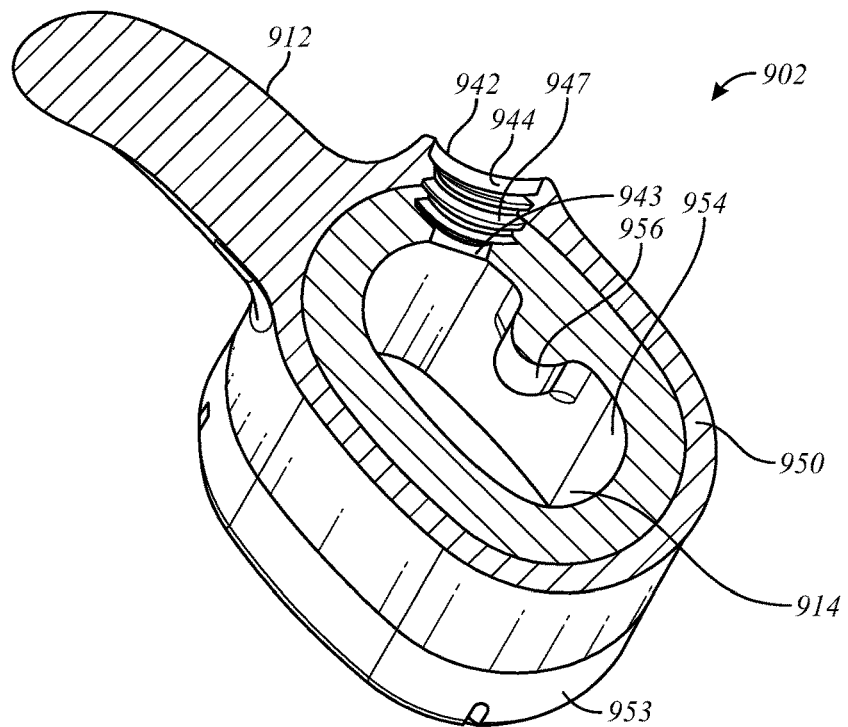
FIG. 37E depicts a first perspective view of a cross-section of the enclosing element 902.
Figure 37F:
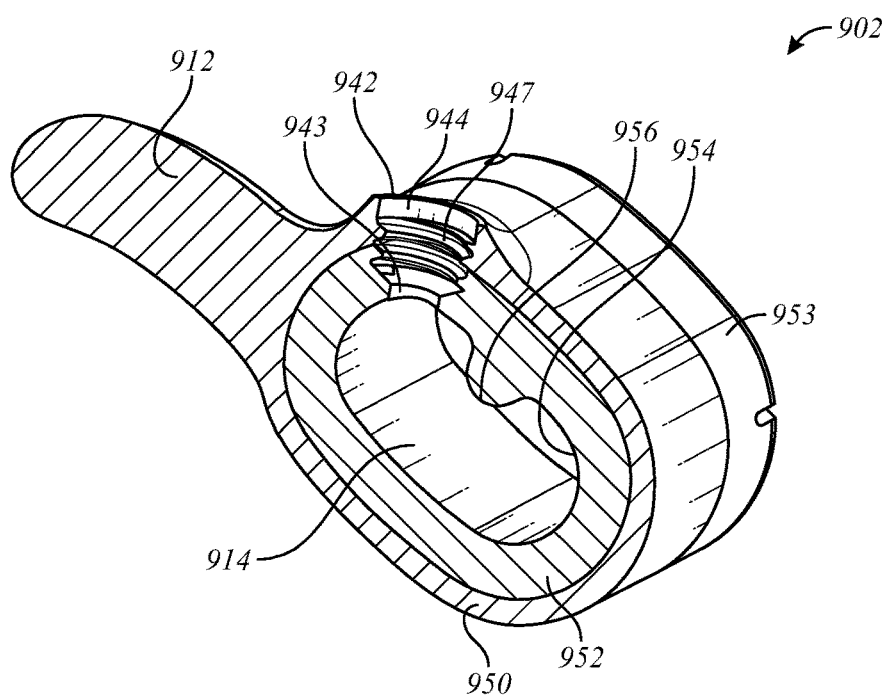
FIG. 37F depicts a second perspective view of a cross-section of the enclosing element 902.
Figure 37G:
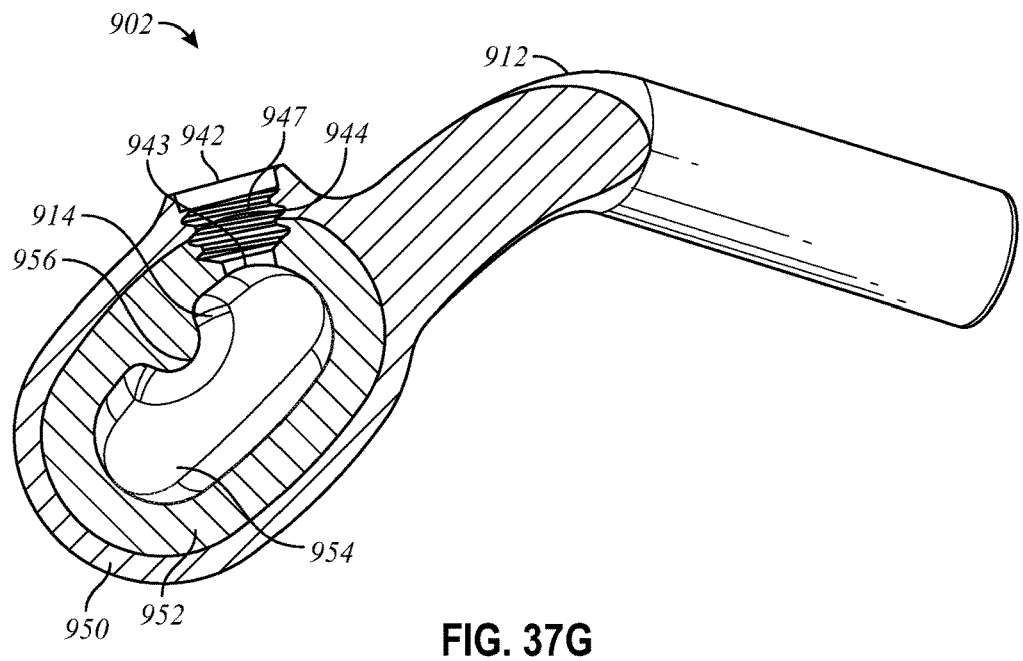
FIG. 37G depicts a fourth cross-sectional view of the enclosing element 902.
Figure 37H:
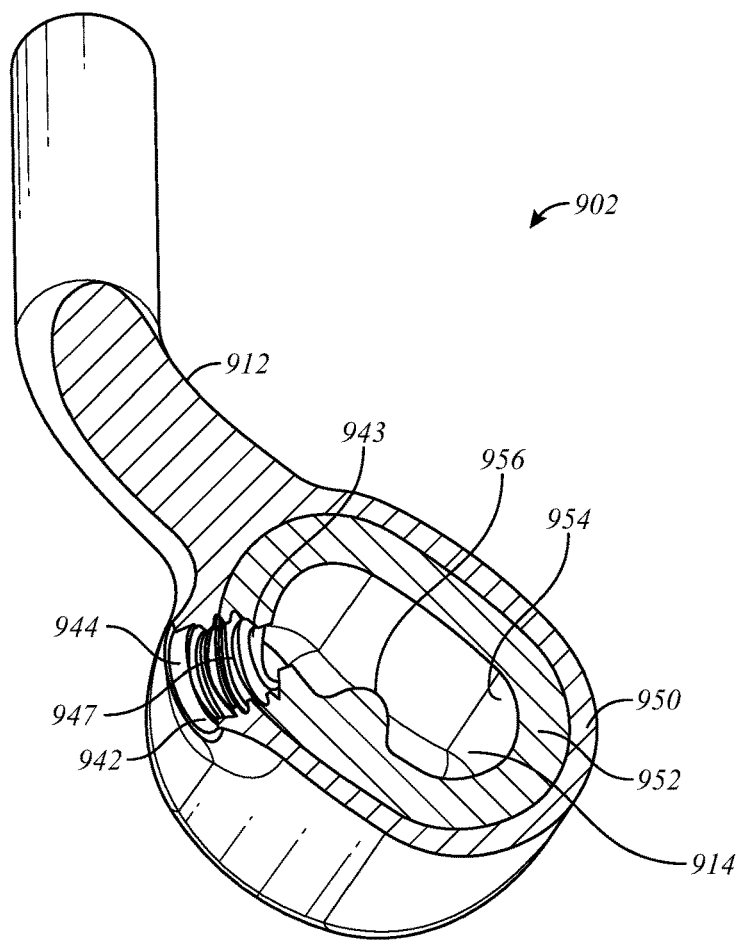
FIG. 37H depicts a third perspective view of a cross-section of the enclosing element 902.
Figure 37I:
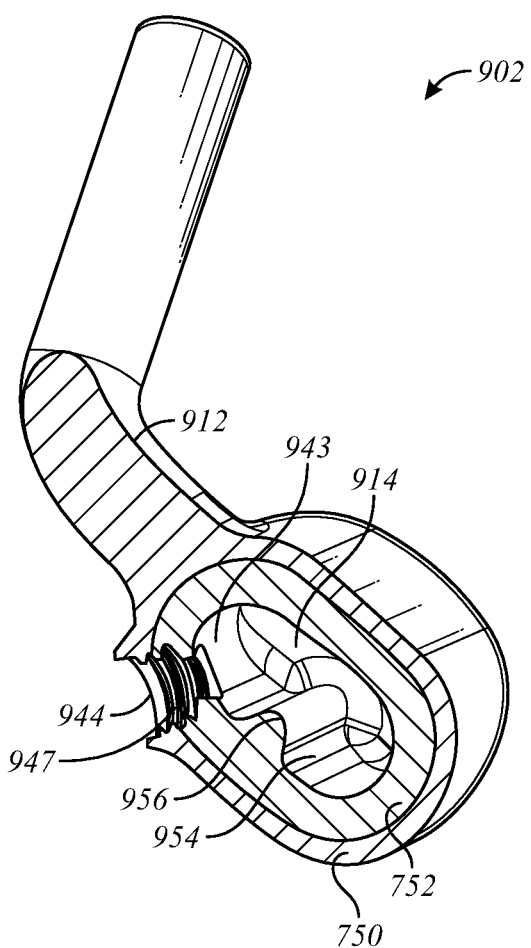
FIG. 37I depicts a fourth perspective view of a cross-section of the enclosing element 902.

FIG. 37A depicts a posterior longitudinal cross-sectional view of the enclosing element 902 taken along line 37A-37A as shown in FIG. 36J. FIG. 37B depicts an anterior longitudinal cross-sectional view of the enclosing element 902 taken along line 37B-37B as shown in FIG. 36J. FIG. 37C depicts a top view of the enclosing element 902. FIG. 37D depicts a bottom cross-sectional view of the enclosing element 902. FIG. 37E depicts a first perspective view of a cross-section of the enclosing element 902. FIG. 37F depicts a second perspective view of a cross-section of the enclosing element 902. FIG. 37G depicts a fourth cross-sectional view of the enclosing element 902. FIG. 37H depicts a third perspective view of a cross-section of the enclosing element 902. FIG. 37I depicts a fourth perspective view of a cross-section of the enclosing element 902.

As shown in FIGS. 37A-I, the enclosing body 906 can include an inner cavity 914 defined by an interior surface 954 of the enclosing body 906. In some embodiments, the interior surface 954 can be an interior surface of the liner 952 of the enclosing body 906.

The inner cavity 914 can be further defined by an opening 1006 of the enclosing body 906. In some embodiments, the opening 1006 is positioned at the superior end 908 of the enclosing body. As shown in FIG. 37A, the opening 1006 is defined by the retainer or retention plate 917. In some embodiments, the opening 1006 can at least partially align with an opening 916 of the outer shell 950 and liner 952. In some embodiments, the inner cavity 914 can be defined by a bottom surface of the retention plate 917.

In some embodiments, the retention plate 917 is formed of a low friction material, such as high molecular weight polyethylene. In some embodiments, the retention plate 917 is formed of ultra-high molecular weight polyethylene. In some embodiments, the retention plate 917 is formed of vitamin E impregnated ultra-high molecular weight polyethylene, which may function as a free radical scavenger.

As shown in FIG. 37A-B, the retention plate 917 can include a base layer 1004 having a lip 1008 configured to be secured within a cavity 973 of the liner 952. In some embodiments, the cavity 973 can be formed by at least partially formed by a lip 971 of the liner 952. In some embodiments, the retention plate can include a top layer 1002 positioned superior to the base layer 1004 and having a smaller cross-sectional area than the base layer 1004.

In some embodiments, the base layer 1004 can at least partially form a barrier to restrict movement of the articulating element 904 within the enclosing body 906. For example, in some embodiments, the base layer 1004 can at least partially form a barrier to restrict movement in a superior direction relative to the enclosing body 906.

In some embodiments, the top layer of the retention plate can couple with the liner 1052 to form a barrier between the inner cavity 914 and the external environment.

In some embodiments, the enclosing body 906 can include a projection 956 extending inwardly relative to a surrounding area 958 of the interior surface 954. In some embodiments, the projection 956 can be generally convex in shape. In some embodiments, the projection 956 is generally parabolic in shape. In some embodiments, the projection 956 can extend from an inferior portion of the enclosing body to a superior portion of the enclosing body 906.

As shown in FIGS. 37A-H, the enclosing body 906 can include a channel 944. The channel 944 can extend through the outer shell 950 and the liner 952. In some embodiments, the channel 944 can be configured to receive fastener or the plug 980.

As shown in FIG. 37B, In some embodiments, a portion of the interior surface 954 of the enclosing body 906 can be shaped to form an articulating surface 928. In some embodiments, the interior surface 954 can be an interior surface of the liner 952 and a portion of the interior surface 954 can be shaped to form the articulating surface 928. In some embodiments, the articulating surface 928 can be concave or at least partially concave. In some embodiments, the articulating surface 928 can be shaped/and or dimensioned to correspond to the shape, size, and/or concavity of an articular surface of a healthy superior articular process. In some embodiments, the articulating surface 928 can be positioned on a surface of the enclosing body 906 generally opposite the projection 956.

As shown in FIGS. 37C-H, the channel 944 can extend between an opening 942 on an exterior surface of the enclosing body 906 and an opening 943 on the interior surface 954 of the enclosing body 906. In some embodiments, the opening 942 is positioned on the exterior surface of the outer shell 950. In some embodiments, the interior surface 954 is an interior surface of the liner 952 and the opening 943 is positioned on the interior surface 954. The channel 944 can include a threaded section 947 configured to engage a threaded section of the plug 980 or a fastener. In some embodiments, at least a portion of the threaded section 947 is formed in the outer shell 950. In some embodiments, at least a portion of the threaded section 947 is formed in the liner 952.

Figure 38A:
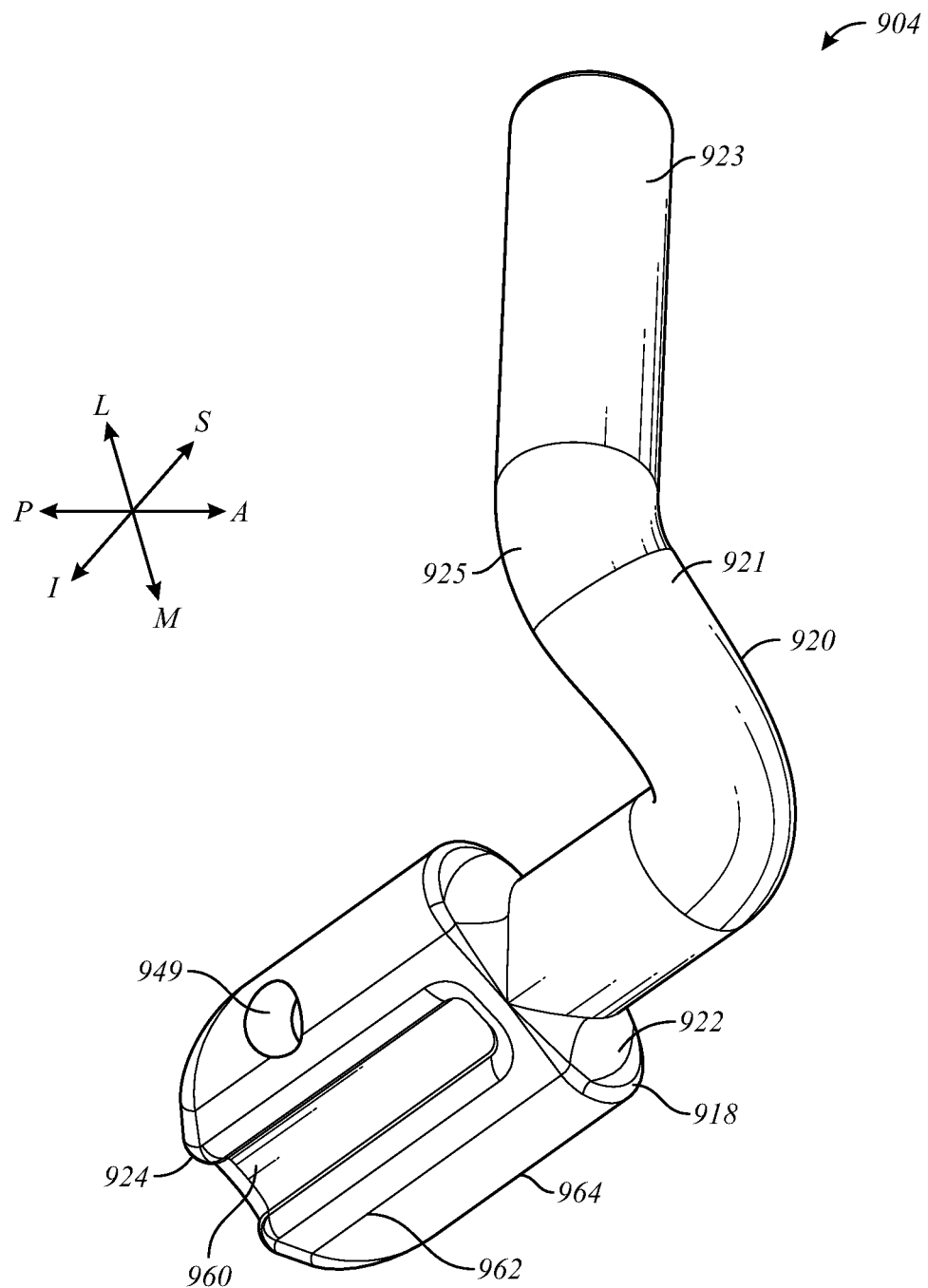
FIG. 38A depicts a top posterior perspective view of an articulating element 904.
Figure 38B:
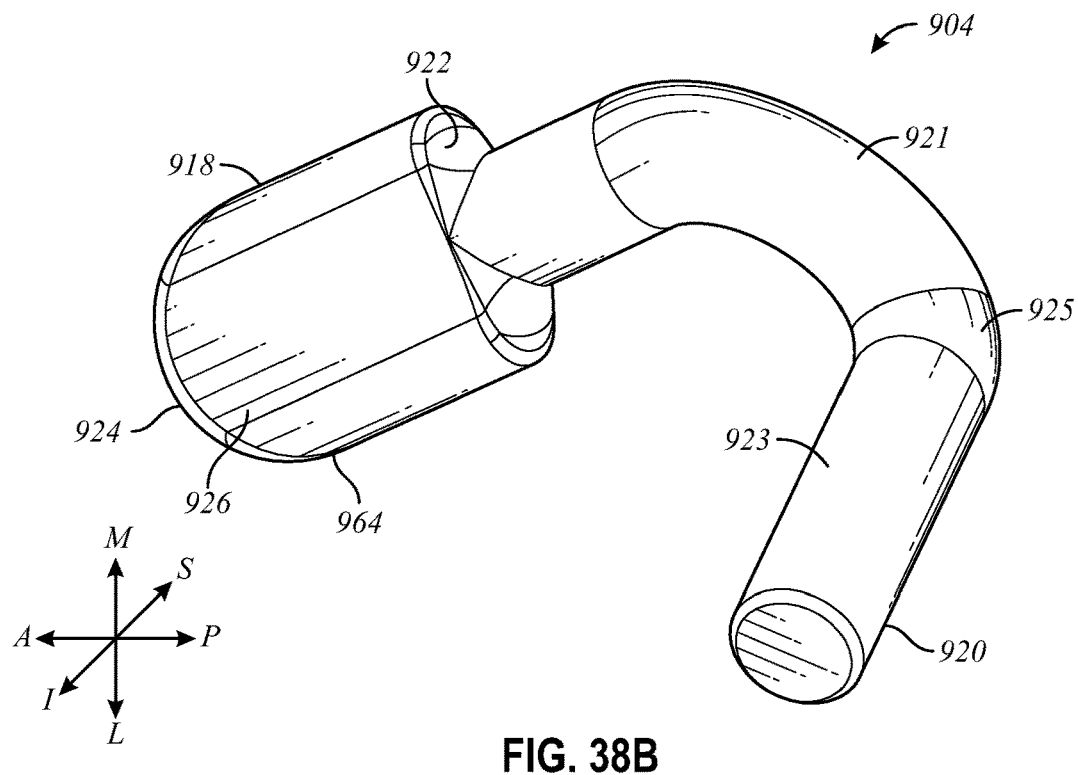
Figure 38C:
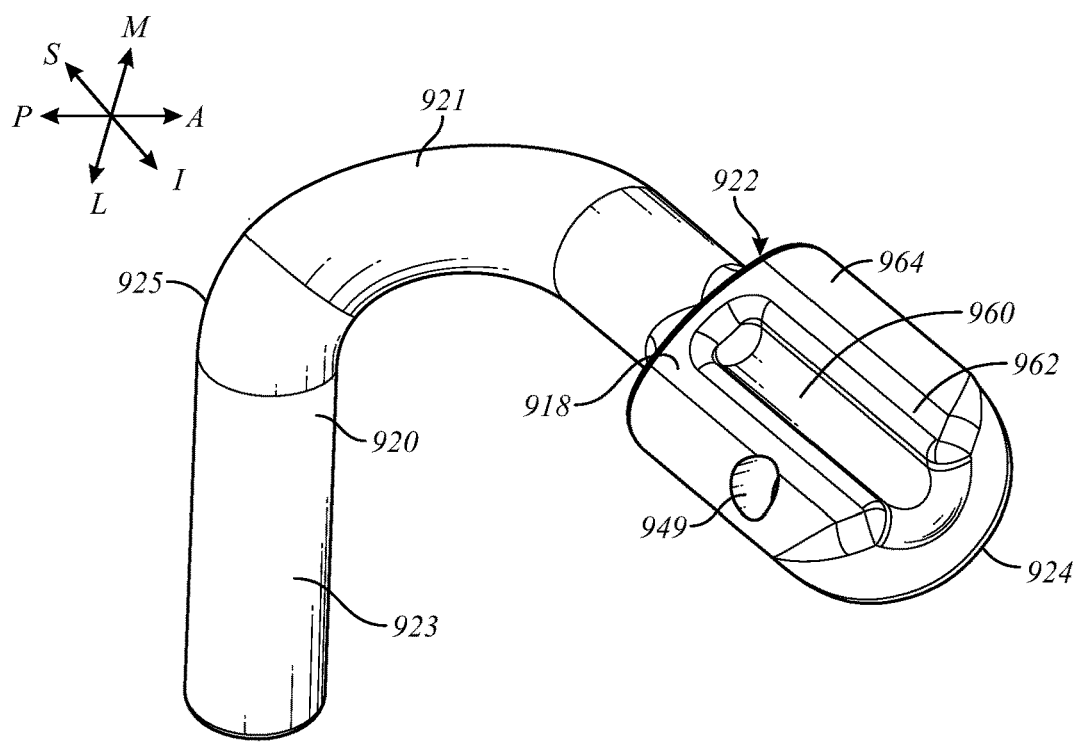
Figure 38D:
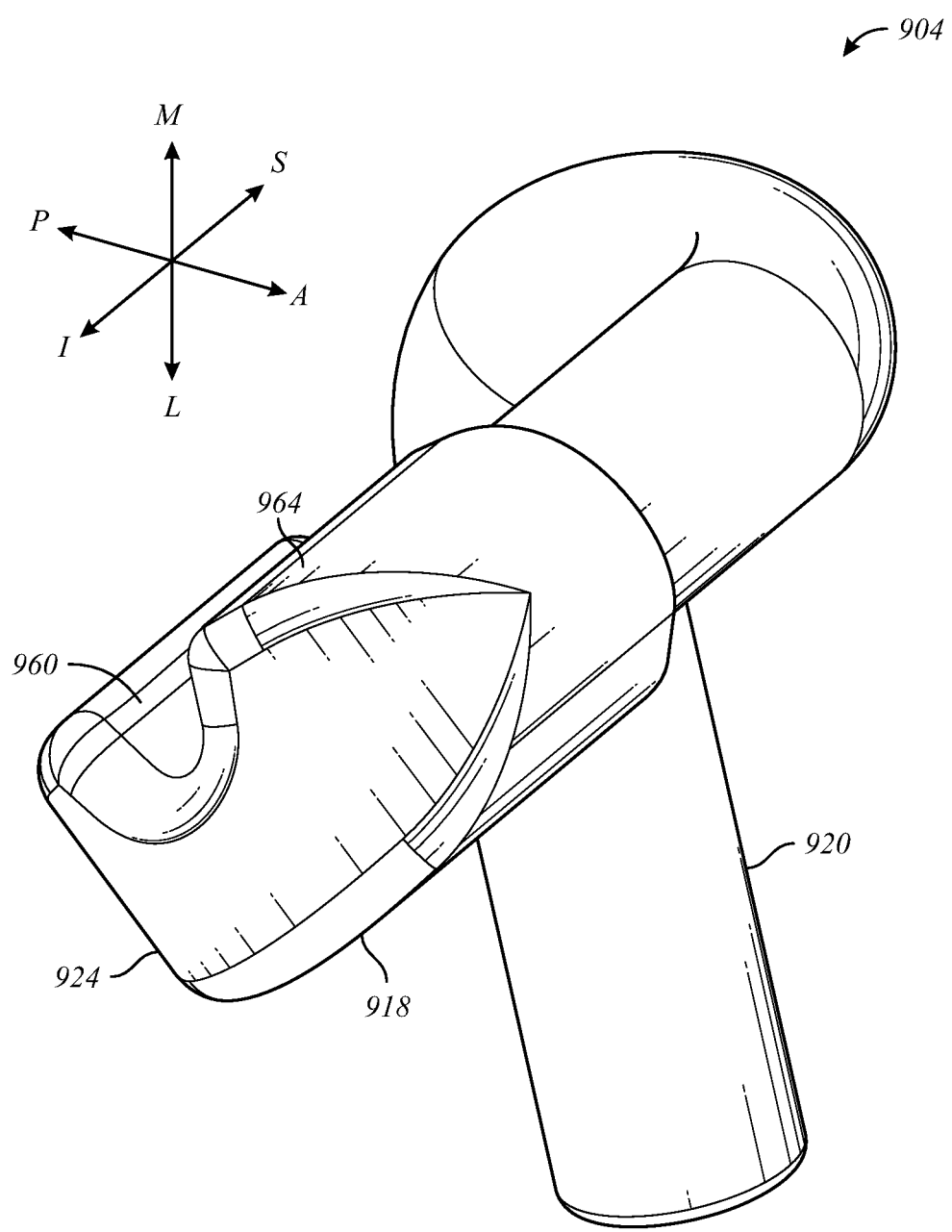

FIGS. 38A-K depict views of the articulating element 904. FIG. 38A depicts a top posterior perspective view of the articulating element 904. FIG. 38B depicts a top anterior perspective view of the articulating element 904. FIG. 38C depicts a bottom posterior perspective view of the articulating element 904. FIG. 38D depicts a bottom anterior perspective view of the articulating element 904.

Figure 38E:
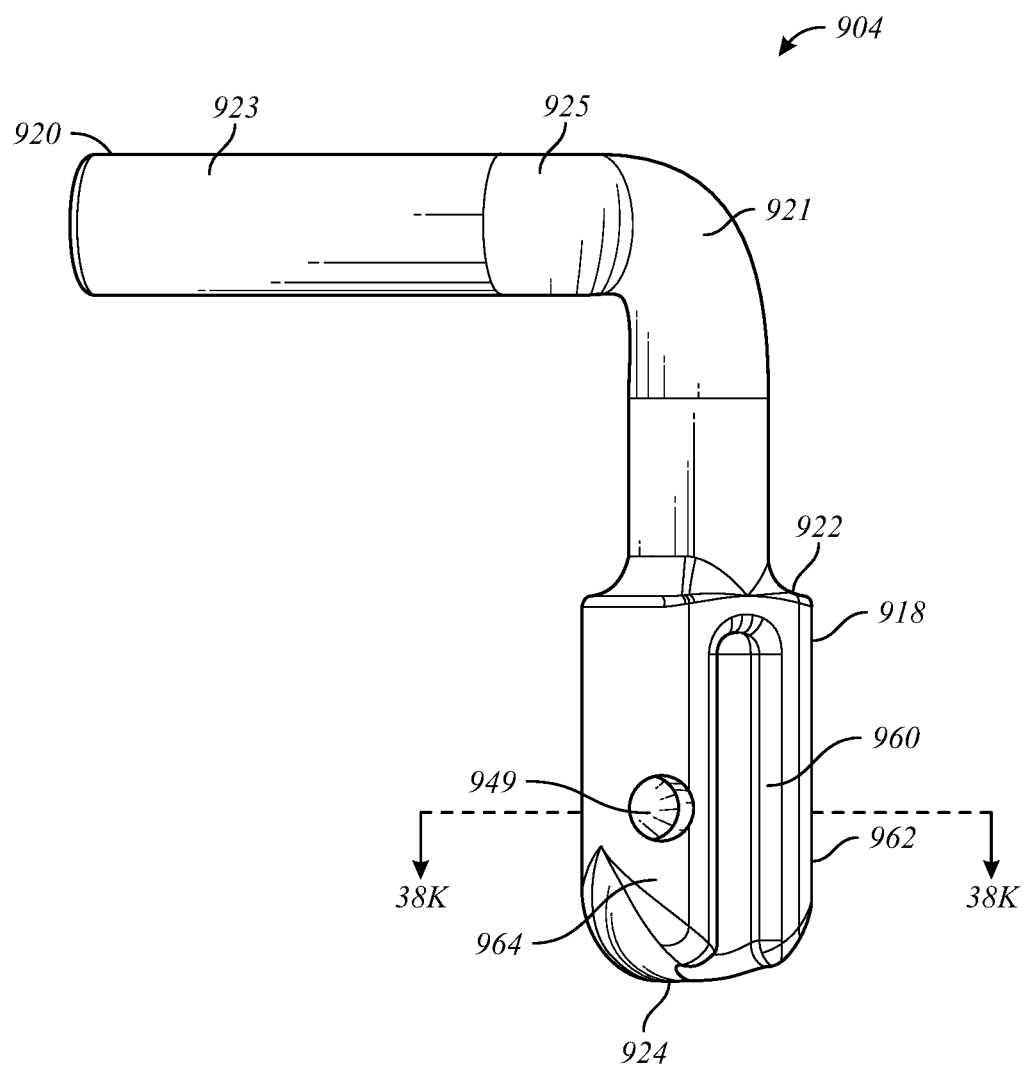
Figure 38F:
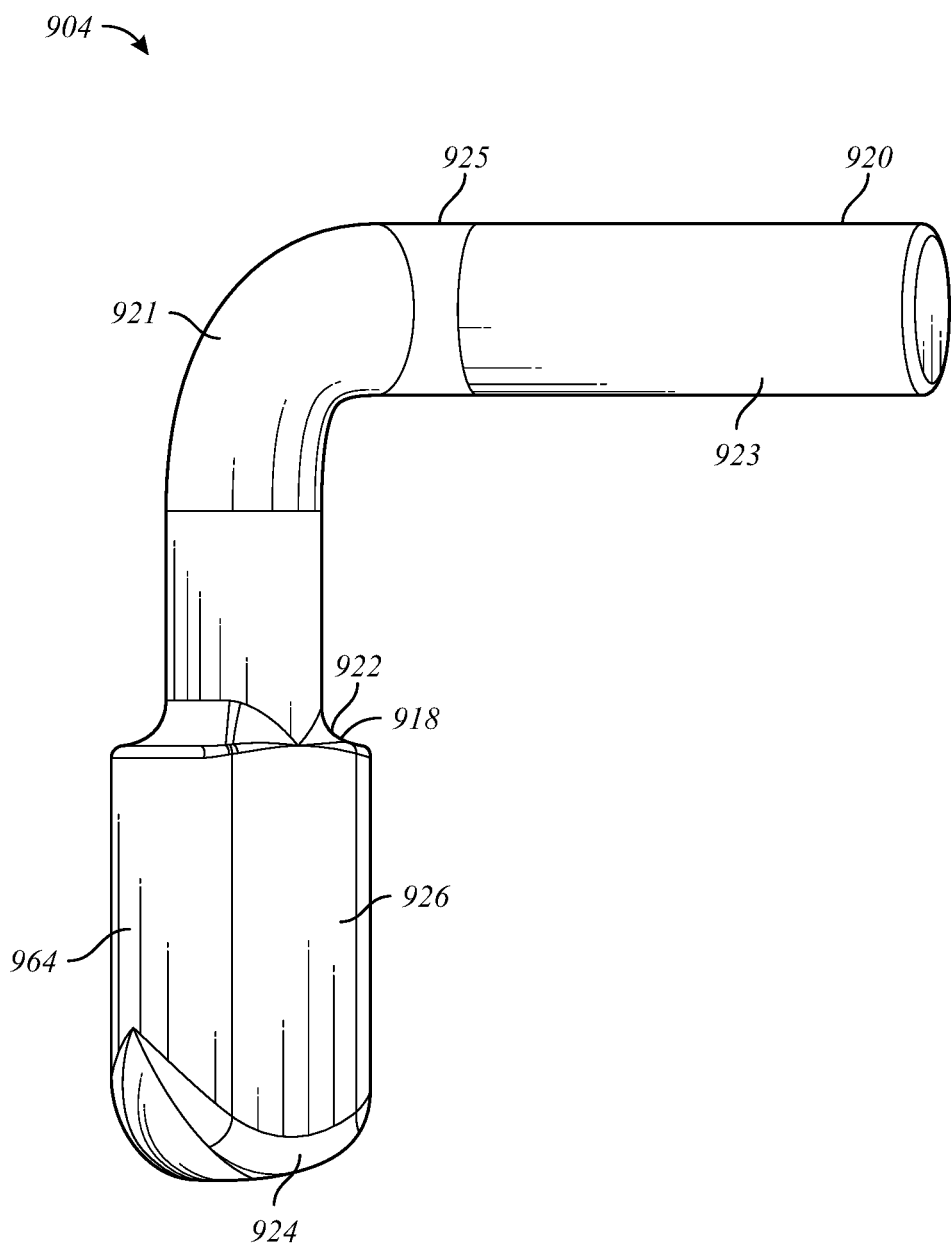
Figure 38G:
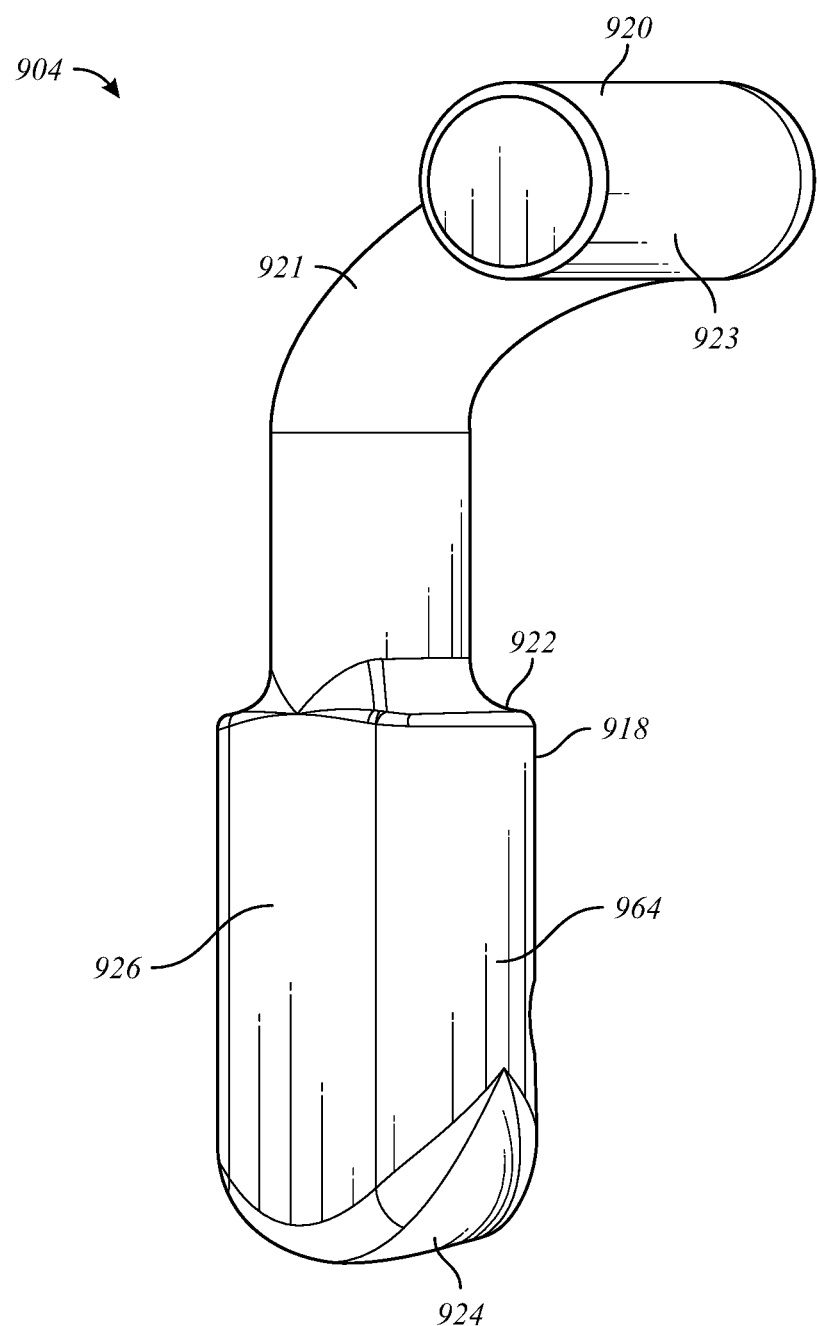
Figure 38H:
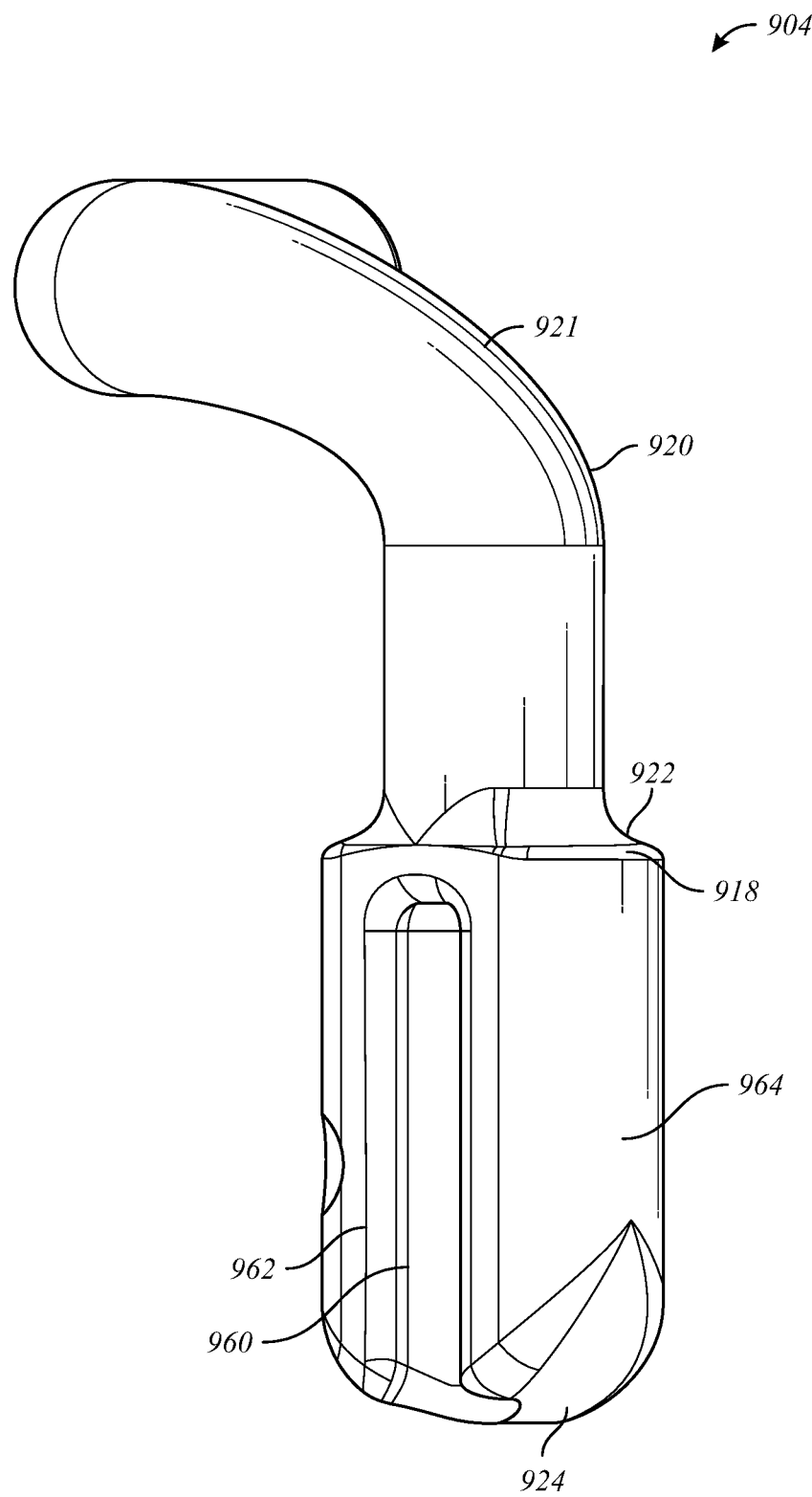
Figure 38I:
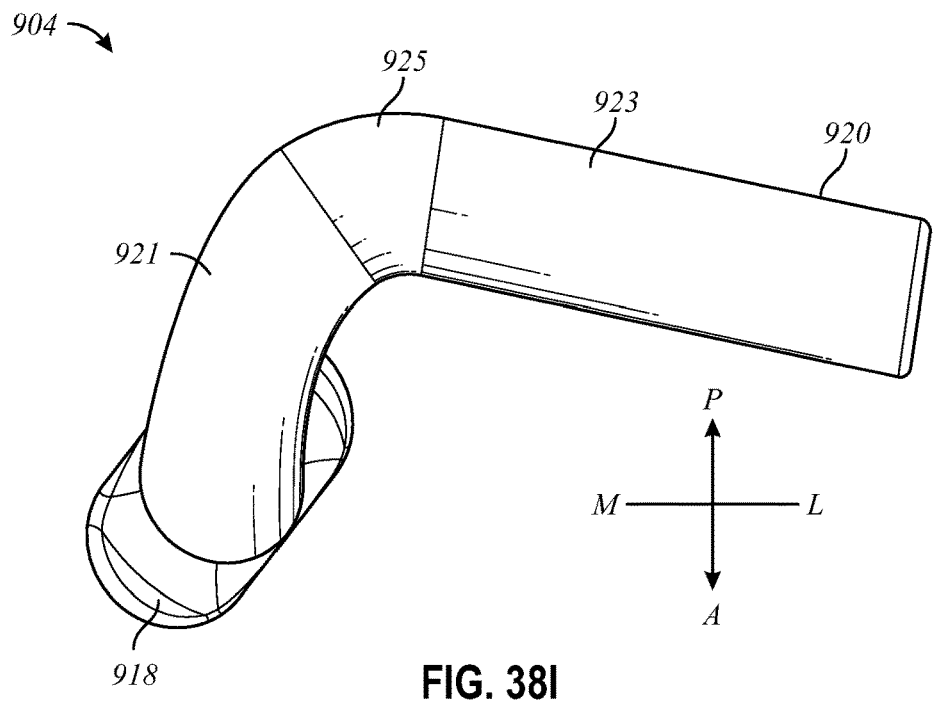
Figure 38J:
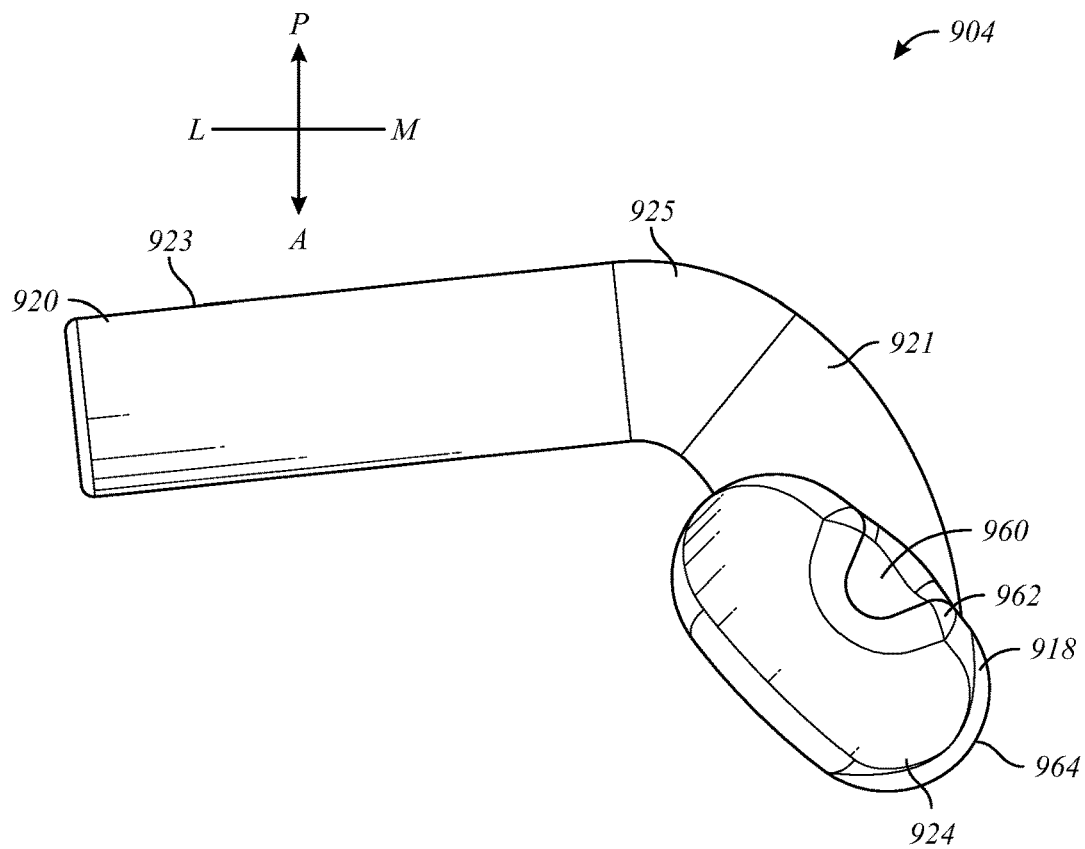
Figure 38K:
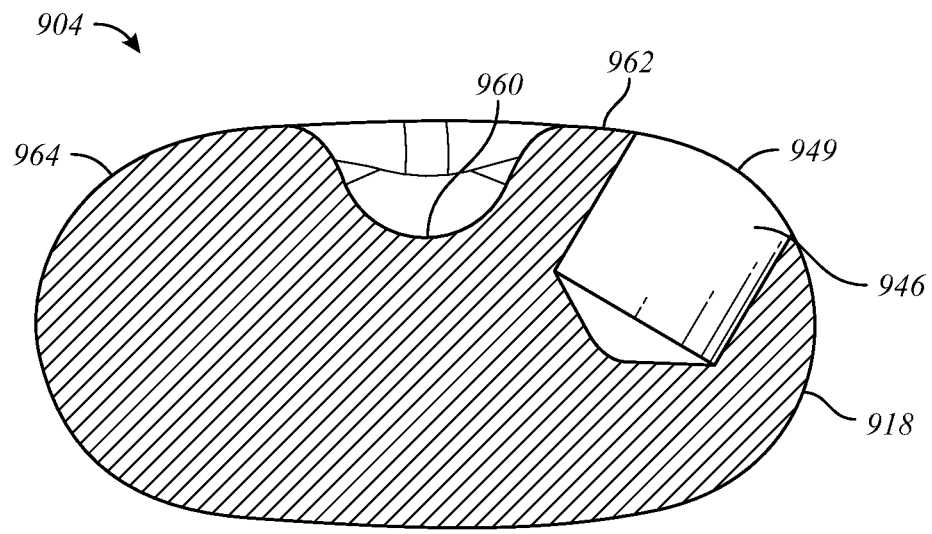

FIG. 38E depicts a posterior view of the articulating element 904. FIG. 38F depicts an anterior view of the articulating element 904. FIG. 38G depicts a first sagittal view of a lateral side of the articulating element 904. FIG. 38H depicts a second sagittal view of a medial side of the articulating element 904. FIG. 38I depicts a top view of the articulating element 904. FIG. 38J depicts a bottom view of the articulating element 904. FIG. 38K depicts a cross-sectional view of the articulating element 904.

As shown in FIGS. 38A-K, the articulating element 904 includes an articulating body 918 and an attachment member 920. As described herein, the articulating body 918 can be at least partially positioned within and configured to move within the inner cavity 914 of the enclosing body 906. The articulating body 918 has a superior end 922 and an inferior end 924.

As shown in FIGS. 38A-K, the attachment member 920 can extend from the superior end 922 of the articulating body 918. In some embodiments, the attachment member 920 can extend superiorly from the articulating body 918. In some embodiments, the attachment member 920 can extend laterally from the articulating body 918. In some embodiments, the attachment member 920 can extend posteriorly from the articulating body 918.

In some embodiments, the attachment member 920 can include a first section 921 and a second section 923. In some embodiments, the first section 921 can extend from the articulating body 918 in superior, lateral, and/or posterior directions. In some embodiments, the second section 923 can extend from the first section in lateral and/or anterior directions. In some embodiments, the first section 921 and the second section 923 can connect at or form a bend 925. In some embodiments, the bend 925 can be positioned lateral to the articulating body.

The attachment member 920 can be shaped and/or dimensioned to facilitate securement of the facet joint replacement device 900 to the spine. As shown in FIGS. 38A-J, the attachment member 920 can be a rod. However, the attachment member 920 can be any shape suitable for fixation directly or indirectly to a vertebral body. In some embodiments, the attachment member 920 can have a diameter of 5.5 mm. In some embodiments, the attachment member 920 can have a diameter of 1 mm, 2 mm, 3 mm, 4 mm, 4.5 mm, 5 mm, 5.5 mm, 6 mm, 6.5 mm, 7 mm, 8 mm, 9 mm, 10 mm, between 2 mm to 8 mm, between 4 mm to 6 mm, between 5 mm to 7 mm, or between 5 mm to 6 mm. In some embodiments, the attachment member 920 can have a length of 1 mm, 2 mm, 3 mm, 4 mm, 5 mm, 6 mm, 7 mm, 8 mm, 9 mm, 10 mm, 15 mm, 20 mm, 25 mm, 30 mm, between 2 mm to 8 mm, between 4 mm to 6 mm, between 5 mm to 10 mm, between 10 mm to 15 mm, between 15 mm to 20 mm, between 20 mm to 25 mm, between 25 mm to 30 mm, between 15 mm to 30 mm, or less than 15 mm.

As shown in FIGS. 38A-K, In some embodiments, a portion of an exterior surface 964 of the articulating body 918 can be shaped to form an articulating surface 926. In some embodiments, the articulating surface 926 can be convex or at least partially convex. In some embodiments, the articulating surface 926 can be shaped/and or dimensioned to correspond to the shape, size, and/or concavity of an articular surface of a healthy inferior articular process.

In some embodiments, the articulating surface 926 of the articulating body and the articulating surface 928 of the enclosing body have complementary surface shapes. In some embodiments, the articulating surface 926 and the articulating surface 928 are elliptical or generally elliptical, circular or generally circular, oval or generally oval, rounded, polygonal, oblong, symmetric, asymmetric, or any other suitable shape. In some embodiments, the articulating surface 926 and articulating surface 928 can be shaped such that force is applied symmetrically to the articulating 928 when the articulating element 926 contacts or otherwise applies a force upon the articulating surface 928.

As shown in FIGS. 38A-K, the articulating body 918 can include a slot, groove, or recess 960 extending inwardly relative to a surrounding area 962 of the exterior surface 964. In some embodiments, the projection 956 and recess 960 can be generally concave in shape. In some embodiments, the recess 960 can be generally parabolic in shape. In some embodiments, the recess 960 can extend from an inferior portion of the articulating body to a superior portion of the articulating body 918. In some embodiments, the articulating surface 926 can be positioned on a face of the articulating body 918 generally opposite the recess 960.

As shown in FIGS. 38A-K, the articulating body 918 can include an opening 949 on the exterior surface 964 of the articulating body 918. The opening 949 can be dimensioned, positioned, or otherwise configured to align with the opening 943 of the enclosing body 906 while the articulating body 918 is located at a particular position within the enclosing body 906. As shown in FIG. 38J, a channel 946 extends from the opening 949 into the interior of the articulating body 918. The channel 946 can be shaped, dimensioned, or otherwise configured to receive a fastener. In some embodiments, the channel 946 can include a threaded portion configured to couple with a threaded portion of a fastener.

In some embodiments, the articulating body 918 is formed of or formed partially of one or more metals or metal alloys. In some embodiments, the articulating body 918 is formed of cobalt-chrome. For example, the articulating body 918 can be formed of cobalt-chromium, titanium, titanium-based alloys, or any other suitable metals or metal alloys. In some embodiments, the articulating body 918 can be ceramic or partially ceramic. In some embodiments, the articulating body 918 can include super-hard ceramics.

In some embodiments, the articulating element 904 can be integrally or monolithically formed. Thus, the articulating element 904 can differ from the articulating element 704 which the attachment portion 720 is a separate component releasably or permanently coupled to the articulating body 718.

Figure 39:
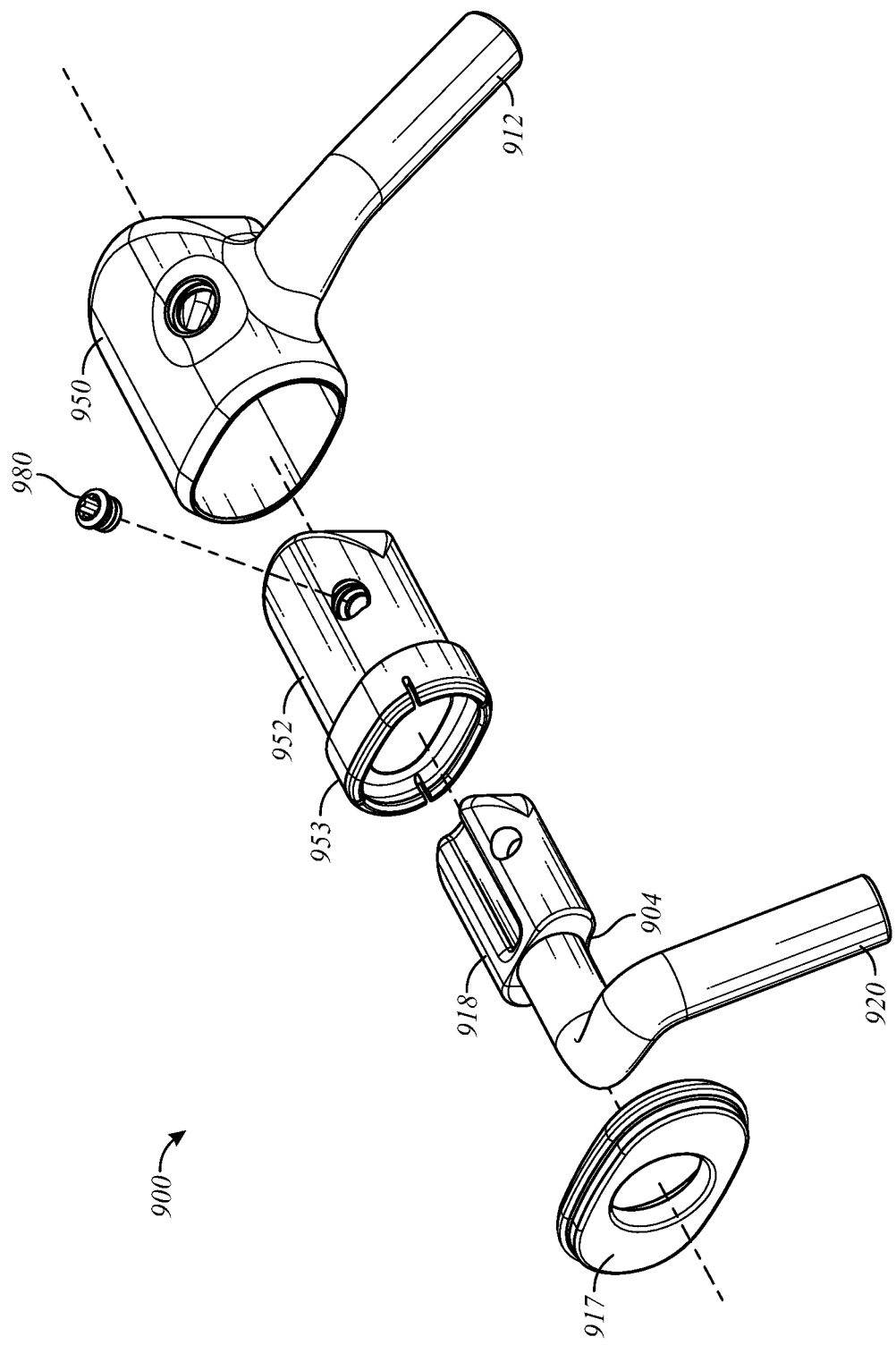

FIG. 39 is an exploded view of a facet joint replacement device 900. FIGS. 40A-C depict posterior-medial cross sectional views of the facet joint replacement device 900.

The articulating body 918 is configured to move within the enclosing body 906 in at least one direction. When the attachment member 920 is secured to a superior vertebral body and the attachment member 912 is secured to an inferior vertebral body, movement between the superior and inferior vertebral bodies can cause movement of the attachment member 920 with respect to the position of the enclosing body 906 resulting from the attachment member 912 being secured to the inferior vertebral body. Movement of the attachment member 920 with respect to the enclosing body 906 causes movement of the articulating body 918 within the enclosing body 906 generally along the interior surface 954 of the enclosing body 906.

In certain embodiments, the articulating body 918 can move along an axis of articulation, such as axis 703 shown with respect to FIGS. 29A-D. The axis of articulation represents an axis of articulation of the articulating body 918 within the enclosing body 906 and/or an axis of articulation of the articulating surfaces 926 and 928 relative to one another. The articulating body 918 can be configured to move along the axis of articulation within the enclosing body. In some embodiments, the axis of articulation can be parallel with a superior-inferior anatomical axis when the facet joint replacement device 900 is implanted within a patient. In some embodiments, the axis of articulation can be parallel with an angle formed between the articulating surfaces 926 and 928.

In some embodiments, the attachment member 920 is configured to move along the axis of articulation towards and away from the enclosing body 906. When the attachment member 920 moves towards the enclosing body 906 along the axis of articulation, the attachment member 920 moves along the axis of articulation in an inferior direction. When the attachment member 920 moves away from the enclosing body 906 along the axis of articulation, the attachment member 920 moves along the axis of articulation in a superior direction. The articulating body 918 moves along the axis of articulation in the same manner when the attachment member 920 moves along the axis of articulation. Although relative movement of the attachment member 920 towards and away from the enclosing body 906 is discussed, one of skill in the art would understand that movement between the enclosing body 906 and attachment member 920 could be described as movement of the enclosing body 906 towards or away from the attachment member 920 or movement of the enclosing body 906 and attachment member 920 towards or away from each other.

In some embodiments, a spring coil can be positioned, for example within or as a portion of the external surface of the enclosing body 906 adjacent the inferior aspect of the device 910 of the enclosing body 906, and/or otherwise configured such that when a threshold extension force is applied when the inferior articulating body 922 is advancing inferiorly within the enclosing body, the spring coil actuates from an initial position to decrease an angle between the attachment member 912 and the enclosing body 906 from an initial angle to a decreased angle. When the amount of force applied is no longer above the threshold extension force, the spring coil can be configured to return to the initial configuration such that the initial angle between the enclosing body and the attachment member 912 is restored.

Movement of the attachment member 920 with respect to the enclosing body 906 causes movement of the articulating surface 926 with respect to the articulating surface 928. In some embodiments, movement of the attachment member 920 with respect to the enclosing body 906 causes movement of the articulating surface 926 along the axis of articulation relative to the articulating surface 928. In some embodiments, the articulating surface 926 can be configured to articulate relative to the articulating surface 928 by moving substantially only parallel to an angle formed by the two juxtaposed articulating surfaces 926 and 978. Although relative movement of the articulating surface 926 relative to the articulating surface 928 is discussed, one of skill in the art would understand that movement between the articulating surface 926 and the articulating surface 928 could be described as movement of the articulating surface 928 relative to the articulating surface 928 or movement of the articulating surfaces 926 and 928 relative to each other. The axis of articulation can represent the direction of relative movement between the articular surfaces of a healthy facet joint. In some embodiments, the articulating surfaces 926 and 928 can be configured to articulate relative each other by moving substantially only parallel to an angle formed by the two juxtaposed articulating surfaces 926 and 978.

In some embodiments, the enclosing body 906 acts to limit relative movement between the articulating surface 926 and the articulating surface 928 along the axis of articulation. In some embodiments, the enclosing body 906 acts to limit relative movement of the articling surface 926 and articulating surface 928 perpendicular to the axis of articulation. In some embodiments, the enclosing body 906 can act to limit relative movement between the articulating surfaces 926 and 928 to correspond to the limitations of movement of the articular surfaces of a healthy facet joint. In some embodiments, the enclosing body 906 can act to limit movement between the articulating surfaces 926 and 928 to correspond to the limitations of movement provided by the facet joint capsule of a healthy facet joint. In any of the embodiments described above or elsewhere in this specification, the enclosing body can be configured to restrict movement of the articulating body within the enclosing body such that the articulating surface 926 moves only along an axis parallel with the superior/inferior axis of the patient. In some embodiments, the enclosing body 906 can be configured to restrict movement of the articulating body 918 within the enclosing body such that the articulating body 918 moves only along an axis parallel with an angle formed by the juxtaposed articulating surface 926 and articulating surface 928. In some embodiments, the enclosing body 906 can be configured to restrict movement of the articulating body 918 within the enclosing body 906 such that the articulating surface 926 moves only along an axis parallel with an angle formed by the juxtaposed articulating surfaces 926 and 928.

When the articulating body 918 moves within the enclosing body 906, the articulating surface 926 can contact the articulating surface 928. The articulating surface 926 can articulate against the articulating surface 928. In some embodiments, the articulating surfaces 926 and 928 may apply an axial load to one another during articulation. In some embodiments, the outer shell 950 and/or liner 952 may have a sufficient thickness at articulating surface 928 to receive an axial load supplied by the articulating body 918 to the articulating surface 928 due to movement of the articulating body 918 within the enclosing body 906. In some embodiments, the articulating body 918 may have a sufficient thickness at articulating surface 926 to receive an axial load supplied by the enclosing body 906 to the articulating surface 928 due to movement of the articulating body 918 within the enclosing body 906.

Although articulation between the articulating surface 926 and the articulating surface 928 is discussed herein, it is contemplated that articulation between any or all of the exterior surfaces of the articulating body 918 and any or all of the interior surfaces of the enclosing body 906 could occur alternatively or in addition to articulating between the articulating surface 926 and the articulating surface 928.

In some embodiments, the enclosing body 906 and articulating body 918 are configured such that a maximum distance between a center point of the articulating surface 926 and the articulating surface 928 is 0.5 mm, 1.0 mm, 1.5 mm, 1.75 mm, 2.0 mm, 2.25 mm, 2.5 mm, 3.0 mm, 3.5 mm, 4.0 mm, 5.0 mm, less than 2.0 mm, less than 3.0 mm, less than 4.0 mm, between 1.0 mm and 3.0 mm, between 1.0 mm and 2.0 mm, between 2.0 mm and 3.0 mm, between 1.5 mm and 2.5 mm, or between 1.75 mm and 2.25 mm.

As shown in FIGS. 29A-D, in some embodiments, a portion of the articulating body 918 can extend or align with the opening 1006 of the enclosing body 906. In some embodiments, the opening 1006 is dimensioned, shaped, or otherwise configured to prevent removal of the articulating body 918 through the opening 1006. For example, in some embodiments, at least some sections of the articulating body 918 are wider than the opening 1006. In some embodiments, the superior end 908 can be shaped, dimensioned, or otherwise configured to prevent removal of the articulating body 918 from the enclosing body 906. For example, in some embodiments, the retention plate 917 of the enclosing body is shaped and positioned to prevent a cross-section of at least a portion of the articulating body 918 from removal through the opening 1006.

In some embodiments, the enclosing body 906 is shaped, dimensioned, or otherwise configured to circumferentially enclose the articulating surface 926 and the articulating surface 928. In some embodiments, the enclosing body 906 encloses an entire circumferential portion of the articulating body 918 that includes the articulating surface 926. In some embodiments, the liner 952 is shaped, dimensioned, or otherwise configured to circumferentially enclose the articulating surface 926 and the articulating surface 928. In some embodiments, the liner 952 encloses an entire circumferential portion of the articulating body 918 that includes the articulating surface 926.

FIG. 40A depicts the articulating body 918 at a neutral position within the enclosing body 906. The neutral position can refer to a position in which the opening 949 and/or channel 946 of the articulating body 918 is aligned with the opening 943 and/or channel 944 of the enclosing body 906. In some embodiments, the neutral position is a mid-position between a superior-most articulating position and an inferior-most articulating position over which the articulating body 918 can move within the enclosing body 906. FIG. 40B shows the articulating body 918 at a position superior to the neutral position within the enclosing body 906. FIG. 40C shows the articulating body 918 at a position inferior to the neutral position within the enclosing body 906. As shown in FIG. 40A-C, the articulating body 918 can move along the axis of articulation within the enclosing body. In some embodiments, the articulating body 918 can move along the axis of articulation within the enclosing body while the plug 980 is positioned within the channel 944 of the enclosing body.

When the articulating body 918 is positioned within the enclosing body 906, the recess 960 receives the projection 956. In other words, the projection 956 is positioned within the recess 960. In some embodiments, the recess 960 and the projection 956 can have complementary shapes and/or dimensions. The recess 960 and/or projection 956 can be shaped, dimensioned, or otherwise configured to prevent relative rotation of the articulating body 918 within the enclosing body 906 when the projection 956 is received within the recess 960. The recess 960 and/or projection 956 can be shaped, dimensioned, or otherwise configured to allow relative movement between the articulating surface 926 and the articulating surface 928 along the axis of articulation. In some embodiments, the axis of articulation can be generally aligned with a longitudinal axis of the recess 960. The recess 960 can be configured to move superiorly and inferiorly relative to the projection 956, and/or the projection 956 can be configured to move superiorly and inferiorly within the recess 960.

Although a single projection 956 and a single recess 960 are shown, any number of projections and recesses may be utilized to prevent relative rotation of the articulating body 918 within the enclosing body 906.

In some embodiments, the enclosing body 906 is configured to protect the surrounding anatomy from friction, damage, or wear products due to the movement of components, including the articulating surface 926 and articulating surface 928 in the interior of the enclosing body 906, for example, by acting as a physical barrier. For example, the enclosing body 906 can protect an adjacent thecal sac and adjacent nerve roots from involvement with the articulating surfaces 926 and 928 during relative movement between the articulating surfaces 926 and 928. In some embodiments, the enclosing body 906 is configured to protect the components within the interior of the enclosing body 906 from damage, wear, or fibrosis due to the surrounding anatomy, for example, by acting as a physical barrier.

FIGS. 41A-C depict a top perspective, bottom perspective, and front view of the retention plate 917. As described above, the retention plate 917 can include the base layer 1004. The base layer 1004 can include a lip 1008 configured to be secured within the cavity 973 of the liner 952. In some embodiments, the retention plate can include the top layer 1002 positioned superior to the base layer 1004. In some embodiments, the top layer 1002 can having a smaller cross-sectional area than the base layer 1004. As described above with respect to FIGS. 37A-B, the retention plate 917 can couple to the liner 952 and/or shell 950 to form the enclosing body. The retention plate 917 can also define the opening 1006.

In certain embodiments, the facet joint replacement device 900 can be implanted in the same or similar manner and in the same or a similar location as described with respect to the facet joint replacement device 700, for example with respect to FIGS. 34A-G. For example, the attachment member 920 can be affixed to the pedicle 240 of the superior vertebra or superior vertebral body 205 by the fastener 874 and the attachment member 912 can be affixed to the pedicle 242 of the interior vertebra or inferior vertebral body 210 by a fastener 876.

When the facet joint replacement device 900 is implanted, the articulating surface 926 can be shaped, dimensioned, or otherwise configured to face at least partially in an anterior and lateral direction. When the facet joint replacement device 900 is implanted, the articulating surface 926 can be shaped, dimensioned, or otherwise configured to face in a direction that corresponds to that of an inferior articular surface of a healthy facet joint. When the facet joint replacement device 900 is implanted, the articulating surface 928 can be shaped, dimensioned, or otherwise configured to face at least partially in a posterior and medial direction. When the facet joint replacement device 900 is implanted, the articulating surface 928 can be shaped, dimensioned, or otherwise configured to face in a direction that corresponds to that of a superior articular surface of a healthy facet joint. In some embodiments, when the facet joint replacement device 900 is implanted, the enclosing body 906 can be located at an anatomical location corresponding to that of a healthy facet joint. In some embodiments, when the attachment member 912 is fixed relative to the inferior vertebral body and the attachment member 920 is fixed relative to the superior vertebral body, the attachment member 912 and/or the attachment member 920 can be shaped, dimensioned, or otherwise configured to locate the articulating surfaces 926 and 928 at a location corresponding to the location of the articular surfaces within the a healthy facet joint.

One of skill in the art would understand that a facet joint replacement device, such as facet joint replacement device 900, can be implanted on either lateral side of a motion segment, or two facet joint replacement devices can be implanted bilaterally, one on each side of a particular motion segment, for example, as described with respect to FIG. 12. One of skill in the art would further understand that two facet joint replacement devices, such as facet joint replacement device 900, can be implanted ipsilaterally, as described with respect to FIG. 20.

As described herein, the components of the facet joint replacement device 900 can be shaped and/or dimensioned to correspond to the anatomy of a healthy facet joint and related spinal motion segment. While lumbar facet joints are shown and described herein, applications of the facet joint replacement device 900 are not limited to the lumbar spine. In some embodiments, the facet joint replacement device 900 can be shaped and/or dimensioned to correspond to the anatomy of the thoracic spine. In some embodiments, a vertical distance between the superior end 908 of the enclosing body and the inferior end 910 of the enclosing body is between 20 mm to 44 mm, between 24 mm to 40 mm, between 28 mm and 36 mm, or between 30 mm and 34 mm. In some embodiments a vertical distance between the superior end 908 of the enclosing body and the inferior end 710 of the enclosing body is 28 mm, 29 mm, 30 mm, 31 mm, 32 mm, 33 mm, 34 mm, 35 mm, or 36 mm. In some embodiments, the facet joint replacement device 900 can be shaped and/or dimensioned to correspond to the anatomy of the cervical spine.

In some embodiments, one or both of the articulating surface 928 and articulating surface 926 can have a major axis length of 10 mm, 11 mm, 12 mm, 13 mm, 14 mm, 15 mm, 16 mm, 17 mm, 18 mm, between 10 mm to 25 mm, between 9 to 14 mm, between 10 to 14 mm, or between 12 mm to 14 mm. In some embodiments, one or both of the articulating surface 128 and articulating surface 126 can have a minor axis length of 8 mm, 9 mm, 10 mm, 11 mm, 12 mm, 13 mm, 14 mm, 15 mm, 16 mm, 17 mm, 18 mm, between 8 mm to 25 mm, between 8 mm to 14 mm, between 9 mm to 14 mm, or between 12 mm to 14 mm.

FIGS. 34A-G show a unilateral implantation of a facet joint replacement device 700. One of skill in the art would understand that a facet joint replacement device, such as facet joint replacement device 700, can be implanted on either lateral side of a motion segment, or two facet joint replacement devices can be implanted bilaterally, one on each side of a particular motion segment, for example, as described with respect to FIG. 12. One of skill in the art would further understand that two facet joint replacement devices, such as facet joint replacement device 700, can be implanted ipsilaterally, as described with respect to FIG. 20.

As described herein, the components of the facet joint replacement device 700 can be shaped and/or dimensioned to correspond to the anatomy of a healthy facet joint and related spinal motion segment. While lumbar facet joints are shown and described herein, applications of the facet joint replacement device 700 are not limited to the lumbar spine. In some embodiments, the facet joint replacement device 700 can be shaped and/or dimensioned to correspond to the anatomy of the thoracic spine. In some embodiments, a vertical distance between the superior end 708 of the enclosing body and the inferior end 710 of the enclosing body is between 20 mm to 44 mm, between 24 mm to 40 mm, between 28 mm and 36 mm, or between 30 mm and 34 mm. In some embodiments a vertical distance between the superior end 708 of the enclosing body and the inferior end 710 of the enclosing body is 28 mm, 29 mm, 30 mm, 31 mm, 32 mm, 33 mm, 34 mm, 35 mm, or 36 mm. In some embodiments, the facet joint replacement device 700 can be shaped and/or dimensioned of correspond to the anatomy of the cervical spine.

In some embodiments, one or both of the articulating surface 128 and articulating surface 126 can have a major axis length of 10 mm, 11 mm, 12 mm, 13 mm, 14 mm, 15 mm, 16 mm, 17 mm, 18 mm, between 10 mm to 25 mm, between 9 to 14 mm, between 10 to 14 mm, or between 12 mm to 14 mm. In some embodiments, one or both of the articulating surface 128 and articulating surface 126 can have a minor axis length of 8 mm, 9 mm, 10 mm, 11 mm, 12 mm, 13 mm, 14 mm, 15 mm, 16 mm, 17 mm, 18 mm, between 8 mm to 25 mm, between 8 mm to 14 mm, between 9 mm to 14 mm, or between 12 mm to 14 mm.

As shown in FIG. 35 with respect to facet joint replacement device 700, the axis 790 parallel to a sagittal anatomic plane can extend through a center point of the articulating surface 926, the axis 792 parallel to a frontal anatomic plane can extend through a center point of the articulating surface 926, and the axis 794 can extending through the center point of the articulating surface 926 and perpendicular to a tangent of the articulating surface 926 at the center point. As described above, an angle $\alpha$ extends between the axis 790 and the axis 794. An angle $\beta$ extends between the axis 792 and 794. In some embodiments, the angle $\alpha$ can be between 30° and 60°, between 35° and 55°, between 40° and 50°, or any other suitable range. In some embodiments, the angle $\alpha$ can be 30°, 35°, 40°, 45°, 50°, 55°, 60°, or any other suitable angle. In some embodiments, the angle $\beta$ can be between 30° and 60°, between 35° and 55°, between 40° and 50°, or any other suitable range. In some embodiments, the angle $\beta$ can be 30°, 35°, 40°, 45°, 50°, 55°, 60°, or any other suitable angle. In some embodiments, an angle between an axis extending through the center point of the articulating surface 926 parallel to a transverse anatomic plane and the axis 794 can be between 75° and 105°, between 80° to 100°, between 85° to 95° or any other suitable angle. In some embodiments, an angle between an axis extending through the center point of the articulating surface 926 parallel to a transverse anatomic plane and the axis 794 can be 75°, 80°, 85°, 90°, 95°, 100°, 105° or any other suitable angle.

Similarly, in some embodiments, an angle between an axis parallel to a frontal anatomic plane and extending through a center point of the articulating surface 928 and an axis extending through the center point of the articulating surface 928 and perpendicular to a tangent of the articulating surface 928 at the center point can be between 30° and 60°, between 35° and 55°, between 40° and 50°, or any other suitable range. In some embodiments, an angle between an axis parallel to a frontal anatomic plane and extending through a center point of the articulating surface 928 and an axis extending through the center point of the articulating surface 928 and perpendicular to a tangent of the articulating surface 928 at the center point can be 30°, 35°, 40°, 45°, 50°, 55°, 60°, or any other suitable angle. In some embodiments, an angle between an axis parallel to a sagittal anatomic plane and extending through a center point of the articulating surface 928 and an axis extending through the center point of the articulating surface 928 and perpendicular to a tangent of the articulating surface 928 at the center point can be between 30° and 60°, between 35° and 55°, between 40° and 50°, or any other suitable range. In some embodiments, an angle between an axis parallel to a sagittal anatomic plane and extending through a center point of the articulating surface 928 and an axis extending through the center point of the articulating surface 928 and perpendicular to a tangent of the articulating surface 928 at the center point can be 30°, 35°, 40°, 45°, 50°, 55°, 60°, or any other suitable angle. In some embodiments, an angle between an axis parallel to a transverse anatomic plane and extending through a center point of the articulating surface 928 and an axis extending through the center point of the articulating surface 928 and perpendicular to a tangent of the articulating surface 728 at the center point can be between 75° and 105°, between 80° to 100°, between 85° to 95° or any other suitable angle. In some embodiments, an angle between an axis parallel to a transverse anatomic plane and extending through a center point of the articulating surface 728 and an axis extending through the center point of the articulating surface 928 and perpendicular to a tangent of the articulating surface 928 at the center point can be 75°, 80°, 85°, 90°, 95°, 100°, 105°, or any other suitable angle.

In some embodiments, the axis of articulation can be perpendicular to a transverse anatomic plane. In some embodiments, the axis of articulation can be parallel to a sagittal anatomic plane. In some embodiments, the axis of articulation can be parallel to a frontal anatomic plane.

As described herein, in some embodiments, the implant 900 can be shaped and/or dimensioned to correspond to the anatomy of the lumbar spine, thoracic spine, or cervical spine.

In some embodiments, an angle between the transverse anatomic plane and a mean orientation of the articulating surface 926 can be between 0° and 98°, between 10° and 88°, between 20° and 78°, or any other suitable angle for a facet joint replacement device 700 implanted within the cervical spine. In some embodiments, an angle between the transverse anatomic plane and a mean orientation of the articulating surface 926 can be between 35° and 100°, between 45° and 90°, between 55° and 80°, or any other suitable angle for a facet joint replacement device 900 implanted within the thoracic spine. In some embodiments, an angle between the transverse anatomic plane and a mean orientation of the articulating surface 926 can be between 62° and 106°, between 72° and 96°, between 82° and 86°, or any other suitable angle for a facet joint replacement device 900 implanted within the lumbar spine. In some embodiments, the transverse anatomic plane may be referred to as the 0° transverse plane. In some embodiments, the foregoing angles between the transverse anatomic plane and a mean orientation of the articulating surface 926 may be referred to as inclination angles of the articulating surface 926 within the sagittal anatomic plane.

In some embodiments, an angle between the sagittal anatomic plane and a mean orientation of the articulating surface 926 can be between 50° and 116°, between 60° and 106°, between 70° and 96°, or any other suitable angle for a facet joint replacement device 700 implanted within the cervical spine. In some embodiments, an angle between the sagittal anatomic plane and a mean orientation of the articulating surface 926 can be between 65° and 140°, between 75° and 130°, between 85° and 120°, or any other suitable angle for a facet joint replacement device 700 implanted within the thoracic spine. In some embodiments, an angle between the sagittal anatomic plane and a mean orientation of the articulating surface 926 can be between 0° and ° 90, between 5° and 80°, between 15° and 70°, or any other suitable angle for a facet joint replacement device 900 implanted within the lumbar spine. In some embodiments, the sagittal anatomic plane may be referred to as the 0° sagittal plane. In some embodiments, the foregoing angles between the sagittal anatomic plane and a mean orientation of the articulating surface 926 may be referred to as inclination angles of the articulating surface 926 within the transverse anatomic plane.

In some embodiments, the articulating surface 926 can be configured to articulate relative to the articulating surface 928 by moving substantially only parallel to an axis defined by the inclination angles of the articulating surface 926 within the sagittal and transverse anatomic planes.

In some embodiments, an angle between the transverse anatomic plane and a mean orientation of the articulating surface 928 can be between 0° and 98°, between 10° and 88°, between 20° and 78°, or any other suitable angle for a facet joint replacement device 900 implanted within the cervical spine. In some embodiments, an angle between the transverse anatomic plane and a mean orientation of the articulating surface 928 can be between 35° and 100°, between 45° and 90°, between 55° and 80°, or any other suitable angle for a facet joint replacement device 900 implanted within the thoracic spine. In some embodiments, an angle between the transverse anatomic plane and a mean orientation of the articulating surface 928 can be between 62° and 106°, between 72° and 96°, between 82° and 86°, or any other suitable angle for a facet joint replacement device 900 implanted within the lumbar spine. In some embodiments, the transverse anatomic plane may be referred to as the 0° transverse plane. In some embodiments, the foregoing angles between the transverse anatomic plane and a mean orientation of the articulating surface 928 may be referred to as inclination angles of the articulating surface 928 within the sagittal anatomic plane.

In some embodiments, an angle between the sagittal anatomic plane and a mean orientation of the articulating surface 928 can be between 50° and 116°, between 60° and 106°, between 70° and 96°, or any other suitable angle for a facet joint replacement device 900 implanted within the cervical spine. In some embodiments, an angle between the sagittal anatomic plane and a mean orientation of the articulating surface 928 can be between 65° and 140°, between 75° and 130°, between 85° and 120°, or any other suitable angle for a facet joint replacement device 700 implanted within the thoracic spine. In some embodiments, an angle between the sagittal anatomic plane and a mean orientation of the articulating surface 728 can be between 0° and ° 90, between 5° and 80°, between 15° and 70°, or any other suitable angle for a facet joint replacement device 900 implanted within the lumbar spine. In some embodiments, the sagittal anatomic plane may be referred to as the 0° sagittal plane. In some embodiments, the foregoing angles between the sagittal anatomic plane and a mean orientation of the articulating surface 928 may be referred to as inclination angles of the articulating surface 928 within the transverse anatomic plane.

In some embodiments, the articulating surface 928 can be configured to articulate relative to the articulating surface 926 by moving substantially only parallel to an axis defined by the inclination angles of the articulating surface 928 within the sagittal and transverse anatomic planes.

FIGS. 42A-F depict a device holder 1040 according to one embodiment. FIG. 42A depicts a perspective view of the device holder 1040. FIG. 42B depicts a front view of the device holder 1040. FIG. 42C depicts a side view of the device holder 1040.

As shown in FIGS. 42A-C, in some embodiments, the device holder 1040 can include a handle 1042. In some embodiments, the handle 1042 can be shaped, dimensioned, and/or otherwise configured to be grasped and manipulated by a user.

In some embodiments, the device holder can include a fastener or fastening head 1046. In some embodiments, the device holder 1040 can include a shaft 1044. The shaft 1044 can extend between the handle 1042 and the fastening head 1046.

FIG. 42D depicts a top perspective enlarged view of a portion of the device holder 1040 showing the fastening head 1046. FIG. 42E depicts a bottom perspective enlarged view of a portion of the device holder 1040 showing the fastening head 1046.

As shown in FIGS. 42D-E, the fastening head 1046 can include an externally threaded portion 1048, a generally cylindrical portion 1050, and a tip 1052. In some embodiments, the fastening head 1046 can have generally the same or similar shape as the fastener 740. In some embodiments, the fastening head 1046 can include any of the same features or functions as the fastener 740. In some embodiments, the fastening head 1046 can be used for any of the uses of the fastener 740 described herein.

In some embodiments, the device holder 1040 can be configured to couple to a facet joint replacement device such as facet joint replacement device 700 or facet joint replacement device 900. FIG. 42F depicts a perspective view of the device holder 1040 coupled to the facet joint replacement device 900. FIG. 42G depicts an enlarged cross-sectional view of a portion of the device holder 1040 coupled to the facet joint replacement device 900.

As shown in FIG. 42G, the fastening head 1046 can be received within the channels 944 and 946 of the enclosing body 906 and articulating element 918. As shown in FIG. 42G, the externally threaded section 1048 of the fastening head 1046 can removably secure to the internally threaded section 947 of the channel 944. In some embodiments, the externally threaded section 1048 of the fastening head 1046 can removably secure to an internally threaded section of the channel 946. In some embodiments, the handle 1042 can be used to apply torque to the fastening head 1046 to thread and unthread the threaded section 1048 of the fastening head 1046 with the internally threaded section 947 of the channel 944 or with an internally threaded section of the channel 946. When positioned within the channels 944 and 946, the fastening head 1046 can prevent movement of the articulating body 918 relative to the enclosing body 906. When positioned within the channels 944 and 946, the fastening head 1046 can maintain the articulating body 918 at the neutral position within the channels 944 and 946.

In some embodiments, the device holder 1040 or one or more components of the device holder 1040, such as the handle 1042, the shaft 1044, and the fastening head 1046, can be formed of or formed partially of one or more metals or metal alloys. For example, the device holder 1040 or one or more components of the device holder 1040, such as the handle 1042, the shaft 1044, and the fastening head 1046, can be formed of cobalt-chromium, titanium, titanium-based alloys, stainless steel, or any other suitable metals or metal alloys. In some embodiments, the device holder 1040 or one or more components of the device holder 1040, such as the handle 1042, the shaft 1044, and the fastening head 1046, can be ceramic or partially ceramic. In some embodiments, the device holder 1040 or one or more components of the device holder 1040, such as the handle 1042, the shaft 1044, and the fastening head 1046, can include super-hard ceramics.

In some embodiments, the device holder 1040 can be coupled to a facet joint replacement device, such as the facet joint replacement devices 700 and 900 at the time of manufacturing, prior to shipping the facet joint replacement device, or prior to installation of the facet joint replacement device to prevent movement of an articulating body, such has articulating bodies 718 and 918, within an enclosing body, such as enclosing bodies 706 and 906. The implant holder 1040 can also be used to position the facet joint replacement device within the body, for example, by a user manipulating the handle 1042. The facet joint replacement device can be secured within the body, for example, using fasteners such as fasteners 874 and 876, while the implant holder 1040 is coupled to the facet joint replacement device. After the facet joint replacement device is secured, the handle 1042 can be manipulated to unthread the threaded portion 1048 from the facet joint replacement device and remove the device holder 1040 from the surgical site.

FIGS. 43A-D depict an embodiment of a plug assembly 1020. FIG. 43A is a top perspective view of the plug assembly 1020. FIG. 43B is a bottom perspective view of the plug assembly 1020. FIG. 43C is a first enlarged cross-sectional view of the plug assembly 1020. FIG. 43D is a second enlarged cross-sectional view of the plug assembly 1020 showing the plug assembly 1020 separated into two pieces.

In some embodiments, the plug assembly 1020 includes the plug 980 described herein with respect to FIGS. 33A-33D. In some embodiments, the plug assembly 1020 can include a plug insertion section 1022. The plug insertion section 1022 and the plug 980 can be coupled at a joint or connection 1028. In some embodiments, the plug insertion section 1022 and the plug 980 are integrally formed. In some embodiments, the connection 1028 is a frangible connection. The connection 1028 can be configured to break, shear, tear, and/or otherwise separate in response to application of a force to the plug assembly 1020, such as for example, a rotational force. In some embodiments, the connection 1028 can be configured to break, shear, tear, and/or otherwise separate in response to application of a force to the plug insertion section 1022, such as for example, a rotational force. In some embodiments, the connection 1028 can be configured to break, shear, tear, and/or otherwise separate in response to application of a force to the plug insertion section 1022, such as for example, a rotational force, while the plug 980 is maintained in a fixed position. As shown in FIG. 43D, the plug assembly 1020 can be separated at the connection 1028 so that the plug 980 is separated from the plug insertion section 1022.

In some embodiments, a channel 1024 can extend through the plug insertion section 1022 and at least partially into the plug 980. In some embodiments, the plug insertion section 1022 can include an internally threaded portion 1024.

In certain embodiments, the plug assembly 1020 can be configured to receive a tool or instrument for inserting the plug 980 into a facet joint replacement device, such as facet joint replacement device 700 and facet joint replacement device 900. For example, in certain embodiments, the threads 1026 can be configured to engage with corresponding threads of an instrument or tool for inserting the plug 980 into a facet joint replacement device.

In some embodiments, the plug assembly 1020 can be configured to couple with the device holder 1040. In some embodiments, the device holder 1040 can be a plug inserter. FIG. 44A depicts a perspective view of the device holder 1040 coupled to the plug insertion portion 1020. FIG. 44B depicts an enlarged cross-sectional view showing a portion of the device holder 1040 coupled to the plug assembly 1020. FIG. 44C is a front view showing the device holder 1040 coupled to the plug insertion portion 1022 after separation of the plug insertion portion 1022 from the plug 980.

In some embodiments, as shown in FIG. 44B, in some embodiments, the plug assembly 1020 can be configured to receive the fastening head 1046 of the device holder 1040 within the channel 1024. In some embodiments, the internal threads 1026 of the plug insertion section 1022 can be configured to mate with the external threads 1048 of the fastening head 1046.

In certain embodiments, the plug 980 can be used in the same or a similar fashion as the plug 780 described herein. For example, the plug 980 can be positioned within the channel 744 of the facet joint replacement device 700 as shown in FIGS. 33C-D. The plug 980 can similarly be positioned within the channel 944 of the facet joint replacement device 900.

The externally threaded section 981 of the plug 980 can removably secure to the internally threaded section 747 of the channel 744 or the internally threaded section 947 of the channel 944. In some embodiments, the plug is shaped, dimensioned, or otherwise configured to extend through only a portion of the channel 744 or 944. The plug 980 can be dimensioned, shaped, or otherwise configured such that when the plug 980 is positioned within the facet joint replacement device 700 or 900, the plug 980 does not extend into the channel 746 or 946. When the plug 980 is positioned within the facet joint replacement device 700 or 900, the plug 980 does not restrict movement of the articulating body 718 or 918 within the enclosing body 706 or 906. In some embodiments, the plug 980 is shaped, dimensioned, or otherwise configured to fit flush with an exterior surface of the enclosing body 706 or 906.

When positioned within the enclosing body 706 or 906, the plug 980 can seal the opening 742 or 942 and/or channel 744 or 944 relative to the surrounding anatomy. By sealing the opening 742 or 942 and/or channel 744 or 944, the plug 980 can act as a physical barrier along with enclosing body 706 or 906 to protect the surrounding anatomy from friction, damage, or infection due to the movement of components, including the articulating surface 726 or 926 and articulating surface 728 or 928 in the interior of the enclosing body 706 or 906. For example, the enclosing body 706 or 906 and plug 980 can protect an adjacent thecal sac and adjacent nerve roots from involvement with the articulating surfaces 726 and 728 or 926 and 928 during relative movement between the articulating surfaces 726 and 728 or 026 and 028. In some embodiments, the plug 980 and enclosing body 706 or 906 are configured to protect the components within the interior of the enclosing body 706 from damage, wear, or fibrosis due to the surrounding anatomy, for example, by acting as a physical barrier.

In certain embodiments, the device holder 1040 can be used to position the plug 980 within a facet joint replacement device, such as facet joint replacement devices 700 and 900, while the plug assembly 1020 is coupled to the device holder 1040. In some embodiments, the handle 1042 can be manipulated to thread the externally threaded section 981 of the plug 980 with the internally threaded section 747 of the channel 744 or the internally threaded section 947 of the channel 944. In some embodiments, after the externally threaded section 981 of the plug 980 is mated with the internally threaded section 747 of the channel 744 or the internally threaded section 947 of the channel 944, the handle 1042 can be used to turn the plug assembly 1020 in the same direction as used for mating the externally threaded section 981 of the plug 980 with the internally threaded section 747 of the channel 744 or the internally threaded section 947 of the channel 944 to apply a shearing force to the connection 1028 to cause the plug insertion section 1022 to shear off from the plug 980 as shown in FIG. 44C. After the plug insertion section 1022 is disconnected from the plug 980, the insertion section 1022 can be removed from the body by removing the device holder 1040.

As shown herein, in some embodiments, a fastening head 1046 can be used as both a fastener to prevent movement of the articulating element 918 within the enclosing body 906 and as a plug inserter. In other embodiments, the device holder 1040 may include a first end having a first fastening head 1046 for use a fastener to prevent movement of the articulating element 918 within the enclosing body 906 and a second end having a second fastening head 1046 for use as a plug inserter. Such an embodiment may be beneficial if different threading patterns are required to mate with the threaded sections of the plug assembly 1020 and the facet joint replacement device 900.

In some embodiments, facet joint replacement devices 900 may be available in a plurality of different sizes. FIG. 45A depicts a posterior view of a facet joint replacement device 900A having a first size. FIG. 45B depicts a posterior view of an articulating element 904A of the facet joint replacement device 900A. FIG. 45C depicts a posterior view of a facet joint replacement device 900B having a second size greater than the first size of FIGS. 45A-B. FIG. 45D depicts a posterior view of an articulating element 904B of the facet joint replacement device 900B. FIG. 45E depicts a posterior view of a facet joint replacement device 900C having a third size greater than the second size of FIGS. 45C-D. FIG. 45F depicts a posterior view of an articulating element 904C of the facet joint replacement device 900C.

As shown in FIGS. 45A-F, the facet joint replacement devices 900A-C can include generally the same or similar components as the facet joint replacement device 900. For example, the facet joint replacement devices 900A-C include attachments members 920A-C, enclosing elements 902A-C, enclosing bodies 906A-C, attachment members 912A-C, shells 950A-C, lines 952A-C, superior ends 908A-C, inferior ends 910A-C, channels 944A-C, first sections 911A-C, second sections 913A-C, bends 915A-C, openings 949A-C, first sections 921A-C, second sections 923A-C, bends 925A-C, superior ends 922A-C, inferior ends 924A-C, recesses 960A-C, surrounding areas 962A-C, and exterior surfaces 964A-C, as shown in FIGS. 45A-F. The components of the facet joint replacement devices 900A-C can have generally the same or similar features or functions as those of the facet joint replacement device 900.

In some embodiments, a distance between the superior end of the attachment member 920A and the inferior end of the attachment member 912A can be between 20 mm and 27 mm, 21 mm to 26 mm, 22 mm to 25 mm, 23 mm to 24 mm, or any other suitable range when the articulating body 918A is in the neutral position. In some embodiments, the distance between the superior end of the attachment member 920A and the inferior end of the attachment member 912A can be 20 mm, 21 mm, 22 mm, 23 mm, 23.5 mm, 24 mm, 25 mm, 26 mm, 27 mm, or any other suitable distance when the articulating body 918A is in the neutral position.

In some embodiments, a distance between the superior end of the attachment member 920B and the inferior end of the attachment member 912B can be between 25 mm and 32 mm, 26 mm to 31 mm, 27 mm to 30 mm, 28 mm to 29 mm, or any other suitable range when the articulating body 918B is in the neutral position. In some embodiments, the distance between the superior end of the attachment member 920B and the inferior end of the attachment member 912B can be 25 mm, 26 mm, 27 mm, 28 mm, 28.5 mm, 29 mm, 30 mm, 31 mm, 32 mm, or any other suitable distance when the articulating body 918B is in the neutral position.

In some embodiments, a distance between the superior end of the attachment member 920C and the inferior end of the attachment member 912C can be between 30 mm and 37 mm, 31 mm to 36 mm, 32 mm to 35 mm, 33 mm to 34 mm, or any other suitable range when the articulating body 918C is in the neutral position. In some embodiments, the distance between the superior end of the attachment member 920C and the inferior end of the attachment member 912C can be 30 mm, 31 mm, 32 mm, 33 mm, 33.5 mm, 34 mm, 35 mm, 36 mm, 37 mm, or any other suitable distance when the articulating body 918C is in the neutral position.

In some embodiments, a distance between the superior end of the attachment member 920B and the inferior end of the attachment member 912B can be 5 mm or about 5 mm greater than a distance between the superior end of the attachment member 920A and the inferior end of the attachment member 912A, when the articulating bodies 918A and 918B are in the neutral position.

In some embodiments, a distance between the superior end of the attachment member 920C and the inferior end of the attachment member 912C can be 5 mm or about 5 mm greater than a distance between the superior end of the attachment member 920B and the inferior end of the attachment member 912B, when the articulating bodies 918B and 918C are in the neutral position.

In some embodiments, the shape and size of the enclosing element 902A can be the same or generally the same shape and size as the enclosing element 902B except that the attachment member 912A extends from the enclosing body 906A at a position superior to a position at which the attachment member 912B extends form the enclosing body 906B, for example at a position 5 mm or about 5 mm superior to the position at which the attachment member 912B extends from the enclosing body 906B.

In some embodiments, the shape and size of the enclosing element 902B and the enclosing element 902C can be the same or generally the same, and the attachment member 920C can extend a greater distance from the superior end 922C of the articulating body 906C than the attachment member 920B extends from the superior end 922B of the articulating body 906B. For example, in some embodiments, the attachment member 920C can extend a distance 5 mm or generally 5 mm farther from the superior end 922C of the articulating body 906C than the attachment member 920B extends from the superior end 922B of the articulating body 906B.

In some embodiments, a method for implanting facet joint replacement device 700 or 900 into a patient begins with the administration of general endotracheal anesthesia. Following the administration of anesthesia, the patient is placed into a prone position and intraoperative fluoroscopy is used to identify a desired location for making a skin incision for implanting the facet joint replacement device 700 or 900. After the desired location is selected, a midline lumbarsacral incision is made at the desired location, and subperiosteal dissection is utilized to expose a desired lamina, facet joint, and entry points to cannulate the ipsilateral pedicles of the superior and inferior vertebral bodies associated with the facet joint to be replaced. In some alternative embodiments, minimally invasive surgical techniques can be employed for exposure of the desired lamina, facet joint, and entry points to cannulate the ipsilateral pedicles. After exposure of the desired structures, intraoperative fluoroscopy is utilized to confirm desired levels of exposure. After the desired levels of exposure are confirmed, a self-retaining retractor system is placed to maintain the desired level of exposure.

After the retractor system is in place, removal of one or more sections of the facet joint and surrounding bone is performed. In some embodiments, the lamina or portion of the lamina in the motion region to be treated is removed. Removal can be performed using bone biters, angled curets, and/or bone punches. In some embodiments, a ligamentum flavum or a portion of the ligamentum flavum in the motion segment to be treated is removed. Removal of the ligamentum flavum can be performed using bone punches. The facet joint or a portion of the facet joint to be treated is also removed. Removal of the facet joint can be performed using a high speed drill, bone biters, and/or bone punches. After removal of the facet joint to be treated, further decompression of the lateral recess can be performed and adjacent nerve roots can be identified. Additional bone may be removed as necessary to prevent mechanical compression of the nerve roots.

Following removal of the desired bone, the pedicles of the superior vertebral body and inferior vertebral body of the motion segment to be treated and desired points of entry to cannulate the pedicles are identified, for example, using intraoperative fluoroscopy. A high speed drill or bone awl is then used to perforate the cortical bone overlying the optimal entry points to cannulate each of the pedicles. The pedicles are then probed and tapped under fluoroscopic guidance. Tulip head bone screws, such as the tulip head bone screws of fasteners 874 and 876, are then screwed into the previously tapped pedicles. Additional fixation augmentors, such as methylmethacrylate, can also be used. In some embodiments, a decision to use additional fixation augmentors is made based on apparent bone quality at the time of bone screw insertion. Methylmethacrylate or other fixation augmentors can be placed within the cannulated pedicle prior to placement of the bone screw, for example, to improve the fixation of the bone screw within the implanted pedicle bone.

After fixation of the bone screws to the superior and inferior vertebral bodies, the attachment member 720 or 920 can be placed within a receiving portion of the tulip head portion of the bone screw in the superior vertebral body, and the attachment member 712 or 912 can be placed within a receiving portion of the tulip head portion of the bone screw in the inferior vertebral body. After the attachment member 720 or 920 and attachment member 712 or 912 are received within the tulip head portions of the implanted bone screws, the attachment member 720 or 920 and attachment member 712 or 912 can be secured to the bone screws by fixation of top loading set screws to each of the tulip head portions of the implanted bone screws.

In some embodiments, after ensuring that the implanted bone screws are in proper position and secure, but before the attachment members 720 and 712 or 920 and 912 are placed into the bone screws, distraction or compression can be applied between the implanted bone screws to address any asymmetric loss of the disc space height or malalignment.

In some embodiments, facet joint replacement devices 700 or 900 may be available in a plurality of different sizes, as described herein with respect to FIGS. 45A-F. In such embodiments, after implantation of the tulip head bone screws into the superior and inferior vertebral bodies, a distance is measured between the tulips head portions of the bone screws and a facet joint replacement device can be selected based on the distance measured between the tulip head portions of the bone screws, for example, so that the attachment members of the facet joint replacement device can be securely engaged with the tulip head portions of the implanted bone screws.

In some embodiments, facet joint replacement devices 700 or 900 may be available with articulating surfaces having a plurality of different angular orientations with respect to the sagittal, transverse, and/or frontal anatomic planes, as described further herein. In such embodiments, after implantation of the tulip head bone screws into the superior and inferior vertebral body, a facet joint replacement device is selected based on the desired angular orientations of the articulating surfaces. The desired angular orientations can be selected based on estimated angular orientations of the articular surfaces of a healthy facet joint in the treated motion segment.

In some embodiments, methods of implanting the facet joint replacement device 700 or 900 include securing the articulating body 718 or 918 in a desired position within the enclosing body 706 or 906, such as the neutral position, prior to implantation in the body using the fastener 740 or the device holder 1040. In some embodiments, methods of implanting the facet joint replacement device 700 or 900 include positioning the articulating body 716 or 916 within the enclosing body at a desired position, such as the neutral position, prior to positioning the fastener 740 or the fastening head 1046 in the channel 744 or 944 and the channel 746 or 946.

In some embodiments, methods of implanting the facet joint replacement device 700 or 900 include introducing the facet joint replacement device 700 or 900 into the body while the fastener 740 or fastening head 1046 is positioned within the channel 744 or 944 and the channel 746 or 946 to constrain movement of the articulating body in the enclosing body. In some embodiments, introducing the facet joint replacement device 700 or 900 into the body while the fastener 740 or fastening head 1046 is positioned within the channels 744 and 746 or 944 and 946 can maintain the articulating body 718 or 918 in a desired position within the enclosing body 706 or 906, such as the neutral position, during implantation in the body using the fastener 740 or the fastening head 1046.

In some embodiments, methods of implanting the facet joint replacement device 700 or 900 include securing the facet joint replacement device 700 or 900 relative to a superior vertebral body and relative to an inferior vertebral body of the patient while the fastener 740 or fastening head 1046 is positioned within the channel 744 or 944 and the channel 746 or 946 to constrain movement of the articulating body 718 or 918 within the enclosing body 706 or 906, for example, to maintain the articulating body 718 or 918 in a desired position within the enclosing body 706 or 906, such as the neutral position.

In some embodiments, the fastener 740 can remain positioned within the facet joint replacement device 700 following implantation. In some embodiments, the fastener 740 or fastening head 1046 can be removed after the facet joint replacement device 700 or 900 is secured to the spine to allow for movement of the articulating body 718 or 918 within the enclosing body 706 or 906. In some embodiments, the fastener 740 or fastening head 1046 can be removed from the channel 744 or 944 and the channel 746 or 946 after securing the facet joint replacement device 700 or 900 relative to the superior vertebral body and relative to the inferior vertebral body to allow movement of the articulating body 718 or 918 within the enclosing body 706 or 906. In some embodiments in which removal of the fastener or fastening head 1046 is required, the device holder 1040 may provide the benefit of preventing a surgeon from leaving the fastening head 1046 within the facet joint replacement device 900 due to the shaft 1044 and handle 1042 extending out of the body.

In some embodiments, after removal of the facet joint replacement device 700 or 900, the plug 780 or 980 can be positioned within the opening 742 or 942 and channel 744 or 944. For example, in some embodiments, the plug 980 can be positioned within the opening 742 or 942 and channel 744 or 944 using the device holder 1040. In some embodiments, the fastening head 1046 can be coupled to the device plug assembly 1020. When the plug assembly 1020 is coupled to the fastening head 1046, the device holder 1040 can be used to position the plug 980 within the opening 742 or 942 and the channel 744 and 944. After the plug 980 is positioned within the opening 742 or 942 and the channel 744 and 944, the device holder 1040 can be used to apply a shearing force to separate the plug insertion section 1022 from the plug 980 so that the plug 980 remains within the opening 742 or 942 and the channel 744 and 944, and the plug insertion section is removed using the device holder 1040.

As described herein, when positioned within the enclosing body 706 or 906, the plug 780 or 980 can seal the opening 742 or 942 and/or channel 744 or 944 relative to the surrounding anatomy. By sealing the opening 742 or 942 and/or channel 744 or 944, the plug 780 or 980 can act as a physical barrier along with enclosing body 706 or 906 to protect the surrounding anatomy from friction, damage, or infection due to the movement of components, including the articulating surface 726 or 926 and articulating surface 728 or 928 in the interior of the enclosing body 706 or 906. For example, the enclosing body 706 or 906 and plug 780 or 980 can protect an adjacent thecal sac and adjacent nerve roots from involvement with the articulating surfaces 726 or 926 and 728 or 928 during relative movement between the articulating surfaces 726 or 926 and 728 or 928. In some embodiments, the plug 780 or 980 and enclosing body 706 or 906 are configured to protect the components within the interior of the enclosing body 706 or 906 from damage, wear, or fibrosis due to the surrounding anatomy, for example, by acting as a physical barrier. In combination, the fastener 740 or fastening head 1046 and the plug 780 or 980 can be used to restrict relative movement of the articulating surfaces 726 and 728 or articulating surfaces 926 and 928 during implantation and allow movement of the articulating surfaces after implantation while maintaining a physical barrier to the surrounding anatomy.

While this invention has been particularly shown and described with reference to embodiments thereof, it will be understood by those skilled in the art that various changes in form and details may be made therein without departing from the scope of the invention. For all of the embodiments described above, the steps of the methods need not be performed sequentially.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

It will be apparent to those skilled in the art that various modifications and variations can be made in the present invention without departing from the scope or spirit of the invention. Thus, it is intended that the present invention cover modifications and variations of this invention.

What is claimed is:

1. A facet joint replacement system, comprising:
   a facet joint replacement device comprising:
      an enclosing body comprising:

an interior surface defining an inner cavity of the enclosing body, the interior surface comprising:
a first articulating surface; and
a projection extending inwardly relative to a surrounding area of the interior surface; and
an articulating body positioned within the inner cavity of the enclosing body, the articulating body configured to move within the inner cavity of the enclosing body, wherein the articulating body comprises:
a second articulating surface; and
a recess extending inwardly relative to a surrounding area of the articulating body and aligned with the projection of the interior surface of the enclosing body so as to allow movement of the projection along the recess of the articulating body while constraining rotational motion of the articulating body within the enclosing body.

2. The facet joint replacement system of claim 1, wherein the projection is configured to move within the recess parallel to a longitudinal axis of articulation.

3. The facet joint replacement system of claim 1, wherein the projection is generally convex and the recess is generally concave.

4. The facet joint replacement system of claim 1, further comprising:
a first attachment member extending from the articulating body and configured to be secured relative to a superior vertebral body; and
a second attachment member extending from the enclosing body and configured to be secured relative to an inferior vertebral body.

5. The facet joint replacement system of claim 4, wherein the second attachment member is configured to extend from a lateral surface of the enclosing body;
wherein the first attachment member comprises a lateral bend in a section of the first attachment member; and
wherein the second attachment member includes a bend in a section of the second attachment member lateral to the enclosing body.

6. The facet joint replacement system of claim 4, further comprising a retention plate comprising an opening, wherein the first attachment member extends out of the opening of the retention plate.

7. The facet joint replacement system of claim 6, wherein a cross-sectional area of the opening of the retention plate is less than a cross-sectional area of the articulating body.

8. The facet joint replacement system of claim 1, wherein the second articulating surface is at least partially positioned on an anterior and medial section of the articulating body.

9. The facet joint replacement system of claim 1, wherein the second articulating surface is positioned on a face of the articulating body opposite the recess.

10. A facet joint replacement system, comprising:
a facet joint replacement device comprising:
an enclosing body comprising:
an interior surface defining an inner cavity of the enclosing body, the interior surface comprising a first articulating surface; and
a first channel extending through a portion of the enclosing body; and
an articulating body positioned within the inner cavity of the enclosing body, the articulating body configured to move within the inner cavity of the enclosing body, wherein the articulating body comprises:
a second articulating surface; and
a second channel extending through at least a portion of the articulating body;
a fastener configured to be removably received within the first channel and the second channel, the fastener configured to engage the enclosing body and articulating body to constrain movement of the articulating body within the enclosing body; and
a plug configured to be removably received within the first channel.

11. The facet joint replacement system of claim 10, wherein the plug is configured to seal the first channel relative to an external environment of the enclosing body.

12. The facet joint replacement system of claim 10, wherein the plug comprises external threads configured to be removably secured to complementary threads within the first channel.

13. The facet joint replacement system of claim 10, wherein the plug is dimensioned to extend through only a portion of the first channel and to fit flush with an exterior surface of the enclosing body.

14. The facet joint replacement system of claim 10, further comprising a facet joint replacement device holder comprising:
a handle;
a shaft extending from the handle; and
the fastener, wherein the fastener is integrally formed with the shaft at an end of the shaft opposite the handle.

15. The facet joint replacement system of claim 14, further comprising a plug assembly, the plug assembly comprising the plug and a plug insertion section coupled to the plug at a frangible connection, wherein the plug insertion section is configured to removably couple to the fastener, and wherein the plug insertion section is configured to separate from the plug at the frangible connection in response to a rotational force exerted on the plug insertion section by the fastener while the plug is positioned within the first channel.

16. A facet joint replacement device comprising:
an enclosing body configured to be secured relative to one of a superior vertebral body and an inferior vertebral body, the enclosing body comprising a first articulating surface; and
an articulating body configured to be secured relative to the other of the superior vertebral body and the inferior vertebral body, wherein the articulating body is positioned within an inner cavity of the enclosing body, the articulating body comprising a second articulating surface positioned within the inner cavity configured to articulate relative to the first articulating surface;
wherein when the enclosing body and the articulating body are secured relative to the superior and inferior vertebral bodies, the first articulating surface and the second articulating surface are configured such that they are located approximately at the location of a natural facet joint and are configured to articulate relative to each other by moving substantially only parallel to a superior/inferior axis of the patient.

17. The facet joint replacement device of claim 16, wherein, when the enclosing body and the articulating body are secured relative to the superior and inferior vertebral bodies, the first articulating surface and the second articulating surface are configured such that they are located medial to locations at which the enclosing body and the articulating body are secured relative to the superior vertebral body and inferior vertebral body.

18. The facet joint replacement device of claim 16, wherein the enclosing body comprises:
an outer shell defining an exterior surface of the enclosing body; and a liner covering an interior surface of the outer shell, the liner comprising a low friction material and defining the inner cavity of the enclosing body, a portion of the liner defining the first articulating surface.

19. The facet joint replacement device of claim 18, wherein the liner comprises Vitamin E impregnated ultra-high molecular weight polyethylene.

20. The facet joint replacement device of claim 18, wherein the liner circumferentially encloses the first articulating surface and the second articulating surface during relative movement between the first articulating surface and the second articulating surface; and wherein one or both of the liner and the outer shell include one or more surface features to restrict relative motion between the liner and the outer shell.

* * * * *